US011357801B2

(12) United States Patent
Adams et al.

(10) Patent No.: US 11,357,801 B2
(45) Date of Patent: Jun. 14, 2022

(54) METHODS FOR TREATING AUTISM SPECTRUM DISORDER AND ASSOCIATED SYMPTOMS

(71) Applicant: ARIZONA BOARD OF REGENTS ON BEHALF OF ARIZONA STATE UNIVERSITY, Scottsdale, AZ (US)

(72) Inventors: James Adams, Tempe, AZ (US); Dae-Wook Kang, Phoenix, AZ (US); Rosa Krajmalnik-Brown, Chandler, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 392 days.

(21) Appl. No.: 16/306,240

(22) PCT Filed: Jun. 14, 2017

(86) PCT No.: PCT/US2017/037499
§ 371 (c)(1),
(2) Date: Nov. 30, 2018

(87) PCT Pub. No.: WO2017/218681
PCT Pub. Date: Dec. 21, 2017

(65) Prior Publication Data
US 2019/0134111 A1  May 9, 2019

Related U.S. Application Data

(60) Provisional application No. 62/350,693, filed on Jun. 15, 2016.

(51) Int. Cl.
*A61K 35/741* (2015.01)
*A61K 35/745* (2015.01)
*A61K 35/74* (2015.01)

(52) U.S. Cl.
CPC ............ *A61K 35/741* (2013.01); *A61K 35/74* (2013.01); *A61K 35/745* (2013.01)

(58) Field of Classification Search
None
See application file for complete search history.

(56) References Cited

U.S. PATENT DOCUMENTS

| | | | |
|---|---|---|---|
| 3,192,116 A | 6/1965 | Möse et al. | |
| 3,320,130 A | 5/1967 | Henry | |
| 3,713,836 A | 1/1973 | Carlsson | |
| 4,098,728 A | 7/1978 | Rosenblatt | |
| 4,309,782 A | 1/1982 | Paulin | |
| 4,332,790 A | 6/1982 | Sozzi et al. | |
| 4,335,107 A | 6/1982 | Snoeyenbos et al. | |
| 4,394,377 A | 7/1983 | Spires | |
| 4,452,779 A | 6/1984 | Cockerill | |
| 4,536,409 A | 8/1985 | Farrell et al. | |
| 4,657,762 A | 4/1987 | Mikkola et al. | |
| 4,710,379 A | 12/1987 | Kawai et al. | |
| 4,892,731 A | 1/1990 | Arai et al. | |
| 4,975,286 A | 12/1990 | Hechter | |
| 5,213,807 A | 5/1993 | Chemburkar et al. | |
| 5,266,315 A | 11/1993 | Taguchi et al. | |
| 5,443,826 A | 8/1995 | Borody | |
| 5,599,795 A | 2/1997 | McCann et al. | |
| 5,728,380 A | 3/1998 | Allen et al. | |
| 5,800,821 A | 9/1998 | Acheson et al. | |
| 5,837,238 A | 11/1998 | Casas et al. | |
| 5,858,356 A | 1/1999 | Wolf et al. | |
| 5,902,578 A | 5/1999 | Halpin-Dohnalek et al. | |
| 5,902,743 A | 5/1999 | Luchansky et al. | |
| 6,087,386 A | 7/2000 | Chen et al. | |
| 6,162,464 A | 12/2000 | Jacob et al. | |
| 6,245,740 B1 | 6/2001 | Goldenberg et al. | |
| 6,284,274 B1 | 9/2001 | Merrill et al. | |
| 6,428,783 B1 | 8/2002 | Khachatrian et al. | |
| 6,479,051 B1 | 11/2002 | Bruce | |
| 6,514,531 B1 | 2/2003 | Alaux et al. | |

(Continued)

FOREIGN PATENT DOCUMENTS

| | | |
|---|---|---|
| AU | 2001276160 B2 | 6/2007 |
| CA | 1333564 | 12/1994 |

(Continued)

OTHER PUBLICATIONS

U.S. Appl. No. 12/843,409, filed Jul. 26, 2010.
"ARGF—'Autologous Rehabilitation of Gastrointestinal Flora,'" Medipex Report for Medilink NW, pp. 1-42, n.d., Web, Feb. 10, 2012 <http://www.bacteriotherapy.org/docs/medipex-report.pdf>.
"Autoimmune Disease List," American Autoimmune Related Diseases Association, pp. 1-4 (2017) <https://www.aarda.org/disease-list/>.
"Certain infectious and parasitic diseases (A00-B99)," International Statistical Classification of Diseases and Related Health Problems, 10th Revision (ICD-10)-WHO Version, Chapter 1, pp. 1 (2016) <www.apps.who.int/classifications/icd10/browse/2016/en#/I>.
"Frequently Asked Questions about Clostridium difficile for Healthcare Providers," Healthcare-associated Infections (HAIs), Centers for Disease Control and Prevention, pp. 1-6, Nov. 25, 2010, updated Mar. 6, 2012, Web, May 19, 2014 <http://www.cdc.gov/HAI/organisms/cdiff/Cdiff_faqs_HCP.html>.

(Continued)

*Primary Examiner* — Robert J Yamasaki
(74) *Attorney, Agent, or Firm* — Arnold & Porter Kaye Scholer LLP

(57) ABSTRACT

The present disclosure relates to compositions and methods for treating autism spectrum disorder (ASD) by restoring an ASD patient's gut microbiota. These methods can be used with ASD patient with or without ongoing gastrointestinal symptoms. Provided here is a method for modulating the abundance of one or more gut microorganisms in a subject in need thereof, said method comprising administering to said subject a therapeutically effective amount of a pharmaceutical composition comprising a fecal microbe preparation to achieve at least a 2-fold change of the abundance of said one or more fecal microorganisms, wherein said one or more gut microorganisms are selected from the group consisting of *Bifidobacterium*, *Prevotella*, *Desulfovibrio*, *Copprococcus*, *Clostridium*, and *Bacteroides*.

20 Claims, 62 Drawing Sheets

(56) References Cited

U.S. PATENT DOCUMENTS

| | | | |
|---|---|---|---|
| 6,645,530 B1 | 11/2003 | Borody |
| 6,649,397 B1 | 11/2003 | Nakamura |
| 6,756,032 B1 | 6/2004 | Tepper et al. |
| 6,926,907 B2 | 8/2005 | Plachetka |
| 6,979,674 B1 | 12/2005 | Goldenberg et al. |
| 6,984,513 B2 | 1/2006 | Brown et al. |
| 7,018,629 B2 | 3/2006 | Jacob et al. |
| 7,374,753 B1 | 5/2008 | Farmer et al. |
| 7,541,091 B2 | 6/2009 | Sisson et al. |
| 7,749,509 B2 | 7/2010 | Cobb et al. |
| 7,763,276 B1 | 7/2010 | Shodai et al. |
| 7,799,341 B2 | 9/2010 | Porzio et al. |
| 7,815,956 B2 | 10/2010 | Lee et al. |
| 7,846,475 B2 | 12/2010 | Shiraishi et al. |
| 7,888,062 B1 | 2/2011 | Garner et al. |
| 7,998,510 B2 | 8/2011 | Caswell |
| 8,168,171 B2 | 5/2012 | Mogna et al. |
| 8,460,648 B2 | 6/2013 | Borody |
| 8,586,029 B2 | 11/2013 | Kasper et al. |
| 8,637,297 B2 | 1/2014 | Fernandez et al. |
| 8,658,153 B2 | 2/2014 | Daube et al. |
| 8,771,673 B2 | 7/2014 | Cobb et al. |
| 8,906,668 B2 | 12/2014 | Henn et al. |
| 9,040,036 B2 | 5/2015 | Borody |
| 9,050,358 B2 | 6/2015 | Borody |
| 9,308,226 B2 | 4/2016 | Borody |
| 9,320,763 B2 | 4/2016 | Borody |
| 9,408,872 B2 | 8/2016 | Borody |
| 9,468,658 B2 | 10/2016 | Borody |
| 9,572,841 B2 | 2/2017 | Borody |
| 9,572,842 B2 | 2/2017 | Borody |
| 9,610,308 B2 | 4/2017 | Borody |
| 9,623,056 B2 | 4/2017 | Borody |
| 9,719,144 B2 | 8/2017 | Krajmalnik-Brown et al. |
| 2001/0014322 A1 | 8/2001 | Chen et al. |
| 2002/0013270 A1 | 1/2002 | Bolte |
| 2002/0022019 A1 | 2/2002 | Laulund |
| 2002/0039599 A1 | 4/2002 | Lin et al. |
| 2003/0092163 A1 | 5/2003 | Collins et al. |
| 2003/0092724 A1 | 5/2003 | Kao et al. |
| 2003/0147858 A1 | 8/2003 | Renaud et al. |
| 2004/0062757 A1 | 4/2004 | Finegold |
| 2004/0167062 A1 | 8/2004 | Bolte |
| 2004/0170617 A1 | 9/2004 | Finegold |
| 2004/0223956 A1 | 11/2004 | Naidu et al. |
| 2006/0076536 A1 | 4/2006 | Barshied |
| 2006/0099197 A1 | 5/2006 | Farmer |
| 2006/0115465 A1 | 6/2006 | Macfarlane et al. |
| 2006/0177424 A1 | 8/2006 | Cobb et al. |
| 2006/0275223 A1 | 12/2006 | Burr |
| 2007/0059296 A1 | 3/2007 | Chen |
| 2008/0254009 A1 | 10/2008 | Finegold |
| 2008/0299197 A1 | 12/2008 | Toneguzzo et al. |
| 2010/0112003 A1 | 5/2010 | Collins et al. |
| 2010/0178349 A1 | 7/2010 | Kolter et al. |
| 2010/0178413 A1 | 7/2010 | Gorris |
| 2010/0184785 A1 | 7/2010 | Kolter et al. |
| 2010/0222311 A1 | 9/2010 | Thommes et al. |
| 2010/0226866 A1 | 9/2010 | Yamashiro et al. |
| 2010/0233278 A1 | 9/2010 | Ookawa et al. |
| 2010/0239667 A1 | 9/2010 | Hemmingsen et al. |
| 2010/0247489 A1 | 9/2010 | Saur-Brosch et al. |
| 2010/0247665 A1 | 9/2010 | Takahashi |
| 2010/0255231 A1 | 10/2010 | Chau et al. |
| 2010/0255307 A1 | 10/2010 | Gonze et al. |
| 2010/0278930 A1 | 11/2010 | Okumura et al. |
| 2010/0285164 A1 | 11/2010 | Schaible et al. |
| 2010/0289164 A1 | 11/2010 | Porzio et al. |
| 2010/0297031 A1 | 11/2010 | Ubeda Perez et al. |
| 2011/0008554 A1 | 1/2011 | Chen et al. |
| 2011/0045222 A1 | 2/2011 | Peters |
| 2011/0081320 A1 | 4/2011 | Westall et al. |
| 2011/0091431 A1 | 4/2011 | Olmstead |
| 2011/0200570 A1 | 8/2011 | Mosbaugh et al. |
| 2011/0218216 A1 | 9/2011 | Vivek et al. |
| 2012/0020941 A1 | 1/2012 | Wacklin et al. |
| 2012/0039853 A1 | 2/2012 | Corveleyn et al. |
| 2012/0064133 A1 | 3/2012 | Chauhan et al. |
| 2012/0087895 A1 | 4/2012 | Mazmanian et al. |
| 2012/0129773 A1 | 5/2012 | Geier et al. |
| 2012/0183612 A1 | 7/2012 | Brogmann et al. |
| 2012/0252775 A1 | 10/2012 | Finegold |
| 2013/0022622 A1 | 1/2013 | Ben-Ari et al. |
| 2013/0045274 A1 | 2/2013 | Hlavka |
| 2013/0195804 A1 | 8/2013 | Borody |
| 2013/0259899 A1 | 10/2013 | Allen-Vercoe et al. |
| 2013/0266539 A1* | 10/2013 | Borody .................. A61K 45/06 424/93.3 |
| 2013/0316394 A1 | 11/2013 | Stimpson |
| 2014/0065132 A1 | 3/2014 | Hsiao et al. |
| 2014/0086877 A1 | 3/2014 | Hlavka |
| 2014/0147417 A1 | 5/2014 | Sadowsky et al. |
| 2014/0147425 A1 | 5/2014 | Henn et al. |
| 2014/0234260 A1 | 8/2014 | Borody |
| 2014/0255351 A1 | 9/2014 | Berstad et al. |
| 2014/0328803 A1 | 11/2014 | McKenzie et al. |
| 2014/0341921 A1 | 11/2014 | Honda et al. |
| 2014/0342438 A1 | 11/2014 | Allen-Vercoe et al. |
| 2014/0363397 A1 | 11/2014 | Allen-Vercoe et al. |
| 2014/0363398 A1 | 12/2014 | Jones et al. |
| 2015/0044173 A1 | 2/2015 | Jones et al. |
| 2015/0050246 A1 | 2/2015 | Jones et al. |
| 2015/0093360 A1 | 4/2015 | McKenzie et al. |
| 2015/0143557 A1 | 5/2015 | Honda et al. |
| 2015/0152484 A1 | 6/2015 | Krajmalnik-Brown et al. |
| 2015/0190435 A1 | 7/2015 | Henn et al. |
| 2015/0224152 A1 | 8/2015 | Littman et al. |
| 2015/0238544 A1 | 8/2015 | Jones et al. |
| 2015/0238545 A1 | 8/2015 | Borody |
| 2015/0238546 A1 | 8/2015 | Borody |
| 2015/0297642 A1 | 10/2015 | Borody |
| 2015/0306144 A1 | 10/2015 | Borody |
| 2015/0306155 A1 | 10/2015 | Borody |
| 2015/0306156 A1 | 10/2015 | Borody |
| 2015/0374761 A1 | 12/2015 | Sadowsky et al. |
| 2016/0089363 A1 | 3/2016 | Borody |
| 2016/0151429 A1 | 6/2016 | Borody |
| 2016/0151431 A1 | 6/2016 | Borody |
| 2016/0151432 A1 | 6/2016 | Borody |
| 2016/0151433 A1 | 6/2016 | Borody |
| 2016/0158294 A1 | 6/2016 | Von Maltzahn et al. |
| 2016/0279178 A1 | 9/2016 | Borody |
| 2016/0279179 A1 | 9/2016 | Borody |
| 2016/0339065 A1 | 11/2016 | Adams et al. |
| 2017/0216378 A1 | 8/2017 | Honda et al. |
| 2017/0246220 A1 | 8/2017 | Sato et al. |
| 2017/0348360 A1 | 12/2017 | Borody |
| 2018/0153943 A1 | 6/2018 | Borody |
| 2018/0256652 A1 | 9/2018 | Borody |
| 2019/0015460 A1 | 1/2019 | Borody |
| 2019/0015461 A1 | 1/2019 | Borody |
| 2019/0015462 A1 | 1/2019 | Borody |
| 2019/0046589 A1 | 2/2019 | Borody |

FOREIGN PATENT DOCUMENTS

| | | |
|---|---|---|
| CA | 2 391 422 A1 | 1/2004 |
| CN | 1561387 A | 1/2005 |
| CN | 101496819 A | 8/2009 |
| CN | 201441672 U | 4/2010 |
| DE | 2 134 179 A1 | 1/1973 |
| EP | 0 303 426 A2 | 2/1989 |
| EP | 0 456 418 A2 | 11/1991 |
| EP | 0 433 299 B1 | 5/1998 |
| EP | 1 514 572 A2 | 3/2005 |
| EP | 1 514 572 A3 | 11/2006 |
| EP | 1 800 688 A1 | 6/2007 |
| EP | 1 514 572 B1 | 12/2008 |
| EP | 2 823 822 B1 | 10/2016 |
| FR | 1275 M | 5/1962 |
| FR | 2427 M | 3/1964 |
| FR | 2828 M | 10/1964 |
| FR | 5528 M | 11/1967 |
| FR | 2 244 464 A1 | 4/1975 |

(56) References Cited

FOREIGN PATENT DOCUMENTS

| | | |
|---|---|---|
| GB | 1 271 674 A | 4/1972 |
| JP | 64-67192 | 3/1989 |
| JP | H05-306221 A | 11/1993 |
| JP | H07-242539 A | 9/1995 |
| JP | H07-242557 A | 9/1995 |
| JP | 3 144 556 B2 | 3/2001 |
| JP | 2004-501095 | 1/2004 |
| JP | 2005-118544 A | 5/2005 |
| JP | 2008-106066 | 5/2008 |
| JP | 2010-513359 | 4/2010 |
| JP | 2010-520234 A | 6/2010 |
| KR | 10-0913405 B1 | 8/2009 |
| WO | WO 90/01335 A1 | 2/1990 |
| WO | WO 95/33046 A1 | 12/1995 |
| WO | WO 96/11014 A1 | 4/1996 |
| WO | WO 98/13068 A1 | 4/1998 |
| WO | WO 00/07571 A2 | 2/2000 |
| WO | WO 2000/015760 | 3/2000 |
| WO | WO 00/42168 A2 | 7/2000 |
| WO | WO 02/07741 A1 | 1/2002 |
| WO | WO 2003/033681 A2 | 4/2003 |
| WO | WO 2005/017095 A2 | 2/2005 |
| WO | WO 2006/127355 A2 | 11/2006 |
| WO | WO 2008/077614 A2 | 7/2008 |
| WO | WO 2008/105715 A2 | 9/2008 |
| WO | WO 2008/117266 A2 | 10/2008 |
| WO | WO 2008/117267 A2 | 10/2008 |
| WO | WO 2008/077614 A3 | 1/2009 |
| WO | WO 2009/024429 A2 | 2/2009 |
| WO | WO 2009/026306 A2 | 2/2009 |
| WO | WO 2009/055362 A1 | 4/2009 |
| WO | WO 2010/040020 A1 | 4/2010 |
| WO | WO 2011/033310 A1 | 3/2011 |
| WO | WO 2011/094027 A1 | 8/2011 |
| WO | WO 2011/110347 A2 | 9/2011 |
| WO | WO 2011/151941 A1 | 12/2011 |
| WO | WO 2011/152566 | 12/2011 |
| WO | WO 2012/013861 A2 | 2/2012 |
| WO | WO 2012/045150 A1 | 4/2012 |
| WO | WO 2012/048152 | 4/2012 |
| WO | WO 2013/037067 A1 | 3/2013 |
| WO | WO 2013/090825 A1 | 6/2013 |
| WO | WO 2013/176774 | 11/2013 |
| WO | WO 2014/070014 A1 | 5/2014 |
| WO | WO 2014/078911 A1 | 5/2014 |
| WO | WO 2014/152338 A1 | 9/2014 |
| WO | WO 2014/152484 | 9/2014 |
| WO | WO 2015/006355 A2 | 1/2015 |
| WO | WO 2015/051323 A1 | 4/2015 |
| WO | WO 2015/077794 A1 | 5/2015 |
| WO | WO 2015/095241 A2 | 6/2015 |
| WO | WO 2015/124637 A1 | 8/2015 |
| WO | WO 2016/133450 A1 | 2/2016 |
| WO | WO 2016/183577 A1 | 11/2016 |
| WO | WO 2016/191356 | 12/2016 |
| WO | WO 2017/075098 A1 | 5/2017 |
| WO | WO 2017/152137 A2 | 9/2017 |
| WO | WO 2017/218681 | 12/2017 |
| WO | WO 2018/089794 | 5/2018 |

OTHER PUBLICATIONS

"Functional Anatomy of Prokaryotic and Eukaryotic Cells," printed Mar. 16, 2017 from <http://classes.midlandstech.edu/carterp/courses/bio225/chap04/lecture2.htm>.
"Monilia," Def. 1, *Stedman's Medical Dictionary*, n.d., Web, Nov. 22, 2005.
"Probiotic," Def. 1, *MSN Encarta—Dictionary*, Encarta, n.d., Web, Dec. 1, 2005.
"Spore-Forming Gram-Positive Bacilli: *Bacillus* and *Clostridium* Species," Jawetz, Melnick, & Adelberg's Medical Microbiology, 26th Edition, Chapter 11, pp. 1-15 (2012).
"Autism Treatment Evaluation Checklist (ATEC)," *Autism Research Institute*, <https://www.autism.com/ind_atec>.
"Studies confirm validity of ATEC Report," *Autism Research Institute*. <https://www.autism.com/ind_atec_report>.
Aas et al., "Recurrent Clostridium difficile Colitis: Case Series Involving 18 Patients Treated with Donor Stool Administered via a Nasogastric Tube," *Clinical Infectious Diseases*, 36(5):580-585 (2003).
Abrams, "Open-Label, Uncontrolled Trial of Bowel Sterilization and Repopulation with Normal Bowel Flora for Treatment of Inflammatory Bowel Disease," Current Therapeutic Research, 58(12):1001-1012 (1997).
Acha et al., "Changes of viability and composition of the *Escherichia coli* flora in faecal samples during long time storage," *Journal of Microbiological Methods*, Elsevier, 63(3):229-238 (2005).
Adams et al., "Effect of a Vitamin/Mineral Supplement on Children with Autism," BMC Pediatrics, 11:111 (2011).
Adams et al., "Gastrointestinal flora and gastrointestinal status in children with autism-comparisons to typical children and correlation with autism severity," BMC Gastroenterology, 11:22 (2011).
Adams et al., "Mercury in first-cut baby hair of children with autism versus typically-developing children," Toxicological & Environmental Chemistry, 90(4): 739-753 (2008).
Adams et al., "The Severity of Autism is Associated with Toxic Metal Body Burden and Red Blood Cell Glutathione Levels," *J. Toxicol*, 2009:532640 (2009).
Agrawal et al., "'Global warming' to *Mycobacterium avium* subspecies paratuberculosis," *Future Microbiol*, 90:829-832 (2014).
Agrawal et al., "A Long-Term Follow-Up Study of the Efficacy and Safety of Fecal Microbiota Transplant (FMT) for Recurrent/Severe/Complicated *C. difficile* Infection (CDI) in the Elderly," *Gastroenterol*, 146(5)(Suppl 1):S42-43 (2014).
Aitken et al., "Demonstration of Intracellular *Mycobacterium* Species in Crohn's Disease Using Novel Technologies," Poster Presentation—2015 ACG Annual Scientific Meeting, Honolulu, Hawaii, USA (2015).
Akao et al., "A Purgative Action of Barbaloin is Induced by *Eubacterium* sp. Strain BAR, a Human Intestinal Anaerobe, Capable of Transforming Barbaloin to Aloe-Emodin Anthrone," *Biol. Pharm.*, 18(1):136-138 (1996).
Al-Eidan et al., "Clostridium difficile-associated diarrhoea in hospitalised patients," *J. Clin. Pharm. Ther.*, 25(2):101-109 (2000).
Al-Nassir et al., "Comparison of Clinical and Microbiological Response to Treatment of Clostridium difficile-Associated Disease with Metronidazole and Vancomycin," *Clin Infect Dis.*, 47(1):56-62 (2008).
Aman et al., "Outcome Measures for Clinical Drug Trials in Autism," *CNS Spectr.*, 9(1):36-47 (2004).
Aman et al., "Psychometric Characteristics of the Aberrant Behavior Checklist," *Am. J. Ment. Defic.*, 89(5):492-502 (1985).
Anand et al., "Epidemiology, clinical manifestations, and outcome of Clostridium difficile-associated diarrhea," *Am J Gastroenterol.*, 89(4):519-23 (1994).
Ananthakrishnan et al., "Excess hospitalisation burden associated with Clostridium difficile inpatients with inflammatory bowel disease," *Gut*, 57(2):205-210 (2007).
Anderson et al., "Systematic review: faecal microbiota transplantation in the management of inflammatory bowel disease," *Aliment. Pharmacol. Ther.*, 36:503-16 (2012).
Andoh et al., "Terminal restriction fragment polymorphisum analyses of fecal microbiota in five siblings including two with ulcerative colitis," Journal of Clinical Gastroenterology, 2:343-345 (2009).
Andrews et al., "'Putting back the bugs': Bacterial Treatment Relieves Chronic Constipation and Symptoms of Irritable Bowel Syndrome," *Med. J. Aust.*, 159(9):633-634 (1993).
Andrews et al., "Bacteriotherapy for Chronic Constipation—A Long Term Follow-Up," *Gastroenterol*, 108:A563 Abstract (1995).
Andrews et al., "Chronic Constipation (CC) may be reversed by Bacteriotherapy," *Gastroenterol*, 106:A459 (1994).
Andrews et al., "Chronic constipation reversed by restoration of bowel flora. A case and a hypothesis," *European Journal of Gastroenterology & Hepatology*, 4:245-247 (1992).
Anorexia nervosa, Encyclopedia Index A, healthAtoZ, Medical Network, Inc., pp. 1-7, n.d., Web, Nov. 23, 2005 <http://www.healthatoz.com/healthatoz/Atoz/ency/anorexia_nervosa.jsp>.

(56) References Cited

OTHER PUBLICATIONS

Arkkila et al., "Fecal Bacteriotherapy for Recurrent *Clostridium difficile* Infection," *Gastroenterology*, 138(5):S1-S5 (2010).
Aroniadis et al., "Intestinal Microbiota and the Efficacy of Fecal Microbiota Transplantation in Gastrointestinal Disease," Gastroenterology and Hepatology, 10(4):230-7 (2014).
Aroniadis et al., "Long-Term Follow-up Study of Fecal Microbiota Transplantation (FMT) for Severe or Complicated *Clostridium difficile* Infection (CDI)," *Gasfroenterol*, 144(Suppl 1):S185 (2013).
Arumugam et al., "Enterotypes of the human gut microbiome," Nature, 473:174-180 (2011).
Atarashi et al., "Induction of Colonic Regulatory T Cells by Indigenous *Clostridium* Species," Science, 331(6015):337-341, published online Dec. 23, 2010.
Atarashi et al., "Treg induction by a rationally selected mixture of Clostridia strains from the human microbiota," Nature, 500(7461):232-236 (2013).
Atarashi et al., "WS/PP-064-03 Regulation of colonic regulatory T cells by *Clostridium* species," International Immunology, 22(Suppl 1, Part 3), pp. 1-3 (2010).
Atarashi et al., WS-064 Mucosal immunity: homeostasis, 14th ICIC Abstract book, 14th International Congress of Immunology, pp. iii131-iii133 (2010).
Autism, Health Encyclopedia—Diseases and Conditions, The Health Scout Network, pp. 1-5, n.d., Web, Nov. 22, 2005 <www.healthscout.com>.
Autism, Treatment, Prognosis, Healthcommunities.com, Inc., pp. 1-4, n.d., Web. Jan. 28, 2009 <http://www.neurologychannel.com/common/PrintPage.php>.
Autism: Mayo Clinic.com, Mayo Foundation for Medical Education and Research, pp. 1-7, May 31, 2008, Web. Jan. 28, 2009 <http://www.mayoclinic.com/print/autism/DS00348/METHOD=print&DSECTION=all>.
Backhed et al., "Host-bacterial mutualism in the human intestine," *Science*, 307(5717):1915-1920 (2005).
Backhed et al., "Mechanisms underlying the resistance to diet-induced obesity in germ-free mice," *PNAS USA*, 104(3):979-984 (2007).
Backhed et al., "The gut microbiota as an environmental factor that regulates fat storage," *PNAS USA*, 101(44):15718-15723 (2004).
Bakken et al., "Fecal bacteriotherapy for recurrent Clostridium difficile infection," *Anaerobe*, 15(6):285-289 (2009).
Bakken et al., "Treating Clostridium difficile Infection with Fecal Microbiota Transplantation," *Clinical Gastroenterology and Hepatology*, 9(12):1044-1049 (2011).
Bartlett et al., "Clinical recognition and diagnosis of Clostridium difficile infection," *Clin Infect Dis.*, 46(Suppl 1):S12-S18 (2008).
Bartlett, "Clostridium difficile-associated Enteric Disease," *Curr Infect Dis Rep.*, 4(6):477-483 (2002).
Belkaid et al., "Natural regulatory T cells in infectious disease," Nature Immunology, 6(4):353-360 (2005).
Bengmark et al., "Bioecological control of inflammatory bowel disease," *Clinical Nutrition*, 26(2):169-181 (2007).
Bennet et al., "Treatment of ulcerative colitis by implantation of normal colonic flora," *Lancet*, 333(8630):164 (1989).
Benson et al., "Changing epidemiology of Clostridium difficile-associated disease in children," *Infect Control Hosp Epidemiol.*, 28(11):1233-1235 (2007).
Berg, "The indigenous gastrointestinal microflora," Trends Microbiol., 4(11):430-435 (1996).
Bergey's Manual of Systematic Bacteriology, Second Edition, vol. Three, The Firmicutes, pp. 1-16 (2009).
Blaser et al., "What are the consequences of the disappearing human microbiota?" *Nat. Rev. Microbiol.*, 7(12):887-894 (2009).
Blaser, "Who are we? Indigenous microbes and the ecology of human diseases," *EMBO Rep*, 7(10):956-960 (2006).
Bolte, "Autism and *Clostridium tetani*," *Medical Hypotheses*, 51(2):133-144 (1998).
Bolte, "Therapies for Gastrointestinal and Neurological Disorders," U.S. Appl. No. 60/214,813, filed Jun. 28, 2000.
Borody et al., "The GI Microbiome and its Role in Chronic Fatigue Syndrome: a Summary of Bacteriotherapy," *ACNEM Journal*, 31(3):3-8 (2012).
Borody et al., "Anti-MAP Rescues Anti-TNF Failures for Over 4 Years," *Gastroenterol*, 136(5)Suppl 1:A-681 (2009).
Borody et al., "Anti-MAP Therapy for Pediatric Crohn's Disease," *Am J Gastroenterol*, 108(Suppl 1):S516 (2013).
Borody et al., "Anti-MAP Therapy in the Treatment of Active Crohn's Disease," *J Gastroenterol & Hepatol*, 20(Suppl):A2 (2005).
Borody et al., "Anti-mycobacterial therapy in Crohn's disease heals mucosa with longitudinal scars," *Digestive & Liver Disease*, 39(5):438-444 (2007).
Borody et al.,"Anti-*Mycobacterium avium* SS *Paratuberculosis* (MAP) Therapy and Fistula Closure in Patients with Severe Crohn's Disease," *Am J Gast*, A101:S440 (2006).
Borody et al., "Bacteriothempy in Chronic Fatigue Syndrome (CFS): A retrospective review," *Am J Gastro*, 107(S1):A1481 (2012).
Borody et al., "Bacteriotherapy Using Fecal Flora: toying with human motions" *J. Clin. Gastroenterol.*, 38(6):475-483 (2004).
Borody et al., "Bowel-flora alteration: a potential cure for inflammatory bowel disease and irritable bowel syndrome?" *Med. J. Aust.*, 150:604 (1989).
Borody et al., "Changes in Crohn's Disease Activity Index and C-Reactive Protein Levels During Anti-MAP Therapy," *AM J Gastro*, 104(S3):A1293 (2009).
Borody et al., "*Clostridium difficile* Complicating Inflammatory Bowel Disease: Pre- and Post-Treatment Findings," *Gastroenterol*, 134(4)Suppl 1:A-361 (2008).
Borody et al., "Could fecal microbiota transplantation cure all Clostridium difficile infections?," *Future Microbiol*, 9:1-3 (2014).
Borody et al., "*Entamoeba histolytica*: another cause of Crohn's Disease," *AM J Gastro*, 104(S3):A990 (2009).
Borody et al., "Faecal bacteriotherapy (FB) for chronic *C. difficile* (*Cd*) *syndromes*," *J Gastroenterol Hepatol*, 18(Suppl.):B8 (Abstract) (2003).
Borody et al., "Fecal bacteriotherapy in the treatment of recurrent C. difficile infection," *UpToDate*, pp. 1-6 (2006).
Borody et al., "Fecal Microbiota Transplantation (FMT) in Multiple Sclerosis (MS)," *AM J Gastro*, 106(S2):A942 (2011).
Borody et al., "Fecal microbiota transplantation and emerging applications," *Nat. Rev. Gastroenterol. Hepatol.*, 9(2):88-96 (2011).
Borody et al., "Fecal microbiota transplantation for *Clostridium difficile* infection: A surgeon's perspective" *Seminars in Colon and Rectal Surgery*, 25:163-166 (2014).
Borody et al., "Fecal microbiota transplantation in gastrointestinal diseases—What practicing physicians should know," *Polish Archives of Internal Medicine*, 125(11):852-858 (2015).
Borody et al. "Fecal microbiota transplantation in the treatment of recurrent Clostridium difficile infection," *UpToDate*, pp. 1-4, (2015).
Borody et al., "Fecal Microbiota Transplantation in Ulcerative Colitis: Review of 24 Years Experience," *Am J Gastro*, 107(Suppl 1):A1644 (2012).
Borody et al., "Fecal microbiota transplantation: A new standard treatment option for *Clostridim difficile* infection," *Expert Rev Anti Infect Ther.*, 11(5):447-449 (2013).
Borody et al., "Fecal microbiota transplantation: current status and future directions," *Expert Review of Gastroenterology & Hepatology*, 5(6):653-655 (2011).
Borody et al., "Fecal Microbiota Transplantation: Expanding Horizons for *Clostridium difficile* Infections and Beyond," *Antibiotics*, 4:254-266 (2015).
Borody et al., "Fecal Microbiota Transplantation: Indications, Methods, Evidence, and Future Directions," *Curr Gastroenterol Rep*, 15:337-344 (2013).
Borody et al., "Fecal Microbiota Transplantation: Techniques, Applications, and Issues," *Gastroenterol Clin North Am*, 41:781-803 (2012).
Borody et al., "Irritable Bowel Syndrome and *Dientamoeba Fragilis*," *ASM Sydney National Conference*, pp. 4-5 (2002).
Borody et al., "Is Crohn's Disease Ready for Fecal Microbiota Transplantation?," *J Clin Gastroenterol*, 48(7):582-583 (2014).

(56) References Cited

OTHER PUBLICATIONS

Borody et al., "Myocolonus-dystonia affected by GI Microbiota?," *AM J Gastro*, 106(S2):A940 (2011).
Borody et al., "Novel appearance of healing mucosa following anti-*Mycobacterium avium paratuberculosis* therapy for Crohn's disease," *J Gastroenterol Hepatol*, 19(Suppl):A210 (2004).
Borody et al., "Reversal of Idiopathic Thrombocytopenic Purpura [ITP] with Fecal Microbiota Transplantation [FMT], *AM J Gastro*, 106(S2):A941 (2011).
Borody et al., "Reversal of Inflammatory Bowel Disease (IBD) with Recurrent Faecal Microbiota Transplants (FMT)," *AM J Gastro*, 106(S2):A979 (2011).
Borody et al., "Severe recurrent Crohn's Disease of ileocolonic anastomosis and antimicrobial (anti-mycobacterial therapy)," *Gut*, 55:1211 (2006).
Borody et al., "Therapeutic faecal microbiota transplantation: current status and future developments," *Curr Opin Gastroenterol*, 30:97-105 (2014).
Borody et al., "Treatment of chronic constipation and colitis using human probiotic infusions," *Proceedings of Prebiotics and Probiotics and the New Foods Conference*, 2-4:228 Abstract (2001).
Borody et al., "Treatment of First-time Clostridium difficile Infection with Fecal Microbiota Transplantation," Poster Presentation, *2015 ACG Annual Scientific Meeting*, Honolulu, Hawaii, USA (2015).
Borody et al., "Treatment of Severe Constipation Improves Parkinson's Disease (PD) Symptoms," *AM J Gastro*, 104(S3):A999 (2009).
Borody et al., "Treatment of Severe Crohn's Disease (CD)—Using Rifabutin-Macrolide-Clofazimine Combination: Results at 30-37 Months," *Gastroenterology*, 118(4):A1334 Abstract (2000).
Borody et al., Treatment of Severe Crohn's Disease Using Rifabutin-Macrolide-Clofazimine Combination—Results at 38-43 Months, *J Gastroenterol & Hepatol*, 15 (Suppl.):J102 (2000).
Borody et al., "Treatment of Severe Crohn's disease using antimycobacterial triple therapy—approaching a cure?," *Digest Liver Dis*, 34(1):29-38 (2002).
Borody et al., "Treatment of ulcerative colitis using fecal bacteriotherapy," *J. Clin. Gastroenterol.*, 37(1):42-47 (2003).
Borody, "Bacteriotherapy for Chronic Fatigue Syndrome—A Long Term Follow-Up Study," Proceedings of ACMA Complementary Medicine Sydney, p. 1 (1995).
Borody, "Flora Power—Fecal Bacteria Cure Chronic C. difficile Diarrhoea," *Am J Gastroenterol*, 95(11):3028-3029 (2000).
Borody "Is the Infected Patient too 'Difficile' to Treat?," The Australian Society for Microbiology 2009 Perth, SY03 & SY03.1, p. 27 & 56, (2009).
Borody, "Letter to the Editor—Response to Drs. Famularo et al.," *AJG*, 96(7):2262-2264 (2001).
Borriello, "Clostridial Disease of the Gut" *Clinical Infectious Diseases*, The University of Chicago, 20(Suppl 2):S242-S250 (1995).
Bowden et al., "Pseudomembraneous enterocolitis: mechanism of restoring floral homeostasis," *Am Surg.*, 47(4):178-183 (1981).
Brandt et al., "Long-Term Follow-Up Study of Fecal Microbiota Transplantation (FMT) for Ulcerative Colitis (UC)," Am. J. Gastroenterol., 107(Suppl):S657 (2012).
Brandt et al., "Endoscopic Fecal Microbiota Transplantation. "First-Line" Treatment for Severe Clostridium difficile Infection?" *J. Clin. Gastroenterol.*, 45(8):655-657 (2011).
Brandt et al., "Fecal microbiota transplantation for recurrent *Clostridium difficile* infection," *J Clin Gastroenterol.*, 45(Suppl):S159-S167 (2011).
Brandt et al., Safety of Fecal Microbiota Transplantation (FMT) in Immunocompromised (Ic) Patients with Inflammatory Bowel Disease (IBD), *Am J Gastroenterol*, 108(Suppl 1):S556 (2013).
Browne et al., "Culturing of 'unculturable' human microbiota reveals novel taxa and extensive sporulation," Nature, 533(7604):543-546 (2016).
Bryant et al., "Bacteroides *Ruminicola N*. Sp. and the new Genus and Species *Succinimonas amylolytica*," Journal of Bacteriol, 76:15-23 (1958).

Bueche et al., "Quantification of Endospore-Forming Firmicutes by Quantitative PCR with the Functional Gene spo0A," Applied and Environmental Microbiology, 79(17):5302-5312 (2013).
Buie et al., "Evaluation, Diagnosis, and Treatment of Gastrointestinal Disorders in Individuals With ASDs: A Consensus Report," Pediatrics, 125:S1-S18 (2010).
Cammarota et al., "Randomised clinical trial: faecal microbiota transplantation by colonoscopy vs. vancomycin for the treatment of recurrent Clostridium difficile infection," Alimentary Pharmacology & Therapeutics, 41(9):835-843 (2015).
Cammorata et al., "Review article: biofile formation by Helicobacter pylori as a target for eradication of resistant infection," Aliment Pharmacol Ther, 36:222-30 (2012).
Campbell et al., "The many faces of Crohn's Disease: Latest concepts in etiology," *OJIM*, 2(2):107-115 (2012).
Cangelosi et al., "Dead or Alive: Molecular Assessment of Microbial Viability," *Appl. Environ. Microbiol.*, 80(19):5884-5891 (2014).
Cano et al., "Revival and identification of bacterial spores in 25-40 million year old Dominican Amber Science," *Science*, 268(5213):1060-1064 (1995).
Cato et al.,"*Clostridium oroticum* comb. nov. amended description," International Journal of Systematic Bacteriology, 17(1):9-13 (1968).
Celik et al., "Factors influencing the stability of freeze-dried stress-resilient and stress-sensitive strains of bifidobacteria," *J. Dairy Sci.*, 96(6):3506-16 (2013).
Center for Disease Control, "Severe Clostridium difficile-associated disease in populations previously at low risk—four states, 2005." *Morbidity and Mortality Weekly Report*, 54(47):1201-1205 (2005).
Chamberlain et al., "Map-associated Crohn's Disease, MAP, Koch's postulates, causality and Crohn's Disease," *Digestive and Liver Disease*, 39:790-794 (2007).
Chamberlin et al., "Primary treatment of Crohn's disease: combined antibiotics taking center stage," *Expert Rev. Clin. Immunol.*, 7(6):751-760 (2011).
Chang et al., "Decreased diversity of the fecal Microbiome in recurrent Clostridium difficile-associated diarrhea," *J. Infect. Dis.*, 197(3):435-438 (2008).
Chao et al., "Estimating the Nimber via Sample Coverage," Journal of the American Statistical Association, 87(417):210-217 (1992).
Chen et al., "A mouse model of Clostridium difficile-associated disease," *Gastroenterology*, 135(6):1984-1992 (2008).
Cherif et al., "Thuricin 7: a novel bacteriocin produced by Bacillus thuringiensis BMG1.7, a new strain isolated from soil," Letters in Applied Microbiology, 32:243-7 (2001).
Chibani-Chennoufi et al., "In Vitro and in Vivo Bacteriolytic Activities of *Escherichia coli* Phages: Implications for Phage Therapy," *Antimicrobial Agents and Chemotherapy*, 48(7):2558-2569 (2004).
Choi et al., "Fecal Microbiota Transplantation: Current Applications, Effectiveness, and Future Perspectives," Clin. Endosc., 49:257-265 (2016).
Chopra et al., "Recent epidemiology of Clostridium difficile infection during hematopoietic stem cell transplantation," *Clin Transplant.*, 25(1):E82-E87 (2011).
Chu et al., "Profiling Living Bacteria Informs Preparation of Fecal Microbiota Transplantations," PLOS One, 1-16 (2017).
Citron et al., "In Vitro Activities of CB-183,315, Vancomycin, and Metronidazole against 556 Strains of *Clostridium difficile*, 445 Other Intestinal Anaerobes, and 56 *Enterobacteriaceae* Species," *Antimicrob Agents Chemother.*, 56(3):1613-1615 (2012).
Claesson et al., "Comparison of two next-generation sequencing technologies for resolving highly complex microbiota composition using tandem variable 16S rRNA gene regions," *Nucleic Acids Research*, 38(22):1-13 (2010).
Clancy et al., "Anti-MAP Therapy Induces and Maintains Remission in Severe Crohn's Disease," *Ann NY Acad Sci*, p. 1 (2005).
Claus et al., "Colonization-induced host-gut microbial metabolic interaction," *MBio*, 2(2):e00271-00210 (2011).
Claus et al., "Systemic multicompartmental effects of the gut microbiome on mouse metabolic phenotypes," *Mol. Syst. Biol.*, 4(1):219 (2008).
Cohen et al., "The PDD Behavior Inventory: a Rating Scale for Assessing Response to Intervention in Children with Pervasive Development Disorder," *J. Autism Dev. Disord.*, 33(1):31-45 (2003).

(56) References Cited

OTHER PUBLICATIONS

Cohen et al., "Clinical practice guidelines for Clostridium difficile infection in adults: 2010 update by the society for healthcare epidemiology of America (SHEA) and the infectious diseases society of America (IDSA)," Infect Control Hosp Epidemiol., 31(5):431-55 (2010).

Cole et al., "Psychological Risk Factors for HIV Pathogenesis: Mediation by the Autonomic Nervous System," Society of Biological Psychiatry, 54:1444-1456 (2003).

Cole et al., "The Ribosomal Database Project (RDP-II): previewing a new autoaligner that allows regular updates and the new prokaryotic taxonomy," Nucleic Acids Research 31(1): 442-443 (2003).

Cole, J.R. et al., "The Ribosomal Database Project: improved alignments and new tools for rRNA analysis," Nucleic Acids Research, 37:D141-D145 (2008).

Collins & Bercik, "The Relationship Between Intestinal Microbiota and the Central Nervous System in Normal Gastrointestinal Function and Disease," Gastroenterology, 136:2003-2014 (2009).

Collins et al., "The Phylogeny of the Genus *Clostridium*: Proposal of Five New Genera and Eleven New Species Combinations," International Journal of Systematic Bacteriology, pp. 812-826 (1994).

Constantino et al., "Validation of a Brief Quantitative Measure of Autistic Traits: Comparison of the Social Responsiveness Scale with the Autism Diagnostic Interview-Revised," J. Autism Dev. Disord., 33(4):427-433 (2003).

Crohn's Disease, Prevention, Health Guide A-Z, WebMDHealth, pp. 1-2, n.d., Web, Oct. 23, 2005 <http://mywebmd.com/hw/inflammatory sub.--bowel/uf6012.asp>.

Crowther, "Transport and Storage of Faeces for Bacteriological Examination," Journal of Applied Bacteriology, 34(2):477-483 (1971).

Cutolo et al., "Fecal feedings as a therapy in *Staphylococcus enterocolitis*," NY State J Med, 59:3831-3833 (1959).

Dale et al., "Molecular interactions between bacterial symbionts and their hosts," Cell, 126(3):453-465 (2006).

Dan et al., "Comparison of preservation media and freezing conditions for storage of specimens of faeces," J. Med Microbiology, 28:151-154 (1989).

De Giulio et al., "Use of Algiinate and Cryo-Protective Sugars to Improve the Viability of Lactic Acid Bacteria After Freezing and Freeze-Drying," World Journal of Microbiology & Biotechnology, 21:739-746 (2005).

Defang et al., "In vitro and in vivo evaluation of two extended release preparations of combination metformin and glipizide," Drug Develop. & Indust. Pharm., 31:677-685 (2005).

Definition of Kit, Merriam-Webster, pp. 1-10., Web., 2019 <https://www.merriam-webster.com/dictionary/kit>.

Dendukuri et al., "Probiotic therapy for the prevention and treatment of Clostridium difficile-associated diarrhea: a systematic review," CMAJ, 173(2):167-170 (2005).

Derrien et al., "*Akkermansia muciniphila* gen. nov., sp. Nov., a human intestinal mucin-degrading bacterium," International Journal of Systematic and Evolutionary Microbiology, 54:1469-1476 (2004).

Derwent Abstract Accession No. 98-230427/20, WO 98/13068 A, (Kuperman VB) Apr. 2, 1998.

Dethlefsen et al., "An ecological and evolutionary perspective on human-microbe mutualism and disease," Nature, 449(7164):811-818 (2007).

D'Eufemia et al., "Abnormal intestinal permeability in children with autism," Acta Paediatr, 85:1076-1079 (1996).

Dewhirst et al., "Phylogeny of the Defind Murine Microbiota: Altered Schaedler Flora," Applied and Environmental Microbiology, 65(8):3287-3292 (1999).

Dieterle et al., "Renal biomarker qualification submission: a dialog between the FDA-EMEA and Predictive Safety Testing Consortium," Nature Biotechnology 28(5):455-462 (2010).

Dorn et al., "Invasion of Human Oral Epithelial Cells by Prevotella intermedia," 66(12):6054-6057 (1998).

Duncan et al., "Acetate Utilization and Butyryl Coenzyme A (CoA): Acetate-CoA Transferase in Butyrate-Producing Bacteria from the Human Large Intestine," Applied and Environmental Microbiology, 68(10):5186-5190 (2002).

DuPont, "The search for effective treatment of Clostridium difficile infection," N Engl J Med., 364(5):473-475 (2011).

Eckburg et al., "Diversity of the human intestinal microbial flora," Science, 308(5728):1635-1638 (2005).

Edgar, "Search and clustering orders of magnitude faster than BLAST," Bioinformatics 26(19):2460-2461 (2010).

Eiseman et al., "Fecal enema as an adjunct in the treatment of pseudomembranous enterocolitis," Surgery, 44(5):854-859 (1958).

Eller et al., "Anaerobic Roll Tube Media for Nonselective Enumeration and Isolation and Bacteria in Human Feces," Applied Microbiology 1971, vol. 22, p. 522-529.

Extended European Search Report dated Apr. 3, 2014, in European Patent Application No. 11813951.8.

Extended European Search Report dated Mar. 16, 2018, in European Patent Application No. 17203052.0.

Extended European Search Report dated Nov. 30, 2016, in European Patent Application No. 16193790.9.

Faust et al., "Treatment of recurrent pseudomembranous colitis (RPMC) with stool transplantation (ST): Report of six (6) cases," Can J Gastroenterol., 16:A43 (2002).

Fenton et al., "Pseudomembranous colitis associated with antibiotic therapy—an emerging entity," Can Med Assoc J., 111(10):1110-1111 (1974).

Filippo et al., "Impact of diet in shaping gut microbiota revealed by a comparative study in children from Europe and rural Africa," PNAS, 107(33):14691-14696 (2010).

Finegold et al., "Gastrointestinal Microflora Studies in Late-Onset Autism," Clinical Infectious Diseases 35:S6 (2002).

Finegold et al., "Pyrosequencing study of fecal microflora of autistic and control children," Anaerobe 16:444-453 (2010).

Floch et al., "Probiotics and Dietary Fiber, The Clinical Coming of Age of Intestinal Microecology," J. Clin. Gastroenterology, 27(2):99-100 (1998).

Floch, "Fecal Bacteriotherapy, Fecal Transplant, and the Microbiome," J. Clin. Gastroenterol., 44(8):529-530 (2010).

Flotterod et al. "Refractory Clostridium difficile infection. Untraditional treatment of antibiotic-induced colitis," Tidsskr Nor Laegeforen, 111:1364-1365 (1991).

Fogarty et al., Comparison of Bacteroides-Provetella 16S rRNA Genetic Markers for Fecal Samples from Different Animal Species, Applied and Environmental Microbiology, 71(10):5999-6007 (Oct. 2005).

Frank et al., "Molecular-phylogenetic characterization of microbial community imbalances in human inflammatory bowel diseases," PNAS, 104(34):13780-13785 (2007).

Frantzen et al., "Empirical evaluation of preservation methods for faecal DNA," Molecular Ecology, 7(10):1423-1428 (1998).

Freeman et al., "The changing epidemiology of Clostridium difficile infections," Clin Microbiol. Rev., 23(3):529-549 (2010).

Frese et al., "The evolution of host specialization in the vertebrate gut symbiont Lactobacillus reuteri," PloS Genet., 7(2):e1001314 (2011).

Gaboriau-Routhiau et al., "The Key Role of Segmented Filamentous Bacteria in the Coordinated Maturation of Gut Helper T Cell Responses," Immunity, 31(4):677-689 (2009).

Garborg et al., "Results of faecal donor instillation therapy for recurrent Clostridium difficile-associated diarrhoea," Scand J Infect Dis., 42(11-12):857-61 (2010).

Garcia-Pena et al., "Anaerobic digestion and co-digestion processes of vegetable and fruit residues: Process and microbial ecology," Bioresource Technology 102:9447-9455 (2011).

Garey et al., "Meta-analysis to assess risk factors for recurrent Clostridium difficile infection," J. Hosp. Infect., 70(4):298-304 (2008).

Geier et al., "A Comparison of the Autism Treatment Evaluation Checklist (ATEC) and the Childhood Autism Rating Scale (CARS) for the Quantitative Evaluation of Autism," Journal of Mental Health Research in Intellectual Disabilities, 6:255-67 (2013).

(56) References Cited

OTHER PUBLICATIONS

Gerding, "Management of Clostridium difficile infection: thinking inside and outside the box," *Clin Infect Dis.*, 51(11):1306-13 (2010).
Geuking et al., "Intestinal Bacterial Colonization Induces Mutualistic Regulatory T Cell Respones," Immunity, 34:794-806 (2011).
Gill et al., "Metagenomic Analysis of the Human Distal Gut Microbiome", Science, 312(5778):1355-1359 (2006).
Gitlin et al., "*Mycobacterium avium ss paratuberculosis*-associated Diseases: Piecing the Crohn's Puzzle Together," *J Clin Gastroenterol*, 46(8):649-655 (2012).
Goehler et al., "Campylobacter jejuni infection increases anxiety-like behavior in the holeboard: possible anatomical substrates for viscerosensory modulation of exploratory behavior," Brain Behavior Immunology, 22(3):354-366 (2008).
Gondalia et al., "Faecal microbiota of individuals with autism spectrum disorder," Electronic Journal of Applied Psychology, 6(2):24-29 (2010).
Gough et al., "Systematic review of intestinal microbiota transplantation (fecal bacteriotherapy) for recurrent Clostridium difficile infection," *Clin. Infect. Dis.*, 53(10):994-1002 (2011).
Gregersen et al., "Duodenal administered seal oil for patients with subjective food hypersensitivity: an explorative open pilot study," *International Journal of General Medicine*, 2010(3):383-92.
Grehan et al., "Durable alteration of the colonic microbiota by the administration of donor fecal flora," *Journal of Clinical Gastroenterology*, 44(8):551-561 (2010).
Guarner et al., "Gut flora in health and disease," *Lancet*, 361(9356):512-519 (2003).
Gustafsson et al., "Faecal Short-Chain Fatty Acids in Patients with Antibiotic-Associated Diarrhoea, before and after Faecal Enema Treatment," *Scand J Gastroenterol*, 33:721-727 (1998).
Gustafsson et al., "The Effect of Faecal Enema on Five Microflora-Associated Characteristics in Patients with Antibiotic-Associated Diarrhoea," Scandinavian Journal of Gastroenterology, 34:580-586 (1999).
Hamilton et al., "Change in microbial community composition of in patients with recalcitrant Clostridium difficile colitis treated with fecal bacteriotherapy," International Human Microbiome Congress, Poster and Presentation, Vancouver, ON, Canada, Mar. 9-11, 2011.
Hamilton et al., "High-throughput DNA sequence analysis reveals stable engraftment of gut microbiota following transplantation of gut microbiota following transplantation of previously frozen fecal bacteria," *Gut Microbes*, 4(2):1-11 (2013).
Hamilton et al., "Standardized Frozen Preparation for Transplantation of Fecal Microbiota for Recurrent Clostridium difficile Infection," Article and Supplementary Material, *Am. J. Gastroenterol.*, 107(5):761-767 (2012).
Hanley & McNeil,"The Meaning and Use of the Area under a Receiver Operating Characteristic Curve," Radiology 143:29-36 (1982).
Hayashi et al., "Phylogenetic Analysis of the Human Gut Microbiota Using 16S rDNA Clone Libraries and Strictly Anaerobic Culture-Based Methods," Microbiol. Immunol., 46(8):535-548 (2002).
Hayashi et al., "*Prevotella copri* sp. nov. and *Prevotella stercorea* sp. nov., isolated from human faeces," International Journal of Systematic and Evolutionary Microbiology, 57:941-946 (2007).
Hecker et al., "Fecal Microbiota Transplantation by Freeze-Dried Oral Capsules for Recurrent Clostridium difficile Infection," Open Forum Infect Dis, 3(2): 1-2 (2016).
Hellemans et al., "Fecal transplantation for recurrent Clostridium difficile colitis, an underused treatment modality," *Acta Gastroenterol Belg.*, 72(2):269-70 (2009).
Henriksson et al., "Probiotics under the regulatory microscope," *Expert Opin. Drug Saf.*, 4(6):1-9 (2005).
Hensel et al., "Vagal Ascent and Distribution of 125 I-Tetanus Toxin after Injection into the Anterior Wall of the Stomach," *Naunyn-Schmiedeberg's Arch. Pharmacol*, 276:395-402 (1973).
Holst et al., "Biochemistry and cell biology of bacterial endotoxins," FEMS Immunology and Medical Microbiology, 16:83-104 (1996).
Honda et al., "Regulation of T Cell Responses by Intestinal Commensal Bacteria," Journal of Intestinal Microbiology, vol. 25, 2nd Edition:104 (2011).
Hongliang et al., "Freeze-dried, Capsulized Fecal Microbiota Transplantation for Relapsing Clostridium difficile Infection," *Journal of Clinical Gastroenterology*, 43(6):537-538 (2015).
Hooper et al., "How host-microbial interactions shape the nutrient environment of the mammalian intestine," *Annu. Rev. Nutr.*, 22:283-307 (2002).
Hope et al., "Sporadic colorectal cancer-role of the commensal microbiota," *FEMS Microbiol. Lett.*, 244:1-7 (2005).
Horvath et al., "Gastrointestinal abnormalities in children with autistic disorder," Journal of Pediatrics 135(5):559-563 (1999).
Hota et al., "Determining Mortality Rates Attributable to Clostridium difficile Infection," *Emerg. Infect. Dis.*, 18(2):305-307 (2012).
Hota et al., "Oral Vancomycin Followed by Fecal Transplant Versus Tapering Oral Vancomycin," U.S. National Institutes of Health, Clinical Study No. NCT01226992, Oct. 20, 2010, last updated Jan. 14, 2013, Web, May 20, 2014, pp. 1-4 <http://clinicaltrials.gov/ct2/show/NCT01226992>.
Hsu et al., "IL-10 Potentiates Differentiation of Human Induced Regulatory T Cells via STAT3 and Foxol," *The Journal of Immunology*, 3665-3674 (2015).
Hu et al., "Prospective derivation and validation of a clinical prediction rule for recurrent Clostridium difficile infection," *Gastroenterology*, 136:1206-1214 (2009).
Huang et al., "Once-daily propranolol extended-release tablet dosage form: formulation design and in vitro/in vivo investigation," *European J. of Pharm. & Biopharm.*, 58:607-614 (2004).
Huttenhower et al., "Structure, function and diversity of the healthy human microbiome," The Human Microbiome Project Consortium, *Nature*, 486:207-214 (2012).
Huws et al., "As yet uncultured bacteria phylogenetically classified as Prevotella, Lachnospiraceae incertae sedis and unclassified Bacteroidales, Clostridiales and Ruminococcaceae may play a predominant role in ruminal biohydrogenationemion", Environmental Microbiology, 13(6):1500-1512 (2011).
Immunology in the 21st Century: Defeating Infection, Autoimmunity, Allergy, and Cancer, ICI 2010 Wrap-up Report, 14th International Congress of Immunology, pp. 1 (2010).
Inflammatory Bowel Disease Facts, Disease Prevention and Treatment Strategies, Crohn's Disease and Inflammatory Bowel Disease (IBD), HealingWithNutrition.com, pp. 1-4, n.d., Web, Oct. 23, 2005 <http://www.HealingWithNutrition.com/disease/inflambowels/chrohns.html>.
Information Disclosure Statement filed Nov. 28, 2017, in U.S. Appl. No. 15/487,553.
International Preliminary Examination Report completed Nov. 19, 2002, in International Application No. PCT/AU2001/000907, 19 pgs.
International Preliminary Report on Patentability completed Dec. 12, 2012, in International No. PCT/AU2011/000987, 35 pgs.
International Preliminary Report on Patentability completed Mar. 12, 2015, in International Application No. PCT/AU2013/001362, 29 pgs.
International Preliminary Report on Patentability dated Sep. 10, 2013, in International Application No. PCT/US2012/028484, 10 pgs.
International Search Report and the Written Opinion dated Aug. 22, 2016, in International Application No. PCT/US2016/033747.
International Search Report and Written Opinion (WO) dated Feb. 2, 2018 in International Application No. PCT/US2017/055618.
International Search Report and Written Opinion (WO) dated Feb. 2, 2018 in International Application No. PCT/US2017/056131.
International Search Report and Written Opinion (WO) dated Feb. 21, 2018 in International Application No. PCT/US2017/056129.
International Search Report and Written Opinion (WO) dated Jan. 17, 2018, in International Application No. PCT/US2017/045092.
International Search Report and Written Opinion (WO) dated Jan. 31, 2018 in International Application PCT/US2017/056126.
International Search Report and Written Opinion dated Aug. 17, 2018, in International Application No. PCT/US2018/034673.

(56) References Cited

OTHER PUBLICATIONS

International Search Report and Written Opinion dated Aug. 2, 2018, in International Application No. PCT/US2018/026074.
International Search Report and Written Opinion dated Jul. 30, 2018, in International Application No. PCT/US2018/026080.
International Search Report and Written Opinion dated Aug. 8, 2016, in International Application No. PCT/US2016/032695, 10 pgs.
International Search Report and Written Opinion dated Feb. 5, 2014, in International Application No. PCT/AU2013/001362, 17 pgs.
International Search Report and Written Opinion dated Jan. 5, 2017, in International Application No. PCT/US2016/058938.
International Search Report and Written Opinion dated Jul. 31, 2014, in International Application No. PCT/US2014/027391, 16 pgs.
International Search Report and Written Opinion dated Oct. 28, 2011, in International No. PCT/AU2011/000987, 18 pgs.
International Search Report dated Aug. 10, 2012, in International Application No. PCT/US2012/028484, 7 pgs.
International Search Report dated Jul. 29, 2014, in International Application No. PCT/AU2014/000478, 7 pgs.
International Search Report dated Jul. 5, 2013, in International Application No. PCT/US2013/032668, 4 pages.
International Search Report dated Sep. 22, 2017, in International Application No. PCT/US2017/040591, 12 pgs.
Irrgang et al., "The historical Development of Mutaflor therapy," Ardeypharm GmbH, pp. 1-38 (1988) <http://www.ardeypharm.de/pdfs/en/mutaflor_historical_e.pdf?>.
Irritable Bowel Syndrome (IBS), Health A to Z, InteliHealth, pp. 1-4, n.d., Web, Oct. 23, 2005 <http://www.intelihealth.com>.
Issa et al., "Clostridium difficile and Inflammatory Bowel Disease," *Inflamm Bowel Dis.*, 14(10):1432-1442 (2008).
Issa et al., "Impact of Clostridium difficile on inflammatory bowel disease," *Clin. Gastroenterol. Hepatol.*, 5(3):345-351 (2007).
Itoh et al., "Characterization of clostridia isolated from faeces of limited flora mice and their effect on caecal size when associated with germ-free mice," Laboratory Animals, 19:111-118 (1985).
Itoh et al., "Intestinal bacteria antagonistic to Clostridium difficile in mice," Laboratory Animals, 21:20-25 (1987).
Ivanov et al., "Induction of intestinal Th17 cells by segmented filamentous bacteria," Cell, 139(3):485-498 (2009).
Ivanov et al., "Specific Microbiota Direct the Differentiation of IL-17-Producing T-Helper Cells in the Mucosa of the Small Intestine," Cell Host & Microbe, 4:337-349 (2008).
Jacob et al., "Single Delivery of High-Diversity Fecal Microbiota Preparation by Colonoscopy is Safe and Effective in Increasing Microbial Diversity in Active Ulcerative Colitis," Inflamm Bowel Dis., 0(0):1-9 (2017).
James et al., "Metabolic biomarkers of increased oxidative stress and impaired methylation capacity in children with autism," American Journal of Clinical Nutrition, 80:1611-1617 (2008).
Janeway et al., "Adaptive Immunity to Infection," Immunobiology, 6th Edition, Chapter 10, pp. 414 (2005).
Janeway, Jr. et al., "Autoimmune responses are directed against self antigens," Immunobiology: The Immune System in Health and Disease, 5th Edition, pp. 1-4 (2001).
Jarvis et al., "National point prevalence of Clostridium difficile in US health care facility inpatients, 2008," *Am. J. Infect. Control*, 37:263-270 (2009).
Jia et al., "Gut microbiota: a potential new territory for drug targeting," Nature Reviews—Drug Discovery, 7:123-129 (2008).
Johnson et al., "Interruption of Recurrent Clostridium difficile-Associated Diarrhea Episodes by Serial Therapy with Vancomycin and Rifaximin," *Clin. Infect. Dis.*, 44(6):846-848 (2007).
Johnson et al., "Rifaximin Redux: Treatment of recurrent Clostridium difficile infections with Rifaximin immediately post-vancomycin treatment," Anaerobe, 15(6):290-291 (2009).

Kageyama et al., "Emendation of genus *Collinsella* and proposal of *Collinsella stercoris* sp. nov. and *Collinsella intestinalis* sp. nov.," *International Journal of Systematic and Evolutionary Microbiology*, 50:1767-1774 (2000).
Kageyama et al., "Phylogenetic and phenotypic evidence for the transfer of *Eubacterium aerofaciens* to the genus *Collinsella* as *Collinsella aerofaciens* gen. nov., comb. nov.," *International Journal of Systematic Bacteriology*, 49:557-565 (1999).
Kakihana et al., "Fecal microbiota transplantation for patients with steriod-resistant acute graft-versus-host disease of the gut," Blood, 128(16):2083-2088 (2016).
Kamboj et al., "Relapse versus reinfection: surveillance of Clostridium difficile infection," *Clin Infect Dis.*, 53(10):1003-1006 (2011).
Kang et al., "Microbiota Transfer Therapy alters gut ecosystem and improves gastrointestinal and autism symptoms: and open-label study," *Microbiome*, 5:10, 16 pages (2017).
Kang et al., "Reduced Incidence of *Prevotella* and Other Fermenters in Intestinal Microflora of Autistic Children," *PLOS One*, 8(7):e68322, 14 pages (2013).
Kaper et al., "Pathogenic *Escherichia coli*," Nature Reviews—Microbiology, 2:123-140 (2004).
Karas et al., "A review of mortality due to Clostridium difficile infection," *J Infect.*, 61(1):1-8 (2010).
Kassam et al., "Fecal transplant via retention enema for refractory or recurrent Clostridium difficile infection," *Arch Intern Med.*, 172(2):191-193 (2012).
Kelly et al., "Commensal gut bacteria: mechanisms of immune modulation," Trends in Immunology, 26(6):326-333 (2005).
Kelly et al., "Clostridium difficile—more difficult than ever," *N. Engl. J. Med.*, 359(18):1932-1940 (2008).
Kelly et al., "Clostridium difficile colitis," *N. Engl. J. Med.*, 330(4):257-62 (1994).
Kelly et al., "Fecal Microbiota Transplant for Treatment of *Clostridium difficile* Infection in Immunocompromised Patients," *Am J Gastroenterol*, 109:1065-1071 (2014).
Kelly et al., "Fecal microbiota transplantation for relapsing Clostridium difficile infection in 26 patients: methodology and results," *J. Clin. Gastroenterol.*, 46(2):145-149 (2012).
Keynan et al., "The Role of Regulatory T Cells in Chronic and Acute Viral Infections," Clinical Infectious Diseases, 46:1046-1052 (2008).
Khanna et al., "A Novel Microbiome Therapeutic Increases Gut Microbial Diversity and Prevents Recurrent Clostridium difficile Infection," *The Journal of Infectious Diseases*, 214:173-81 (2016).
Khanna et al., "The epidemiology of community-acquired Clostridium difficile infection: a population-based study," *Am J Gastroenterol.*, 107(1):89-95 (2012).
Khanna et al., "The growing incidence and severity of Clostridium difficile infection in inpatient and outpatient settings," *Expert Rev Gastroenterol Hepatol.*, 4(4):409-16 (2010).
Kharidia et al., "The Activity of a Small Lytic Peptide PTP-7 on *Staphylococcus aureus* Biofilms," *J. Microbiol.*, 49(4):663-668 (2011).
Khoruts et al., "Changes in the composition of the human fecal microbiome after bacteriotherapy for recurrent Clostridium difficile-associated diarrhea," *J. Clin. Gastroenterol.*, 44(5):354-360 (2010).
Khoruts et al., "Therapeutic transplantation of the distal gut microbiota," *Mucosal Immunol.*, 4(1):4-7 (2011).
Kim et al., "Effect of Rifampin on the Plasma Concentration and the Clinical Effect of Haloperidol Concomitantly Administered to Schizophrenic Patients," *Journal of Clinical Psychopharmacology*, 16(3):247-252 (1996).
Kim et al., "In Vitro Culture Conditions for Maintaining a Complex Population of Human Gastrointestinal Tract Microbiota," *Journal of Biomedicine and Biotechnology*, 2011(Article ID 838040):1-10 (2011) <http://www.hindawi.com/journals/bmri/2011/838040/>.
Kitajka et al., "Effects of dietary omega-3 polyunsaturated fatty acids on brain gene expression," PNAS, 101(30):10931-10936 (2004).
Klaenhammer, "Bacteriocins of lactic acid bacteria," Biochimie, 70:337-49 (1988).
Kleiman et al., "Comparison of two coprological methods for the veterinary diagnosis of fasciolosis," *Arquivo Brasileiro de Medicina Veterinária e Zootécnica*, 55(2):181-185 (2005).

(56) References Cited

OTHER PUBLICATIONS

Kobashi et al., "Metabolism of Sennosides by Human Intestinal Bacteria," *Journal of Medicinal Plant Research*, 40(3):225-236 (1980).
Koch, "What size should a bacterium be? A question of scale," *Annu. Rev. Microbiol.*, 50:317-48 (1996).
Kostic et al., "Genomic analysis identifies association of Fusobacterium with colorectal carcinoma," Genome Research 22:292-298 (2011).
Krogius-Kurikka et al., "Sequence analysis of percent G+C fraction libraries of human faecal bacterial DNA reveals a high number of Antinobacteria," BMC Microbiology, 9(68):1-13 (2009).
Kuijper et al. "Update of Clostridium difficile Infection due to PCR Ribotype 027 in Europe, 2008," *Euro. Surveill.*, 13(31):Article 5 (2008).
Kuksal et al., "Formulation and In Vitro, In Vivo Evaluation of Extended-release Matrix Tablet of Zidovudine: Influence of Combination of Hydrophilic and Hydrophobic Matrix Formers," *AAPS Pharm.*, 7(1):E1-E9 (2006).
Kunde et al., "Safety, Tolerability, and Clinical Response After Fecal Transplantation in Children and Young Adults With Ulcerative Colitis," *JPNG*, 56(6):597-601 (2013).
Kushak et al., "Intestinal disaccharidase activity in patients with autism," Autism, 15(3):285-294 (2011).
Kyne et al., "Association between antibody response to toxin A and protection against recurrent Clostridium difficile diarrhea," Lancet, 357(9251):189-93 (2001).
Kyne et al., "Asymptomatic carriage of Clostridium difficile and serum levels of IgG antibody against toxin A," *N Engl J Med.*, 342(6):390-397 (2000).
Kyne et al., "Factors associated with prolonged symptoms and severe disease due to Clostridium difficile," *Age and Ageing*, 28(2):107-13 (1999).
Kysela et al., "Serial analysis of V6 ribosomal sequence tags (SARST-V6): a method for efficient, high-throughput analysis of microbial community composition," *Environmental Microbiology*, 7(3):356-364 (2005).
Kyselova et al., "Alterations in the Serum Glycome Due to Metastatic Prostate Cancer," Journal of Proteome Research, 6:1822-1832 (2007).
Labbé et al., "Clostridium difficile infections in a Canadian tertiary care hospital before and during a regional epidemic associated with the BI/NAP1/027 strain," *Antimicrob Agents Chemother.*, 52(9):3180-7 (2008).
Lamontagne et al., "Impact of emergency colectomy on survival of patients with fulminant Clostridium difficile colitis during an epidemic caused by a hypervirulent strain," *Ann. Surg.*, 245(2):267-272 (2007).
Larsen et al. "Gut Microbiota in Human Adults with Type 2 Diabetes Differs from Non-Diabetic Adults," *PLoS ONE*, 5(2): e9085 (2010).
Lau et al., "Bacteraemia caused by Anaerotruncus colihominisand emended description of the species," J Clin Pathol, 59:748-752 (2006).
Lawson et al., "*Anaerotruncus colihominis* gen. nov., sp. nov., from human faeces," International Journal of Systematic and Evoluntionary Microbiology, 54:413-417 (2004).
Lawson et al., "Anaerotruncus," Bergey's Manual of Systematics of Archae and Bacteria, pp. 1-4 (2009).
Lederberg, "Infectious History", Science, 288(5464):287-293 (2000).
Lee & Mazmanian, "Has the Microbiota Played a critical Role in the Evolution of the Adaptive Immune System?," 330:1768-1773 (2010).
Lee et al., "Discriminative prediction of mammalian enhancers from DNA sequence," Genome Research 21:2167-2180 (2011).
Lee et al., "Prioritizing candidate disease genes by network-based boosting of genome-wide association data," Genome Research, 21(1):1109-1121 (2011).
Lee et al., "The outcome and long-term follow-up of 94 patients with recurrent and refractory *Clostridium difficile* infection using single to multiple fecal microbiota transplantation vie retention enema," *European Journal Clinical Microbiology Infect Dis.*, 33:1425-1428 (2014).
Lee, "A Prospective Randomized Multi-Centre Trial of Fresh vs. Frozen-and-Thawed Human Biotherapy (Fecal Transplant) for Recurrent Clostridium difficile Infection," U.S. National Institutes of Health, Clinical Study No. NCT01398969, pp. 1-4, last updated Feb. 27, 2014, Web, May 20, 2014 <http://clinicaltrials.gov/ct2/show/NCT01398969>.
Leis et al., "Fecal microbiota transplantation: A 'How-To' guide for nurses," *Collegian*, 22:445-451 (2015).
Leslie et al., "Trehalose and Sucrose Protect Both Membranes and Proteins in Intact Bacteria during Drying," Applied and Environmental Microbiology, 61:3592-3597 (1995).
Lewis et al., "Stool form scale as a useful guide to intestinal transit time," *Scand. J. Gastroenterol.*, 32(9):920-924 (1997).
Ley et al., "Ecological and evolutionary forces shaping microbial diversity in the human intestine," *Cell*, 124:837-848 (2006).
Ley et al., "Evolution of mammals and their gut microbes," *Science*, 320(5883):1647-1651 (2008).
Ley et al., "Microbial ecology: human gut microbes associated with obesity," *Nature*, 444(7122):1022-3 (2006).
Ley et al., "Worlds within worlds: evolution of the vertebrate gut microbiota," *Nat. Rev. Microbiol.*, 6(10):776-788 (2008).
Lin et al., "Twelve Week Storage Trial of Microbial Viability in Lyophilized and Frozen Fecal Microbiota Preparations," Poster Presentation—Digestive Disease Week 2015, Washington, D.C. USA.
Longstreth, "Irritable bowel syndrome: A multibillion-dollar problem," *Gastroenterology*, 109(6):2029-2031 (1995).
Lonsdale et al., "Treatment of autism spectrum children with thiamine tetrahydrofurfuryl disulfide: A pilot study," Neuroendocrinology Letters, 23:303-308 (2002).
Loo et al., "A predominantly clonal multiinstitutional outbreak of Clostridium difficile-associated diarrhea with high morbidity and mortality," *N Engl J Med*, 353(23):2442-9 (2005).
Loo et al., "Host and pathogen factors for Clostridium difficile infection and colonization," *N Engl J Med*, 365(18):1693-703 (2011).
Louie et al., "Fidaxomicin versus vancomycin for Clostridium difficile infection," *N. Engl. J. Med.*, 364(5):422-431 (2011).
Louie et al., "Home-based fecal flora infusion to arrest multiply-recurrent C. difficile infection," ICAAC/IDSA Conference, Abstract #K-4201 (2008).
Louis et al., "Diversity, metabolism and microbial ecology of butyrate-producing bacteria from the human large intestine," FEMS Microbiology Letters, 294:1-8 (2009).
Lu, "Taboo transplant: How new poo defeats superbugs," *Science News*, 1:90-91 (2011).
Ludwig et al., "Taxonomic outline of the phylum Firmicutes," Bergey's Manual of Systematic Bacteriology, 3:15-17 (2009).
Lund-Tonnesen et al., "Clostridium difficile-associated diarrhea treated with homologous faeces," *Tidsskr Nor Lageforen*, 118:1027-1030 (1998).
MacConnachie et al., "Faecal transplant for recurrent Clostridium difficile-associated diarrhoea: a UK case series," *QJM*, 102(11):781-784 (2009).
MacDonald et al., "Formation of Ursodeoxycholic Acid from Chenodeoxycholic Acid by a 7β-Hydroxysteroid Dehydrogenase-Elaborating *Eubacterium aerofaciens* Strain Cocultured with 7α-Hydroxysteroid Dehydrogenase-Elaborating Organisms," *Applied and Environmental Microbiology*, 44(5):1187-1195 (1982).
MacFabe et al., "Short-chain fatty acid fermentation products of the gut microbiome: implications in autism spectrum disorders," Microbial Ecology in Health & Disease, 23:19260 (2012).
Macpherson et al., "Induction of Protective IgA by Intestinal Dendritic Cells Carrying Commensal Bacteria," *Science*, 303:1662-1665 (2004).
Madsen, "The use of probiotics in gastrointestinal disease," *Can J Gastroenterol*, 15(12):817-22 (2001).
Magistris et al., "Alterations of the Intestinal Barrier in Patients with Autism Spectrum Disorders and in Their First-degree Relatives," Gastroenterology 51(4):418-424 (2010).

(56) References Cited

OTHER PUBLICATIONS

Maizels et al., "Regulatory T cells in Infection," Advances in Immunology, Chapter 3, 112:73-136 (2011).
Manichanh et al., "Reshaping the gut microbiome with bacterial transplantation and antibiotic intake," Genome Research 20:1411-1419 (2010).
Marchesi et al., "The normal intestinal microbiota," *Curr. Opin. Infect. Dis.*, 20(5):508-513 (2007).
Martin, "Development and Delivery of a Treatment for Clostridium difficile," *Bacteriotherapy*, pp. 1-2, n.d., Web, Feb. 10, 2012 <www.bacteriotherapy.org>.
Martin-Dejardin et al., "A way to follow the viability of encapsulated Bifidobacterium bifidum subjected to a freeze-drying process in order to target the colon: Interest of flow cytometry," *European Journal of Pharmaceutical Sciences*, 49:166-74 (2013).
Maslowski et al., "Diet, gut microbiota and immune responses," *Nat Immunol.*, 12(1):5-9 (2011).
McDonald et al., "An Epidemic, Toxin Gene-Variant Strain of Clostridium difficile," *N Engl J Med.*, 353(23):2433-41 (2005).
McDonald et al., "Clostridium difficile Infection in Patients Discharged from US Short-stay Hospitals, 1996-2003" *Emerg. Infect. Dis*, 12(3):409-415 (2006).
McFarland et al., "Breaking the Cycle: Treatment Strategies for 163 Cases of Recurrent Clostridium difficile Disease," *Am. J. Gastroenterol.*, 97(7):1769-1775 (2002).
McFarland et al., "Implications of the changing face of Clostridium difficile disease for health care practitioners," *Am J Infect Control.*, 35(4):237-253 (2007).
McFarland et al., "Meta-Analysis of Probiotics for the Prevention of Antibiotic Associated Diarrhea and the Treatment of Clostridium difficile Disease," *Am J Gastroenterol.*, 101(4):812-22 (2006).
McFarland et al., "Nosocomial Acquisition of Clostridium Difficile Infection," *N Engl J Med.*, 320(4):204-210 (1989).
McFarland et al., "Recurrent Clostridium Difficile Disease: Epidemiology and Clinical Characteristics," *Infect Control Hosp Epidemiol.*, 20(1):43-50 (1999).
McFarland et al., "Renewed interest in a difficult disease: Clostridium difficile infections—epidemiology and current treatment strategies," *Curr Opin Gastroenterol.*, 25(1):24-35 (2008).
Meadows, "Gut Bacteria May Override Genetic Protections against Diabetes," PLOS Biology, 9(12):e1001215 (2011).
Miller et al., "Health care-associated Clostridium difficile infection in Canada: patient age and infecting strain type are highly predictive of severe outcome and mortality," Clin Infect Dis., 50(2):194-201 (2010).
Miller et al., "Long-term follow-up of patients with fulminant Clostridium difficile colitis," *J. Gastrointest. Surg.*, 13(5):956-959 (2009).
Miller et al., "Morbidity, mortality, and healthcare burden of nosocomial Clostridium difficile-associated diarrhea in Canadian hospitals," *Infect Control Hosp Epidemiol.*, 23(3):137-40 (2002).
Miller, "The fascination with probiotics for Clostridium difficile infection: lack of evidence for prophylactic or therapeutic efficacy," *Anaerobe*, 15(6):281-284 (2009).
Minami et al., "Effects of lipopolysaccharides and chelator onmercuiy content in the cerebrum of thimerosal administered mice," Environmental Toxicology and Pharmacology, 24:316-320 (2007).
Minami et al., "Roles of nitric oxide prostaglandins in the increased permeability of the blood-brain barrier caused by lipopolysaccharide," Environmental Toxicology and Pharmacology, 5:35-41 (1998).
Moayyedi et al., "Fecal Microbiota Transplantation Induces Remission in Patients With Active Ulcerative Colitis in a Randomized Controlled Trial," *Gastroenterology*, 149(1):102-9 (2015).
Molecular Studies in Autism, 2004 Funding Cycle, Cure Autism Now, Cure Autism Now Foundation, pp. 1-7 (2005) <www.cureautismnow.org>.
Molloy & Manning-Courtney, "Prevalence of chronic gastrointestinal symptoms in children with autism and autistic spectrum disorders," Autism 7(2):165-171 (2003).

Momose et al., "16S rRNA gene sequence-based analysis of clostridia related to conversion of germfree mice to the normal state," Journal of Applied Microbiology, 107:2088-2097 (2009).
Morris et al., "Clostridium difficile Colitis: An Increasingly Aggressive Iatrogenic Disease?" *Arch Surg.*, 137(10):1096-1100 (2002).
Mucosal immunity: homeostasis (WS-064): Chairpersons: Toshiaki Ohteki, Makoto Iwata, *International Immunology*, 22: Suppl 1 Pt. 3, 1-9 (2010).
Mullard, "Microbiology: The Inside Story," *Nature*, 453:578-580 (2008).
Mulloy et al., "Gluten-free and casein-free diets in the treatment of autism spectrum disorders: A systematic review," Research in Autism Spectrum Disorders, 4:328-339 (2010).
Murai et al., "Interleukin 10 acts on regulatory T cells to maintain expression of the transcription factor Foxp3 and suppressive function in mice with colitis," *Nat Immunol.*, pp. 1-20 (2009).
Mutaflor, "Brief Summary of Therapeutic Principles," Ardeypharm GmbH 0796 D-58313 Herdecke Germany, 6 pgs (2006).
Mutaflor, "For Functional and Inflammatory Bowel Diseases for Extraintestinal Manifestations for Activation of the Body's In-Built Defences," Ardeypharm GmbH 0796, D-58313 Herdecke Germany, 8 pgs (2006).
Mutaflor, "Safety of Therapy," Ardeypharm GmbH 0796, D-58313 Herdecke Germany, 4 pgs (1988).
Muto et al., "A Large Outbreak of Clostridium difficile-Associated Disease with an Unexpected Proportion of Deaths and Colectomies at a Teaching Hospital Following Increased Fluoroquinolone Use," *Infect Control Hosp Epidemiol.*, 26(3):273-80 (2005).
Niehus & Lord, "Early Medical History of Children with Autism Spectrum Disorders," Journal of Developmental Behavioral Pediatrics, 27(2):S120-S127 (2006).
Nieuwdorp et al., ["Treatment of recurrent Clostridium difficile-associated diarrhoea with a suspension of donor faeces"], *Ned Tijdschr Geneeskd*, 152(35):1927-32 (2008).
Niu et al., "Prevalence and Impact of Bacteriophages on the Presence of *Escherichia coli* O157:H7 in Feedlot Cattle and Their Environment," *Applied and Environmental Microbiology*, 75(5): 1271-8 (2009).
O'Hara et al., "The gut flora as a forgotten organ," *EMBO Rep.*, 7(7):688-693 (2006).
O'Brien et al., "The emerging infectious challenge of clostridium difficile-associated disease in Massachusetts hospitals: clinical and economic consequences," Infect Control Hosp Epidemiol., 28(11):1219-27 (2007).
Ochoa-Reparaz et al., "Gut Bugs, and Brain: Role of Commensal Bacteria in the Control of Central Nervous System Disease", Annals Neurology, 69:240-247 (2011).
O'Connor et al., "Clostridium difficile Infection Caused by the Epidemic Bi/NAP1/027 Strain," *Gastroenterology*, 136(6):1913-1924 (2009).
Office Action dated Sep. 18, 2015, in European Patent Application No. 11 728 077.6.
O'Garra et al., "IL-10—producing and naturally occuring CD4+ Tregs: limiting collateral damage," The Journal of Clinical Investigation, 114:1372-1378 (2004).
O'Hara et al., "Functional modulation of human intestinal epithelial cell responses by Bifidobacterium infantis and Lactobacillus salivarius," Immunology 118:202-215 (2006).
Okada et al., "Effects of Fecal Microorganisms and Their Chloroform-Resistant Variants Derived from Mice, Rats, and Humans on Immunological and Physiological Characteristics of the Intestines of Ex-germfree Mice," Infection and Immunity, 62(12):5442-5446 (1994).
Olson et al., "The Gut Microbiota Mediates the Anti-Seizure Effects of the Ketogenic Diet," Cell, 173:1728-1741 (2018) <https://linkinghub.elsevier.com/retrieve/pii/S0092867418305208>.
Ott et al., "Efficacy of Sterile Fecal Filtrate Transfer for Treating Patients With Clostridium difficile Infection," *Gastroenterology*, 152(4):799-811 (2017).
Paramsothy et al., "Multidonor intensive faecal microbiota transplantation for active ulcerative colitis: a randomised placebo-controlled trial," The Lancet, published online, 11 pages (2017).

(56) References Cited

OTHER PUBLICATIONS

Paramsothy et al., "Gastroenterologist perceptions of faecal microbiota transplantation," *World J Gastroenterol*, 21(38): 10907-10914 (2015).
Parracho et al., "Differences between the gut microflora of children with autistic spectrum disorders and that of healthy children," Journal of Medicine Microbiology, 54:987-991 (2005).
Paterson et al., "Putting back the bugs: Bacterial treatment relieves chronic diarrhoea," *Med J Aus*, 160:232-233 (1994).
Patterson et al., "Special organism isolation: attempting to bridge the gap," *Infect Control Hosp Epidemiol.*, 15(5):335-338 (1994).
Pearce et al., "Modification of the colonic microflora using probiotics: The way forward?," *Gut*, 41(Suppl 3):A63 (1997).
Pearce et al., "The use of probiotic therapy as a novel approach to the management of irritable bowel syndrome: a preliminary study," *J Gastroenterol & Hepatol*, 12(Suppl):A129 (1997).
Pépin et al., "Clostridium difficile-associated diarrhea in a region of Quebec from 1991 to 2003: a changing pattern of disease severity," *CMAJ*, 171(5):466-472 (2004).
Pépin et al., "Emergence of Fluoroquinolones as the Predominant Risk Factor for Clostridium difficile-Associated Diarrhea: A Cohort Study During an Epidemic in Quebec," *Clin Infect Dis.*, 41(9):1254-1260 (2005).
Pépin et al., "Management and Outcomes of a First Recurrence of Clostridium difficile-Associated Disease in Quebec, Canada," *Clin. Infect. Dis.*, 42:758-764 (2006).
Persky et al., "Treatment of recurrent Clostridium difficile-associated diarrhea by administration of donated stool directly through a colonoscope," *Am J Gastroenterol.*, 95(11):3283-3285 (2000).
Petrof et al., "Stool substitute transplant therapy for the eradication of Clostridium difficile infection: 'RePOOPulating' the gut," *Microbiome*, 1:3 (2013).
Petrof, "Harnessing the healthy gut microbiota to cure patients with recurrent C. difficile infection," U.S. National Institutes of Health, Clinical Study No. NCT01372943, pp. 1-2, last updated Nov. 6, 2013, Web, May 22, 2014 <http://clinicaltrials.gov/ct2/show/NCT01372943>.
Pillai et al., "Probiotics for treatment of Clostridium difficile-associated colitis in adults (Review)," *Cochrane Database Syst Rev.*, (1):CD004611 (2008).
Porter, "Coating of pharmaceutical dosage forms," In D.B. Troy (Ed.), *Remington: The Science and Practice of Pharmacy*, Chapter 46, pp. 929-938 (2005).
Poster 064-03 presented at the 14$^{th}$ International Congress of Immunology, Aug. 22-27, 2010, in Kyoto (Atarashi et al., Regulation of colonic regulatory T cells by *Clostridium* species).
Prakash et al., "Colon-targeted delivery of live bacterial cell biotherapeutics including microencapsulated live bacterial cells," *Biologics: Targets & Therapy*, 2(3):355-378 (2008).
Prevention of Sudden Infant Death Syndrome, Healthtouch.com, Thomson MICROMEDEX, pp. 1-4, n.d., Web, Nov. 23, 2005.
Qin et al., "A human gut microbial gene catalogue established by metagenomic sequencing," Nature 464:59-67 (2010).
Qiu et al., "Faecalibacterium prausnitzii upregulates regulatory T cells and anti-inflammatory cytokines in treating TNBS-induced colitis," Journal of Crohn's and Colitis, 7:e558-e568 (2013).
Rabeneck et al., "Bleeding and perforation after outpatient colonoscopy and their risk factors in usual clinical practice," *Gastroenterology*, 135(6):1899-1906 (2008).
Rager et al., "Evaluation of rumen transfaunation after surgical correction of left-sided displacement of the abomasum in cows," *J. Am. Vet. Med. Assoc.*, 225(6):915-920 (2004).
Ramesh et al., "Prevention of Clostridium difficile-induced ileocecitis with Bacteriophage," Anaerobe, 5:69-78 (1999).
Rao et al., "Evaluation of gastrointestinal transit in clinical practice: position paper of the American and European Neurogastroenterology and Motility Societies," *Neurogastroenterol. Motil.*, 23(1):8-23 (2011).
Rautava, "Potential uses of probiotics in the neonate," Seminars in Fetal & Neonatal Medicine, 12:45-53 (2007).
Rea et al., "Gut solutions to a gut problem: bacteriocins, probiotics and bacteriophage for control of *Clostridium difficile* infection," *Journal of Medical Microbiology*, 62:1369-1378 (2013).
Redelings et al., "Increase in Clostridium difficile-related mortality rates, United States, 1999-2004," *Emerg Infect Dis.*, 13(9):1417-1419 (2007).
Response to Office Action filed Feb. 25, 2014, in European Patent Application No. 11 728 077.6.
Response to Office Action filed Jan. 28, 2015, in European Patent Application No. 11 728 077.6.
Response to Office Action filed Nov. 18, 2015, in European Patent Application No. 11 728 077.6.
Rex et al., "American College of Gastroenterology guidelines for colorectal cancer screening 2008," *Am. J. Gastroenterol.*, 104(3):739-750 (2009).
Ricciardi et al., "Increasing prevalence and severity of Clostridium difficile colitis in hospitalized patients in the United States," *Arch Surg.*, 142(7):624-631 (2007).
Roberts, Generation and Development Microbial Drug Products, CSO Vedanta Biosciences, 1st Microbiome Drug Development Summit, pp. 1-17 (2016).
Robertson et al., "Intestinal Permeability and Glucagon-like peptide-2 in Children with Autism: A Controlled Pilot Study", Journal of Autism Development Disorder, 38:10661071 (2008).
Robinson et al., "Characterization of the Cecal Bacteria of Normal Pigs", Applied and Environmental Microbiology, 41(4):950-955 (1981).
Rodemann et al., "Incidence of Clostridium difficile infection in inflammatory bowel disease," *Clin Gastroenterol Hepatol.*, 5(3):339-344 (2007).
Rohlke et al., "Fecal flora reconstitution for recurrent Clostridium difficile infection: results and methodology," *J Clin Gastroenterol.*, 44(8):567-570 (2010).
Roid et al., *Leiter International Performance Scale—Revised*, Stoelting (1997).
Rolfe et al., "Bacterial interference between Clostridium difficile and normal fecal flora," *J Infect Dis.*, 143(3):470-475 (1981).
Rossen et al., "Findings From a Randomized Controlled Trial of Fecal Transplantation for Patients with Ulcerative Colitis," *Gastroenterology*, 149(1):110-8 (2015).
Round et al., "Inducible Foxp3+ regulatory T-cell development by a commensal bacterium of the intestinal microbiota," *PNAS*, 107(27):12204-12209 (2010).
Round et al., "The Toll-like receptor pathway establishes commensal gut colonization," Science, 332(6032):974-977 (2011).
Round et al., "The gut microbiota shapes intestinal immune responses during health and disease," *Nat. Rev. Immunol.*, 9(5):313-323 (2009).
Rupnik et al., "Clostridium difficile infection: new developments in epidemiology and pathogenesis," *Nat. Rev. Microbiol.*, 7(7):526-536 (2009).
Russell et al., "Fecal bacteriotherapy for relapsing Clostridium difficile infection in a child: a proposed treatment protocol," *Pediatrics*, 126(1):e239-42 (2010).
Salazar et al, "Exopolysaccharides Produced by Intestinal Bifidobacterium Strains Act as Fermentable Substrates for Intestinal Bacteria", Applied and Environmental Microbiology, 74(15):4737-4745 (2008).
Sambol et al., "Colonization for the prevention of *Clostridium difficile* disease in hamsters," *J. Infect. Dis.*, 186(12):1781-1789 (2002).
Sanchez et al., "The Role of Natural Regulatory T cells in Infection," Immunol Res., 49(0):124-134 (2011).
Sandler et al., "Possible Gut-Brain Interaction Contributing to Delayed Onset Autism Symptomatology," *Fourth Int. Symp. Brain-Gut Interactions*, Blackwell Science Ltd., 10(4):33 (1998).
Sandler et al., "Short-Term Benefit From Oral Vancomycin Treatment of Regressive-Onset Autism," *Journal of Child Neurology*, 15(7):429-435 (2000).
Sara, et al., "Vineland Adaptive Behavior Scales, Second Edition (Vineland™-II)", *Pearson Publishing* (2005).
Sartor, "Therapeutic correction of bacterial dysbiosis discovered by molecular techniques," PNAS, 105(43):16413-16414 (2008).

(56) References Cited

OTHER PUBLICATIONS

Schauer & Falkow, "Attaching and Effacing Locus of a Citrobacter freundii Biotype That Cuases Transmissible Murine Colonic Hyperplasia," Infection and Immunity, 61(6):2486-2492 (1993).
Schiller, "Review article," the therapy of constipation, *Ailment Pharmacol. Ther.*, 15:749-763 (2001).
Schloss et al., "Introducing mothur: Open-Source, Platform-Independent, Community-Supported Software for Describing and Comparing Microbial Communities," Applied and Environmental Microbiology, 75(23):7537-7541 (2009).
Schneider et al., "Oral Human Immunoglobulin for Children with Autism and Gastrointestinal Dysfunction: A Prospective, Open-Label Study," Journal of Autism Development Disorder, 36:1053-1064 (2006).
Schopler et al., *Childhood autism rating scale-second edition (CARS2)*. Western Psychological Services, 4-5, 93 (2010).
Schwan et al., "Relapsing *Clostridium difficile* Enterocolitis Cured by Rectal Infusion of Homologous Faeces," *The Lancet*, 322(8354):845 (1983).
Schwan et al., "Relapsing *Clostridium difficile* Enterocolitis Cured by Rectal Infusion of Normal Faeces," *Scand. J. Infect. Dis.*, 16(2):211-215 (1984).
Seeff et al., "How many endoscopies are performed for colorectal cancer screening? Results from CDC's survey of endoscopic capacity," *Gastroenterology*, 127:1670-1677 (2004).
Sekirov et al., "Gut microbiota in health and disease," *Physiol. Rev.*, 90(3):859-904 (2010).
Sell et al., "Bacteriophage and Bacteriocin Typing Scheme for Clostridium difficile," Journal of Clinical Microbiology, 17(6):1148-1152 (1983).
Setlow, "I Will Survive: Protecting and Repairing Spore DNA," *Journal of Bacteriology*, 174(9):2737-2741 (1992).
Setlow, "The bacterial spore: nature's survival package," *Culture*, 26(2):1-4 (2005).
Sghir et al., "Quantification of Bacterial Groups within Human Fecal Flora by Oligonucleotide Prode Hybridization," Applied and Environmental Microbiology, 66(5):2263-2266 (2000).
Shannon, et al., "The mathematical theory of communication," *The University of Illinois Press, Urbana*, 117pp (1948).
Shi et al., "Fecal Microbiota Transplantation for Ulcerative Colitis: A Systematic Review and Meta-Analysis," *PLOS One*, 1-18 (2016).
Shim et al., "Primary symptomless colonisation by *Clostridium difficile* and decreased risk of subsequent diarrhea," *The Lancet*, 351(9103):633-666 (1998).
Silverman et al., "Success of self-administered home fecal transplantation for chronic Clostridium difficile infection," *Clin. Gastroenterol. Hepatol.*, 8(5):471-473 (2010).
Simor et al., "Clostridium difficile in long-term-care facilities for the elderly," *Infect Control Hosp Epidemiol.*, 23(11):696-703 (2002).
Singh et al., "Do NSAIDs, antibiotics, infections, or stress trigger flares in IBD?" *Am J Gastroenterol.*, 104(5):1298-1313 (2009).
Sleator, "The human superorganism—of microbes and men," *Med. Hypotheses*, 74(2):214-215 (2010).
Smits et al., "Therapeutic potential of fecal microbiota transplantation," *Gastroenterology*, 145:946-953 (2013).
Sokol et al., Faecalibacterium prausnitzii is an anti-inflammatory commensal bacterium identified by gut microbiota analysis of Crohn disease patients, Proceedings of the National Academy of Sciences, 105(43):16731-16736 (2008).
Sokol et al., "Low Counts of Faecalibacterium prausnitzii in Colitis Microbiota," Inflamm Bowel Dis., pp. 1-7 (2009).
Song et al, "Real-Time PCR Quant tation of Clostridia in Feces of Autistic Children" Applied and Environmental Microbiology, 70(11):6459-6465 (2004).
Sparrow et al., "Vineland Adaptive Behavior Scales," *2nd Edition American Guidance Service*, 3 (2005).
Stocks, "Mechanism and Use of the Commercially Available Viability Stain, BacLight," *Cytometry Part A*, 61(A):189-195 (2004).

Sullivan et al., "Effect of supplement with lactic-acid producing bacteria on fatigue and physical activity in patients with chronic fatigue syndrome," Nutritional Journal, 8(4):1-6 (2009).
Sun et al., "Tag-Encoded FLX Amplicon Pyrosequencing for the Elucidation of Microbial and Functional Gene Diversity in Any Environment", Methods and Applications, Methods in Molecular Biology, 733:129-141 (2011).
Sunil et al., "Design and evaluation of lornoxicam bilayered tablets for biphasic release," Brazilian Journal of Pharmaceutical Sciences, 48(4):609-19 (2012).
Surawicz et al., "Treatment of refractory and recurrent Clostridium difficile infection," *Nat. Rev. Gastroenterol. Hepatol.*, 8(6):330-339 (2011).
Surawicz, "Reining in Recurrent Clostridium difficile Infection—Who's at Risk?," *Gastroenterology*, 136:1152-1154 (2009).
Sutherland et al., "Lyophilized Clostridium perfringens 3 alpha- and Clostridium bifermentans 7 alpha-hydroxysteroid dehydrogenases: two new stable enzyme preparations for routine bile acid analysis," *Biochim Biophys Acta*, 962(1):116-121 (1988).
Svedlund et al., *Dig. Dis. Sci.*, 33(2):129-34 (1988).
Takaishi et al., "Imbalance in intestinal microflora constitution could be involved in the pathogenesis of inflammatory bowel disease," J. Med. Microbiol., 298:463-472 (2008).
Takeda et al., "Serum Haloperidol Levels of Schizophrenics Receiving Treatment for Tuberculosis," *Clinical Neuropharmacology*, 9(4):386-397 (1986).
Tannock et al., "A new macrocyclic antibiotic, fidaxomicin (OPT-80), causes less alteration to the bowel microbiota of Clostridium difficile-infected patients than does vancomycin," *Microbiology*, 156(11):3354-3359 (2010).
Tanoue et al., "Immune response to gut microbiota-commensals and pathogens," Gut. Microbes, 1(4):224-233 (2010).
Tap et al., "Towards the human intestinal microbiota phylogenetic core," Environmental Microbiology, 11(10):2574-2584 (2009).
Taras et al., "Reclassification of Eubacterium formicigenerans Holdeman and Moore 1974 as *Dorea formicigenerans* gen. nov., comb. nov., and description of *Dorea longicatena* sp. nov., isolated from human faeces," *International Journal of Systematic and Evolutionary Microbiology*, 52:423-428 (2002).
Teasley et al., "Prospective randomised trial of metronidazole versus vancomycin for Clostridium-difficile-associated diarrhoea and colitis," *The Lancet*, 2(8358):1043-1046 (1983).
Tian et al., "Freeze-dried, Capsulized Fecal Microbiota Transplantation for Relapsing Clostridium difficile Infection," *Journal of Clinical Gastroenterology*, 49(6):537-538 (2015).
Tilg et al., "Gut microbiome, obesity, and metabolic dysfunction," *J. Clin. Invest.*, 121(6):2126-2132 (2011).
Trent et al., "Diversity of endotoxin and its impact on pathogenesis," Journal Endotoxin Research, 12(4):205-223 (2006).
Turnbaugh et al., "A core gut microbiorne in obese and lean twins," Nature, 457(7228):480-484 (2009).
Tvede et al., "Bacteriotherapy for chronic relapsing Clostridium difficile diarrhea in six patients," *The Lancet*, 1:1156-1160 (1989).
Udall et al., "Development of Gastrointestinal Mucosal Barrier. I. The Effect of Age on Intestinal Permeability to Macromolecules," Journal of Pediatric Research, 15:241-244 (1981).
Van Andel et al., "Interleukin-12 Has a Role in Mediating Resistance of Murine Strains to Tyzzer's Disease," *Infect. Immun.*, 66(10):4942-4946 (1998).
Van der Waaij et al., "Direct Flow Cytometry of Anaerobic Bacteria in Human Feces," *Cytometry*, 16:270-279 (1994).
Van Immerseel et al., "Butyric acid-producing anaerobic bacteria as a novel probiotic treatment approach for inflammatory bowel disease," Journal of Medical Microbiology, 59:141-143 (2010).
Van Nood et al., "Struggling with Recurrent Clostridium difficile Infections: Is Donor Faeces the Solution?," *Euro Surveill.*, 14(34):1-6 (2009).
Van Nood, "Duodenal infusion of donor feces for recurrent Clostridium difficile," *New England Journal of Medicine*, 368(5):407-415 (2013).
Van Passel et al., "The Genome of Akkermansia muciniphila, a Dedicated Intestinal Mucin Degrader, and Its Use in Exploring Intestinal Metagenomesvan," Plos One 6(3):e16876 (2011).

(56) References Cited

OTHER PUBLICATIONS

Vaughn et al., "Novel treatment options for ulcerative colitis," *Future Science*, 1-20 (2013).
Veldhuyzen van Zanten et al., "Drug Treatment of Functional Dyspepsia: A Systematic Analysis of Trial Methodology with Recommendations for Design of Future Trials," *Am. Gastroenterol.*, 91(4):660-673 (1996).
Veldhuyzen van Zanten et al., "Validation of a 7-point Global Overall Symptom scale to measure the severity of dyspepsia symptoms in clinical trials," *Ailment Pharmacol. Ther.*, 23(4):521-529 (2006).
Venugopal et al., "Fidaxomicin: A Novel Macrocyclic Antibiotic Approved for Treatment of Clostridium difficile Infection," *Clin Infect Dis*, 54(4):568-74 (2012).
Vidhyalakshmi et al.,"Encapsulation "The Future of Probiotics"—A Review," Advances in Biological Research, 3(3-4):96-103 (2009).
Vrieze et al., "The environment within: how gut microbiota may influence metabolism and body composition," *Diabetologia*, 53(4):606-613 (2010).
Vulevic et al., "Modulation of the fecal microflora profile and immune function by a novel trans-galactooligosaccharide mixture (B-GOS) in healthy elderly volunteers," Am J Clin Nutr, 88:1438-46 (2008).
Wachsmann et al., "Characterization of an Orotic Acid Fermenting Bacterium, *Zymobacterium oroticum*, nov. gen., nov. spec.," Journal of Bacteriology, 68(4):400-404 (1954).
Walter et al., "Host-microbial symbiosis in the vertebrate gastrointestinal tract and the Lactobacillus reuteri paradigm," PNAS USA, 108(Suppl 1):4645-4652 (2011).
Wang et al., "Low Relative Abundances of the Mucolytic Bacterium *Akkermansia muciniphila* and *Bifidobacterium* spp. In Feces of Children with Autism," Applied and Environmental Microbiology, 77(18):6718-6721 (2011).
Warnock & Peck, "A roadmap for biomarker qualification," Nature Biotechnology, 28(5):444-445 (2010).
Warny et al., "Toxin production by an emerging strain of Clostridium difficile associated with outbreaks of severe disease in North America and Europe," *Lancet*, 366(9491):1079-84 (2005).
Warren et al., "*Clostridium aldenense* sp. nov. and *Clostridium citroniae* sp. nov. Isolated from Human Clinical Infections," Journal of Clinical Microbiology, 44(7):2416-2422 (2006).
Wasfy et al., "Comparison of Preservation Media for Storage of Stool Samples," *Journal of Clinical Microbiology*, 33(8):2176-2178 (1995).
Weingarden et al., "Dynamic changes in short- and long-term bacterial composition following fecal microbiota transplantation for recurrent Clostridium difficile infection," *Microbiome*, 3(10), 8 pages (2015).
Weissman et al., "Stool Transplants: Ready for Prime Time?," *Current Gastroenterology Reports*, 14:313-316 (2012).
Wells et al., "Clostridia: Sporeforming Anaerobic Bacilli," Medical Microbiology—NCBI Bookshelf, 4th Edition, Chapter 18, pp. 1-20 (1996) <https://www.ncbi.nlm.nih.gov/books/NBK8219/?report=printable>.
Wenisch et al., "Comparison of Vancomycin, Teicoplanin, Metronidazole, and Fusidic Acid for the Treatment of Clostridium difficile-Associated Diarrhea," *Clin Infect Dis.*, 22(5):813-818 (1996).
Wettstein et al., "Fecal Bacteriotherapy—An effective Treatment for Relapsing Symptomatic Clostridium difficile Infection," Abstract, 15th United European Gastroenterology Week (UEGW) Poster presentations, United European Gastroenterology Federation, France, A303 (2007).
Wettstein et al., "Skewered diverticulum: another cause of abdominal pain," *Internal Med J*, 31(8):495-496 (2001).
Wikoff et al., "Metabolomics analysis reveals large effects of gut microflora on mammalian blood metabolites," *PNAS*, 106(10):3698-3703 (2009).

Williams et al., "Impaired Carbohydrate Digestion and Transport and Mucosal Dysbiosis in the Intestines of Children with Autism and Gastrointestinal Disturbances," PLoS ONE, 6(9):e24585 (Sep. 2011).
Willing et al., "Shifting the balance: antibiotic effects on host-microbiota mutualism," Nature Reviews—Microbiology, 9:233-243 (2011).
Wilson et al., "Human Colonic Biota Studied by Ribosomal DNA Sequence Analysis," *Appl. Environ. Microbiol.*, 62(7):2273-2278 (1996).
Wolcott et al., "Evaluation of the bacterial diversity among and within individual venous leg ulcers using bacterial tag-encoded FLX and Titanium amplicon pyrosequencing and metagenomic approaches," BMC Microbiology, 9:226 (2009).
Wu et al., "Focused Evolution of HIV-1 Neutralizing Antibodies Revealed by Structures and Deep Sequencing," Science, 333:1593-1602 (2011).
Yoon et al., "Treatment of Refractory/Recurrent C. difficile-associated Disease by Donated Stool Transplanted Via Colonoscopy: A Case Series of 12 patients," *J Clin Gastroenterol.*, 44(8):562-566 (2010).
You et al., "Successful treatment of fulminant Clostridium difficile infection with fecal bacteriotherapy," *Ann. Intern. Med.*, 148(8):632-633 (2008).
Youngster et al., "Oral, Capsulized, Frozen Microbiota Transplantation for Relapsing Clostridium difficile Infection," *American Medical Association*, 312 (174) 1772-1778 (2014).
Youngster et al., "Oral, Frozen fecal microbiota transplant (FMT) capsules for recurrent *Clostridium difficile* infection," *BMC Medicine*, 14:134 (2016).
Yue et al., "Similarity Measure Based on Species Proportions," *Commun. Stat. Theor. Methods*, 34(11):2123-2131 (2005).
Zar et al., "A Comparison of Vancomycin and Metronidazole for the Treatment of Clostridium difficile-Associated Diarrhea, Stratified by Disease Severity," *Clin Infect Dis.*, 45(3):302-307 (2007).
Zhang et al., "Influence of Microbiota on Intestinal Immune System in Ulcerative Colitis and Its Intervention," Frontiers in Immunology, 8(Article 1674):1-11 (2017).
Zhang et al., "Altered gut microbiome composition in children with refractory epilepsy after ketogenic diet," *Epilepsy Research* (2018) <https://doi.org/10.1016/j.eplepsyres.2018.06.15>.
Zhang et al., "Human gut microbiota in obesity and after gastric bypass," *PNAS*, 106(7):2365-2370 (2009).
Zhou et al., "Total fecal microbiota transplantation alleviates high-fat diet-induced steatohepatitis in mice via beneficial regulation of gut microbiota," Scientific Reports (Nature), 7(1529):1-11 (2017).
Zhu et al., "Altered giutathione homeostasis in animals prenatally exposed to lipopolysaccharide," *Neurochemistry International*, 50(4):671-680 (2007).
Zilberberg et al., "Clostridium difficile Infections among Hospitalized Children, United States, 1997-2006," *Emerg. Infect. Dis*, 16(4):604-609 (2010).
Zilberberg et al., "Clostridium difficile-related Hospitalizations among US Adults, 2006," *Emerg. Infect. Dis*, 15(1):122-124 (2009).
Zilberberg et al., "Increase in Adult Clostridium difficile-related Hospitalizations and Case-Fatality Rate, United States, 2000-2005," *Emerg. Infect. Dis*, 14(6):929-931 (2008).
Zilberberg et al., "Increase in Clostridium difficile-related Hospitalizations Among Infants in the United States, 2000-2005," *Pediatr Infect Dis J.*, 27(12):1111-1113 (2008).
Zoppi et al., "Oral Bacteriotherapy in Clinical Practice," *Eur J. Pediatr*, 139(1):18-21 (1982).
Zoppi et al., "Oral Bacteriotherapy in Clinical Practice," *Eur J. Pediatr*, 139(1):22-24 (1982).
Zoppi et al., "The Intestinal Ecosystem in Chronic Functional Constipation," ACTA Paediatr, Scandinavian University Press, p. 836-841 (1998).
Abstract Book. IHMC: 5th International Human Microbiome Congress. (2015).
Adams, J., et al., "*Gut Bacteria in Children with Autism,* " 1st International Symposium on the Microbiome in Health and Disease with a Special Focus on Autism, 2014.

(56) References Cited

OTHER PUBLICATIONS

Balfour Sartor R (2004). "Therapeutic manipulation of the enteric microflora in inflammatory bowel diseases: antibiotics, probiotics, and prebiotics," Gastroenterology, 126(6): 1620-1633.
Baumgart D et al. (2007). "Inflammatory bowel disease: cause and immunobiology," The Lancet, 369(9573): 1627-1640.
Borody T et al. (2013). "Therapeutic Potential of the Human Gastrointestinal Microbiome," Drug Development Research 74: 385-392.
Bryant R et al. (2014). "Systematic review: Histological remission in inflammatory bowel disease. Is 'complete' remission the new treatment paradigm? An IOIBD initiative," Journal of Crohn's and Colitis, 8(12): 1582-1597.
Cammarota G (2016). "Principles of DNA-Based Gut Microbiota Assessment and Therapeutic Efficacy of Fecal Microbiota Transplantation in Gastrointestinal Diseases," Digestive Diseases 34(3): 279.
Cenit M et al. (2014). "Rapidly expanding knowledge on the role of the gut microbiome in health and disease," Biochimica et Biophysica Acta—Molecular Basis of Disease, 1842(10): 1981-1992.
Chaidez, V., et al., (2014). "Gastrointestinal Problems in Children with Autism, Development Delays or Typical Development." J. Autism Dev Disord, 44:1117-1127.
Clemente J et al. (2012). "The Impact of the Gut Microbiota on Human Health: An Integrative View," Cell, 148(6): 1258-1270.
Colman R et al. (2014). "Fecal microbiota transplantation as therapy for inflammatory bowel disease: A systematic review and meta-analysis," Journal of Crohn's and Colitis, 8(12): 1569-1581.
Critchfield J et al. (2011). "The Potential Role of Probiotics in the Management of Childhood Autism Spectrum Disorders," Gastroenterology Research and Practice, 1(1): 1-8.
Damman C (2012). "The microbiome and inflammatory bowel disease: is there a therapeutic role for fecal microbiota transplantation?" The American Journal of Gastroenterology 107(10): 1452.
De Angelis, M, et al., (2013). "Fecal Microbiota and Metabolome of Children with Autism and Pervasive Development Disorder Not Otherwise Specified," PLOS One. 8(10); e76993.
Ferre-Aracil C et al. (2015). "Fecal microbiota transplantation: something more than merely a therapeutic curiosity," Revista Espanola de Enfermedades Digestivas. 107(7): 399-401.
Finegold, S, et al., (2012). "Microbiology of regressive autism," Anaerobe, 18:260-262.
Garrett W et al. (2010). "Homeostasis and Inflammation in the Intestine," Cell, 140(6): 859-870.
Gilbert J et al. (2013). "Towards effective probiotics for autism and other neurodevelopmental disorders," Cell, 155: 1446-1448.
Hollister E et al. (2014). "Compositional and Functional Features of the Gastrointestinal Microbiome and Their Effects on Human Health," Gastroenterology, 146(6): 1449-1458.
Holmes E et al. (2012). "Therapeutic Modulation of Microbiota-Host Metabolic Interactions," Science Translational Medicine, 4(137): 137rv6.
Hsiao E et al. (2013). "Microbiota Modulate Behavioral and Physiological Abnormalities Associated with Neurodevelopmental Disorders," Cell 155: 1451-1463.
Kantarcioglu A et al. (2016). "Microbiota-Gut-Brain Axis: Yeast Species Isolated from Stool Samples of Children with Suspected or Diagnosed Autism Spectrum Disorders and In Vitro Susceptibility Against Nystatin and Fluconazole," Mycopathologia, 181(1): 1-7.
Khoruts A et al. (2014). "Emergence of fecal microbiota transplantation as an approach to repair disrupted microbial gut ecology," Immunol Lett. 162(2A):77-81.
Li Q et al. (2014). "Therapeutic modulation and reestablishment of the intestinal microbiota with fecal microbiota transplantation resolves sepsis and diarrhea in a patient," The American Journal of Gastroenterology 109(11): 1832.
Li Q et al. (2016). "The microbiota-gut-brain axis and its potential therapeutic role in autism spectrum disorder," Neuroscience, 324: 131-139.
Liu X et al. (2015). "Modulation of Gut Microbiota-Brain Axis by Probiotics, Prebiotics, and Diet," J. Agric. Food Chem., 63(36): 7885-7895.
Mangiola F et al. (2016). "Gut microbiota in autism and mood disorders," World J Gastroenterol., 22(1): 361-368.
Neish A (2009). "Microbes in Gastrointestinal Health and Disease," Gastroenterology, 136(1): 65-80.
Owyang C et al. (2014). "The Gut Microbiome in Health and Disease," Gastroenterology, 146(6): 1433-1436.
Petrof E (2013). "Microbial ecosystems therapeutics: a new paradigm in medicine?" Beneficial Microbes, 4(1): 53-65.
Petrof E et al. (2014). "From Stool Transplants to Next-Generation Microbiota Therapeutics," Gastroenterology, 146(6): 1573-1582.
Reddy B (2015). "Autism and our intestinal microbiota," Journal of Mol. Microbio. and Biotech. 25(1): 51.
Rosenfeld C (2015). "Microbiome Disturbances and Austin Spectrum Disorders," Drug Metabolism and Disposition, 43(10): 1557.
Shanahan F et al. (2014). "Manipulation of the Microbiota for Treatmenet of IBS and IBD—Challenges and Controversies," Gastroenterology, 146(6): 1554-1563.
Sun J et al. (2014). "Exploring gut microbes in human health and disease: Pushing the envelope," Genes & Diseases, 1(2): 132-139.
Swidsinski A et al. (2002). "Mucosal flora in inflammatory bowel disease," Gastroenterology, 122(1): 44-54.
U.S. Securities and Exchange Commission, Form 8-K Report, Assembly Bioscience, Inc., Feb. 24, 2015.
Ursell L et al. (2014). "The Intestinal Metabolome: An Intersection Between Microbiota and Host," Gastroenterology 146:1470-1476.
West, C., et al., "The gut microbiota and inflammatory noncommunicable diseases: Associations and potentials for gut microbiota therapies" Journal of Allergy and Clinical Immunology, vol. 135, Issue 1, Jan. 2015, pp. 3-13.
Yarandi S et al (2016). "Modulatory Effects of Gut Microbiota on the Central Nervous System: How Gut Could Play a Role in Neuropsychiatric Health and Diseases," J Neurogastroenterol Motil., 22(2): 201-212.

\* cited by examiner

|  | % CHANGE | p-VALUE |
|---|---|---|
| IRRITABILITY | -25% | 0.03 |
| LETHARGY | -33% | 0.003 |
| STEREOTOPY | -21% | 0.03 |
| HYPERACTIVITY | -28% | 0.0005 |
| INAPPROPRIATE SPEECH | -22% | 0.01 |
| TOTAL ABC | -27% | 0.001 |

FIG. 4

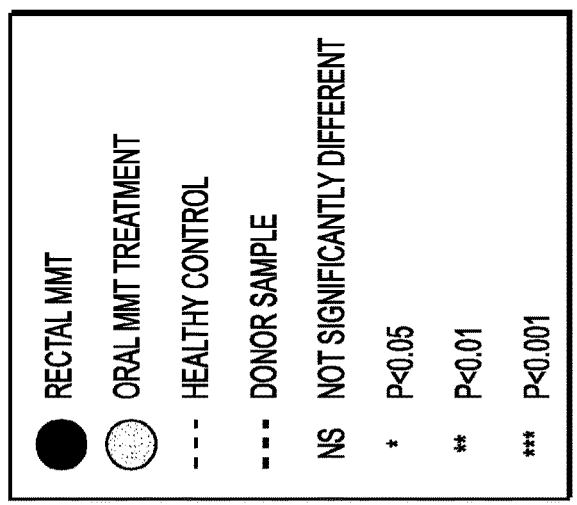
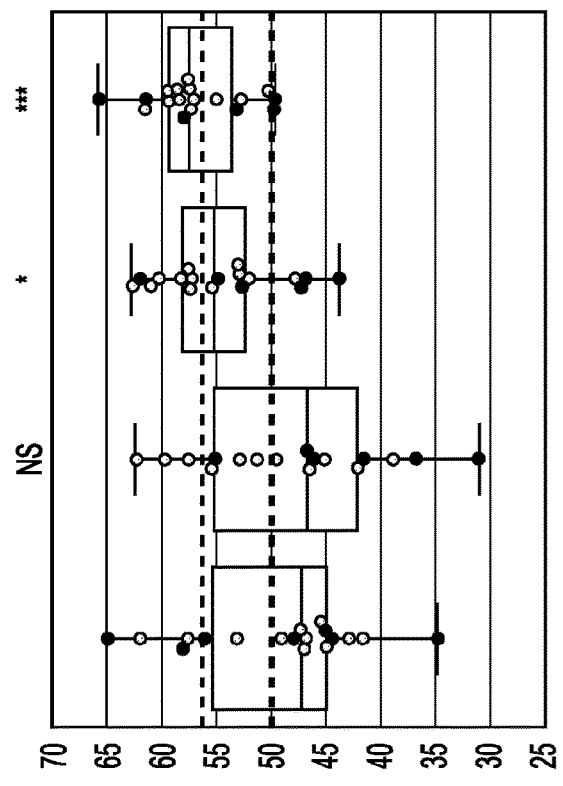
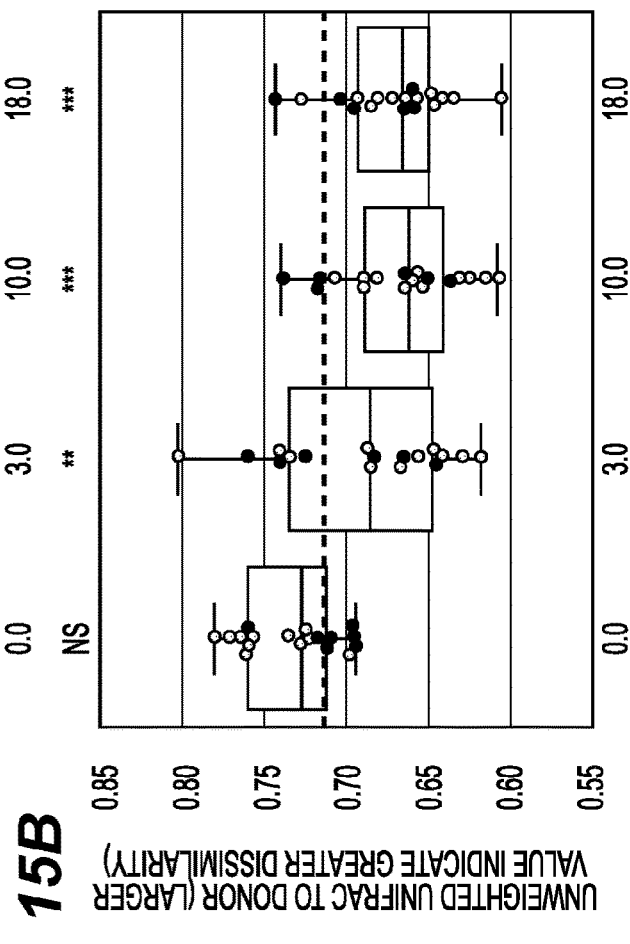
FIG. 15A
FIG. 15B

ORAL VS. RECTAL ADMINISTRATION

| OBSERVED OTUS | MEDIAN | | 2-TAILED P-VALUE □ |
| --- | --- | --- | --- |
| | ORAL (N=10) | RECTAL (N=6) | |
| MEDIAN | 1085 | 823 | 0.09 |

| PD | MEDIAN | | 2-TAILED P-VALUE □ |
| --- | --- | --- | --- |
| | ORAL (N=10) | RECTAL (N=6) | |
| MEDIAN | 37 | 53 | 0.11 |

*FIG. 30C*

MALE VS. FEMALE ADMINISTRATION

OBSERVED OTUS

| | MEDIAN | | 2-TAILED P-VALUE |
|---|---|---|---|
| | FEMALE (N=2) | MALE (N=14) | |
| MEDIAN | 702 | 1059 | NA |

PD

| | MEDIAN | | 2-TAILED P-VALUE |
|---|---|---|---|
| | FEMALE (N=2) | MALE (N=14) | |
| MEDIAN | 37 | 53 | NA |

*FIG. 30D*

METHODS FOR TREATING AUTISM SPECTRUM DISORDER AND ASSOCIATED SYMPTOMS

CROSS-REFERENCE TO RELATED APPLICATIONS

This application is a U.S. National Stage of International Application No. PCT/US2017/037499, filed Jun. 14, 2017, which claims priority to U.S. Provisional Application No. 62/350,693, filed Jun. 15, 2016, both of which are herein incorporated by reference in their entireties.

BACKGROUND

The present disclosure relates to methods of modulating gut microbiome and methods for treating autism spectrum disorder (ASD). Autism spectrum disorder (ASD) is a complex neurodevelopmental condition characterized by widespread abnormalities of social interactions and communication, as well as restricted interests and repetitive behaviors. ASD typically appears during the first three years of life and manifests in characteristic symptoms or behavioral traits. A diagnosis of ASD now includes several conditions that used to be diagnosed separately: autistic disorder, pervasive developmental disorder not otherwise specified (PDD-NOS), and Asperger syndrome. All of these conditions are now encompassed by the diagnostic criteria for autism spectrum disorder as set forth in the American Psychiatric Association's Diagnostic & Statistical Manual of Mental Disorders, Fifth Edition (DSM-V).

In addition to the spectrum of symptoms seen within these principal diagnostic criteria, ASD individuals display a wide range of neurological comorbidities, including intellectual disability, epilepsy, and anxiety and mood disorders, as well as non-neurological comorbidities, including blood hyperserotonemia, immune dysregulation, and GI dysfunction (e.g., chronic constipation, diarrhea, abdominal pain, and gastroesophageal reflux).

To date, there are no FDA-approved treatments for reducing or eliminating the core symptoms of autism spectrum disorder. The only two medications approved by the FDA for treating autism, risperidone (sold under Risperdal®) and aripiprazole (sold under Abilify®), are specifically indicated for reducing irritability in subjects having ASD. Accordingly, there remains a need in the art for improved methods for treating and reducing the severity and incidence of symptoms associated with autism spectrum disorder. This application provides a method for treating an ASD patient (with or without a GI symptom) by transferring beneficial fecal bacteria to replace, restore, or rebalance the ASD patient's gut microbiota, a treatment referred to here as Microbiota Transfer Therapy (MTT). This application further provides a method for treating an ASD in a patient by selectively modulating the abundance of certain fecal microbes (e.g., bacteria) or bacteriophages.

BRIEF DESCRIPTION OF THE DRAWINGS

FIG. 4 presents Aberrant Behavior Checklist (ABC) data for MTT trial participants.

FIG. 15 (including panels a and b) describes stool microbiota changes in ASD patients received MTT and further classified according to the oral or rectal administration of MIVIT. Panel a. Changes in Faith's Phylogenetic Diversity (PD) in the ASD microbiota as measured from stool samples. Orange line indicates median PD of the donor samples, and green line indicates median PD of neurotypical controls at week 0. Panel b. Unweighted UniFrac distances between ASD gut microbiota and most relevant donor sample (initial donor sample at weeks 0 and 3, most recent maintenance dose sample at weeks 10 and 18). Green line indicates the median interpersonal variation between neurotypical controls and illustrates that prior to treatment the difference in gut microbiota composition between MTT recipients and donors is on the order of normal interpersonal variation. Following treatment, the MTT recipients are more similar to donors than normal interpersonal variation.

SUMMARY

Figure 1:
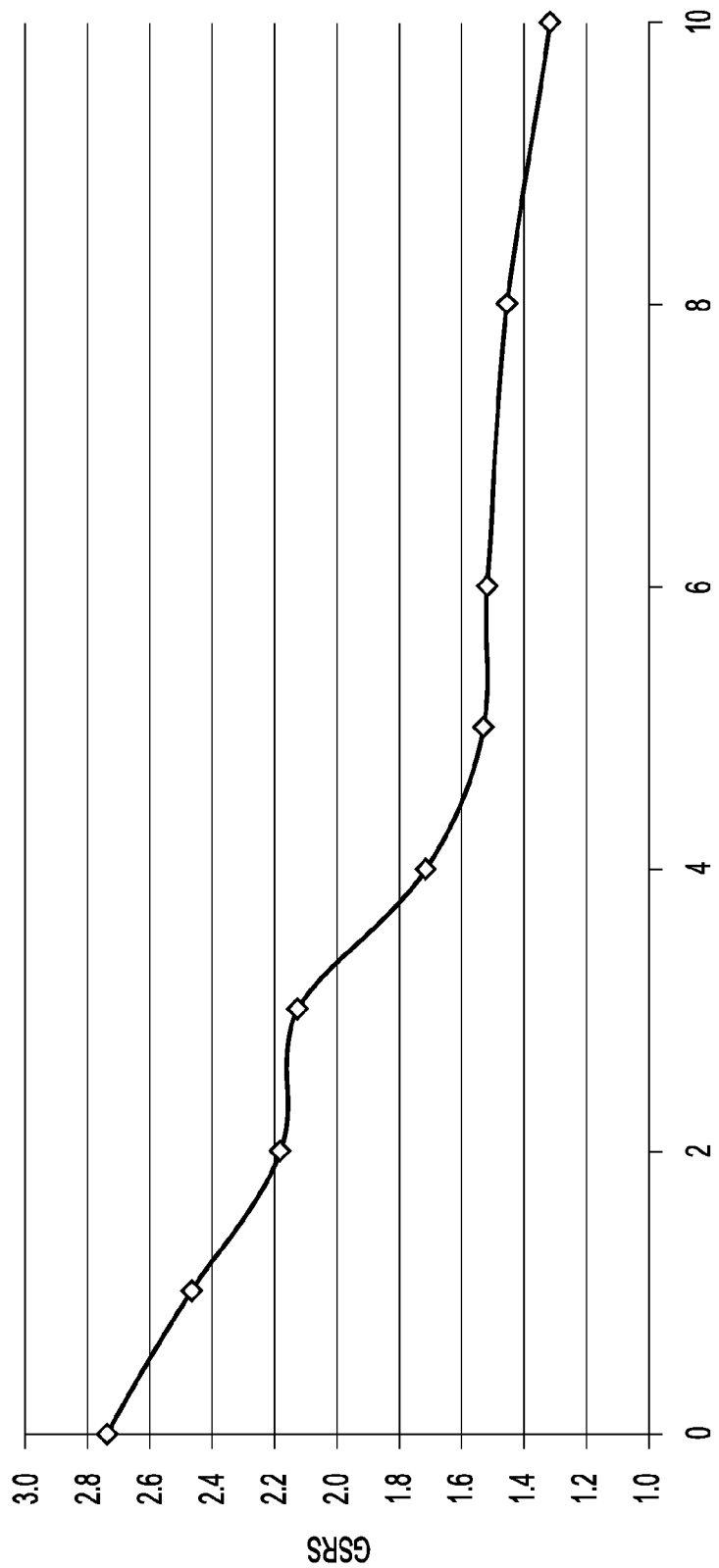
FIG. 1 presents Gastrointestinal Symptom Rating Scale (GSRS) data for trial participants.

In one aspect, this application provides a method for increasing the abundance of one or more gut microorganisms in a subject in need thereof, the method comprising treating the subject by administering a therapeutically effective amount of a pharmaceutical composition comprising a fecal microbe preparation, wherein the subject exhibits at least a 2-fold increase of the abundance of the one or more fecal microorganisms after the treatment as compared to before initiating the treatment, wherein the one or more gut microorganisms are from a genus selected from the group consisting of *Bifidobacterium, Prevotella*, and *Desulfovibrio*.

In another aspect, this application provides a method for increasing the phylogenetic diversity of fecal microbiota, fecal phage virome, or both, of a subject in need thereof, the method comprising administering to the subject a therapeutically effective amount of a pharmaceutical composition comprising a fecal microbe preparation, wherein the subject exhibits at least a two-fold increase of fecal microbiota or fecal phage virome diversity after the treatment as compared to before initiating the treatment.

In one aspect, this application provides a method comprising: determining the relative abundance of one or more gut microorganisms in a subject having an ASD or having an ASD sibling, and administering a therapeutically effective amount of a pharmaceutical composition comprising a fecal microbe preparation to achieve at least a 2-fold change of the abundance of the one or more fecal microorganisms, wherein the one or more gut microorganisms are from a genus selected from the group consisting of *Clostridium, Bacteroides, Eggerthella, Bifidobacterium, Prevotella*, and *Desulfovibrio*.

In another aspect, this application provides a method for modulating the abundance of one or more gut microorganisms in a subject in need thereof, the method comprising administering to the subject a therapeutically effective amount of a pharmaceutical composition comprising a fecal microbe preparation to achieve at least a 2-fold change of the abundance of the one or more fecal microorganisms, wherein the one or more gut microorganisms are selected from the group consisting of *Bifidobacterium, Prevotella, Desulfovibrio, Copprococcus, Clostridium, Eggerthella*, and *Bacteroides*.

DETAILED DESCRIPTION

Unless defined otherwise, all technical and scientific terms used herein have the same meaning as commonly understood by one of ordinary skill in the art to which this disclosure belongs.

All publications, patents, and patent applications mentioned in this specification are herein incorporated by reference to the same extent as if each individual publication, patent, or patent application is specifically and individually indicated to be incorporated by reference.

As used herein and in the appended claims, the singular forms "a," "an," and "the" include plural referents unless the context clearly dictates otherwise. As used herein, the term "substantially" as in, for example, the phrase "substantially all peptides of an array," refers to at least 90%, preferably at least 95%, more preferably at least 99%, and most preferably at least 99.9%, of the peptides of an array. Other uses of the term "substantially" involve an analogous definition.

Where a range of values is provided, it is understood that each intervening value, between the upper and lower limit of that range and any other stated or intervening value in that stated range is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either both of those included limits are also included in the disclosure.

As used herein, the term "treating" refers to (i) completely or partially inhibiting a disease, disorder or condition, for example, arresting its development; (ii) completely or partially relieving a disease, disorder or condition, for example, causing regression of the disease, disorder and/or condition; or (iii) completely or partially preventing a disease, disorder or condition from occurring in a patient that may be predisposed to the disease, disorder and/or condition, but has not yet been diagnosed as having it. Similarly, "treatment"

refers to both therapeutic treatment and prophylactic or preventative measures. In the context of autism spectrum disorder, "treat" and "treating" encompass alleviating, ameliorating, delaying the onset of, inhibiting the progression of, or reducing the severity of one or more symptoms associated with an autism spectrum disorder. In one aspect, treating can also mean modulating the abundance of selected bacterial genera.

As used herein, a "subject" can be a human or animal including, but not limited to, a dog, cat, horse, cow, pig, sheep, goat, chicken, rodent, e.g., rats and mice, and primate, e.g., monkey. Preferred subjects are human subjects. The human subject may be a pediatric, adult or a geriatric subject.

As used herein, a "microbiota" and "flora" refer to a community of microbes that live in or on a subject's body, both sustainably and transiently, including eukaryotes, archaea, bacteria, and viruses (including bacterial viruses (i.e., phage)). A "fecal microbiota" or "fecal microbiota preparation" refers to a community of microbes present in or prepared from a subject's feces. A non-selective fecal microbiota refers to a community or mixture of fecal microbes derived from a donor's fecal sample without selection and substantially resembling microbial constituents and population structure found in such fecal sample.

As used herein, "therapeutically effective amount" or "pharmaceutically active dose" refers to an amount of a composition which is effective in treating the named disease, disorder or condition.

As used herein, "isolated" or "purified" refers to a bacterium or other entity or substance that has been (1) separated from at least some of the components with which it is associated when initially produced (whether in nature or in an experimental setting), and/or (2) produced, prepared, purified, and/or manufactured by the hand of man. Isolated or purified bacteria can be separated from at least about 10%, about 20%, about 30%, about 40%, about 50%, about 60%, about 70%, about 80%, about 90%, or more of the other components with which they are initially associated.

As used herein, the terms "non-pathogenic" in reference to a bacterium or any other organism or entity includes any such organism or entity that is not capable of causing or affecting a disease, disorder or condition of a host organism containing the organism or entity.

As used herein, "spore" or a population of "spores" includes bacteria (or other single-celled organisms) that are generally viable, more resistant to environmental influences such as heat and bacteriocidal agents than vegetative forms of the same bacteria, and typically capable of germination and out-growth. "Spore-formers" or bacteria "capable of forming spores" are those bacteria containing the genes and other necessary abilities to produce spores under suitable environmental conditions.

As used herein, "colony forming units" (cfu) refers to an estimate of the number of viable microorganism cells in a given sample. The number of cfu can be assessed by counting the number of colonies on an agar plate as in standard methods for determining the number of viable bacterial cells in a sample.

As used herein, "viable" means possessing the ability to multiply. The viability of bacterial populations can be monitored as a function of the membrane integrity of the cell. Cells with a compromised membrane are considered to be dead or dying, whereas cells with an intact membrane are considered live. For example, SYTO 9 and propidium iodide are used to stain and differentiate live and dead bacteria. See Stocks, *Cytometry A*. 2004 October; 61(2):189-95. Cell viability can also be evaluated via molecular viability analyses, e.g., a PCR-based approach, which can differentiate nucleic acids associated with viable cells from those associated with inactivated cells. See Cangelosi and Mescheke, *Appl Environ Microbiol*. 2014 October; 80(19): 5884-5891.

As used herein, "Shannon Diversity Index" refers to a diversity index that accounts for abundance and evenness of species present in a given community using the formula $H=-\Sigma_{i=1}^{R} p_i \ln p_i$, where H is Shannon Diversity Index, R is the total number of species in the community, and $p_i$ is the proportion of R made up of the ith species. Higher values indicate diverse and equally distributed communities, and a value of 0 indicates only one species is present in a given community. For further reference, see Shannon and Weaver, (1949) *The mathematical theory of communication*. The University of Illinois Press, Urbana. 117 pp.

As used herein, "antibiotic" refers to a substance that is used to treat and/or prevent bacterial infection by killing bacteria, inhibiting the growth of bacteria, or reducing the viability of bacteria.

Autism spectrum disorder (ASD) is a neurodevelopmental disorder that is characterized by impairments in social interaction and communication, restricted interests, and repetitive behavior. Individuals on the autism spectrum experience widely varying degrees and types of impairments, from mild to severe. Although early detection and interventions are encouraged to maximize the benefits and reduce the severity of the symptoms, individuals of any age can benefit from interventions and therapies that can reduce symptoms and increase skills and abilities. Appropriate subjects for the methods described herein include, without limitation, humans diagnosed as having or suspected of having autism spectrum disorder. In some cases, appropriate subjects for the methods provided herein are considered to be at increased risk (e.g., moderate or high risk) of developing ASD. In some cases, the subject has been diagnosed as having a condition meeting diagnostic criteria for ASD as set forth in the DSM-V. In other cases, the subject has a well-established DSM-IV diagnosis of autistic disorder, Asperger's disorder, or pervasive developmental disorder not otherwise specified (PDD-NOS).

The methods provided herein result in, or are aimed at achieving a detectable improvement in one or more indicators or symptoms of ASD including, without limitation, including, but not limited to, changes in eye tracking, skin conductance and/or EEG measurements in response to visual stimuli, difficulties engaging in and responding to social interaction, verbal and nonverbal communication problems, repetitive behaviors, intellectual disability, difficulties in motor coordination, attention issues, sleep disturbances, and physical health issues such as gastrointestinal disturbances.

Several screening instruments are known in the art for evaluating a subject's social and communicative development and thus can be used as aids in screening for and detecting changes in the severity of impairment in communication skills, social interactions, and restricted, repetitive and stereotyped patterns of behavior characteristic of autism spectrum disorder. Evaluation can include neurologic and genetic assessment, along with in-depth cognitive and language testing. Additional measures developed specifically for diagnosing and assessing autism include the Autism Diagnosis Interview-Revised (ADI-R), the Autism Diagnostic Observation Schedule (ADOS-G) and the Childhood Autism Rating Scale (CARS).

According to CARS, evaluators rate the subject on a scale from 1 to 4 in each of 15 areas: Relating to People; Imitation;

Emotional Response; Body Use; Object Use; Adaptation to Change; Visual Response; Listening Response; Taste, Smell, and Touch Response and Use; Fear; Verbal Communication; Nonverbal Communication; Activity; Level and Consistency of Intellectual Response; and General Impressions.

A second edition of CARS, known as the Childhood Autism Rating Scale—2 or CARS-2, is developed by Schopler et al. (Childhood Autism Rating Scale—Second edition (CARS2): Manual. Los Angeles: Western Psychological Services, 2010). The original CARS is developed primarily with individuals with co-morbid intellectual functioning and is criticized for not accurately identifying higher functioning individuals with ASD. CARS-2 retained the original CARS form for use with younger or lower functioning individuals (now renamed the CARS2-ST for "Standard Form"), but also includes a separate rating scale for use with higher functioning individuals (named the CARS2-HF for "High Functioning") and an unscored information-gathering scale ("Questionnaire for Parents or Caregivers" or CARS2-QPC) that has utility for making CARS2ST and CARS2-HF ratings.

Another symptom rating instrument useful for assessing changes in symptom severity before, during, or following treatment according to a method provided herein is the Aberrant Behavior Checklist (ABC). See Aman et al., Psychometric characteristics of the aberrant behavior checklist. *Am J Ment Defic.* 1985 March; 89(5):492-502. The ABC is a symptom rating checklist used to assess and classify problem behaviors of children and adults in a variety of settings. The ABC includes 58 items that resolve onto five subscales: (1) irritability/agitation, (2) lethargy/social withdrawal, (3) stereotypic behavior, (4) hyperactivity/noncompliance, and (5) inappropriate speech.

The present inventors observed that autistic individuals, regardless of the presence or absence of comorbid gastrointestinal distress, have fewer species of gut bacteria as compared to neurotypical individuals. The present inventors also found that restoring the species diversity of gut bacteria helps to treat autistic symptoms in patients in need thereof.

In one aspect, this application provides a method for increasing the abundance of one or more gut microorganisms in a subject in need thereof, the method comprising treating the subject by administering a therapeutically effective amount of a pharmaceutical composition comprising a fecal microbe preparation, wherein the subject exhibits at least a 50-fold increase of the abundance of the one or more fecal microorganisms after the treatment as compared to before initiating the treatment, wherein the one or more gut microorganisms are from a genus selected from the group consisting of *Bifidobacterium, Prevotella,* and *Desulfovibrio*. In one aspect, a subject being treated exhibits at least 2-fold, 3-fold, 4-fold, 5-fold, 10-fold, 20-fold, 30-fold, 40-fold, 50-fold, 60-fold, 70-fold, 80-fold, 90-fold, 100-fold, 110-fold, 120-fold, 130-fold, 140-fold, 150-fold, 160-fold, 170-fold, 180-fold, 190-fold, or 200-fold increase of the abundance of one or more *Bifidobacterium, Prevotella,* or *Desulfovibrio* species after a treatment as compared to before initiating the treatment. In another aspect, this application provides a method for modulating the abundance of one or more gut microorganisms in a subject in need thereof, the method comprising administering to the subject a therapeutically effective amount of a pharmaceutical composition comprising a fecal microbe preparation to achieve at least a 2-fold, 5-fold, 10-fold, 20-fold, 30-fold, 40-fold, 50-fold, 60-fold, 70-fold, 80-fold, 90-fold, 100-fold, 110-fold, 120-fold, 130-fold, 140-fold, 150-fold, 160-fold, 170-fold, 180-fold, 190-fold, or 200-fold change of the abundance of the one or more fecal microorganisms, wherein the one or more gut microorganisms are selected from the group consisting of *Bifidobacterium, Prevotella, Desulfovibrio, Coprococcus, Clostridium, Eggerthella,* and *Bacteroides.* In a further aspect, a treated subject exhibit a bacterial abundance fold increase (e.g., *Bifidobacterium, Prevotella,* or *Desulfovibrio*) of between 2 and 10, between 3 and 10, between 4 and 10, between 5 and 10, between 6 and 10, between 10 and 20, between 10 and 30, between 10 and 40, between 10 and 50, between 10 and 60, between 10 and 70, between 10 and 80, between 10 and 90, between 20 and 30, between 20 and 40, between 20 and 50, between 20 and 60, between 20 and 70, between 20 and 80, between 20 and 90, between 30 and 40, between 30 and 50, between 30 and 60, between 30 and 70, between 30 and 80, between 30 and 90, between 40 and 50, between 40 and 60, between 40 and 70, between 40 and 80, between 40 and 90, between 50 and 60, between 50 and 70, between 50 and 80, between 50 and 90, between 50 and 100, between 50 and 150, between 50 and 200, between 50 and 250, between 50 and 300 fold after 8 or more weeks of treatment as compared to before initiating the treatment.

*Prevotella* is an anaerobic, non-spore forming, non-motile, rod that stains Gram-negative. *Desulfovibrio* is a gram negative, rod shaped, sulfate reducing bacterium, which is an anaerobe and which may compete with the host for sulfur. Its metal corroding ability has led to numerous health and safety concerns; and its production of $H_2S$ and endotoxin can lead to genotoxic and other toxic-related problems. *Bifidobacterium* is an Gram-positive, non-acid-fast, non-sporeforming, and nonmotile anaerobe. *Eggerthella* are Gram-positive obligately anaerobic bacilli, which are non-motile and do not produce endospores. *Prevotella* and *Bifidobacterium* are generally believed to be beneficial intestinal bacteria, but the role of *Desulfovibrio* is less understood. This application illustrates that increases in all three are beneficial in children with ASD.

Figure 20:
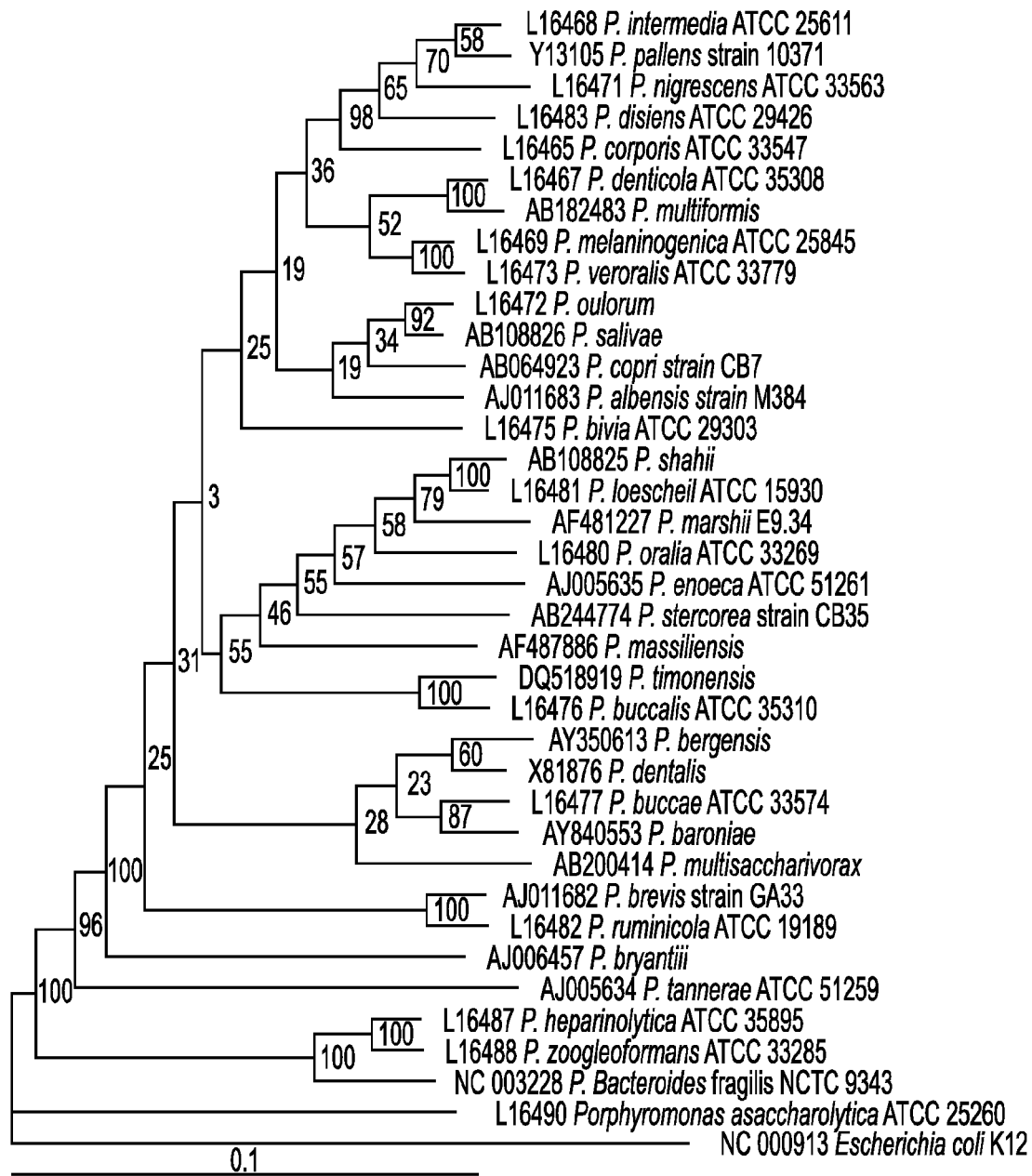
FIG. 20 provides a neighbor-joining phylogenetic tree of 16S rRNA gene sequences of the type strains of *Prevotella* species deposited in GenBank to show the relationships of strains within the genus. Bootstrap values (expressed as percentages of 1000 replicates) are shown at the nodes. The numbers that precede each strain are the GenBank accession numbers, while those that follow the species names are the Culture Collection numbers. The type species of *Bacteroides* (*Bacteroides fragilis*, NCTC 9343) and *Porphyromonas* (*Porphyromonas asaccharolytica*, ATCC 25260), both former members of the same genus, and *Escherichia coli* (K12) are included for comparison.
Figure 21:
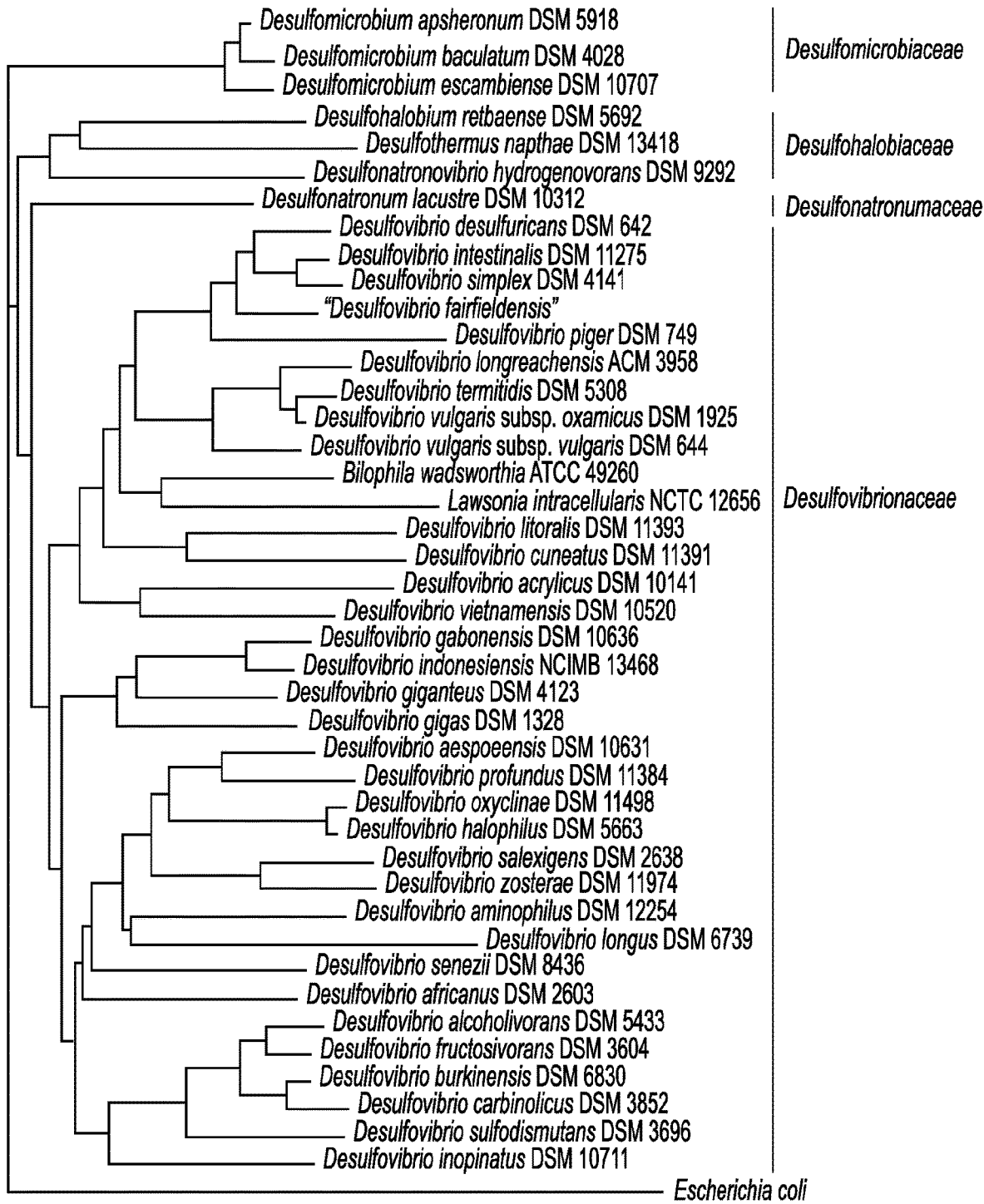
FIG. 21 describes phylogenetic relationships based on 16S rRNA gene sequence analyses of the taxa within the order Desulfovibrionales for which 16S rRNA gene sequences are available. The scale bar represents 10 inferred nucleotide substitutions per 100 nucleotides. The dendrogram is reconstructed from distance matrices using the neighbor-joining method.
Figure 22:
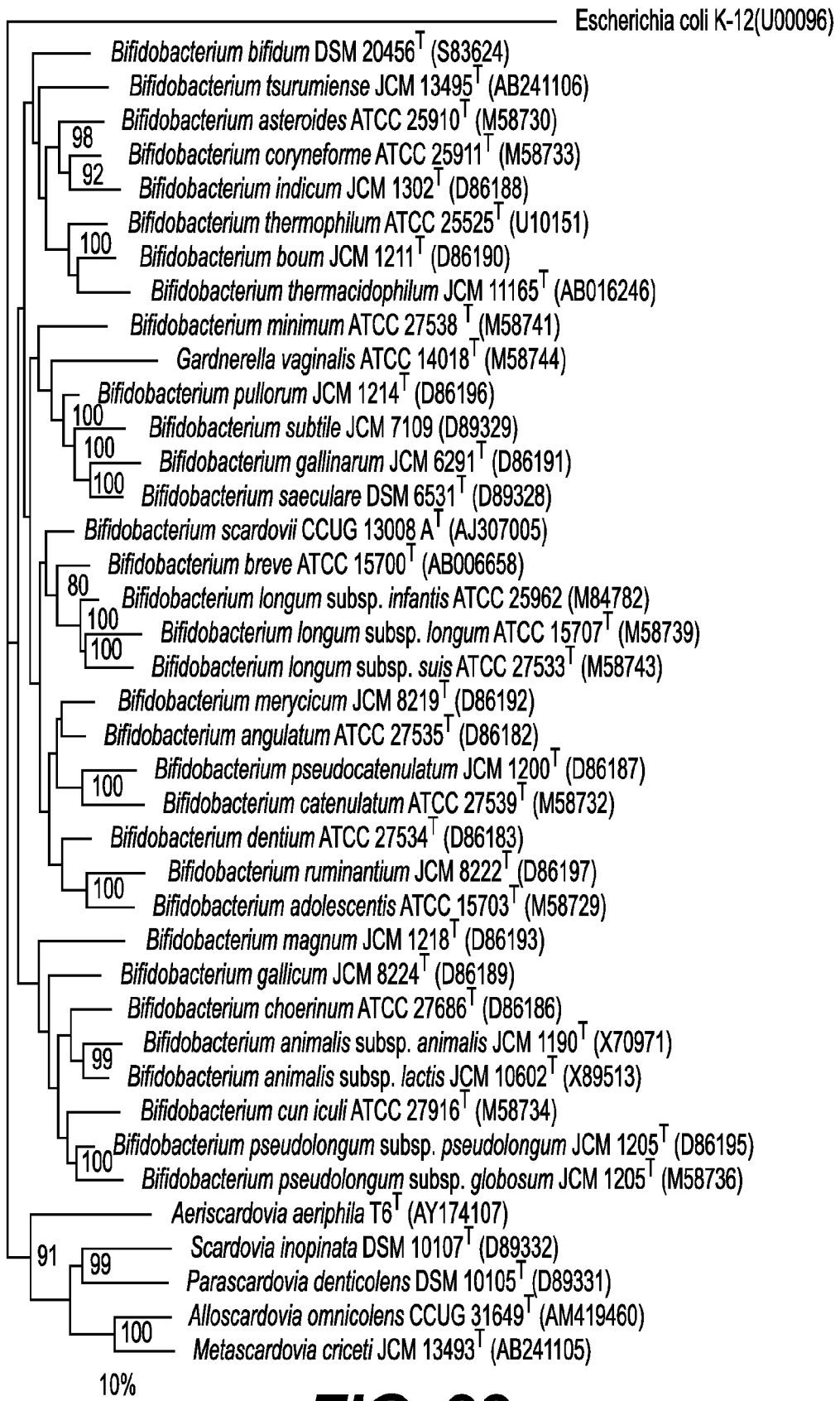
FIG. 22 describes a phylogenetic tree constructed from partial 16S rRNA gene sequences of members of the family Bifidobacteriaceae. The tree is rooted with *Escherichia coli*, and constructed by using the neighbor-joining method with bootstrap values calculated from 1000 trees (represented as percentages and given at each branch). For each species, the GenBank accession number for the respective 16S rRNA gene sequence is indicated. The scale bar shows the number of nucleotide substitutions per site.

In one aspect, an increase in *Prevotella* abundance is an increase of one or more, two or more, three or more, four or more, five or more, six or more, or seven or more species selected from the group consisting of *P. intermedia, P. pallens, P. nigrescens, P. disiens, P. corporis, P. denticola, P. multiformis, P. melaninogenica, P. veroralis, P. oulorum, P. salivae, P. copri, P. albensis, P. bivia, P. shahii, P. loescheii, P. marshii, P. oralia, P. enoeca, P. stercorea, P. massiliensis, P. timonensis, P. buccalis, P. bergensis, P. dentalis, P. buccae, P. baroniae, P. multisaccharivorax, P. brevis, P. ruminicola, P. bryantiii, P. tannerae, P. heparinolytica,* and *P. zoogleoformans.* In one aspect, an increase in *Prevotella* abundance is an increase of one or more, two or more, three or more, four or more, five or more, six or more, or seven or more species listed in FIG. 20. In one aspect, an increase in *Desulfovibrio* abundance is an increase of one or more, two or more, three or more, four or more, five or more, six or more, or seven or more *Desulfovibrio* species listed in FIG. 21. In one aspect, an increase in *Bifidobacterium* abundance is an increase of one or more, two or more, three or more, four or more, five or more, six or more, or seven or more *Bifidobacterium* species selected from the group consisting of *B. adolescentis, B. angulatum, B. animalis, B. asteroides, B. bifidum, B. bourn, B. breve, B. catenulatum, B. choerinum, B. coryneforme, B. cuniculi, B. denticolens, B. dentium, B. gallicum, B. gallinarum, B. indicum, B. inopinatum, B. infantis, B. lactis, B. longum, B. magnum, B. merycicum, B. minimum, B. pseudocatenulatum, B. pseudolongum, B. pullorum, B. ruminantium, B. saeculare, B. subtile, B. thermacidophilum, B. thermophilum,* and *B. tsurumiense.* In one aspect, an increase in *Bifidobacterium* abundance is an increase of one or more, two or more, three or more, four or more, five or more, six or more, or seven or more *Bifidobacterium* species listed in FIG. 22. In one aspect, a change in *Eggerthella* abundance is an decrease of one or more or two or more *Eggerthella* species selected from the group consisting of *Eggerthella lenta*, *Eggerthella sinensis*, and *Eggerthella hongkongensis*.

In one aspect, a bacterial abundance change (e.g., increase of *Bifidobacterium*, *Prevotella*, or *Desulfovibrio*, or decrease of *Bacteroides* or *Eggerthella*) is ongoing during a treatment or sustained after finishing or discontinuing a treatment. In one aspect, a bacterial abundance change (e.g., increase of *Bifidobacterium*, *Prevotella*, or *Desulfovibrio*, or decrease of *Bacteroides* or *Eggerthella*) is assessed at a specific time point during or post treatment, e.g., about 2, 4, 6, 8, 12, 18, 24, 32, 40, 48 weeks after initiating a treatment, or about 2, 4, 6, 8, 12, 18, 24, 32, 40, 48 weeks after finishing or discontinuing a treatment. In another aspect, a bacterial abundance change (e.g., increase of *Bifidobacterium*, *Prevotella*, or *Desulfovibrio*, or decrease of *Bacteroides* or *Eggerthella*) is assessed about 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, or 110 weeks after initiating a treatment, or about 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, or 110 weeks after finishing or discontinuing a treatment.

In one aspect, a method further comprises determining in a subject a relative abundance of one or more gut microorganisms selected from the group consisting of *Bifidobacterium*, *Prevotella*, *Desulfovibrio*, *Copprococcus*, *Clostridium*, *Eggerthella*, and *Bacteroides*. In one aspect, a relative abundance is determined via an assay selected from the group consisting of qPCR, RT-qPCR, clone libraries, DGGE, T-RFLP, ARISA, microarrays, FIFH, dot-blot hybridization, and a DNA hybridization method. In another aspect, a relative abundance is determined via 16S rDNA-targeted pyrosequencing. In a further aspect, a relative abundance is determined via a DNA hybridization assay based on a 16S rDNA sequence. In one aspect, a relative abundance is determined via detecting one or more proteins or metabolites specific to one or more gut microorganisms. In another aspect, a relative abundance is determined via an assay selected from the group consisting of 2-Dimensional Gel Electrophoresis, 2-Diminsional Difference Gel Electrophoresis (2D-DIGE), MALDI TOF-MS, (2D-) LC-ESI-MS/MS, AQUA and 1TRAQ.

In one aspect, this application provides a method for modulating the abundance of *Eggerthella* or *Bacteroides* in a subject in need thereof, the method comprising treating the subject by administering a therapeutically effective amount of a pharmaceutical composition comprising a fecal microbe preparation, wherein the subject exhibits at least a 20% change in the abundance of *Eggerthella* or *Bacteroides* after the treatment as compared to before initiating the treatment. In one aspect, a subject being treated exhibits at least 10%, 20%, 30%, 40%, 50%, 60%, 70%, 80%, or 90% change in *Eggerthella* or *Bacteroides* abundance after a treatment as compared to before initiating the treatment. In one aspect, a subject being treated exhibits between 20% and 30%, between 20% and 40%, between 20% and 50%, between 20% and 60%, between 20% and 70%, between 20% and 80%, between 20% and 90%, between 30% and 40%, between 30% and 50%, between 30% and 60%, between 30% and 70%, between 30% and 80%, between 30% and 90%, between 40% and 50%, between 40% and 60%, between 40% and 70%, between 40% and 80%, between 40% and 90%, between 50% and 60%, between 50% and 70%, between 50% and 80%, or between 50% and 90% change in *Eggerthella* or *Bacteroides* abundance after a treatment as compared to before initiating the treatment. In one aspect, a change in *Eggerthella* or *Bacteroides* abundance is an abundance increase. In one aspect, a change in *Eggerthella* or *Bacteroides* abundance is an abundance decrease.

In another aspect, this application provides a method for increasing the phylogenetic diversity of fecal microbiota, fecal phage virome, or both, of a subject in need thereof, the method comprising administering to the subject a therapeutically effective amount of a pharmaceutical composition comprising a fecal microbe preparation, wherein the subject exhibits at least a two-fold increase of fecal microbiota or fecal phage virome diversity after the treatment as compared to before initiating the treatment.

In one aspect, a subject being treated exhibits at least 2-fold, 3-fold, 4-fold, 5-fold, 10-fold, 20-fold, 30-fold, 40-fold, 50-fold, 60-fold, 70-fold, 80-fold, 90-fold, 100-fold, 110-fold, 120-fold, 130-fold, 140-fold, 150-fold, 160-fold, 170-fold, 180-fold, 190-fold, or 200-fold increase of fecal microbiota or fecal phage virome diversity after a treatment as compared to before initiating the treatment. In another aspect, a treated subject exhibit an increase in fecal microbiota or fecal phage virome diversity of between 2 and 10, between 3 and 10, between 4 and 10, between 5 and 10, between 6 and 10, between 10 and 20, between 10 and 30, between 10 and 40, between 10 and 50, between 10 and 60, between 10 and 70, between 10 and 80, between 10 and 90, between 20 and 30, between 20 and 40, between 20 and 50, between 20 and 60, between 20 and 70, between 20 and 80, between 20 and 90, between 30 and 40, between 30 and 50, between 30 and 60, between 30 and 70, between 30 and 80, between 30 and 90, between 40 and 50, between 40 and 60, between 40 and 70, between 40 and 80, between 40 and 90, between 50 and 60, between 50 and 70, between 50 and 80, between 50 and 90, between 50 and 100, between 50 and 150, between 50 and 200, between 50 and 250, between 50 and 300 fold after 8 or more weeks of treatment as compared to before initiating the treatment. In one aspect, an increase in fecal microbiota or fecal phage virome diversity is ongoing during a treatment or sustained after finishing or discontinuing a treatment. In one aspect, a subject being treated exhibits at least 10%, 20%, 30%, 40%, 50%, 60%, 70%, 80%, or 90% increase of fecal microbiota or fecal phage virome diversity after a treatment as compared to before initiating the treatment. In another aspect, a treated subject exhibit an increase in fecal microbiota or fecal phage virome diversity of between 20% and 30%, between 20% and 40%, between 20% and 50%, between 20% and 60%, between 20% and 70%, between 20% and 80%, between 20% and 90%, between 30% and 40%, between 30% and 50%, between 30% and 60%, between 30% and 70%, between 30% and 80%, between 30% and 90%, between 40% and 50%, between 40% and 60%, between 40% and 70%, between 40% and 80%, between 40% and 90%, between 50% and 60%, between 50% and 70%, between 50% and 80%, or between 50% and 90% after 8 or more weeks of treatment as compared to before initiating the treatment. In one aspect, an increase in fecal microbiota or fecal phage virome diversity is ongoing during a treatment or sustained after finishing or discontinuing a treatment. In another aspect, an increase in fecal microbiota or fecal phage virome diversity is assessed at a specific time point during or post treatment, e.g., about 2, 4, 6, 8, 12, 18, 24, 32, 40, 48 weeks after initiating a treatment, or about 2, 4, 6, 8, 12, 18, 24, 32, 40, 48 weeks after finishing or discontinuing a treatment. In another aspect, an increase in fecal microbiota or fecal phage virome diversity is assessed at 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, or 110 weeks after initiating a treatment, or about 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, or 110 weeks after finishing or discontinuing a treatment.

In one aspect, fecal microbiota or fecal phage virome diversity is assessed using Shannon's Index. In another aspect, fecal microbiota or fecal phage virome diversity is assessed using Faith phylogenetic diversity. In another aspect, fecal microbiota or fecal phage virome diversity is assessed using an observed OTUs metric. In one aspect, fecal microbiota or fecal phage virome diversity is assessed using a qualitative non-phylogenetic metric (Jaccard distance), a quantitative non-phylogenetic diversity metric (Bray-Curtis distance), a qualitative phylogenetic diversity metric (unweighted UniFrac), or a quantitative phylogenetic diversity metric (weighted UniFrac).

In one aspect, this application provides a method comprising: determining the relative abundance of one or more gut microorganisms in a subject having an ASD or having an ASD sibling, and administering a therapeutically effective amount of a pharmaceutical composition comprising a fecal microbe preparation to achieve at least a 2-fold, 3-fold, 4-fold, 5-fold, 10-fold, 20-fold, 30-fold, 40-fold, 50-fold, 60-fold, 70-fold, 80-fold, 90-fold, 100-fold, 110-fold, 120-fold, 130-fold, 140-fold, 150-fold, 160-fold, 170-fold, 180-fold, 190-fold, or 200-fold change of the abundance of the one or more fecal microorganisms, wherein the one or more gut microorganisms are from a genus selected from the group consisting of *Clostridium, Bacteroides, Eggerthella, Bifidobacterium, Prevotella*, and *Desulfovibrio*. In another aspect, a subject exhibits an abundance change of one or more gut microorganisms selected from the group consisting of *Clostridium, Bacteroides, Eggerthella, Bifidobacterium, Prevotella*, and *Desulfovibrio*, of between 3 and 10, between 4 and 10, between 5 and 10, between 6 and 10, between 10 and 20, between 10 and 30, between 10 and 40, between 10 and 50, between 10 and 60, between 10 and 70, between 10 and 80, between 10 and 90, between 20 and 30, between 20 and 40, between 20 and 50, between 20 and 60, between 20 and 70, between 20 and 80, between 20 and 90, between 30 and 40, between 30 and 50, between 30 and 60, between 30 and 70, between 30 and 80, between 30 and 90, between 40 and 50, between 40 and 60, between 40 and 70, between 40 and 80, between 40 and 90, between 50 and 60, between 50 and 70, between 50 and 80, between 50 and 90, between 50 and 100, between 50 and 150, between 50 and 200, between 50 and 250, between 50 and 300 fold after 8 or more weeks. In one aspect, a subject having an ASD exhibits no gastrointestinal symptom. In another aspect, a subject having an ASD does not exhibit one or more, two or more, three or more, four or more gastrointestinal symptoms selected from the group consisting of abdominal pain, reflux, indigestion, irritable bowel syndrome, chronic persistent diarrhoea, diarrhoea, flatulence, constipation, and alternating constipation/diarrhoea. In a further aspect, a subject having an ASD exhibits no gastrointestinal symptom selected from the group consisting of abdominal pain, reflux, indigestion, irritable bowel syndrome, chronic persistent diarrhoea, diarrhoea, flatulence, constipation, and alternating constipation/diarrhoea. In one aspect, one or more gut microorganisms with abundance change are from *Clostridium*, and wherein the *Clostridium* microorganisms increase their abundance by at least 2 fold. In another aspect, one or more gut microorganisms with abundance change are from *Bacteroides*, and wherein the *Bacteroides* microorganisms decrease their abundance by at least 2 fold. In another aspect, one or more gut microorganisms with abundance change are from *Eggerthella*, and wherein the *Eggerthella* microorganisms decrease their abundance by at least 2 fold. In another aspect, one or more gut microorganisms with abundance change are from *Bifidobacterium*, and wherein the *Bifidobacterium* microorganisms increase their abundance by at least 2 fold. In another aspect, one or more gut microorganisms with abundance change are from *Prevotella*, and wherein the *Prevotella* microorganisms increase their abundance by at least 2 fold. In another aspect, one or more gut microorganisms with abundance change are from *Desulfovibrio*, and wherein the *Desulfovibrio* microorganisms increase their abundance by at least 2 fold.

In one aspect, a subject being treated has an ASD and the treatment improves one or more ASD symptoms. In one aspect, a subject exhibits at least a 10% reduction in ASD symptom severity after the treatment as compared to before initiating the treatment, and based on an assessment system selected from the group consisting of Childhood Autism Rating Scale (CARS), Childhood Autism Rating Scale 2—Standard Form (CARS2-ST), Childhood Autism Rating Scale 2—High Functioning (CARS2-HF), Aberrant Behavior Checklist (ABC), Social Responsiveness Scale (SRS), and Vineland Adaptive Behavior Scale II (VABS-II).

In one aspect, a treatment results in an improvement of at least 10%, 20%, 30%, 40%, 50%, 60%, 70%, 80%, or 90% based on the Leiter International Performance Scale (see Roid, G. H., & Miller, L. J. (1997). Leiter International Performance Scale—Revised. Wood Dale, Ill.: Stoelting) in an ASD patient. In another aspect, a Leiter score improvement is measured after at least 8, 16, 24, 32, 40, 50, 60, or 80 weeks of treatment and compared to a Leiter score prior to the treatment.

One of ordinary skill in the art understands that the foregoing assessment systems are only exemplary tools for evaluating ASD-related social and cognitive symptoms. Other similar tools can be used or designed to evaluate core ASD-related symptoms. For example, in one aspect, a treatment results in an improvement of at least 10%, 20%, 30%, 40%, 50%, 60%, 70%, 80%, or 90% based on Autism Treatment Evaluation Checklist (ATEC). See Rimland and Edelson: Autism Treatment Evaluation Checklist: Statistical Analyses. Autism Research Institute 2000. In another aspect, a treatment results in an improvement of at least 10%, 20%, 30%, 40%, 50%, 60%, 70%, 80%, or 90% based on Pervasive Developmental Disorders Behavior Inventory (PDD-BI). See Cohen et al., The PDD Behavior Inventory: a rating scale for assessing response to intervention in children with pervasive developmental disorder. *J Autism Dev Disord.* 2003 33(1):31-45. In yet another aspect, a treatment results in an improvement of at least 10%, 20%, 30%, 40%, 50%, 60%, 70%, 80%, or 90% based on Severity of Autism Scale (SAS). See Adams et al., The severity of autism is associated with toxic metal body burden and red blood cell glutathione levels. *J Toxicol.* 2009, 2009:532640. In a further aspect, an improvement of autism-related symptoms or an symptom severity reduction is assessed based on any one of the system or scale mentioned in Aman et al., Outcome Measures for Clinical Drug Trials in Autism, *CNS Spectr.* 9(1): 36-47 (2004). In a further aspect, an improvement of autism-related symptoms or an symptom severity reduction is assessed based on any one of the symptom characterization systems listed in Table 1. In another aspect, a method described here achieve an improvement of autism-related symptoms or an symptom severity reduction of at least 1, 2, 3, 4, 5, 6, 7, 8, 9, or 10 graduations in a scale described here (e.g., in Table 1). In another aspect, a method described here achieve an improvement of autism-related symptoms or an symptom severity reduction of between 1 and 10, between 2 and 10, between 3 and 10, between 4 and 10, between 5 and 10, between 6 and 10, between 1 and 9, between 2 and 9, between 3 and 9, between 4 and 9, between 5 and 9, between 6 and 9, between 1 and 8, between 2 and 8, between 3 and 8, between 4 and 8, between 5 and 8, between 6 and 8, between 1 and 7, between 2 and 7, between 3 and 7, between 4 and 7, between 5 and 7, between 6 and 7, between 1 and 6, between 2 and 6, between 3 and 6, between 4 and 6, between 5 and 6, between 1 and 5, between 2 and 5, between 3 and 5, between 4 and 5, between 1 and 4, between 2 and 4, between 3 and 4, between 1 and 3, between 2 and 3, or between 1 and 2 graduations in a scale described here (e.g., CARS, CARS2-ST, CARS2-HF, ABC, SRS, VABS-II, PGI-R2, or a scale in Table 1). In one aspect, an symptom improvement over any one of the foregoing systems is measured after at least 8, 16, 24, 32, 40, 50, 60, or 80 weeks of treatment and compared to a Leiter score prior to the treatment. In one aspect, an symptom improvement over any one of the foregoing systems is measured after discontinuing treatment for at least 2, 4, 6, 8, 10 or more weeks and compared to a measurement prior to the treatment.

TABLE 1

Selected outcome measures that can be used to monitor core ASD-related social and cognitive symptoms.
Validated Outcome Measures

| Tool | Description | Rater |
| --- | --- | --- |
| | Autism Symptoms | |
| ADOS | The Autism Diagnostic Observation Schedule (ADOS) is a gold standards instrument for diagnosing ASD with the largest evidence base and highest sensitivity and specificity | Trained Examiner |
| OACIS | The Ohio Autism Clinical Impression Scale was developed to be sensitive to subtle, but clinically-meaningful changes in core and associated ASD symptoms using a focused scaling system that assesses severity and improvement in ASD behaviors similar to the widely used Clinical Global Impression Scale. | Clinician |
| SRS | The Social Responsiveness Scale is a standardized and validated quantitative scale that measures the severity and type of social impairments that are characteristic of ASD | Parent or Teacher |
| SCQ | Social Communication Questionnaire is brief instrument that evaluates communication skills and social functioning. Both the current and lifetime editions will be used as appropriate | Parent or Teacher |
| AIM | The Autism Impact Measure is a recently developed parent-report measure that assesses both frequency and impact of current core ASD symptoms during the past 2-weeks. Initial studies have demonstrated excellent psychometric properties and construct validity | Parent |
| | Behavior | |
| ABC | The Aberrant Behavior Checklist is a validated questionnaire that rates symptoms of hyperactivity, irritability, lethargy, and stereotypic behavior in individuals with developmental disabilities. It has been used in multiple clinical trials in ASD and has convergent and divergent validity | Parent or Teacher |

TABLE 1-continued

Selected outcome measures that can be used to monitor core ASD-related social and cognitive symptoms.
Validated Outcome Measures

| Tool | Description | Rater |
| --- | --- | --- |
| CBCL | Child Behavior Checklist is an easy to complete standardized questionnaire that assesses a wide range of behaviors associated with ASD symptoms, including anxiety, depression, withdraw, sleep problems, somatic problems, and aggressive and destructive behavior | Parent or Teacher |
| BASC | The Behavioral Assessment System for Children provides scales of cognition function, behavior, social function, and academic problems. This scale measures a wide range of behaviors including hyperactivity, attention, depression, anxiety, and executive function. | Parent or Teacher |
| | Language | |
| CELF | The Clinical Evaluations of Language Fundamentals is one of the only standardized, well-validated language assessment instruments that spans the age range of most participants (using both CELF-preschool-2 and CELF-4). It assesses a wide range of language skills that are only partially measured by other language tests, including high-level language skills that are abnormal in individuals with ASD, such as language pragmatics and has been used in several recent studies focusing on core language deficits in ASD | Trained Examiner |
| PLS | The Preschool Language Scale-4 is used in conjunction with the CELF since it is also a standardized, well-validated language assessment instrument and can measure subtle changes in language in children with poor language abilities | Trained Examiner |
| | Adaptive Behavior | |
| VABS | The Vineland Adaptive Behavior Scale is a widely used standardized, well-validated assessment tool for children with developmental delays that measures functional abilities within several domains. It is particularly useful for children with intellectual disability which commonly co-occurs with ASD and has valid measures of social impairments in children with ASD | Trained Interviewer |
| | Intellect | |
| Leiter-R | The Leiter-R, due to its non-verbal nature, is an excellent unbiased measure of intellect when language impairment exists. It assesses a wide range of ages (2-21 years) and contains attention and memory batteries which are skills often disrupted in ASD. The Leiter-R is designed to measure growth in all domains it assesses, making it sensitive to change due to treatment. Studies have shown good psychometric properties and verified that it is generally recommended for use in children with ASD | Trained Examiner |
| WISC/ WPPSI | The Wechsler Intelligence Scale for Children is one of the oldest and most widely used tests of intelligence for children. For children younger than 6 years the Wechsler Preschool and Primary Scale of Intelligence test is used. One disadvantage when using this with children with ASD is its reliance on language. | Trained Examiner |

In one aspect, a treatment described here achieves at least 10%, 20%, 30%, 40%, 50%, 60%, 70%, 80%, or 90% reduction in ASD symptom severity after 2 or more weeks of treatment as compared to before initiating the treatment, where the ASD symptom severity is assessed by a method selected from the group consisting of CARS, CARS2-ST, CARS2-HF, ABC, SRS, and VABS-II. In one aspect, a treatment achieves at least 10%, 20%, 30%, 40%, 50%, 60%, 70%, 80%, or 90% reduction in ASD symptom severity after 4 or more weeks of treatment as compared to before initiating the treatment, where the ASD symptom severity is assessed by a method selected from the group consisting of CARS, CARS2-ST, CARS2-HF, ABC, SRS, and VABS-II. In one aspect, a treatment achieves at least 10%, 20%, 30%, 40%, 50%, 60%, 70%, 80%, or 90% reduction in ASD symptom severity after 6 or more weeks of treatment as compared to before initiating the treatment, where the ASD symptom severity is assessed by a method selected from the group consisting of CARS, CARS2-ST, CARS2-HF, ABC, SRS, and VABS-II. In one aspect, a treatment achieves at least 10%, 20%, 30%, 40%, 50%, 60%, 70%, 80%, or 90% reduction in ASD symptom severity after 8 or more weeks of treatment as compared to before initiating the treatment, where the ASD symptom severity is assessed by a method selected from the group consisting of CARS, CARS2-ST, CARS2-HF, ABC, SRS, and VABS-II.

In another aspect, a treatment achieves between 10% and 20%, between 10% and 30%, between 10% and 40%, between 10% and 50%, between 10% and 60%, between 10% and 70%, between 10% and 80%, between 10% and 90%, between 20% and 30%, between 20% and 40%, between 20% and 50%, between 20% and 60%, between 20% and 70%, between 20% and 80%, between 20% and 90%, between 30% and 40%, between 30% and 50%, between 30% and 60%, between 30% and 70%, between 30% and 80%, between 30% and 90%, between 40% and 50%, between 40% and 60%, between 40% and 70%, between 40% and 80%, between 40% and 90%, between 50% and 60%, between 50% and 70%, between 50% and 80%, or between 50% and 90% reduction in ASD symptom severity after 8 or more weeks of treatment as compared to before initiating the treatment, where the ASD symptom severity is assessed by a method selected from the group consisting of CARS, CARS2-ST, CARS2-HF, ABC, SRS, and VABS-II. In another aspect, a treatment achieves between 10% and 90%, between 20% and 80%, between 30% and 70%, or between 40% and 60% reduction in ASD symptom severity after 8 or more weeks of treatment as compared to before initiating the treatment, where the ASD symptom severity is assessed by a method selected from the group consisting of CARS, CARS2-ST, CARS2-HF, ABC, SRS, and VABS-II. In another aspect, a treatment achieves between 10% and 90%, between 20% and 80%, between 30% and 70%, or between 40% and 60% reduction in ASD symptom severity after 12 or more weeks of treatment as compared to before initiating the treatment, where the ASD symptom severity is assessed by a method selected from the group consisting of CARS, CARS2-ST, CARS2-HF, ABC, SRS, and VABS-II. In another aspect, a treatment achieves between 10% and 90%, between 20% and 80%, between 30% and 70%, or between 40% and 60% reduction in ASD symptom severity after 18 or more weeks of treatment as compared to before initiating the treatment, where the ASD symptom severity is assessed by a method selected from the group consisting of CARS, CARS2-ST, CARS2-HF, ABC, SRS, and VABS-II. In another aspect, a treatment achieves between 10% and 90%, between 20% and 80%, between 30% and 70%, or between 40% and 60% reduction in ASD symptom severity after 24 or more weeks of treatment as compared to before initiating the treatment, where the ASD symptom severity is assessed by a method selected from the group consisting of CARS, CARS2-ST, CARS2-HF, ABC, SRS, and VABS-II.

In one aspect, a treatment achieves at least 10%, 20%, 30%, 40%, 50%, 60%, 70%, 80%, or 90% reduction in ASD symptom severity and substantially maintains the symptom severity reduction for at least 8, 12, 16, 20, 24, or 28 weeks after discontinuing the treatment, where the ASD symptom severity is assessed by CARS. In one aspect, a treatment achieves at least 10%, 20%, 30%, 40%, 50%, 60%, 70%, 80%, or 90% reduction in ASD symptom severity and substantially maintains the symptom severity reduction for at least 8, 12, 16, 20, 24, or 28 weeks after discontinuing the treatment, where the ASD symptom severity is assessed by CARS2-ST. In one aspect, a treatment achieves at least 10%, 20%, 30%, 40%, 50%, 60%, 70%, 80%, or 90% reduction in ASD symptom severity and substantially maintains the symptom severity reduction for at least 8, 12, 16, 20, 24, or 28 weeks after discontinuing the treatment, where the ASD symptom severity is assessed by CARS2-HF. In one aspect, a treatment achieves at least 10%, 20%, 30%, 40%, 50%, 60%, 70%, 80%, or 90% reduction in ASD symptom severity and substantially maintains the symptom severity reduction for at least 8, 12, 16, 20, 24, or 28 weeks after discontinuing the treatment, where the ASD symptom severity is assessed by ABC. In one aspect, a treatment achieves at least 10%, 20%, 30%, 40%, 50%, 60%, 70%, 80%, or 90% reduction in ASD symptom severity and substantially maintains the symptom severity reduction for at least 8, 12, 16, 20, 24, or 28 weeks after discontinuing the treatment, where the ASD symptom severity is assessed by SRS. In one aspect, a treatment achieves at least 10%, 20%, 30%, 40%, 50%, 60%, 70%, 80%, or 90% reduction in ASD symptom severity and substantially maintains the symptom severity reduction for at least 8, 12, 16, 20, 24, or 28 weeks after discontinuing the treatment, where the ASD symptom severity is assessed by VABS-II.

In one aspect, a treatment achieves at least 10%, 20%, 30%, 40%, 50%, 60%, 70%, 80%, or 90% reduction in ASD symptom severity and substantially maintains the symptom severity reduction for at least 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, or 110 weeks after discontinuing the treatment, where the ASD symptom severity is assessed by CARS. In one aspect, a treatment achieves at least 10%, 20%, 30%, 40%, 50%, 60%, 70%, 80%, or 90% reduction in ASD symptom severity and substantially maintains the symptom severity reduction for at least 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, or 110 weeks after discontinuing the treatment, where the ASD symptom severity is assessed by CARS2-ST. In one aspect, a treatment achieves at least 10%, 20%, 30%, 40%, 50%, 60%, 70%, 80%, or 90% reduction in ASD symptom severity and substantially maintains the symptom severity reduction for at least 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, or 110 weeks after discontinuing the treatment, where the ASD symptom severity is assessed by CARS2-HF. In one aspect, a treatment achieves at least 10%, 20%, 30%, 40%, 50%, 60%, 70%, 80%, or 90% reduction in ASD symptom severity and substantially maintains the symptom severity reduction for at least 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, or 110 weeks after discontinuing the treatment, where the ASD symptom severity is assessed by ABC. In one aspect, a treatment achieves at least 10%, 20%, 30%, 40%, 50%, 60%, 70%, 80%, or 90% reduction in ASD symptom severity and substantially maintains the symptom severity reduction for at least 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, or 110 weeks after discontinuing the treatment, where the ASD symptom severity is assessed by SRS. In one aspect, a treatment achieves at least 10%, 20%, 30%, 40%, 50%, 60%, 70%, 80%, or 90% reduction in ASD symptom severity and substantially maintains the symptom severity reduction for at least 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, or 110 weeks after discontinuing the treatment, where the ASD symptom severity is assessed by VABS-II.

In one aspect, an ASD subject being treated exhibits no gastrointestinal (GI) symptom prior to initiating a treatment. In another aspect, an ASD subject being treated exhibits one or more GI symptoms prior to initiating a treatment. In one aspect, an ASD subject being treated exhibits at least a 20%, 30%, 40%, 50%, 60%, 70%, 80%, or 90% reduction in GI symptom severity after a treatment as compared to before initiating the treatment. In one aspect, GI symptom severity is assessed by the Gastrointestinal Symptom Rating Scale (GSRS). In another aspect, a treatment achieves between 20% and 30%, between 20% and 40%, between 20% and 50%, between 20% and 60%, between 20% and 70%, between 20% and 80%, between 20% and 90%, between 30% and 40%, between 30% and 50%, between 30% and 60%, between 30% and 70%, between 30% and 80%, between 30% and 90%, between 40% and 50%, between 40% and 60%, between 40% and 70%, between 40% and 80%, between 40% and 90%, between 50% and 60%, between 50% and 70%, between 50% and 80%, or between 50% and 90% reduction in GI symptom severity in an ASD patient after 8 or more weeks of treatment as compared to before initiating the treatment, where the GI symptom severity is assessed by one or more symptom assessment systems selected from the group consisting of Gastrointestinal Severity Index (GSI) (Schneider et al., *J Autism Dev Disord* 2006; 36: 1053-64); 6-item Gastrointestinal Severity Index (6-GSI) (Adams et al., *BMC Gastroenterology* 2011, 11:22); Gastrointestinal Symptom Questionnaire—GISQ (Bovenschen et al., *Dig Dis Sci* (2006) 51:1509-15); GSRS (original) (Svedlund et al., Dig Dis Sci 1988; 33: 129-134); GSRS (Likert version) (Revicki et al., Quality of Life Research. Vol 7. 1998 75-83); GSRS-IBS (Wiklund et al., Scand J Gastroenterol 2003; 38(9): 947-954); PROMIS (Spiegel et al., *Am J Gastroenterol* 2014; 109(11): 1804-1814); PedsQL GI Distress Domain (Varni et al., JPGN 2014; 59: 347-355); Pediatric Functional Gastrointestinal Disorders (PFGD) (Caplan et al., J Pediatric Gastroenterol Nutrition 41, 305-316); Autism Network GI Symptom Inventory (Mazefsky, Autism Treatment Network. Autism Treatment Network GI Symptom Inventory Questionnaire, version 3.0. New York, N.Y.: Autism Speaks; 2005); Questionnaire on Pediatric GI Symptoms (QPGS) (ROME III criteria; Caplan et al., J Pediatric Gastroenterol Nutrition 2005 4, 296-304); GI Symptom Questionnaire (Chandler et al., J Autism Dev Disord 2013; 43: 2737-2747); Birmingham IBS (Roalfe et al., BMD Gastroenterology 2008; 8:30); Gastrointestinal Symptom Score in Kids (GISSK) (Brunner et al., *J Clin Rheumatol* 2005; 11: 194-204); Gastro-Q (Liebbrand et al., *Int J Behav Med* 2002; 9: 155-72); IBS-SSS (Francis et al., *Aliment Pharmacol Ther* 1997; 11: 395-402); and any other similar, corresponding, or modified systems.

The GSRS is a disease-specific instrument of 15 items combined into five symptom clusters depicting Reflux, Abdominal pain, Indigestion, Diarrhoea and Constipation. See Svedlund et al., *Dig. Dis. Sci.*, 33(2):129-34(1988). The GSRS has a seven-point graded Likert-type scale where 0 represents absence of troublesome symptoms and 3 represents an extreme degree of the symptoms with half-steps to increase the sensitivity of the scales. In one aspect, a treatment method provided here reduces, alleviates, or eliminates one or more, two or more, three or more, four or more, five or more, six or more, or seven or more GI symptoms selected from the group consisting of epigastric pain, colicky abdominal pain, dull abdominal pain, undefined abdominal pain, heartburn, acid regurgitation, sucking sensations in the epigastrium, nausea and vomiting, borborygmus, abdominal distension, eructation, increased flatus, decreased passage of stools, increased passage of stools, loose stool, hard stools, urgent need for defecation, feeling of incomplete evacuation.

In one aspect, a treated subject's abdominal pain decreases from a more severe level to a less severe level, where the pain levels are selected from the group consisting of severe or crippling pains with impact on all social activities, prolonged and troublesome aches and pains causing requests for relief and interfering with many social activities, occasional aches and pains interfering with some social activities, and no or transient pain.

In another aspect, a treated subject's heartburn decreases from a more severe level to a less severe level, where the pain levels are selected from the group consisting of continuous discomfort with only transient relief by antacids, frequent episodes of prolonged discomfort; requests for relief, occasional discomfort of short duration, and no or transient heartburn.

In another aspect, a treated subject's acid regurgitation condition improves from a more severe level to a less severe level, where the condition levels are selected from the group consisting of regurgitation several times a day; only transient and insignificant relief by antacids, regurgitation once or twice a day; requests for relief, occasional troublesome regurgitation, and no or transient regurgitation.

In another aspect, a treated subject's sucking sensations in the epigastrium improves from a more severe level to a less severe level, where the condition levels are selected from the group consisting of continuous discomfort; frequent requests for food or antacids between meals, frequent episodes of prolonged discomfort, requests for food and antacids between meals, occasional discomfort of short duration; no requests for food or antacids between meals, and no or transient sucking sensation. As used herein, sucking sensation in the epigastrium represents a sucking sensation in the epigastrium with relief by food or antacids. If food or antacids are not available, the sucking sensations progress to ache, and pains.

In another aspect, a treated subject's nausea or vomiting condition improves from a more severe level to a less severe level, where the condition levels are selected from the group consisting of continuous nausea coupled with frequent vomiting, frequent and prolonged nausea with no vomiting, occasional nausea episodes of short duration, and no nausea.

In another aspect, a treated subject's borborygmus condition improves from a more severe level to a less severe level, where the condition levels are selected from the group consisting of continuous borborygmus severely interfering with social performance, frequent and prolonged episodes which can be mastered by moving without impairing social performance, occasional troublesome borborygmus of short duration, and no or transient borborygmus.

In another aspect, a treated subject's abdominal distension condition improves from a more severe level to a less severe level, where the condition levels are selected from the group consisting of continuous discomfort seriously interfering with social performance, frequent and prolonged episodes which can be mastered by adjusting the clothing, occasional discomfort of short duration, and no or transient distension.

In another aspect, a treated subject's eructation condition improves from a more severe level to a less severe level, where the condition levels are selected from the group consisting of frequent episodes seriously interfering with social performance, frequent episodes interfering with some social activities, occasional troublesome eructation, and no or transient eructation.

In another aspect, a treated subject's increased flatus condition improves from a more severe level to a less severe level, where the condition levels are selected from the group consisting of frequent episodes seriously interfering with social performance, frequent and prolonged episodes interfering with some social activities, occasional discomfort of short duration, and no increase flatus.

In another aspect, a treated subject's decreased stool frequency improves from a more severe level to a less severe level, where the levels are selected from the group consisting of every seventh day or less freluently, every sixth day, every fifth day, every fourth day, every third day, every second day, and once a day.

In another aspect, a treated subject's increased stool frequency improves from a more severe level to a less severe level, where the levels are selected from the group consisting of seven times a day or more frequently, six times a day, five times a day, four times a day, three times a day, twice a day, and once a day.

In another aspect, a treated subject's loose-stool condition improves from a more severe level to a less severe level, where the levels are selected from the group consisting of watery, runny, somewhat loose, and normal consistency.

In another aspect, a treated subject's hard-stool condition improves from a more severe level to a less severe level, where the levels are selected from the group consisting of hard and fragmented with occasional diarrhoea, hard, somewhat hard, and normal consistency.

In another aspect, a treated subject's urgency for defecation improves from a more severe level to a less severe level, where the levels are selected from the group consisting of inability to control defecation, frequent feelings of urgent need for defecation with sudden need for a toilet interfering with social performance, occasional feelings of urgent need for defecation, and normal control of defecation.

In another aspect, a treated subject's feeling of incomplete evacuation improves from a more severe level to a less severe level, where the levels are selected from the group consisting of defecation extremely difficult with regular feelings of incomplete evacuation, defecation definitely difficult with often feelings of incomplete evacuation, defecation somewhat difficult; occasional feelings of incomplete evacuation, and feeling of complete evacuation without straining.

In another aspect, a treated subject's one or more additional GI symptoms improve from a more severe level to a less severe level, where these one or more additional GI symptoms are selected from the group consisting of unusually large amount and/or large diameter of stools, unusually foul-smelling stools, unusual color of stool (medium brown is normal). In another aspect, a treated subject's stool also improves to a form corresponding to Type 3 or 4 of the Bristol stool scale or improves from a more irregular type to a type closer of the normal stool form (e.g., from Types 1-2 or Types 5-7 to Type 3 or 4. Bristol stool scale is a medical aid designed to classify the form of human feces into seven types. See Lewis and Heaton, *Scand J Gastroenterol*. 32(9): 920-24 (1997). The seven types of stool are: Type 1: Separate hard lumps, like nuts (hard to pass); Type 2: Sausage-shaped, but lumpy; Type 3: Like a sausage but with cracks on its surface; Type 4: Like a sausage or snake, smooth and soft, Type 5: Soft blobs with clear cut edges (passed easily); Type 6: Fluffy pieces with ragged edges, a mushy stool; and Type 7: Watery, no solid pieces, entirely liquid.

In one aspect, a symptom severity reduction (e.g., for ASD symptoms, GI symptoms, or both) is ongoing during a treatment or sustained after finishing or discontinuing a treatment. In one aspect, a symptom severity reduction (e.g., for ASD symptoms, GI symptoms, or both) is assessed at a specific time point during or post treatment, e.g., about 2, 4, 6, 8, 12, 18, 24, 32, 40, 48 weeks after initiating a treatment, or about 2, 4, 6, 8, 12, 18, 24, 32, 40, 48 weeks after finishing or discontinuing a treatment. In one aspect, a symptom severity reduction (e.g., for ASD symptoms, GI symptoms, or both) is assessed at a specific time point during or post treatment, e.g., about 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, or 110 weeks after initiating a treatment, or about 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, or 110 weeks after finishing or discontinuing a treatment.

In one aspect, a method further comprises administering an antibiotic to a subject prior to administering a pharmaceutical composition comprising a fecal microbe preparation. In another aspect, a method further comprises subjecting a subject to a bowel cleanse.

In another aspect, a pharmaceutical composition used herein comprises a non-selective and substantially complete fecal microbiota supplemented with one or more viable, non-pathogenic microorganisms selected from the group consisting of *Bifidobacterium, Prevotella, Desulfovibrio, Copprococcus*, and *Clostridium*. In another aspect, a pharmaceutical composition used herein comprises a synthetic fecal composition of predetermined flora. In another aspect, a pharmaceutical composition used herein comprises a predetermined flora comprises a preparation of viable flora in proportional content that resembles a normal healthy human fecal flora and comprises no antibiotic resistant populations. In another aspect, a pharmaceutical composition used herein is administered as a solid dosage form selected from the group consisting of capsule, tablet, powder, and granule. In another aspect, a pharmaceutical composition used herein is formulated as an acid resistant capsule.

In another aspect, provided herein is a method of treating an autism spectrum disorder in a human subject. In exemplary aspects, the method comprises or consists essentially of the following steps: administering an antibiotic to a human subject; subjecting the human subject to a bowel cleanse; and administering purified fecal microbiota to the human subject, wherein an autism spectrum disorder is treated in the human subject.

In exemplary aspects, treating ASD comprises alleviating, ameliorating, delaying the onset of, inhibiting the progression of, or reducing the severity of one or more, two or more, three or more, four or more, five or more, six or more, seven or more, eight or more symptoms characteristic of ASD. In one aspect, a treatment alleviates, ameliorates, delays the onset of, inhibits the progression of, or reduces the severity of one or more social and cognitive core ASD-related symptoms. In some aspects, the symptom(s) is selected from the group consisting of: (i) insistence on sameness or resistance to change; (ii) difficulty in expressing needs; (iii) repeating words or phrases in place of normal, responsive language; (iv) laughing, crying, showing distress for reasons not apparent to others; (v) prefers to be alone or aloof manner; (vi) tantrums; (vii) difficulty in mixing with others; (viii) may not want to cuddle or be cuddled; (ix) little or no eye contact; (x) unresponsive to normal teaching methods; (xi) sustained odd play; (xii) apparent over-sensitivity or under-sensitivity to pain; (xiii) little or no real fears of danger; (xiv) noticeable physical over-activity or extreme under-activity; (xv) uneven gross/fine motor skills; and/or (xvi) non-responsiveness to verbal cues. In some aspects, the symptom(s) is selected from the group consisting of compulsive behavior, ritualistic behavior, restricted behavior, stereotypy, sameness, or self-injury. The methods described here can lead to improvement of any combination of the foregoing symptoms.

In exemplary aspects, the human subject exhibits a significant reduction in autism symptom severity as assessed according to a ASD rating scale. In some cases, for example, the human subject exhibits at least a 10% or 20% reduction in autism symptom severity as assessed by the Childhood Autism Rating Scale (CARS) relative to severity as assessed prior to initiating the method.

Subjects appropriate for treatment according to a method provided herein may not present with or report gastrointestinal distress symptoms prior to initiating a method as provided herein. In some cases, for example, a human subject appropriate for treatment according to a method provided herein manifests no gastrointestinal symptoms prior to or at the time at which treatment is begun. In one aspect, an ASD subject treated herein exhibit one or more or two or more GI symptoms selected from the group consisting of abdominal pain, reflux, indigestion, irritable bowel syndrome, chronic persistent diarrhoea, diarrhoea, flatulence, constipation, and alternating constipation/diarrhoea.

Regardless of the presence or absence of gastrointestinal distress symptoms, human subjects appropriate for the methods provided herein typically have significantly fewer species of gut bacteria before the method of treatment as compared to a neurotypical human. In some cases, the human subject to be treated by the method exhibits at least about 20%, 30%, 40%, 50%, 60%, 70%, 80%, or 90% fewer species of gut bacterial prior to administration of the purified fecal microbiota dosage as compared to a neurotypical human.

Also provided herein are methods for reducing autism severity in an autistic human subject. In exemplary aspects, the method comprises or consists essentially of the following steps: orally-administering a non-absorbable antibiotic to an autistic human subject; subjecting the autistic human subject to a bowel cleanse; and administering purified fecal microbiota from a neurotypical human donor to the human subject, wherein the human subject exhibits a significant reduction in autism symptom severity as assessed by the Childhood Autism Rating Scale (CARS) after the method as compared to before initiating the method. In some cases, the human subject exhibits at least a 10% or 20% reduction in autism symptom severity as assessed by the Childhood Autism Rating Scale (CARS) relative to severity as assessed prior to initiating the method.

In one aspect, a fecal microbiota preparation used in a method described here comprises a donor's entire or substantially complete microbiota. In one aspect, a fecal microbiota preparation comprises a non-selective fecal microbiota. In another aspect, a fecal microbiota preparation comprises an isolated or purified population of live non-pathogenic fecal bacteria. In a further aspect, a fecal microbiota preparation comprises a non-selective and substantially complete fecal microbiota preparation from a single donor. In another aspect, a therapeutic composition used herein comprises a mixture of live, non-pathogenic, synthetic bacteria or live, non-pathogenic, purified or extracted, fecal microbiota.

In one aspect, the preparation of a fecal microbiota preparation involves a treatment selected from the group consisting of ethanol treatment, detergent treatment, heat treatment, irradiation, and sonication, or a combination thereof. In one aspect, the preparation of a fecal microbiota preparation involves no treatment selected from the group consisting of ethanol treatment, detergent treatment, heat treatment, irradiation, and sonication. In one aspect, the preparation of a fecal microbiota preparation involves a separation step selected from the group consisting of filtering, sieving, density gradients, filtration, chromatography, and a combination thereof. In one aspect, the preparation of a fecal microbiota preparation does not require one or more separation steps selected from the group consisting of filtering, sieving, density gradients, filtration, and chromatography. In one aspect, a fecal microbiota preparation is substantially free of non-living matter. In one aspect, a fecal microbiota preparation is substantially free of acellular material selected from the group consisting of residual fiber, DNA, viral coat material, and non-viable material. In one aspect, a fecal microbiota preparation is substantially free of eukaryotic cells from the fecal microbiota's donor.

In one aspect, the present disclosure provides a method for treating ASD in a subject in need thereof, where the method comprises administering to the subject a pharmaceutically active dose of a therapeutic composition described herein. In one aspect, the present disclosure provides a method for treating ASD in a subject in need thereof, where the method comprises administering daily to the subject a pharmaceutically active dose of a therapeutic composition described herein. In one aspect, a therapeutic composition is administered to a patient in need thereof at least once daily for at least two consecutive days. In one aspect, a therapeutic composition is administered at least once daily for at least 3, 4, 5, 6, 7, 8, 9, 10, 11, 12, 13, 14, or 15 consecutive days. In another aspect, a therapeutic composition is administered at least once daily for at least 1, 2, 3, 4, 5, 6, 7, 8, 9, 10, 11, or 12 consecutive weeks. In one aspect, a therapeutic composition is administered at least once daily for at most 4, 5, 6, 7, 8, 9, 10, 11, 12, 13, 14, 15, 16, 17, 18, 19, or 20 consecutive days or weeks. In another aspect, a therapeutic composition is administered at least once daily for at most 1, 2, 3, 4, 5, 6, 7, 8, 9, 10, 11, or 12 consecutive weeks or months. In a further aspect, a therapeutic composition is administered at least once for at least 1, 2, 3, 4, 5, 6, 7, 8, 9, 10, 11, or 12 consecutive months or years, chronically for a subject's entire life span, or an indefinite period of time.

In one aspect, a therapeutic composition is administered to a patient in need thereof at least twice daily for at least two consecutive days. In one aspect, a therapeutic composition is administered at least twice daily for at least 3, 4, 5, 6, 7, 8, 9, 10, 11, 12, 13, 14, or 15 consecutive days. In another aspect, a therapeutic composition is administered at least twice daily for at least 1, 2, 3, 4, 5, 6, 7, 8, 9, 10, 11, or 12 consecutive weeks. In one aspect, a therapeutic composition is administered at least twice daily for at most 4, 5, 6, 7, 8, 9, 10, 11, 12, 13, 14, 15, 16, 17, 18, 19, or 20 consecutive days or week. In another aspect, a therapeutic composition is administered at least twice daily for at most 1, 2, 3, 4, 5, 6, 7, 8, 9, 10, 11, or 12 consecutive weeks or months. In a further aspect, a therapeutic composition is administered at least twice for at least 1, 2, 3, 4, 5, 6, 7, 8, 9, 10, 11, or 12 consecutive months or years, chronically for a subject's entire life span, or an indefinite period of time.

In one aspect, a therapeutic composition is administered to a patient in need thereof at least three times daily for at least two consecutive days. In one aspect, a therapeutic composition is administered at least three times daily for at least 3, 4, 5, 6, 7, 8, 9, 10, 11, 12, 13, 14, or 15 consecutive days. In another aspect, a therapeutic composition is administered at least three times daily for at least 1, 2, 3, 4, 5, 6, 7, 8, 9, 10, 11, or 12 consecutive weeks. In one aspect, a therapeutic composition is administered at least three times daily for at most 4, 5, 6, 7, 8, 9, 10, 11, 12, 13, 14, 15, 16, 17, 18, 19, or 20 consecutive days or weeks. In another aspect, a therapeutic composition is administered at least three times daily for at most 1, 2, 3, 4, 5, 6, 7, 8, 9, 10, 11, or 12 consecutive weeks or months. In a further aspect, a therapeutic composition is administered at least three times for at least 1, 2, 3, 4, 5, 6, 7, 8, 9, 10, 11, or 12 consecutive months or years, chronically for a subject's entire life span, or an indefinite period of time.

In one aspect, the present disclosure provides a method for treating ASD in a subject in need thereof, where the method comprises administering orally to the subject a pharmaceutically active dose of a therapeutic composition comprising live, non-pathogenic, synthetic bacterial mixture or live, non-pathogenic, purified or extracted, fecal microbiota, where the dose is administered at a dosing schedule of at least once or twice daily for at least three consecutive days or weeks. In another aspect, a dose is administered at least once, twice, or three times daily for a period between 1 and 12 weeks, between 2 and 12 weeks, between 3 and 12 weeks, between 4 and 12 weeks, between 5 and 12 weeks, between 6 and 12 weeks, between 7 and 12 weeks, between 8 and 12 weeks, between 9 and 12 weeks, between 10 and 12 weeks, between 1 and 2 weeks, between 2 and 3 weeks, between 3 and 4 weeks, between 4 and 5 weeks, between 5 and 6 weeks, between 6 and 7 weeks, between 7 and 8 weeks, between 8 and 9 weeks, between 9 and 10 weeks, or between 10 and 11 weeks.

In one aspect, the present disclosure provides a method for treating ASD in a subject in need thereof by administering a pharmaceutical composition described herein, where the method comprises a first dosing schedule followed by a second dosing schedule. In one aspect, a first dosing schedule comprises a treatment or induction dose. In one aspect, a first dosing schedule comprises a continuous dosing schedule. In another aspect, a second dosing schedule comprises a maintenance dose lower than or equal to a pharmaceutically active dose of a first dosing schedule. In another aspect, a second dosing schedule lasts for at least about 2, 4, 6, 8, 10, 12, 18, 24, 36, 48, 72, or 96 months. In one aspect, a second dosing schedule lasts permanently, for a treated subject's entire life span, or an indefinite period of time. In one aspect, a second dosing schedule is a continuous dosing schedule. In another aspect, a second dosing schedule is an intermittent dosing schedule. In a further aspect, a second dosing schedule is an intermittent dosing schedule comprising a treatment period of at least 1, 2, 3, 4, 5, 6, 7, 8, 9, 10, 11, 12, 13, or 14 days followed by a resting period of at least 1, 2, 3, 4, 5, 6, 7, 8, 9, 10, 11, 12, 13, or 14 days. In another aspect, a second dosing schedule comprises administering a second dose (e.g., a maintenance dose) every other day, every two days, or every 3, 4, 5, 6, 7, 8 days. In another aspect, a maintenance dose is administered for an extended period of time with or without titration (or otherwise changing the dosage or dosing schedule). In one aspect, the interval between a first and a second dosing schedule is at least about 1, 2, 3, 4, 5, 6, 7, 8, 9, 10, 11, or 12 weeks. In another aspect, a second dosing schedule (e.g., a maintenance dose) comprises a dosage about 2, 5, 10, 50, 100, 200, 400, 800, 1000, 5000 or more folds lower than the dosage used in a first dosing schedule (e.g., an initial treatment dose). In another aspect, a second dosing schedule (e.g., a maintenance dosing schedule) has an equal or lower dosing frequency than a first dosing schedule (e.g., an initial treatment dosing schedule). In another aspect, a second dosing schedule (e.g., a maintenance dosing schedule) has a higher dosing interval than a first dosing schedule (e.g., an initial treatment dosing schedule).

In one aspect, a first or second dosing schedule used in a method can be once-a-week, twice-a-week, or thrice-a-week. The term "once-a-week" means that a dose is administered once in a week, preferably on the same day of each week. "Twice-a-week" means that a dose is administered two times in a week, preferably on the same two days of each weekly period. "Thrice-a-week" means that a dose is administered three times in a week, preferably on the same three days of each weekly period. In one aspect, a first or second dosing schedule can use fecal microbiota prepared from two or more different donors. In another aspect, a first dose schedule (e.g., a treatment, induction, or initial loading dose) comprises a fecal microbiota preparation from a donor different from the donor providing the fecal microbiota preparation used in a second dose schedule (e.g., a maintenance dose).

In one aspect, a subject being treated is a subject already with a disorder (e.g., ASD). Administration of a disclosed therapeutic composition to clinically, asymptomatic human subject who is genetically predisposed or prone to a disorder (e.g., ASD) is also useful in preventing the onset of clinical symptoms. A human subject genetically predisposed or prone to ASD can be a human subject having a close family member or relative exhibiting or having suffered a disorder (e.g., ASD). In another aspect, a subject being treated is a subject in which ASD is to be prevented. In another aspect, a subject being treated is predisposed or susceptible to a disorder (e.g., ASD). In another aspect, a subject being treated is a subject diagnosed as having a disorder (e.g., ASD). In one aspect, a subject being treated is a patient in need thereof.

In one aspect, a subject being treated is a human patient. In one aspect, a patient is a male patient. In one aspect, a patient is a female patient. In one aspect, a patient is a premature newborn. In one aspect, a patient is a term newborn. In one aspect, a patient is a neonate. In one aspect, a patient is an infant. In one aspect, a patient is a toddler. In one aspect, a patient is a young child. In one aspect, a patient is a child. In one aspect, a patient is an adolescent. In one aspect, a patient is a pediatric patient. In one aspect, a patient is a geriatric patient. In one aspect, a human patient is a child patient below about 18, 15, 12, 10, 8, 6, 4, 3, 2, or 1 year old. In another aspect, a human patient is an adult patient. In another aspect, a human patient is an elderly patient. In a further aspect, a human patient is a patient above about 30, 35, 40, 45, 50, 55, 60, 65, 70, 75, 80, 85, 90, or 95 years old. In another aspect, a patient is about between 1 and 5, between 2 and 10, between 3 and 18, between 21 and 50, between 21 and 40, between 21 and 30, between 50 and 90, between 60 and 90, between 70 and 90, between 60 and 80, or between 65 and 75 years old. In one aspect, a patient is a young old patient (65-74 years). In one aspect, a patient is a middle old patient (75-84 years). In one aspect, a patient is an old patient (>85 years).

In one aspect, a method comprises administering a therapeutic composition orally, by enema, or via rectal suppository. In one aspect, a pharmaceutical composition is formulated as a geltab, pill, microcapsule, capsule, or tablet. In one aspect, a therapeutic composition is formulated as an enteric coated capsule or microcapsule, acid-resistant capsule or microcapsule, or formulated as part of or administered together with a food, a food additive, a dairy-based product, a soy-based product or a derivative thereof, a jelly, or a yogurt. In another aspect, a therapeutic composition is formulated as an acid-resistant enteric coated capsule. A therapeutic composition can be provided as a powder for sale in combination with a food or drink. A food or drink can be a dairy-based product or a soy-based product. In another aspect, a food or food supplement contains enteric-coated and/or acid-resistant microcapsules containing a therapeutic composition.

In an aspect, a therapeutic composition comprises a liquid culture. In another aspect, a therapeutic composition is lyophilized, pulverized and powdered. It may then be infused, dissolved such as in saline, as an enema. Alternatively the powder may be encapsulated as enteric-coated and/or acid-resistant capsules for oral administration. These capsules may take the form of enteric-coated and/or acid-resistant microcapsules. A powder can preferably be provided in a palatable form for reconstitution for drinking or for reconstitution as a food additive. In a further aspect, a food is yogurt. In one aspect, a powder may be reconstituted to be infused via naso-duodenal infusion.

In another aspect, a therapeutic composition is in a liquid, frozen, freeze-dried, spray-dried, lyophilized, or powder formulation. In a further aspect, a therapeutic composition is formulated as a delayed or gradual enteric release form. In another aspect, a therapeutic composition comprises an excipient, a saline, a buffer, a buffering agent, or a fluid-glucose-cellobiose agar (RGCA) media.

In one aspect, a therapeutic composition further comprises an acid suppressant, an antacid, an H2 antagonist, a proton pump inhibitor or a combination thereof. In one aspect, a therapeutic composition substantially free of non-living matter. In another aspect, a therapeutic composition substantially free of acellular material selected from the group consisting of residual fiber, DNA, viral coat material, and non-viable material.

In one aspect, a therapeutic composition comprises a cryoprotectant. In another aspect, a cryoprotectant comprises, consisting essentially or, or consisting of polyethylene glycol, skim milk, erythritol, arabitol, sorbitol, glucose, fructose, alanine, glycine, proline, sucrose, lactose, ribose, trehalose, dimethyl sulfoxide (DMSO), glycerol, or a combination thereof.

In another aspect, a therapeutic composition comprises a lyoprotectant. In one aspect, the same substance or the same substance combination is used as both a cryoprotectant and a lyoprotectant. Exemplary lyoprotectants include sugars such as sucrose or trehalose; an amino acid such as monosodium glutamate or histidine; a methylamine such as betaine; a lyotropic salt such as magnesium sulfate; a polyol such as trihydric or higher sugar alcohols, e.g. glycerin, erythritol, glycerol, arabitol, xylitol, sorbitol, and mannitol; propylene glycol; polyethylene glycol; Pluronics; and combinations thereof. In one aspect, a lyoprotectant is a non-reducing sugar, such as trehalose or sucrose. In one aspect, a cryoprotectant or a lyoprotectant consisting essentially of, or consisting of, one or more substances mentioned in this paragraph and the paragraph above.

In one aspect, a lyophilized formulation comprises trehalose. In one aspect, a lyophilized formulation comprises 2% to 30%, 3% to 25%, 4% to 20%, 5% to 15%, 6% to 10%, 2% to 30%, 2% to 25%, 2% to 20%, 2% to 15%, or 2% to 10% trehalose. In one aspect, a lyophilized formulation comprises at least 2%, 3%, 4%, 5%, 6%, 7%, 8%, 9%, 10%, or 15% trehalose. In one aspect, a lyophilized formulation comprises at most 2%, 3%, 4%, 5%, 6%, 7%, 8%, 9%, 10%, or 15% trehalose. In one aspect, a lyophilized formulation comprises about 5% trehalose. In one aspect, a lyophilized formulation comprises trehalose and sucrose. In one aspect, a lyophilized formulation comprises between about 8% to 12% trehalose with between about 1.5% to 3.5% sucrose and between about 0.5% to 1.5% NaCl.

In one aspect, a therapeutic composition also comprises or is supplemented with a prebiotic nutrient selected from the group consisting of polyols, fructooligosaccharides (FOSs), oligofructoses, inulins, galactooligosaccharides (GOSs), xylooligosaccharides (XOSs), polydextroses, monosaccharides, tagatose, and/or mannooligosaccharides.

In one aspect, a method further comprises pretreating a subject with an antibiotic composition prior to administering a therapeutic bacterial or microbiota composition. In one aspect, an antibiotic composition comprises an antibiotic selected from the group consisting of rifabutin, clarithromycin, clofazimine, vancomycin, rifampicin, nitroimidazole, chloramphenicol, and a combination thereof. In another aspect, an antibiotic composition comprises an antibiotic selected from the group consisting of rifaximin, rifamycin derivative, rifampicin, rifabutin, rifapentine, rifalazil, bicozamycin, aminoglycoside, gentamycin, neomycin, streptomycin, paromomycin, verdamicin, mutamicin, sisomicin, netilmicin, retymicin, kanamycin, aztreonam, aztreonam macrolide, clarithromycin, dirithromycin, roxithromycin, telithromycin, azithromycin, bismuth subsalicylate, vancomycin, streptomycin, fidaxomicin, amikacin, arbekacin, neomycin, netilmicin, paromomycin, rhodostreptomycin, tobramycin, apramycin, and a combination thereof. In a further aspect, a method further comprises pretreating a subject with an anti-inflammatory drug prior to administration of a therapeutic bacterial or microbiota composition.

In one aspect, every about 200 mg of a pharmaceutical composition comprises a pharmacologically active dose. In one aspect, every about 75, 100, 125, 150, 175, 200, 250, 300, 350, 400, 450, 500, 750, 1000, 1500, or 2000 mg of a pharmaceutical composition comprises a pharmacologically active dose.

In one aspect, a pharmaceutically active or therapeutic effective dose comprises at least about $10^5$, $10^6$, $10^7$, $10^8$, $10^9$, $10^{10}$, $10^{11}$, $10^{12}$, or $10^{13}$ cfu. In another aspect, a pharmaceutically active therapeutic effective dose comprises at most about $10^5$, $10^6$, $10^7$, $10^8$, $10^9$, $10^{10}$, $10^{11}$, $10^{12}$, or $10^{13}$ cfu. In a further aspect, a pharmacologically active therapeutic effective dose is selected from the group consisting of from $10^8$ cfu to $10^{14}$ cfu, from $10^9$ cfu to $10^{13}$ cfu, from $10^{10}$ cfu to $10^{12}$ cfu, from $10^9$ cfu to $10^{14}$ cfu, from $10^9$ cfu to $10^{12}$ cfu, from $10^9$ cfu to $10^{11}$ cfu, from $10^9$ cfu to $10^{10}$ cfu, from $10^{10}$ cfu to $10^{14}$ cfu, from $10^{10}$ cfu to $10^{13}$ cfu, from $10^{11}$ cfu to $10^{14}$ cfu, from $10^{11}$ cfu to $10^{13}$ cfu, from $10^{12}$ cfu to $10^{14}$ cfu, and from $10^{13}$ cfu to $10^{14}$ cfu. In one aspect, a pharmaceutical composition comprises the foregoing pharmaceutically active or therapeutic effective dose in a unit weight of about 0.2, 0.4, 0.6, 0.8 or 1.0 gram, or a unit volume of about 0.2, 0.4, 0.6, 0.8 or 1.0 milliliter.

In one aspect, a pharmaceutically active or therapeutic effective dose comprises at least about $10^5$, $10^6$, $10^7$, $10^8$, $10^9$, $10^{10}$, $10^{11}$, $10^{12}$, or $10^{13}$ cells or spores. In another aspect, a pharmaceutically active or therapeutic effective dose comprises at most about $10^5$, $10^6$, $10^7$, $10^8$, $10^9$, $10^{10}$, $10^{11}$, $10^{12}$, or $10^{13}$ total cells or spores. In a further aspect, a pharmacologically active or therapeutic effective dose is selected from the group consisting of from $10^8$ to $10^{14}$, from $10^9$ to $10^{13}$, from $10^{10}$ to $10^{12}$, from $10^9$ to $10^{14}$, from $10^9$ to $10^{12}$, from $10^9$ to $10^{11}$, from $10^9$ to $10^{10}$, from $10^{10}$ to $10^{14}$, from $10^{10}$ to $10^{13}$, from $10^{11}$ to $10^{14}$, from $10^{11}$ to $10^{13}$, from $10^{12}$ to $10^{14}$, and from $10^{13}$ to $10^{14}$ cells or spores. In an aspect, the pharmaceutically active or therapeutic effective dose cell count is directed to live cells. In one aspect, a pharmaceutical composition comprises the foregoing pharmaceutically active or therapeutic effective dose in a unit weight of about 0.2, 0.4, 0.6, 0.8 or 1.0 gram, or a unit volume of about 0.2, 0.4, 0.6, 0.8 or 1.0 milliliter.

In one aspect, a therapeutic composition described and used here comprises one or more, two or more, three or more, four or more, or five or more isolated, purified, or cultured microorganisms selected from the group consisting of *Clostridium, Bacillus, Collinsella, Bacteroides, Eggerthella, Eubacterium, Fusobacterium, Propionibacterium, Lactobacillus, Ruminococcus, Escherichia coli, Gemmiger, Desulfomonas, Peptostreptococcus, Bifidobacterium, Coprococcus, Dorea,* and *Monilia.*

In one aspect, a fecal microbiota preparation described herein comprises a purified or reconstituted fecal bacterial mixture. In one aspect, a fecal microbiota preparation described and used here comprises one or more, one or more, two or more, three or more, four or more, or five or more live fecal microorganisms are selected from the group consisting of *Acidaminococcus, Akkermansia, Alistipes, Anaerotruncus, Bacteroides, Eggerthella, Bifidobacterium, Blautia, Butyrivibrio, Clostridium, Collinsella, Coprococcus, Corynebacterium, Dorea, Enterococcus, Escherichia, Eubacterium, Faecalibacterium, Haemophilus, Holdemania, Lactobacillus, Moraxella, Parabacteroides, Prevotella, Propionibacterium, Raoultella, Roseburia, Ruminococcus, Staphylococcus, Streptococcus, Subdoligranulum,* and *Veillonella.* In one aspect, a fecal microbiota preparation comprises one or more, one or more, two or more, three or more, four or more, or five or more live fecal microorganisms are selected from the group consisting of *Bacteroides fragilis* ssp. *vulgatus, Collinsella aerofaciens, Bacteroides fragilis* ssp. *thetaiotaomicron, Peptostreptococcus productus* II, *Parabacteroides distasonis, Faecalibacterium prausnitzii, Coprococcus eutactus, Peptostreptococcus productus* I, *Ruminococcus bromii, Bifidobacterium adolescentis, Gemmiger formicilis, Bifidobacterium longum, Eubacterium siraeum, Ruminococcus torques, Eubacterium rectale, Eubacterium eligens, Bacteroides eggerthii, Clostridium leptum, Bacteroides fragilis* ssp. A, *Eubacterium biforme, Bifidobacterium infantis, Eubacterium rectale, Coprococcus comes, Pseudoflavonifractor capillosus, Ruminococcus albus, Dorea formicigenerans, Eubacterium hallii, Eubacterium ventriosum* I, *Fusobacterium russi, Ruminococcus obeum, Eubacterium rectale, Clostridium ramosum, Lactobacillus leichmannii, Ruminococcus callidus, Butyrivibrio crossotus, Acidaminococcus fermentans, Eubacterium ventriosum, Bacteroides fragilis* ssp. *fragilis, Coprococcus catus, Aerostipes hadrus, Eubacterium cylindroides, Eubacterium ruminantium, Staphylococcus epidermidis, Eubacterium limosum, Tissirella praeacuta, Fusobacterium mortiferum* I, *Fusobacterium naviforme, Clostridium innocuum, Clostridium ramosum, Propionibacterium acnes, Ruminococcus flavefaciens, Bacteroides fragilis* ssp. *ovatus, Fusobacterium nucleatum, Fusobacterium mortiferum, Escherichia coli, Gemella morbillorum, Finegoldia magnus, Streptococcus intermedius, Ruminococcus lactaris, Eubacterium tenue, Eubacterium ramulus, Bacteroides clostridiiformis* ssp. *clostridliformis, Bacteroides coagulans, Prevotella oralis, Prevotella ruminicola, Odoribacter splanchnicus,* and *Desuifomonas pigra.*

In one aspect, a fecal microbiota preparation described and used here lacks or is substantially devoid of one or more, one or more, two or more, three or more, four or more, or five or more live fecal microorganisms are selected from the group consisting of *Acidaminococcus, Akkermansia, Alistipes, Anaerotruncus, Bacteroides, Eggerthella, Bifidobacterium, Blautia, Butyrivibrio, Clostridium, Collinsella, Coprococcus, Corynebacterium, Dorea, Enterococcus, Escherichia, Eubacterium, Faecalibacterium, Haemophilus, Holdemania, Lactobacillus, Moraxella, Parabacteroides, Prevotella, Propionibacterium, Raoultella, Roseburia, Ruminococcus, Staphylococcus, Streptococcus, Subdoligranulum,* and *Veillonella.* In one aspect, a fecal microbiota preparation lacks or is substantially devoid of one or more, one or more, two or more, three or more, four or more, or five or live more fecal microorganisms are selected from the group consisting of *Bacteroides fragilis* ssp. *vulgatus, Collinsella aerofaciens, Bacteroides fragilis* ssp. *thetaiotaomicron, Peptostreptococcus productus* II, *Parabacteroides distasonis, Faecalibacterium prausnitzii, Coprococcus eutactus, Peptostreptococcus productus* I, *Ruminococcus bromii, Bifidobacterium adolescentis, Gemmiger formicilis, Bifidobacterium longum, Eubacterium siraeum, Ruminococcus torques, Eubacterium rectale, Eubacterium eligens, Bacteroides eggerthii, Clostridium leptum, Bacteroides fragilis* ssp. A, *Eubacterium biforme, Bifidobacterium infantis, Eubacterium rectale, Coprococcus comes, Pseudoflavonifractor capillosus, Ruminococcus albus, Dorea formicigenerans, Eubacterium hallii, Eubacterium ventriosum* I, *Fusobacterium russi, Ruminococcus obeum, Eubacterium rectale, Clostridium ramosum, Lactobacillus leichmannii, Ruminococcus callidus, Butyrivibrio crossotus, Acidaminococcus fermentans, Eubacterium ventriosum, Bacteroides fragilis* ssp. *fragilis, Coprococcus catus, Aerostipes hadrus, Eubacterium cylindroides, Eubacterium ruminantium, Staphylococcus epidermidis, Eubacterium limosum, Tissirella praeacuta, Fusobacterium mortiferum* I, *Fusobacterium naviforme, Clostridium innocuum, Clostridium ramosum, Propionibacterium acnes, Ruminococcus flavefaciens, Bacteroides fragilis* ssp. *ovatus, Fusobacterium nucleatum, Fusobacterium mortiferum, Escherichia coli, Gemella morbillorum, Finegoldia magnus, Streptococcus intermedius, Ruminococcus lactaris, Eubacterium tenue, Eubacterium ramulus, Bacteroides clostridiiformis* ssp. *clostridliformis, Bacteroides coagulans, Prevotella oralis, Prevotella ruminicola, Odoribacter splanchnicus,* and *Desuifomonas pigra.*

In another aspect, a therapeutic composition comprises a fecal microbiota further supplemented, spiked, or enhanced with a fecal microorganism. In one aspect, a fecal microbiota is supplemented with a non-pathogenic (or with attenuated pathogenicity) bacterium of *Clostridium, Collinsella, Dorea, Ruminococcus, Coprococcus, Prevotella, Veillonella, Bacteroides, Eggerthella, Bacillus,* or a combination thereof. In another aspect, a therapeutic composition comprises a fecal microbiota further supplemented, spiked, or enhanced with a species of *Veillonellaceae, Firmicutes,*

*Gammaproteobacteria, Bacteroidetes*, or a combination thereof. In another aspect, a therapeutic composition comprises a fecal microbiota further supplemented with fecal bacterial spores. In one aspect, fecal bacterial spores are *Clostridium* spores, *Bacillus* spores, or both. In another aspect, a therapeutic composition comprises a fecal microbiota further supplemented, spiked, or enhanced with a *Bacteroides* species selected from the group consisting of *Bacteroides coprocola, Bacteroides plebeius, Bacteroides massiliensis, Bacteroides vulgatus, Bacteroides helcogenes, Bacteroides pyogenes, Bacteroides tectus, Bacteroides uniformis, Bacteroides stercoris, Bacteroides eggerthii, Bacteroides finegoldii, Bacteroides thetaiotaomicron, Bacteroides ovatus, Bacteroides acidifaciens, Bacteroides caccae, Bacteroides nordii, Bacteroides salyersiae, Bacteroides fragilis, Bacteroides intestinalis, Bacteroides coprosuis, Bacteroides distasonis, Bacteroides goldsteinii, Bacteroides merdae, Bacteroides forsythus, Bacteroides splanchnicus, Bacteroides capillosus, Bacteroides cellulosolvens*, and *Bacteroides ureolyticus*.

In an aspect, a therapeutic composition comprises a fecal microbiota from a subject selected from the group consisting of a human, a bovine, a dairy calf, a ruminant, an ovine, a caprine, or a cervine. In another aspect, a therapeutic composition can be administered to a subject selected from the group consisting of a human, a bovine, a dairy calf, a ruminant, an ovine, a caprine, or a cervine. In an aspect, a therapeutic composition is substantially or nearly odourless.

In an aspect, a therapeutic composition provided here comprises a fecal microbiota preparation comprising a Shannon Diversity Index of greater than or equal to 0.3, greater than or equal to 0.4, greater than or equal to 0.5, greater than or equal to 0.6, greater than or equal to 0.7, greater than or equal to 0.8, greater than or equal to 0.9, greater than or equal to 1.0, greater than or equal to 1.1, greater than or equal to 1.2, greater than or equal to 1.3, greater than or equal to 1.4, greater than or equal to 1.5, greater than or equal to 1.6, greater than or equal to 1.7, greater than or equal to 1.8, greater than or equal to 1.9, greater than or equal to 2.0, greater than or equal to 2.1, greater than or equal to 2.2, greater than or equal to 2.3, greater than or equal to 2.4, greater than or equal to 2.5, greater than or equal to 3.0, greater than or equal to 3.1, greater than or equal to 3.2, greater than or equal to 3.3, greater than or equal to 3.4, greater than or equal to 3.5, greater than or equal to 3.6, greater than or equal to 3.7, greater than or equal to 3.8, greater than or equal to 3.9, greater than or equal to 4.0, greater than or equal to 4.1, greater than or equal to 4.2, greater than or equal to 4.3, greater than or equal to 4.4, greater than or equal to 4.5, or greater than or equal to 5.0. In another aspect, a therapeutic composition comprises fecal microbiota comprising a Shannon Diversity Index of between 0.1 and 3.0, between 0.1 and 2.5, between 0.1 and 2.4, between 0.1 and 2.3, between 0.1 and 2.2, between 0.1 and 2.1, between 0.1 and 2.0, between 0.4 and 2.5, between 0.4 and 3.0, between 0.5 and 5.0, between 0.7 and 5.0, between 0.9 and 5.0, between 1.1 and 5.0, between 1.3 and 5.0, between 1.5 and 5.0, between 1.7 and 5.0, between 1.9 and 5.0, between 2.1 and 5.0, between 2.3 and 5.0, between 2.5 and 5.0, between 2.7 and 5.0, between 2.9 and 5.0, between 3.1 and 5.0, between 3.3 and 5.0, between 3.5 and 5.0, between 3.7 and 5.0, between 31.9 and 5.0, or between 4.1 and 5.0. In one aspect, a Shannon Diversity Index is calculated at the phylum level. In another aspect, a Shannon Diversity Index is calculated at the family level. In one aspect, a Shannon Diversity Index is calculated at the genus level. In another aspect, a Shannon Diversity Index is calculated at the species level. In a further aspect, a therapeutic composition comprises a preparation of flora in proportional content that resembles a normal healthy human fecal flora.

In a further aspect, a therapeutic composition comprises fecal bacteria from at least 1, 2, 3, 4, 5, 6, 7, 8, 9, or 10 different families. In an aspect, a therapeutic composition provided here comprises a fecal microbiota comprising a weight ratio between fecal-derived non-living material and fecal-derived biological material of no greater than 0.05%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, or 10%. In another aspect, a therapeutic composition provided here comprises a fecal microbiota comprising a weight ratio between fecal-derived non-living material and fecal-derived biological material of no greater than 20%, 25%, 30%, 35%, 40%, 45%, 50%, 55%, 60%, 65%, 70%, 75%, 80%, 85%, 90%, or 95%. In another aspect, a therapeutic composition provided here comprises, consists of, or consists essentially of, particles of non-living material and/or particles of biological material of a fecal sample that passes through a sieve, a column, or a similar filtering device having a sieve, exclusion, or particle filter size of 2.0 mm, 1.0 mm, 0.5 mm, 0.25 mm, 0.212 mm, 0.180 mm, 0.150 mm, 0.125 mm, 0.106 mm, 0.090 mm, 0.075 mm, 0.063 mm, 0.053 mm, 0.045 mm, 0.038 mm, 0.032 mm, 0.025 mm, 0.020 mm, 0.01 mm, or 0.2 mm. "Non-living material" does not include an excipient, e.g., a pharmaceutically inactive substance, such as a cryoprotectant, added to a processed fecal material. "Biological material" refers to the living material in fecal material, and includes microbes including prokaryotic cells, such as bacteria and archaea (e.g., living prokaryotic cells and spores that can sporulate to become living prokaryotic cells), eukaryotic cells such as protozoa and fungi, and viruses. In one aspect, "biological material" refers to the living material, e.g., the microbes, eukaryotic cells, and viruses, which are present in the colon of a normal healthy human. In an aspect, a therapeutic composition provided or comprises an extract of human feces where the composition is substantially odorless. In an aspect, a therapeutic composition provided or comprises fecal material or a fecal floral preparation in a lyophilized, crude, semi-purified or purified formulation.

In an aspect, a fecal microbiota in a therapeutic composition comprises highly refined or purified fecal flora, e.g., substantially free of non-floral fecal material. In an aspect, a fecal microbiota can be further processed, e.g., to undergo microfiltration before, after, or before and after sieving. In another aspect, a highly purified fecal microbiota product is ultra-filtrated to remove large molecules but retain the therapeutic microflora, e.g., bacteria.

In another aspect, a fecal microbiota in a therapeutic composition used herein comprises or consists essentially of a substantially isolated or a purified fecal flora or entire (or substantially entire) microbiota that is (or comprises) an isolate of fecal flora that is at least about 90%, 91%, 92%, 93%, 94%, 95%, 96%, 97%, 98%, 99%, 99.5%, 99.6%, 99.7%, 99.8% or 99.9% isolated or pure, or having no more than about 0.1%, 0.2%, 0.3%, 0.4%, 0.5%, 0.6%, 0.7%, 0.8%, 0.9% or 1.0% or more non-fecal floral material; or, a substantially isolated, purified, or substantially entire microbiota as described in Sadowsky et al., WO 2012/122478 A1, or as described in Borody et al., WO 2012/016287 A2. In one aspect, a fecal microbiota preparation comprises a weight ratio between fecal-derived non-living material and fecal-derived biological material of no greater than about 0.1%, 0.2%, 0.3%, 0.4%, 0.5%, 0.6%, 0.7%, 0.8%, 0.9%, 1%, 2%, 5%, 8%, 10%, 15%, 20%, 30%, 40$, or 50%.

In an aspect, a fecal microbiota in a therapeutic composition comprises a donor's substantially entire or non-selective fecal microbiota, reconstituted fecal material, or synthetic fecal material. In another aspect, the fecal microbiota in a therapeutic composition comprises no antibiotic resistant population. In another aspect, a therapeutic composition comprises a fecal microbiota and is largely free of extraneous matter (e.g., non-living matter including acellular matter such as residual fiber, DNA, RNA, viral coat material, non-viable material; and living matter such as eukaryotic cells from the fecal matter's donor).

In an aspect, a fecal microbiota in a therapeutic composition used herein is derived from disease-screened fresh homologous feces or equivalent freeze-dried and reconstituted feces. In an aspect, a fresh homologous feces does not include an antibiotic resistant population. In another aspect, a fecal microbiota in a therapeutic composition is derived from a synthetic fecal composition. In an aspect, a synthetic fecal composition comprises a preparation of viable flora which preferably in proportional content, resembles normal healthy human fecal flora which does not include antibiotic resistant populations. Suitable microorganisms may be selected from the following: *Bacteroides, Eggerthella, Eubacterium, Fusobacterium, Propionibacterium, Lactobacillus, Ruminococcus, Escherichia coli, Gemmiger, Clostridium, Desulfomonas, Peptostreptococcus, Bifidobacterium, Collinsella, Coprococcus, Dorea*, and *Ruminococcus*.

In an aspect, a therapeutic composition is combined with other adjuvants such as antacids to dampen bacterial inactivation in the stomach. (e.g., Mylanta, Mucaine, Gastrogel). In another aspect, acid secretion in the stomach could also be pharmacologically suppressed using H2-antagonists or proton pump inhibitors. An example H2-antagonist is ranitidine. An example proton pump inhibitor is omeprazole. In one aspect, an acid suppressant is administered prior to administering, or in co-administration with, a therapeutic composition.

In an aspect, a therapeutic composition is administered in the form of: an enema composition which can be reconstituted with an appropriate diluent; enteric-coated capsules; enteric-coated microcapsules; acid-resistant tablet; acid-resistant capsules; acid-resistant microcapsules; powder for reconstitution with an appropriate diluent for naso-enteric infusion or colonoscopic infusion; powder for reconstitution with appropriate diluent, flavoring and gastric acid suppression agent for oral ingestion; powder for reconstitution with food or drink; or food or food supplement comprising enteric-coated and/or acid-resistant microcapsules of the composition, powder, jelly, or liquid.

In an aspect, a treatment method effects a cure, reduction of the symptoms, or a percentage reduction of symptoms of a disorder (e.g., ASD). The change of flora is preferably as "near-complete" as possible and the flora is replaced by viable organisms which will crowd out any remaining, original flora. Typically the change in enteric flora comprises introduction of an array of predetermined flora into the gastro-intestinal system, and thus in a preferred form the method of treatment comprises substantially or completely displacing pathogenic enteric flora in patients requiring such treatment.

In another aspect, a therapeutic composition can be provided together with a pharmaceutically acceptable carrier. As used herein, a "pharmaceutically acceptable carrier" refers to a non-toxic solvent, dispersant, excipient, adjuvant, or other material which is mixed with a live bacterium in order to permit the formation of a pharmaceutical composition, e.g., a dosage form capable of administration to the patient. A pharmaceutically acceptable carrier can be liquid (e.g., saline), gel or solid form of diluents, adjuvant, excipients or an acid resistant encapsulated ingredient. Suitable diluents and excipients include pharmaceutical grades of physiological saline, dextrose, glycerol, mannitol, lactose, starch, magnesium stearate, sodium saccharin, cellulose, magnesium carbonate, and the like, and combinations thereof. In another aspect, a therapeutic composition may contain auxiliary substances such as wetting or emulsifying agents, stabilizing or pH buffering agents. In an aspect, a therapeutic composition contains about 1%-5%, 5%-10%, 10%-15%, 15-20%, 20%-25%, 25-30%, 30-35%, 40-45%, 50%-55%, 1%-95%, 2%-95%, 5%-95%, 10%-95%, 15%-95%, 20%-95%, 25%-95%, 30%-95%, 35%-95%, 40%-95%, 45%-95%, 50%-95%, 55%-95%, 60%-95%, 65%-95%, 70%-95%, 45%-95%, 80%-95%, or 85%-95% of active ingredient. In an aspect, a therapeutic composition contains about 2%-70%, 5%-60%, 10%-50%, 15%-40%, 20%-30%, 25%-60%, 30%-60%, or 35%-60% of active ingredient.

In an aspect, a therapeutic composition can be incorporated into tablets, drenches, boluses, capsules or premixes. Formulation of these active ingredients into such dosage forms can be accomplished by means of methods well known in the pharmaceutical formulation arts. See, e.g., U.S. Pat. No. 4,394,377. Filling gelatin capsules with any desired form of the active ingredients readily produces capsules. If desired, these materials can be diluted with an inert powdered diluent, such as sugar, starch, powdered milk, purified crystalline cellulose, or the like to increase the volume for convenience of filling capsules.

In an aspect, conventional formulation processes can be used to prepare tablets containing a therapeutic composition. In addition to the active ingredients, tablets may contain a base, a disintegrator, an absorbent, a binder, and a lubricant. Typical bases include lactose, sugar, sodium chloride, starch and mannitol. Starch is also a good disintegrator as is alginic acid. Surface-active agents such as sodium lauryl sulfate and dioctyl sodium sulphosuccinate are also sometimes used. Commonly used absorbents include starch and lactose. Magnesium carbonate is also useful for oily substances. As a binder there can be used, for example, gelatin, gums, starch, dextrin, polyvinyl pyrrolidone and various cellulose derivatives. Among the commonly used lubricants are magnesium stearate, talc, paraffin wax, various metallic soaps, and polyethylene glycol.

In an aspect, for preparing solid compositions such as tablets, an active ingredient is mixed with a pharmaceutical carrier, e.g., conventional tableting ingredients such as corn starch, lactose, sucrose, sorbitol, talc, stearic acid, magnesium stearate, dicalcium phosphate or gums, or other pharmaceutical diluents, e.g. water, to form a solid preformulation composition containing a homogeneous mixture of a composition of the present disclosure. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing a desired amount of an active ingredient (e.g., at least about $10^5$, $10^6$, $10^7$, $10^8$, $10^9$, $10^{10}$, $10^{11}$, $10^{12}$, or $10^{13}$ cfu). A therapeutic composition used herein can be flavored.

In an aspect, a therapeutic composition can be a tablet or a pill. In one aspect, a tablet or a pill can be coated or otherwise compounded to provide a dosage form affording the advantage of prolonged action. For example, a tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

In an aspect, a therapeutic composition is formulated as a delayed or gradual enteric release form. In an aspect, a delayed or gradual enteric release formulation comprises the use of cellulose acetate, polyethylene glycerol, or both. In an aspect, a delayed or gradual enteric release formulation comprises the use of a hydroxypropylmethylcellulose (HPMC), a microcrystalline cellulose (MCC), magnesium stearate, or a combination thereof. In an aspect, a delayed or gradual enteric release formulation comprises the use of a poly(meth)acrylate, a methacrylic acid copolymer B, a methyl methacrylate, a methacrylic acid ester, a polyvinylpyrrolidone (PVP), a PVP-K90, or a combination thereof. In an aspect, a delayed or gradual enteric release formulation comprises the use of a solid inner layer sandwiched between two outer layers; wherein the solid inner layer comprises the pharmaceutical composition and another component selected from the group consisting of a disintegrant, an exploding agent, an effervescent or any combination thereof; wherein the outer layer comprises a substantially water soluble, a crystalline polymer, or both. In an aspect, a delayed or gradual enteric release formulation comprises the use of a non-swellable diffusion matrix.

In another aspect, a delayed or gradual enteric release formulation comprises the use of a bilayer tablet or capsule which comprises a first layer comprising a polyalkylene oxide, a polyvinylpyrrolidone, a lubricant, or a mixture thereof, and a second osmotic push layer comprising polyethylene oxide, carboxy-methylcellulose, or both. In an aspect, a delayed or gradual enteric release formulation comprises the use of a release-retarding matrix material selected from the group consisting of an acrylic polymer, a cellulose, a wax, a fatty acid, shellac, zein, hydrogenated vegetable oil, hydrogenated castor oil, polyvinylpyrrolidine, a vinyl acetate copolymer, a vinyl alcohol copolymer, polyethylene oxide, an acrylic acid and methacrylic acid copolymer, a methyl methacrylate copolymer, an ethoxyethyl methacrylate polymer, a cyanoethyl methacrylate polymer, an aminoalkyl methacrylate copolymer, a poly(acrylic acid), a poly(methacrylic acid), a methacrylic acid alkylamide copolymer, a poly(methyl methacrylate), a poly(methacrylic acid anhydride), a methyl methacrylate polymer, a polymethacrylate, a poly(methyl methacrylate) copolymer, a polyacrylamide, an aminoalkyl methacrylate copolymer, a glycidyl methacrylate copolymer, a methyl cellulose, an ethylcellulose, a carboxymethylcellulose, a hydroxypropylmethylcellulose, a hydroxymethyl cellulose, a hydroxyethyl cellulose, a hydroxypropyl cellulose, a crosslinked sodium carboxymethylcellulose, a crosslinked hydroxypropylcellulose, a natural wax, a synthetic wax, a fatty alcohol, a fatty acid, a fatty acid ester, a fatty acid glyceride, a hydrogenated fat, a hydrocarbon wax, stearic acid, stearyl alcohol, beeswax, glycowax, castor wax, carnauba wax, a polylactic acid, polyglycolic acid, a co-polymer of lactic and glycolic acid, carboxymethyl starch, potassium methacrylate/divinylbenzene copolymer, crosslinked polyvinylpyrrolidone, poly inylalcohols, polyvinylalcohol copolymers, polyethylene glycols, non-crosslinked polyvinylpyrrolidone, polyvinylacetates, polyvinylacetate copolymers, or any combination thereof. In an aspect, a delayed or gradual enteric release formulation comprises the use of a microenvironment pH modifier.

In an aspect, a therapeutic composition can be a drench. In one aspect, a drench is prepared by choosing a saline-suspended form of a therapeutic composition. A water-soluble form of one ingredient can be used in conjunction with a water-insoluble form of the other by preparing a suspension of one with an aqueous solution of the other. Water-insoluble forms of either active ingredient may be prepared as a suspension or in some physiologically acceptable solvent such as polyethylene glycol. Suspensions of water-insoluble forms of either active ingredient can be prepared in oils such as peanut, corn, sesame oil or the like; in a glycol such as propylene glycol or a polyethylene glycol; or in water depending on the solubility of a particular active ingredient. Suitable physiologically acceptable adjuvants may be necessary in order to keep the active ingredients suspended. Adjuvants can include and be chosen from among the thickeners, such as carboxymethylcellulose, polyvinyl pyrrolidone, gelatin and the alginates. Surfactants generally will serve to suspend the active ingredients, particularly the fat-soluble propionate-enhancing compounds. Most useful for making suspensions in liquid nonsolvents are alkylphenol polyethylene oxide adducts, naphthalenesulfonates, alkylbenzene-sulfonates, and the polyoxyethylene sorbitan esters. In addition many substances, which affect the hydrophilicity, density and surface tension of the liquid, can assist in making suspensions in individual cases. For example, silicone anti-foams, glycols, sorbitol, and sugars can be useful suspending agents.

In an aspect, a therapeutic composition comprises non-pathogenic spores of one or more, two or more, three or more, or four or more *Clostridium* species selected from the group consisting of *Clostridium absonum, Clostridium argentinense, Clostridium baratii, Clostridium botulinum, Clostridium cadaveris, Clostridium carnis, Clostridium celatum, Clostridium chauvoei, Clostridium clostridioforme, Clostridium cochlearium, Clostridium fallax, Clostridium felsineum, Clostridium ghonii, Clostridium glycolicum, Clostridium haemolyticum, Clostridium hastiforme, Clostridium histolyticum, Clostridium indolis, Clostridium irregulare, Clostridium limosum, Clostridium malenominatum, Clostridium novyi, Clostridium oroticum, Clostridium paraputrificum, Clostridium perfringens, Clostridium piliforme, Clostridium putrefaciens, Clostridium putrificum, Clostridium sardiniense, Clostridium sartagoforme, Clostridium scindens, Clostridium septicum, Clostridium sordellii, Clostridium sphenoides, Clostridium spiroforme, Clostridium sporogenes, Clostridium subterminale, Clostridium symbiosum, Clostridium tertium, Clostridium tetani, Clostridium welchii,* and *Clostridium villosum*. In an aspect, a therapeutic composition comprises one or more, two or more, three or more, or four or more non-pathogenic *Bacteroides* species selected from the group of *Bacteroides coprocola, Bacteroides plebeius, Bacteroides massiliensis, Bacteroides vulgatus, Bacteroides helcogenes, Bacteroides pyogenes, Bacteroides tectus, Bacteroides uniformis, Bacteroides stercoris, Bacteroides eggerthii, Bacteroides finegoldii, Bacteroides thetaiotaomicron, Bacteroides ovatus, Bacteroides acidifaciens, Bacteroides caccae, Bacteroides nordii, Bacte-*

*roides salyersiae, Bacteroides fragilis, Bacteroides intestinalis, Bacteroides coprosuis, Bacteroides distasonis, Bacteroides goldsteinii, Bacteroides merdae, Bacteroides forsythus, Bacteroides splanchnicus, Bacteroides capillosus, Bacteroides cellulosolvens,* and *Bacteroides ureolyticus*. The foregoing *Clostridium* and *Bacteroides* can be either cultured or purified and can be used in combination in a single combination for a synergistic effect.

In an aspect, a therapeutic composition comprises purified, isolated, or cultured viable non-pathogenic *Clostridium* and a plurality of purified, isolated, or cultured viable non-pathogenic microorganisms from one or more genera selected from the group consisting of *Collinsella, Coprococcus, Dorea, Eubacterium,* and *Ruminococcus*. In another aspect, a therapeutic composition comprises a plurality of purified, isolated, or cultured viable non-pathogenic microorganisms from one or more genera selected from the group consisting of *Clostridium, Collinsella, Coprococcus, Dorea, Eubacterium,* and *Ruminococcus*.

In an aspect, a therapeutic composition comprises two or more genera selected from the group consisting of *Collinsella, Coprococcus, Dorea, Eubacterium,* and *Ruminococcus*. In another aspect, a therapeutic composition comprises two or more genera selected from the group consisting of *Coprococcus, Dorea, Eubacterium,* and *Ruminococcus*. In a further aspect, a therapeutic composition comprises one or more, two or more, three or more, four or more, or five or more species selected from the group consisting of *Coprococcus catus, Coprococcus comes, Dorea longicatena, Eubacterium eligens, Eubacterium hadrum, Eubacterium hallii, Eubacterium rectale,* and *Ruminococcus torques*.

In one aspect, a pharmaceutical composition is in an anaerobic package or container. In another aspect, a pharmaceutical composition further comprises an oxygen scavenger. In one aspect, a container can be made oxygen free by e.g., incorporating into the container a built in or clipped-on oxygen-scavenging mechanism, e.g., oxygen scavenging pellets as described e.g., in U.S. Pat. No. 7,541,091. In another aspect, the container itself is made of an oxygen scavenging material, e.g., oxygen scavenging iron, e.g., as described by O2BLOCK™, or equivalents, which uses a purified and modified layered clay as a performance-enhancing carrier of oxygen-scavenging iron; the active iron is dispersed directly in the polymer. In one aspect, oxygen-scavenging polymers are used to make the container itself or to coat the container, or as pellets to be added; e.g., as described in U.S. Pat. App. Pub. 20110045222, describing polymer blends having one or more unsaturated olefinic homopolymers or copolymers; one or more polyamide homopolymers or copolymers; one or more polyethylene terephthalate homopolymers or copolymers; that exhibit oxygen-scavenging activity. In one aspect, oxygen-scavenging polymers are used to make the container itself or to coat the container, or as pellets to be added; e.g., as described in U.S. Pat. App. Pub. 20110008554, describing compositions comprising a polyester, a copolyester ether and an oxidation catalyst, wherein the copolyester ether comprises a polyether segment comprising poly(tetramethylene-co-alkylene ether). In one aspect, oxygen-scavenging polymers are used to make the container itself or to coat the container, or as pellets to be added; e.g., as described in U.S. Pat. App. Pub. 201000255231, describing a dispersed iron/salt particle in a polymer matrix, and an oxygen scavenging film with oxygen scavenging particulates.

In preferred aspects, purified fecal microbiota is obtained from a carefully screened, healthy, neurotypical human donor. Microbiota is separated from fecal material collected from healthy donors, mixed with a cryopreservative, stored as a frozen liquid suspension with the cryopreservative, and thawed prior to administration in liquid form. Based on the route of administration, the purified fecal microbiota can be provided as fresh, frozen-thawed, or lyophilized live microbiota. In some cases, purified fecal microbiota is administered to a human subject in the form of an oral dose. In other cases, purified fecal microbiota is administered in the form of a rectal dose.

In some cases, the dosage form comprises any suitable form of live microbiota (fresh, frozen, lyophilized, etc.) and is formulated for administration to a human subject orally, by nasogastric tube, by colonoscopy, or anally. In some cases, the dosage is administered as a solution. In other cases, the dosage is administered as solid dosage forms such as, for example, capsules, tablets, powders, and granules. In such solid dosage forms, purified fecal microbiota is admixed with at least one inert excipient (or carrier), a filler or extender (e.g., starches, lactose, sucrose, mannitol, or silicic acid), a binder (e.g., carboxymethylcellulose, alginates, gelatin, polyvinylpyrrolidone, sucrose, or acacia), a humectant (e.g., glycerol), a disintegrating agent (e.g., agar-agar, calcium carbonate, potato or tapioca starch, alginic acid, a silicate, sodium carbonate), an absorption accelerators, a wetting agent (e.g., cetyl alcohol or glycerol monostearate), an adsorbent (e.g., kaolin or bentonite), and/or a lubricant (e.g., talc, calcium stearate, magnesium stearate, solid polyethylene glycols, sodium lauryl sulfate, or mixtures thereof). In the case of capsules and tablets, the dosage forms may also comprise buffering agents.

A tablet comprising purified fecal microbiota can, for example, be made by compressing or molding the active ingredient, optionally with one or more additional ingredients. Compressed tablets can be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets can be made by molding, in a suitable device, a mixture of the active ingredient, a pharmaceutically acceptable carrier, and at least sufficient liquid to moisten the mixture. In exemplary aspects, the dosage form comprises a powder prepared by lyophilization ("freeze drying"), whereby the process involves removing water from purified, frozen fecal microbiota at extremely low pressures.

The specific dosage and dosage range that can be used depends on a number of factors, and the determination of dosage ranges and optimal dosages for a particular patient is well within the ordinary skill of one in the art in view of this disclosure. It is further understood, however, that the specific dose level for any particular human will depend upon a variety of factors including the activity of the specific compound employed, the age, body weight, general health, gender, and diet of the human, the time of administration, the route of administration, the rate of excretion, any drug combination, and the severity of any disorder being treated.

In exemplary aspect, purified fecal microbiota is administered to a subject in multiple doses. For example, purified fecal microbiota can be administered to a subject according to a method provided herein in multiple doses over a time period of about two days to about eight weeks.

Prior to administration of purified fecal microbiota, any suitable antibiotic can be administered to the subject. In exemplary aspects, the antibiotic is a non-absorbed or minimally-absorbed antibiotic such as, for example, vancomycin or rifaximin. Antibiotics are administered to the subject via any appropriate delivery route. One of skill in the art can develop appropriate dose delivery methods. Preferably, the antibiotic is administered to the subject orally. In another aspect, an ASD treatment method requires no antibiotic pretreatment. In a further aspect, an ASD treatment method requires no bowel preparation or bowel cleansing. In another aspect, an ASD treatment method requires neither antibiotic pretreatment nor bowel cleansing prior to administering a pharmaceutical composition comprising a fecal microbiota preparation.

In some cases, the antibiotic is administered in multiple doses before a bowel cleanse is performed. In some cases, administration of the antibiotic is initiated at least seven days (e.g., at least 7, 9, 10, 12, 14, 18, or 21 days) before the bowel cleanse. In preferred aspects, the bowel cleanse is preceded by fasting of the human subject.

Following administration of an antibiotic, the subject undergoes a bowel cleanse. In exemplary aspects, the bowel cleanse comprises administering to the subject a product such as MoviPrep®, a commercial bowel prep for colonoscopy. Preferably, the bowel cleanse removes residual vancomycin and cleanses the lower gastrointestinal tract.

In exemplary aspects, the method further comprises administering to the subject a stomach acid suppressant. Stomach acid suppressants, also known as gastric acid suppressants, suitable for use according to a method provided herein include, without limitation, proton pump inhibitors (PPIs) and histamine blockers. In some cases, the stomach acid suppressant is Prilosec and is administered to the subject one or more days in advance of oral administration of purified fecal microbiota. In some cases, the stomach acid suppressant is administered one week prior to oral administration of purified fecal microbiota.

In another aspect, provided herein are unit dosage forms comprising purified fecal microbiota. In some cases, unit dosage forms described herein are provided as part of a kit. Such a kit could include a purified fecal microbiota dosage and, optionally, a delivery device to administer the composition to the subject or instructions for administering the dosage to a subject via an appropriate delivery route. In some cases, the dosage form comprises any suitable form of live microbiota (fresh, frozen, lyophilized, etc.) and is formulated for administration to a human subject orally, by nasogastric tube, by colonoscopy, or anally. As described herein, dosage forms suitable for kits provided herein include, without limitation, liquid solutions, capsules, tablets, powders, granules, and lyophilized forms.

In a further aspect, provided herein is use of a purified composition for manufacture of a medicament for treating autism spectrum disorder or for reducing the severity of one or more symptoms of autism spectrum disorder.

It will be appreciated that compositions, dosage forms, and medicaments as described herein include combination pharmaceutical compositions in which one or more additional compounds or medications are added to or otherwise co-administered with a purified fecal microbiota composition.

In an aspect, this application provides for the following embodiments:

Embodiment 1

A method for increasing the abundance of one or more gut microorganisms in a subject in need thereof, said method comprising treating said subject by administering a therapeutically effective amount of a pharmaceutical composition comprising a fecal microbe preparation, wherein said subject exhibits at least a 2-fold increase of the abundance of said one or more fecal microorganisms after said treatment as compared to before initiating said treatment, wherein said one or more gut microorganisms are selected from the group consisting of *Bifidobacterium, Prevotella* and *Desulfovibrio*.

Embodiment 2

A method for modulating the abundance of one or more gut microorganisms in a subject in need thereof, said method comprising treating said subject by administering a therapeutically effective amount of a pharmaceutical composition comprising a fecal microbe preparation, wherein said subject exhibits at least a 2-fold change of the abundance of said one or more fecal microorganisms after said treatment as compared to before initiating said treatment, wherein said one or more gut microorganisms are selected from the group consisting of *Bifidobacterium, Prevotella, Desulfovibrio, Copprococcus, Clostridium, Eggerthella,* and *Bacteroides*.

Embodiment 3

The method of Embodiment 1, wherein said method further comprises determining in said subject a relative abundance of said one or more gut microorganisms.

Embodiment 4

The method of Embodiment 3, wherein said relative abundance is determined via an assay selected from the group consisting of qPCR, RT-qPCR, clone libraries, DGGE, T-RFLP, ARISA, microarrays, FIFH, dot-blot hybridization, and a DNA hybridization method.

Embodiment 5

The method of Embodiment 3, wherein said relative abundance is determined via 16S rDNA-targeted pyrosequencing.

Embodiment 6

The method of claim Embodiment 3, wherein said relative abundance is determined via a DNA hybridization assay based on a 16S rDNA sequence.

Embodiment 7

The method of Embodiment 3, wherein said relative abundance is determined via detecting one or more proteins or metabolites specific to said one or more gut microorganisms.

Embodiment 8

The method of Embodiment 7, wherein said relative abundance is determined via an assay selected from the group consisting of 2-Dimensional Gel Electrophoresis, 2-Diminsional Difference Gel Electrophoresis (2D-DIGE), MALDI TOF-MS, (2D-) LC-ESI-MS/MS, AQUA and 1TRAQ.

Embodiment 9

The method of Embodiment 1, wherein said subject has an ASD and said method improves one or more ASD symptoms.

Embodiment 10

The method of Embodiment 9, wherein said one or more ASD symptoms are selected from the group consisting of gastrointestinal (GI) condition, speech, sociability, receptive language, cognition, irritability, mood, anxiety, lethargy, stereotypy, hyperactivity, and play skills.

Embodiment 11

The method of Embodiment 1, wherein said subject exhibits at least a 10% reduction in ASD symptom severity after said treatment as compared to before initiating said treatment, and based on an assessment system selected from the group consisting of Childhood Autism Rating Scale (CARS), Childhood Autism Rating Scale 2—Standard Form (CARS2-ST), Childhood Autism Rating Scale 2—High Functioning (CARS2-HF), Aberrant Behavior Checklist (ABC), Social Responsiveness Scale (SRS), and Vineland Adaptive Behavior Scale II (VABS-II).

Embodiment 12

The method of Embodiment 1, where said at least 2-fold increase is achieved after 2 or more weeks of initiating said treatment.

Embodiment 13

The method of Embodiment 1, where said at least 2-fold increase is maintained for at least 8 weeks after discontinuing said treatment.

Embodiment 14

The method of claim Embodiment 1, where said subject exhibits no gastrointestinal (GI) symptom prior to initiating said treatment.

Embodiment 15

The method of claim Embodiment 1, where said subject further exhibits one or more GI symptoms prior to initiating said treatment.

Embodiment 16

The method of claim Embodiment 15, where said subject exhibits at least a 50% reduction in GI symptom severity based on the Gastrointestinal Symptom Rating Scale (GSRS) after said treatment as compared to before initiating said treatment.

Embodiment 17

The method of claim Embodiment 1, where said method further comprises administering an antibiotic to said subject prior to administering said pharmaceutical composition.

Embodiment 18

The method of claim Embodiment 1, where said method further comprises subjecting said subject to a bowel cleanse.

Embodiment 19

The method of Embodiment 1, where said at least 10% reduction in ASD symptom severity is achieved after 2 or more weeks of initiating said treatment.

Embodiment 20

The method of Embodiment 11, where said at least 10% reduction in ASD symptom severity is maintained for at least 8 weeks after discontinuing said treatment.

Embodiment 21

The method of Embodiment 11, where said subject exhibits no gastrointestinal (GI) symptom prior to initiating said treatment.

Embodiment 22

The method of Embodiment 11, where said subject further exhibits one or more GI symptoms prior to initiating said treatment.

Embodiment 23

The method of Embodiment 22, where said subject exhibits at least a 50% reduction in GI symptom severity based on the Gastrointestinal Symptom Rating Scale (GSRS) after said treatment as compared to before initiating said treatment.

Embodiment 24

The method of Embodiment 11, where said method further comprises administering an antibiotic to said subject prior to administering said pharmaceutical composition.

Embodiment 25

The method of Embodiment 11, where said method further comprises subjecting said subject to a bowel cleanse.

Embodiment 26

The method of Embodiment 11, wherein said ASD is selected from the group consisting of autistic disorder, pervasive developmental disorder not otherwise specified (PDD-NOS), and Asperger syndrome.

Embodiment 27

The method of Embodiment 1, wherein said pharmaceutical composition is administered orally.

Embodiment 28

The method of Embodiment 1, wherein said fecal microbe preparation is lyophilized.

Embodiment 29

The method of Embodiment 1, wherein said fecal microbe preparation comprises a non-selective and substantially complete fecal microbiota from a single donor.

Embodiment 30

The method of Embodiment 29, wherein said non-selective and substantially complete fecal microbiota is supplemented with one or more viable, non-pathogenic microorganisms selected from the group consisting of *Bifidobacterium*, *Prevotella*, *Desulfovibrio*, *Copprococcus*, *Clostridium*, and *Bacteroides*.

Embodiment 31

The method of Embodiment 1, wherein said fecal microbe preparation comprises a synthetic fecal composition of predetermined flora.

Embodiment 32

The method of Embodiment 31, wherein said predetermined flora comprises a preparation of viable flora in proportional content that resembles a normal healthy human fecal flora and comprises no antibiotic resistant populations.

Embodiment 33

The method of Embodiment 1, wherein said pharmaceutical composition is administered as a solid dosage form selected from the group consisting of capsule, tablet, powder, and granule.

Embodiment 34

The method of Embodiment 1, wherein said pharmaceutical composition is formulated as an acid resistant capsule.

Embodiment 35

A method for increasing the phylogenetic diversity of fecal microbiota of a subject in need thereof, said method comprising administering to said subject a therapeutically effective amount of a pharmaceutical composition comprising a fecal microbe preparation, wherein said subject exhibits at least a two-fold increase of fecal microbiota diversity after said treatment as compared to before initiating said treatment.

Embodiment 36

The method of Embodiment 35, wherein said subject has an ASD and said method improves one or more ASD symptoms.

Embodiment 37

A method comprising
a. determining the relative abundance of one or more gut microorganisms in a subject having an ASD or having an ASD sibling, and
b. administering a therapeutically effective amount of a pharmaceutical composition comprising a fecal microbe preparation to achieve at least a 2-fold change of the abundance of said one or more fecal microorganisms, wherein said one or more gut microorganisms are from a genus selected from the group consisting of *Clostridium*, *Bacteroides*, *Bifidobacterium*, *Prevotella*, *Eggerthella*, and *Desulfovibrio*.

Embodiment 38

The method of Embodiment 37, wherein said subject having an ASD exhibits no gastrointestinal symptom.

Embodiment 39

The method of Embodiment 37, wherein said subject having an ASD does not exhibit one or more, two or more, three or more, four or more gastrointestinal symptoms selected from the group consisting of abdominal pain, reflux, indigestion, irritable bowel syndrome, chronic persistent diarrhoea, diarrhoea, flatulence, constipation, and alternating constipation/diarrhoea.

Embodiment 40

The method of Embodiment 37, wherein said subject having an ASD exhibits no gastrointestinal symptom selected from the group consisting of abdominal pain, reflux, indigestion, irritable bowel syndrome, chronic persistent diarrhoea, diarrhoea, flatulence, constipation, and alternating constipation/diarrhoea.

Embodiment 41

The method of Embodiment 37, wherein said one or more gut microorganisms are from *Clostridium*, and wherein said *Clostridium* microorganisms increase their abundance by at least 2 fold.

Embodiment 42

The method of Embodiment 37, wherein said one or more gut microorganisms are from *Bacteroides*, and wherein said *Bacteroides* microorganisms decrease their abundance by at least 2 fold.

Embodiment 43

The method of Embodiment 37, wherein said one or more gut microorganisms are from *Prevotella*, and wherein said *Prevotella* microorganisms increase their abundance by at least 2 fold.

Embodiment 44

The method of Embodiment 37, wherein said one or more gut microorganisms are from *Desulfovibrio*, and wherein said *Desulfovibrio* microorganisms increase their abundance by at least 2 fold.

Embodiment 45

The method of Embodiment 1, where said at least 2-fold increase is maintained for at least 52 weeks after discontinuing said treatment.

Embodiment 46

The method of Embodiment 1, where said at least 2-fold increase is maintained for at least 98 weeks after discontinuing said treatment.

Embodiment 47

The method of Embodiment 11, where said at least 10% reduction in ASD symptom severity is maintained for at least 50 weeks after discontinuing said treatment.

Embodiment 48

The method of Embodiment 11, where said at least 10% reduction in ASD symptom severity is maintained for at least 98 weeks after discontinuing said treatment.

The disclosure may be better understood by reference to the following non-limiting Examples, which are provided as exemplary of the disclosure. The following examples are presented in order to more fully illustrate the preferred aspects of the disclosure and should in no way be construed, however, as limiting the broad scope of the disclosure. Therefore, the scope of the appended claims should not be limited to the description of the aspects contained herein.

EXAMPLES

Example 1: Treating Autistic Children Using Microbiota Transfer Therapy (MTT)

A clinical study (ClinicalTrials.gov Identifier: NCT02504554) of 20 autistic children, ages 7-17, is conducted to evaluate the safety and tolerability of a fecal microbiota-based treatment designed to reduce the symptoms of autism by improving the gastrointestinal microbiota function. This treatment includes transfer of purified gut bacteria from a healthy person to children diagnosed as having autism spectrum disorder. Details of this trial are described in PCT Application No. PCT/US2016/033747 and U.S. application Ser. No. 15/161,654, both filed May 23, 2016 (both incorporated by reference in their entirety).

The general study design is an open-label clinical trial involving 18 children (ages 7-17 years) with ASD who are diagnosed by the Autism Diagnostic Interview-Revised (ADI-R) and have moderate to severe gastrointestinal problems. Each child participates in the study for 18 weeks in total, a 10 week treatment and a follow-up 8 week observation period after the treatment stops. For the fecal material transplant (FMT) treatment, two routes of administration, oral versus rectal, are compared for the initial dose, followed by a lower maintenance dosage given orally for 7-8 weeks.

The protocol is approved by FDA (Investigational new drug number 15886) and the Institutional Review Board of Arizona State University (ASU IRB Protocol #: 00001053). The study is advertised by email to approximately 2500 ASD families in Arizona, using the contact list of the Autism Society of Greater Phoenix and the Autism/Asperger's Research Program at Arizona State University. Families with children who meet the study inclusion and exclusion criteria have a 1-hour individual phone call to discuss the study. After the phone call, families who sign the parent permission form and child assent forms are provided with initial questionnaires to complete. A letter is also sent to them for their personal physician to double-check their medications and for the physician to be aware of the delivery of the vancomycin, Prilosec, and the fecal transplant Beneficial bacteria (a non-selective fecal microbiota preparation) were prepared from human donor stools. Fecal samples were collected from carefully-screened healthy donors (90% of general population rejected) and purified extensively to retain only bacteria. Specifically, the microbiota is separated from fecal material collected from carefully screened, healthy donors, stored in a cryopreservative in a frozen liquid suspension with a cryopreservative, and thawed prior to administration in liquid form. Each purified sample of beneficial bacteria contained 1000 or more bacterial species. By comparison, standard commercially available probiotics include 1 to 10 bacterial species.

Example 2: Subject Recruitment

The study began with a verification of an autism spectrum diagnosis using the Autism Diagnostic Interview-Revised (ADI-R), which involved a phone interview of the parents with our ADI-R evaluator. The study physician assessed general physical health through an initial 30 minute meeting with participants and an extensive review of the participants' last 2 years of medical records and height/weight/growth charts in order to check for exclusion criteria. Participant exclusion criteria include antibiotics in last 6 months and probiotics in last 3 months, single-gene disorder, major brain malformation, tube feeding, severe GI problems that require immediate treatment (life-threatening), Ulcerative Colitis, Crohn's disease, diagnosed Celiac Disease, Eosinophilic Gasteroenteritis, severely underweight/malnourished, and recent/scheduled surgeries. None of the neurotypical children are diagnosed with mental disorders including ASD, ADHD, depression, and anxiety, and neurotypical children do not have first-degree relatives of individuals with ASD. From participants, initial blood, urine, and stool samples are collected and parents are asked to fill in diet diaries of their child for one week at the beginning of the study. Participants are recruited primarily from the greater Phoenix, Ariz. area, but three participants are from outside that area. Neurotypical families are recruited from friends of the ASD families and professionals who work with ASD families.

Example 3: Trial Participants

Eighteen autism participants (each from a different family) ages 7-17 years with moderate to severe GI problems and moderate to high cognitive functioning. Twenty participants are recruited into the study, but two do not enter the treatment phase of the study before the treatment started. One participant is disqualified due to a change in medication, and one decides not to participate. Characteristics of 18 study participants and their medical history are listed in Table 2. All 18 participants that enter the treatment phase complete the 19-week trial. The post-treatment data presented herein is collected for 13 of these 18 participants. In addition, 20 age- and gender-matched neurotypical children from 13 families (6 families had 1 neurotypical participant, and 7 families had 2 neurotypical participants) are also recruited. These 20 neurotypical children are monitored for 18 weeks but not treated.

TABLE 2

Characteristics of study participants and their medical history.

| | Children with ASD | Neurotypical children | p-value |
|---|---|---|---|
| Total Number | 18 | 20 | |
| Male/Female | 16/2 | 18/2 | |
| Age | 11.0 +/− 2.7 | 11.1 +/− 2.5 | n.s. |
| BMI | 19.9 +/− 5.4 | 18.1 +/− 3.4 | n.s. |
| GSRS 4-point scale (sum of all 15 items, minimum score for no symptoms is 15) | 28.1 +/− 4.3 | 18.8 +/− 4.0 | P < 0.001 |
| Born by C-Section | 61% | 16% | P < 0.01 |
| Number of months of breast-feeding exclusively (no formula) | 3.3 +/− 3.9 | 9.3 +/− 7.8 | P < 0.01 |
| % using non-standard formula (soy or other) | 39% | 8% | P < 0.05 |
| Food allergy (moderate or severe) | 56% | 5% | P < 0.01 |
| Other allergies (moderate or severe) | 44% | 10% | P < 0.01 |
| Eczema | 56% | 5% | P < 0.01 |
| Fiber consumption - child | 8.9 +/− 4.3 | 11.8 +/− 4.9 | P = 0.07 |
| Fiber consumption - mother | 6.7 +/− 3.9 | 10.5 +/− 4.5 | P = 0.02 |
| Oral antibiotic use during first 4 years of life (number of rounds) | 4.6 +/− 5.2 | 4.1 +/− 6.0 | n.s. |

Example 4: Trial Protocol

The participants are given oral vancomycin (a non-absorbable broad spectrum antibiotic that stays in the GI tract) for 2 weeks to reduce levels of pathogenic bacteria, and then 1 day of low-volume colonoscopy prep MoviPrep® (a drink that flushes the bowels, to remove most remaining gut bacteria and vancomycin) to clear the residual vancomycin and feces. The vancomycin is intended to kill off harmful bacteria, the fasting is intended to remove any remaining bacteria and to minimize other luminal fecal material, and the colon cleanse helps to remove the vancomycin and cleanse the lower GI Tract.

Following vancomycin treatment and bowel cleanse, participants received either 2 days of high dose oral Microbiota Transfer Therapy (MTT, mixed in a chocolate milk, milk substitute, or juice) (dosage of $2.5 \times 10^{12}$ CFU per day) or a single dose of rectal MTT (dosage of $2.5 \times 10^{12}$ CFU for one given similar to an enema). The rectal dose is administered under the direct supervision of the study physician, and the first oral dose is similarly administered in the presence of the physician. Participants are randomly assigned to either the oral or rectal route of administration. If one administration route is not tolerated, or if the family preferred the other route, then participants had the option of trying the other route. For the participants with initial oral dose, a lower oral maintenance dose ($2.5 \times 10^9$ CFU) is followed for 8 weeks right after the major oral initial dose. Whereas, the major rectal initial dose is followed by waiting period of 1 week followed by a lower oral maintenance dose ($2.5 \times 10^9$ CFU) for 7 weeks. The maintenance SHGM dose is self-administered orally every day up to week 10. After treatment is stopped, participants were monitored for another 8 weeks. Participants are then monitored for a 2-year follow-up.

Prilosec (omeprazole) is administered daily to reduce stomach acid and thereby increase viability of the MTT, starting on the 12th day of oral vancomycin treatment and continuing until the end of the maintenance dose. Table 3 provides a general treatment timeline.

TABLE 3

MTT Treatment Timeline Summary.

| Time (Day) | Initial oral administration | Initial rectal administration |
|---|---|---|
| Day 1-14 | Vancomycin* | |
| Day 12-74 | Prilosec* | |
| Day 15 | MoviPrep* | |
| Day 16 | Major oral dose of MTT** | Major rectal dose of MTT** |
| Day 17 | Major oral dose of MTT | — |
| Day 18-24 | Lower maintenance oral dose of MTT | — |
| Day 25-74 | Lower maintenance oral dose of MTT*** | |
| Day 75-130 | No treatment, observation period | |
| Day 714-834 | No treatment, observation period | |

*Vancomycin: 40 mg/kg P.O. per day, divided into three doses, not to exceed 2 gm per day; Prilosec: 20 mg PO QD; MoviPrep: Standard kit is used with half the dosage being administered at approximately 10 am and the other half at 4 pm on day fifteen only, to cleanse the bowel of vancomycin and feces. The dosage varies proportionally based on the body mass.
**Initial oral route: The dosage for the first 2 days will be $8.3 \times 10^{11}$ cells, t.i.d, for a total daily dose of $2.5 \times 10^{12}$ cells/day, for Day 16 and 17 only; Initial rectal route: $2.5 \times 10^{12}$ cells, 1x (Day 16 only)
***Maintenance dose: $2.5 \times 10^9$ cells, 1x/day P.O.

Example 5: Fecal Microbiota Preparation Used for MTT

A human microbiota preparation, which comprises a highly purified standardized extract from human feces (also called Standardized Human Gut Microbiota (SHGM)) is used. This is a full-spectrum product, containing all the bacteria present in the gut of very healthy donors. First, donors are carefully screened using an extensive health questionnaire and extensive medical testing to ensure optimal GI and overall health; the screening process is so rigorous that 90% of donors are eliminated, leaving only the 10% healthiest portion of the population. The donated material is then extensively filtered and standardized, following FDA Good Manufacturing Processes (GMP). The final product is liquid form which can be frozen, and is proven to be highly effective for treating *C. difficile* (Hamilton et al., Am J Gastroenterol. 2012 May; 107(5):761-7). The SHGM is stored in −80° C. freezers and then delivered to families on dry ice every week during the study. Families are instructed to keep the SHGM in a container with dry ice, and thaw it shortly before use.

Two different doses of SHGM are used; the high major dose and a lower maintenance dose. The high-dose SHGM is at a daily dosage of $2.5 \times 10^{12}$ cells. The rationale for two days of high dose is that after the MoviPrep and 1-day fast is presumably the most critical time in which to provide new beneficial bacteria. The low-dose SHGM is at a dosage of $2.5 \times 10^9$ cells.

Example 6: Toleration of Study Medications

Vancomycin: The vancomycin is associated with two types of minor adverse events. One child develops an allergic rash upon administration of oral vancomycin, but they are switched to vancomycin without orange flavoring and the rash disappeared. Twelve of the 18 children had a behavioral reaction to the vancomycin, starting 1-4 days after the start of the vancomycin, and lasting 1-3 days in most cases, although 1 participant had symptoms lasting for 3 weeks. In 7 cases, the symptoms are mild to moderate increase in hyperactivity, and in 5 cases the symptoms are mild to moderate increase in tantrumming/aggression. After these behavioral symptoms disappeared, GI symptoms and autism symptoms began improving. Similar results are reported in a previous study (Sandler, 2000), and parents of the study subjected had been informed to expect this. The reaction may be due to release of bacterial toxins as the vancomycin kills off harmful bacteria.

Prilosec: This is generally well-tolerated.

MoviPrep®: Many children had difficulty consuming this medication due to taste.

Rectal administration of Microbiota Transfer Therapy (MTT): This is surprisingly well-tolerated by 6 of 6 recipients.

Oral administration of high-dose MTT: This is well-tolerated by 12 of 13 recipients, but 1 participant experienced vomiting and is switched to the rectal route.

Oral administration of maintenance dose MTT: This is well-tolerated by all participants.

CBC/ChemPanel: There are no major concerns regarding changes in Complete Blood Count (CBC) or blood chemistry panel (CBC). The following minor changes are observed. There is a 5% decrease in potassium ($p=0.01$) from beginning to end of treatment, but all levels remain in the normal range. After the vancomycin (2nd week of study), there is a 8% increase in platelets ($p=0.03$). Four subjects had elevated levels at start, and only 2 had elevated levels after vancomycin. There is a 26% drop in blood urea nitrogen (BUN) ($p=0.002$), but all stayed in normal range. There is a 6% increase in albumin to globulin (A/G) ratio ($p=0.03$), with 1 slightly elevated. There is a 17% increase in aspartate amino transferase (AST) (p=0.01), but all remained in normal range. There is a 24% increase in alanine amino transferase (ALT) (p=0.003), where 1 remained elevated and 2 became slightly elevated. All of these values (platelets, BUN, A/G, AST, ALT) returned to similar to baseline at the 3rd and 4th tests. Slight changes (1-2%) in red blood cell indices (Mean corpuscular volume (MCV), Mean corpuscular hemoglobin (MCH), Mean corpuscular hemoglobin concentration (MCHC), and Red cell distribution width (RDW)) are observed.

Example 7: Adverse Effects

Children with ASD experienced temporary adverse effects at the beginning of vancomycin treatment. As listed in Table 4, one participant among the 18 children with ASD (5%) developed an extensive rash, but the rash disappeared when vancomycin is switched from a natural orange flavor to an unflavored form. Within 1-4 days after the start of the vancomycin, 12 children with ASD had a temporary behavioral reaction to the vancomycin either involving hyperactivity (7 out of 12 cases; 39%) or Tantrums/Aggression (5 out of 12 cases; 28%). The symptoms lasted 1-3 days in most cases, except for one participant that had symptoms lasting for 3 weeks. After the symptoms disappeared, GI symptoms and behavioral symptoms began improving, which is similar to what Sandler et al., *Journal of Child Neurology* 15, 429-35, (2000) reported in their oral vancomycin therapy for children with autism. Only one participant does not tolerate the initial high-dose oral SHGM (nausea/vomiting) and is switched to initial rectal administration.

TABLE 4

Adverse effects.

| Adverse effect | % adverse effects |
| --- | --- |
| Rash | 5% (due to natural orange flavor in vancomycin) |
| Hyperactivity | 39%* (temporary: start of vancomycin only) |
| Tantrums/Aggression | 28%* (temporary: start of vancomycin only) |
| Nausea/vomiting | 5% (due to high-dose SHGM) |

*The severity of symptoms ranged from mild to moderate.

Example 8: Assessments of Gastrointestinal Symptoms

Gastrointestinal Symptom Rating Scale (GSRS) is an assessment of GI symptoms during the previous week, based on 15 questions, which are then scored in 5 domains: Abdominal Pain, Reflux, Indigestion, Diarrhea, and Constipation. A score is reported for each domain based on the average within the questions in that domain. The original GSRS used a 4-point scale, but a revised version is used which included 7-point Likert scale which also has simpler language. The GSRS is assessed on days 0, 7, 14, 21, 28, 35, 42, 56, 74, and 130. One of ordinary skill in the art understands that GSRS is only one way to assess GI symptoms. Other similar tools can be used or designed to evaluate GI symptoms.

Daily Stool Records (DSR) are collected at baseline for two weeks, daily during the treatment phase, and the last two weeks of the observation period. These records included a rating of the stool using the Bristol Stool Form scale (1=very hard, 7=liquid).

Example 9: Assessments of Autism and Related Symptoms

Autism Diagnostic Interview-Revised (ADI-R) is a 2-hour structured interview and is one of the primary tools used for clinical diagnosis of autism and autism spectrum disorders. It is not designed to be a measure of autism severity, but higher scores are generally consistent with more severe symptoms. The ADI-R is used to verify the diagnosis of ASD for admission into the study.

Parent Global Impressions—III is introduced here as an expanded version of the PGI-R. See Adams et al., Effect of a Vitamin/Mineral Supplement on Children with Autism, *BMC Pediatrics,* 11:111(2011). The PGI-III evaluates changes in 17 areas (see FIG. 13), and overall, using a 7-point scale ranging from "much worse" to "much better". An "Average Change" is computed by computing the average in all 18 scores of the PGI-2-Final. This tool is chosen because it was found that it is more reliable to ask parents directly about observed changes than to have them estimate symptom severity at beginning and end and then compute a difference. Also, the use of a 7-point scale to detect changes seems to yield a high sensitivity to changes.

Childhood Autism Rating Scale (CARS) is a 15-item scale that can be used to both diagnose autism and ASD and to assess the overall severity of symptoms. The CARS assessment is done subsequent to the ADIR assessment by the same evaluator.

Aberrant Behavior Checklist (ABC) assesses problem behaviors in five areas common in children with ASD, including irritability, lethargy, stereotypy, hyperactivity, and inappropriate speech.

Social Responsiveness Scale (SRS) is a 65-item scale that assesses social impairments, a core issue in autism, including social awareness, social information processing, capacity for reciprocal social communication, social anxiety/avoidance, and autistic preoccupations and traits. See Constantino et al., Validation of a brief quantitative measure of autistic traits: comparison of the social responsiveness scale with the autism diagnostic interview-revised. *J Autism Dev Disord.* 2003 August; 33(4):427-33.

Vineland Adaptive Behavior Scale II (VABS-II) is a measure of the functioning level in four different domains: Communication, Daily Living Skills, Socialization, and Motor Skills, and 11 sub-domains. The raw scores are converted into an age equivalent score. It complements the ABC, which assesses problem behaviors. See Sara et al., Vineland Adaptive Behavior Scales, Second Edition (Vineland™-II), Pearson Publishing, 2005.

The GSRS and PGI-R3 are assessed on days 0, 7, 14, 21, 28, 35, 42, 56, 74, 130, and an average of analysis taken on days 714-834. The Stool Record is assessed every day during the treatment. The CARS, ABC, and SRS are assessed at baseline, at the end of treatment, and at the end of the observation period. The VABS-II is assessed at baseline and at the end of the observation period, and at the 2-year follow-up only, because it is lengthy and believed to be less sensitive to short time periods since it assesses changes in specific adaptive skills. The CARS is assessed by a professional evaluator, and the GSRS, PGI-R2, ABC, SRS, and VABS-II are assessed by parents.

Example 10: Initial Observations

Figure 2:
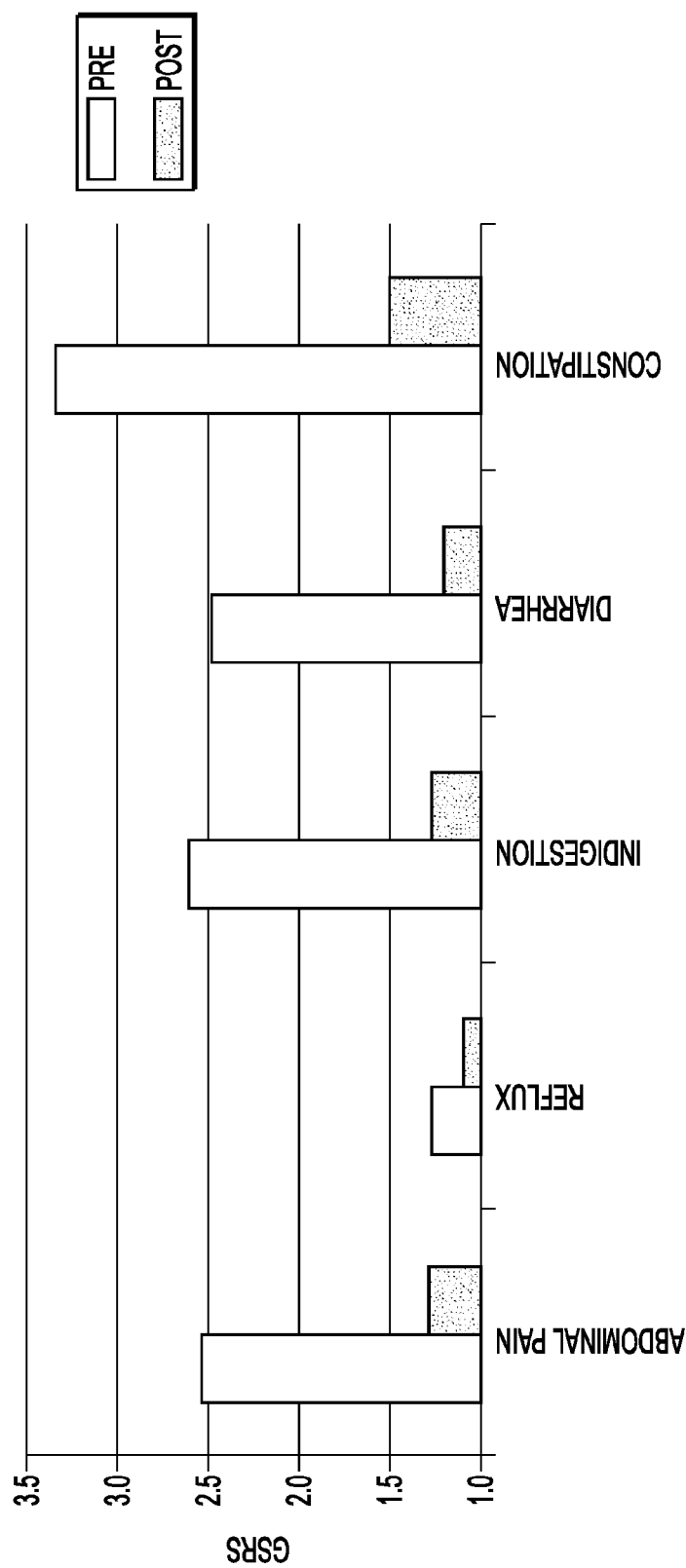
FIG. 2 presents GSRS subscale data collected prior to ("pre") and following ("post") MTT treatment.
Figure 3:
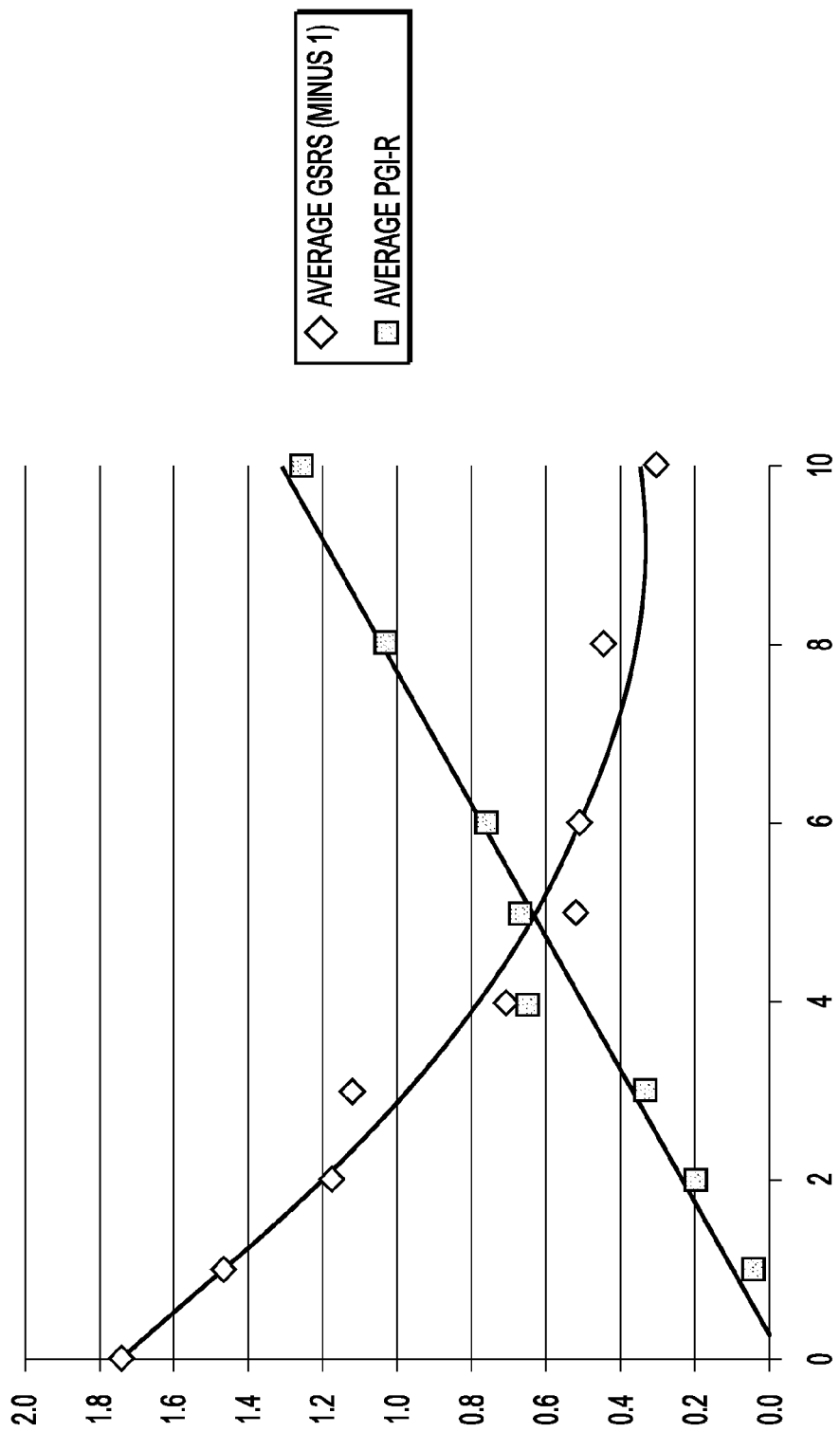
FIG. 3 presents continuous improvements of both average GSRS and average PGI-R scores of the participants.
Figure 5:
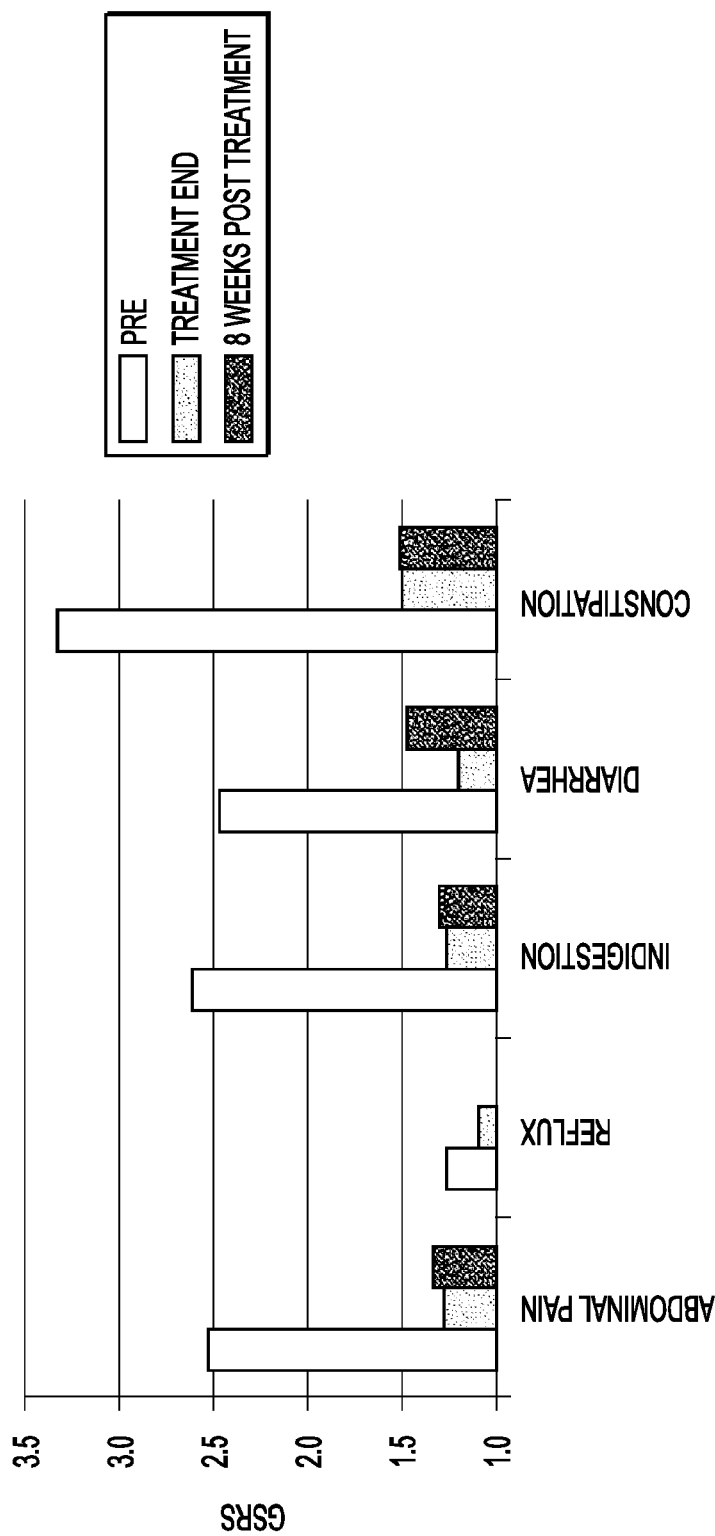
FIG. 5 presents GSRS scores collected 8 weeks post-treatment.

GI Symptoms:

During the 2 weeks of vancomycin and then 8 weeks of beneficial bacteria, there is a rapid improvement in GI symptoms in most children. At the end of treatment there is an 82% reduction in average scores on the Gastrointestinal Symptom Rating Scale (GSRS) (FIG. 1 and FIG. 3). As shown in FIG. 2 and FIG. 5, roughly equal decrease in all 4 GSRS subscale areas (abdominal pain, indigestion, diarrhoea, constipation). There is no change in the reflux subscale because none of the children had a significant reflux problem. Sixteen of 18 children had a 70% or greater reduction, 1 had a 30% reduction, and 1 exhibited no change. Similar results are obtained for both the rectal-administration group and the oral-administration group.

Autism Symptoms:

By the end of the treatment phase, the parents rated their children's autism symptoms on the Overall scale of the Parent Global Impressions as: Much Better—4; Better—8; Slightly Better—5; Little/No change—1. The largest improvements are in GI, speech, sociability, receptive language, cognition, irritability/mood, anxiety, and play skills (FIG. 3). For the Childhood Autism Rating Scale (CARS) rated by our experienced evaluator, there is a 22% decrease in the CARS scores, p<0.001, which is consistent with the observations by the parents. For the Aberrant Behavior Checklist (ABC), there is a 27% reduction in the total score, p=0.001 (FIG. 4). Similar results are obtained for both the rectal-administration group and the oral-administration group.

Figure 7:
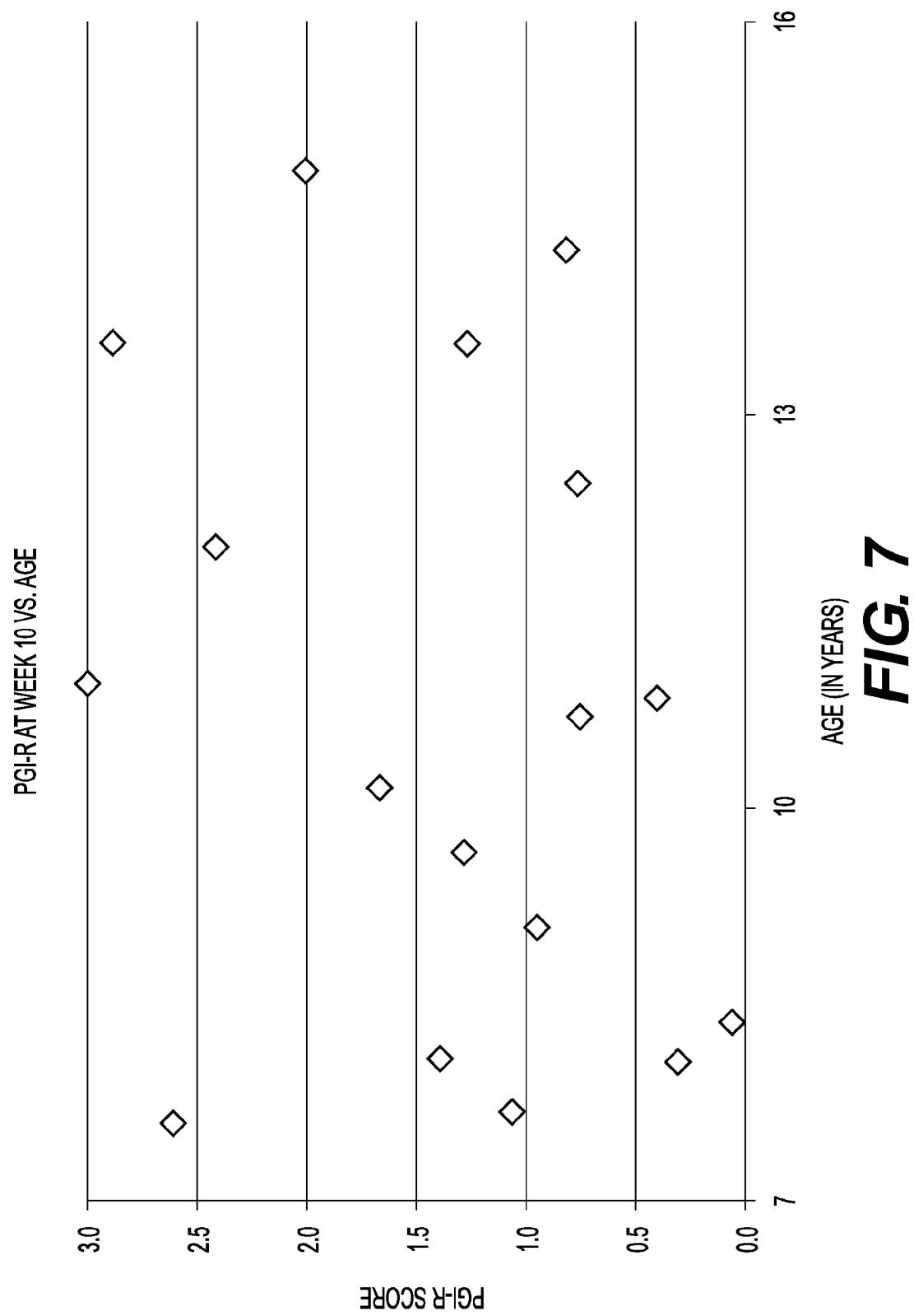
FIG. 7 is a graph demonstrating that end-of-treatment PGI-R scores had little correlation with age.

Post-Treatment:

Among the first 5 participants that completed the 8-week post-treatment observation period, after two months of receiving no treatment, on average no change in improvements of GI symptoms is observed (73% reduction in GSRS at end of treatment vs. start; 71% reduction after 8 weeks of no treatment vs. start). With respect to post-treatment autism symptoms, PGI-Scores continued to improve over those collected at the end of treatment, with medium to large improvements in 3 participants and no detected change in 2 participants. (FIG. 7). With regard to post-treatment CARS scores, these 5 children had a 16% decrease in CARS scores at the end of treatment, and a 25% decrease compared to baseline at the end of the no-treatment (observation) period. So, there appeared to be a surprising continued improvement in symptoms even after treatment stopped.

Figure 6:
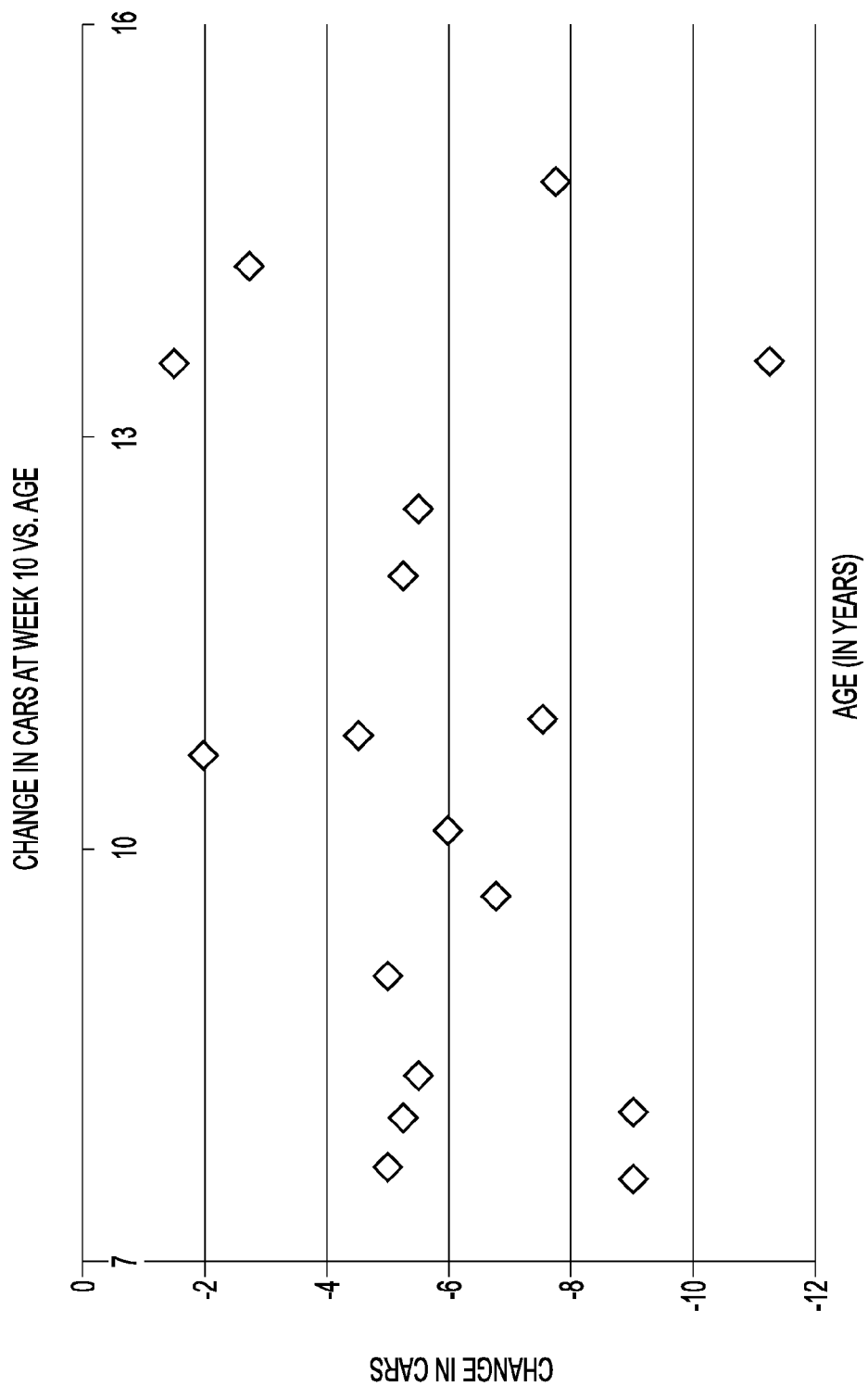
FIG. 6 is a graph demonstrating the lack of correlation between age and the degree of CARS score improvement.
Figure 8:
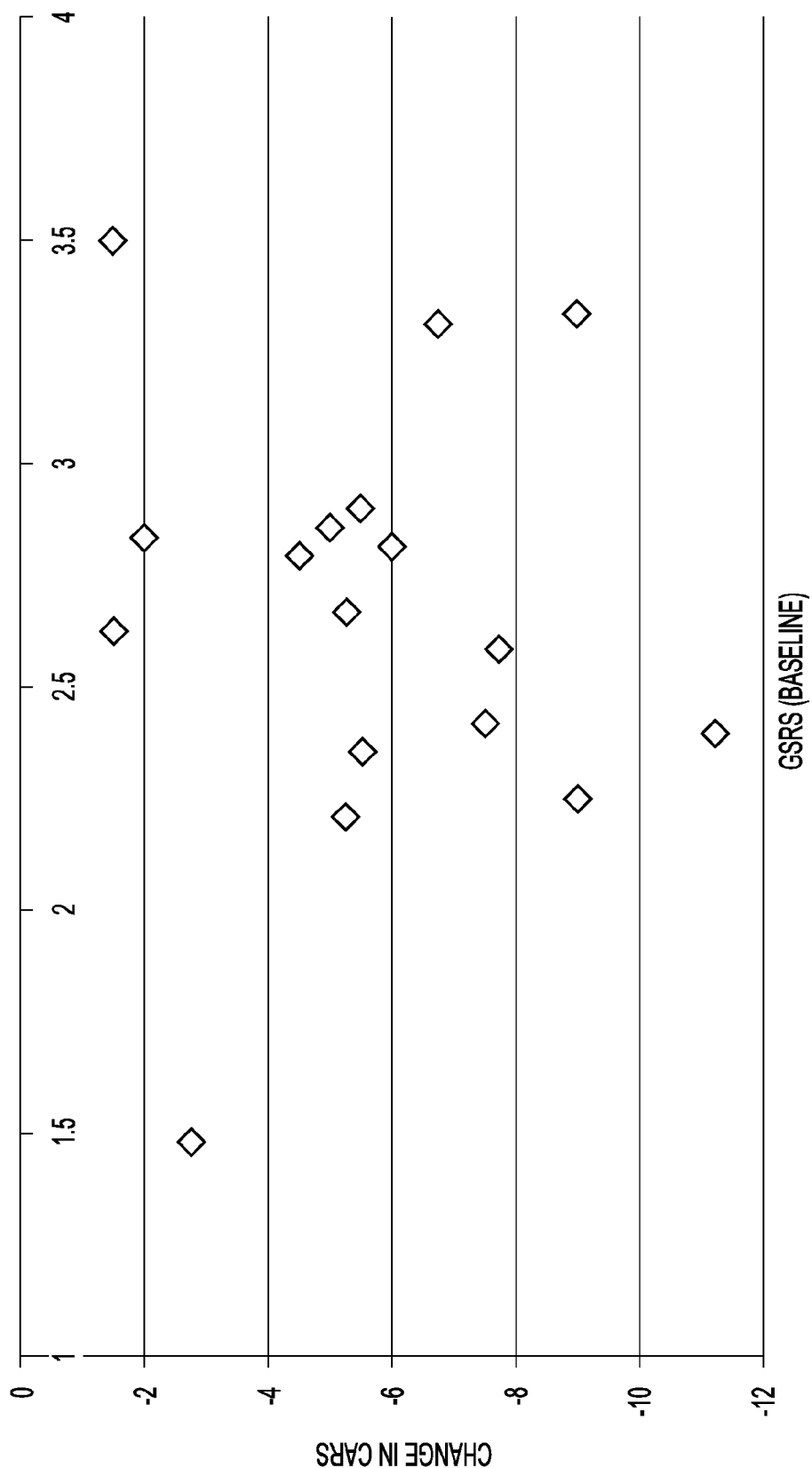
FIG. 8 is a graph demonstrating the lack of correlation between the degree of improvement on CARS and initial GSRS score.
Figure 9A:
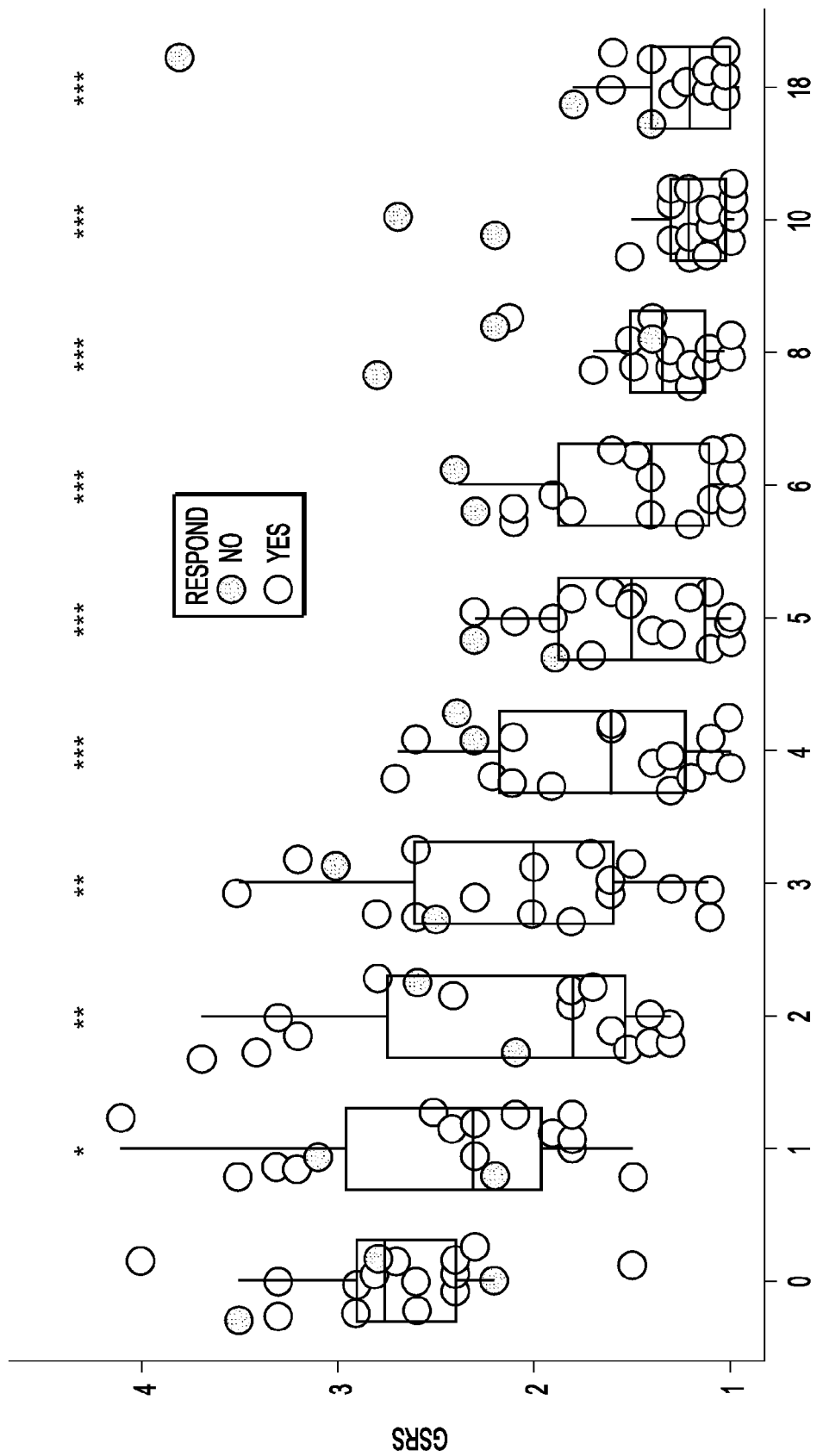
FIG. 9 (including panels a to e) describes the improvement of GI- and core ASD-related symptoms of 18 ASD-afflicted children treated with MTT. Children are treated with vancomycin for two weeks followed by the administering of a fecal bacteria composition for 8 weeks, with a single follow-up evaluation 8 weeks after treatment ended. Panel a. Changes in GSRS scores. GSRS is scored on a Likert scale from 1 (no symptoms) to 7 (very severe discomfort). Panel b. Changes in PGI-R scores (Overall autism/related symptoms). PGI-R is scored from −3 (much worse), −2 (worse), −1 (slightly worse), 0 (no change), 1 (slightly better), 2 (better) to 3 (much better) compared to baseline. Panel c. CARS assessment pre-treatment, post treatment and 8 weeks post treatment. Panel d. Total SRS score pre-treatment, post treatment and 8 weeks post treatment. Panel e. Total ABC score pre-treatment, post treatment and 8 weeks post treatment. The data points represent 18 individual participants, and some data points overlap in the box plot. Asterisks (at the top of the box-plot) indicate whether individuals (at each time points) significantly decrease since pre-treatment (Week 0). ns: not-significant, *: $p<0.05$, : $p<0.01$, *: $p<0.001$ (two-tailed paired t-test). Two participants who had less than 50% improvement in GSRS scores are defined as non-responders and color-coded in grey.
Figure 9B:
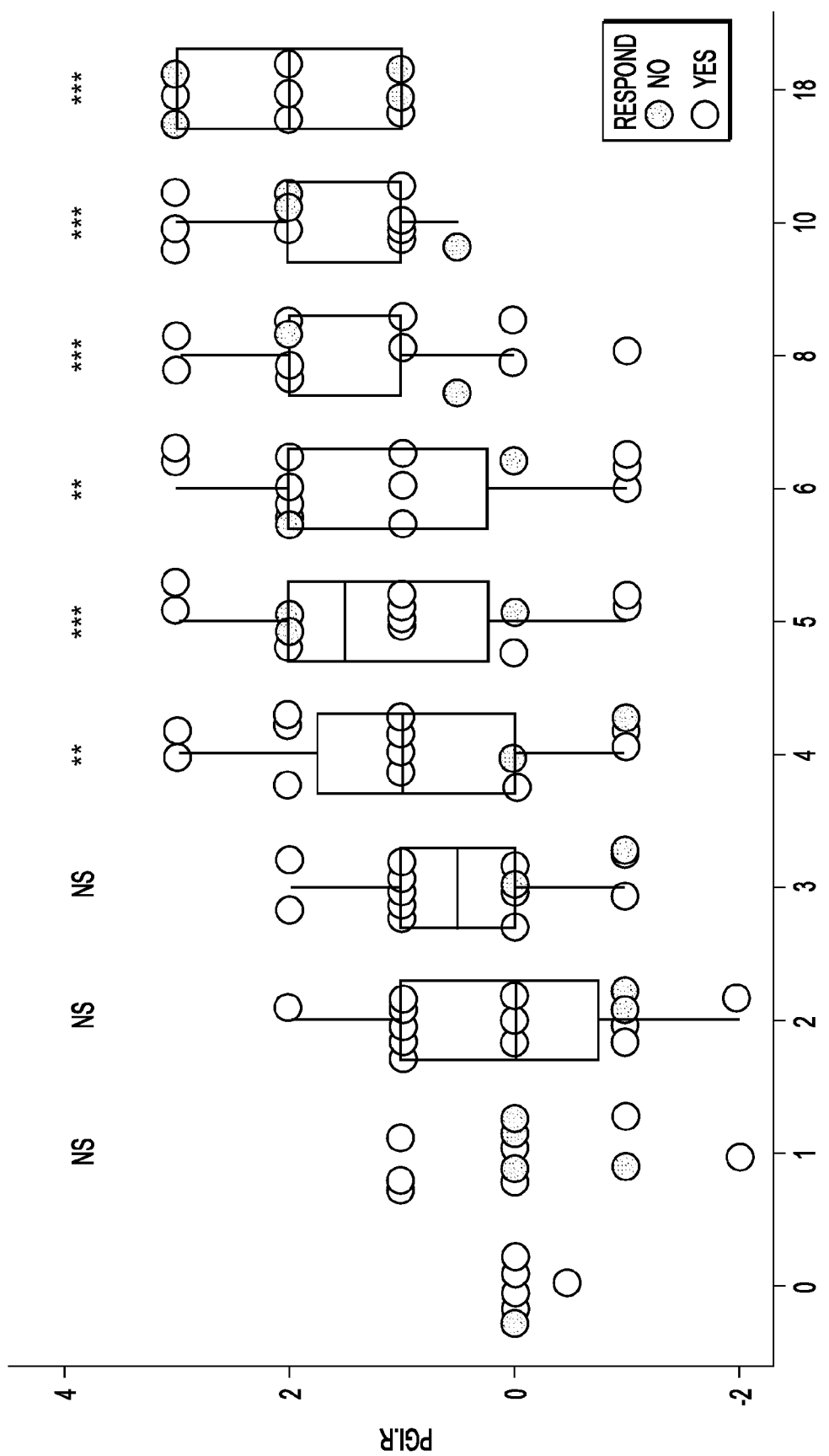
Figure 9C:
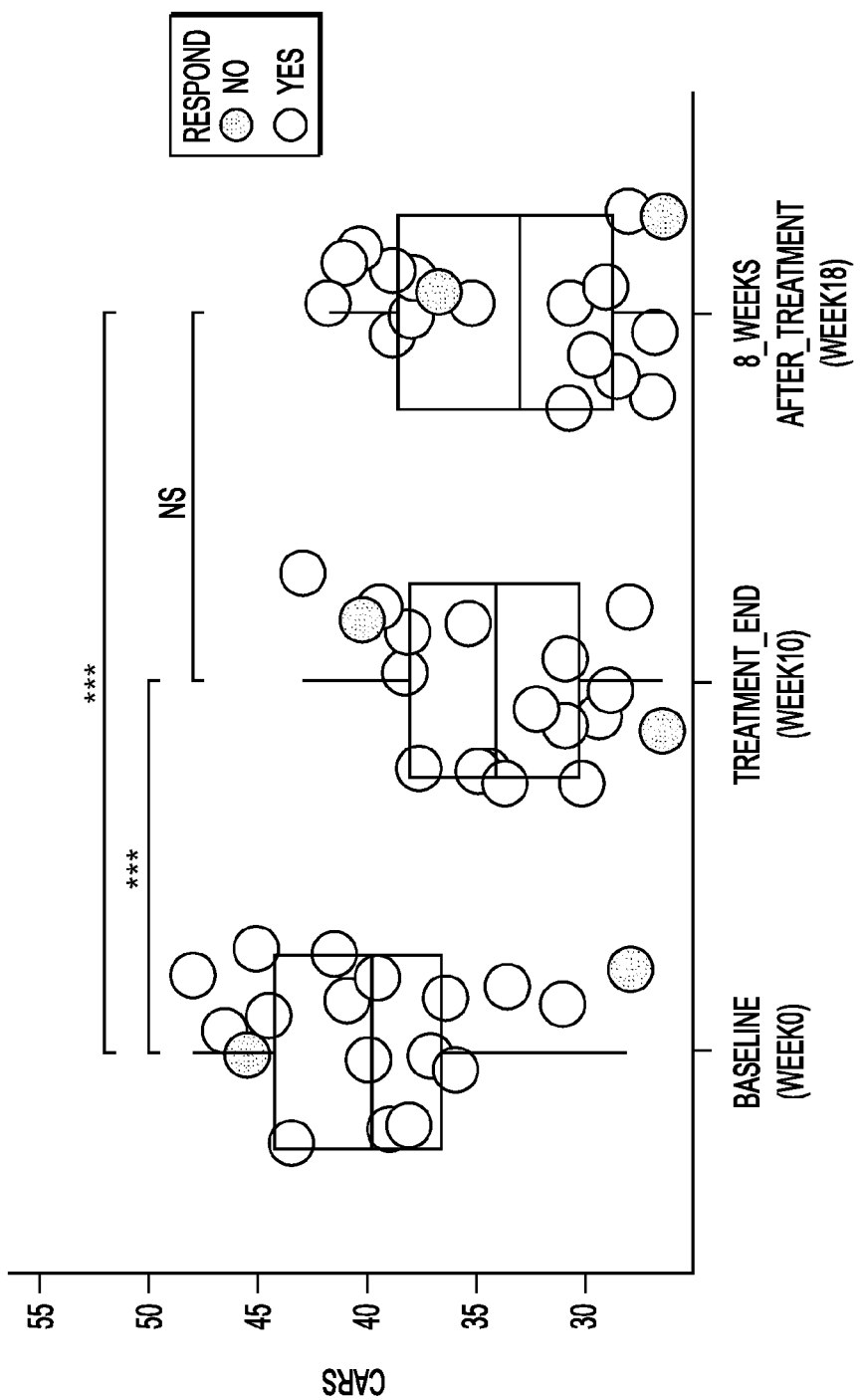
Figure 9D:
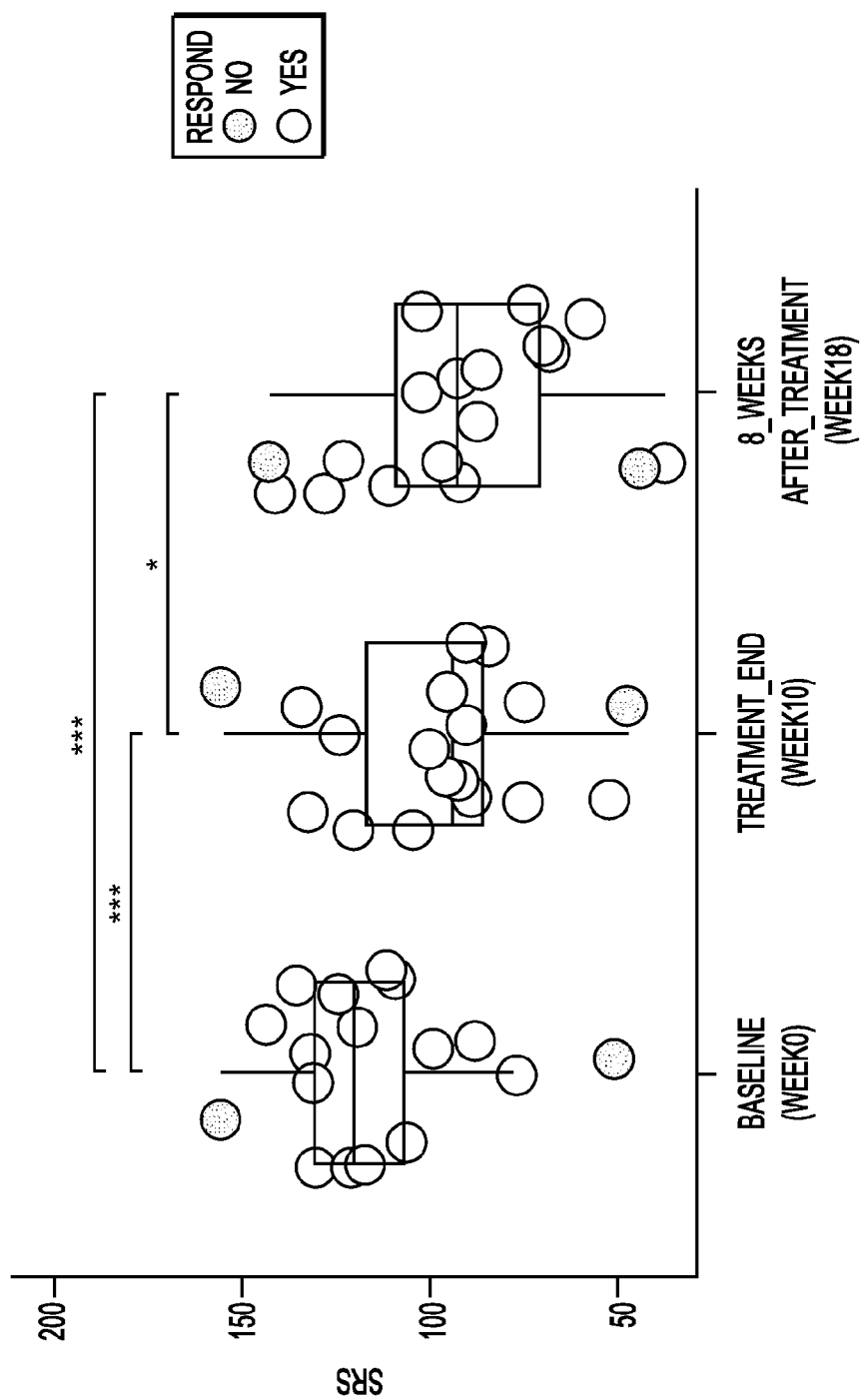
Figure 9E:
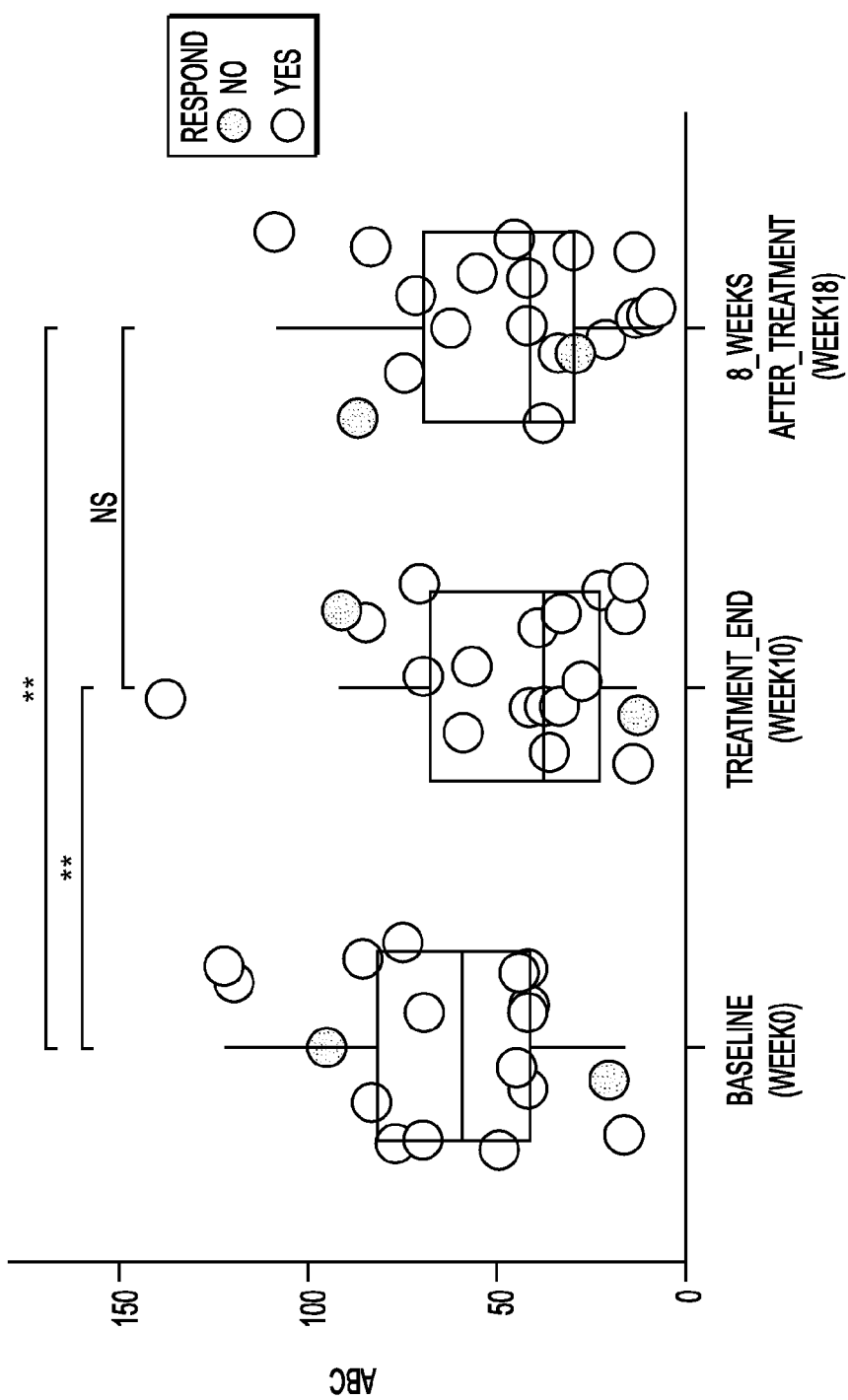

These data demonstrates a 22% reduction in autism severity scores assigned using the Childhood Autism Rating Scale (CARS) after only 10 weeks of the combined therapy (FIG. 3). The degree of improvement on the CARS does not appear to correlate with age (FIG. 6). This suggests that the treatment is useful for both younger children and adults. Furthermore, the degree of improvement on the CARS does not correlate with initial GSRS score (FIG. 8). This suggests that the treatment is helpful to those with mild GI symptoms as well as those without GI symptoms. In other words, the treatment appears to be effective to reduce autism symptoms regardless of the presence or absence of GI symptoms. This observation is consistent with data reported in our previous study (Kang et al., *PLOS One* 8(7):e68322 (2013)), from which it is concluded that children with ASD had a low diversity of gut bacteria that is independent of their gastrointestinal symptoms.

Example 11: Trial Outcome and Analysis

Clinically, this study is broadly successful. First, all ASD participants completed the 18-week study. Second, GI symptoms, as assessed by the Gastrointestinal Symptom Rating Scale (GSRS), significantly improved for abdominal pain, indigestion, diarrhea, and constipation, such that the average GSRS score dropped 82% from the beginning to end of treatment and remained improved (77% decrease from baseline) at 8 weeks after treatment stopped (two-tailed paired t-test t=−9.45, p<0.001, t=−7.64, p<0.001, respectively) (FIG. 9, panel a). A steady and large degree of improvement in most areas of GSRS evaluation including abdominal pain, indigestion, diarrhea, and constipation (FIG. 10, panel a) are observed. There is little change in reflux since no children had significant reflux at the start of the study. Notably, two seemingly opposite GI symptoms-diarrhea and constipation-responded to the MTT treatment effectively.

Figure 10A:
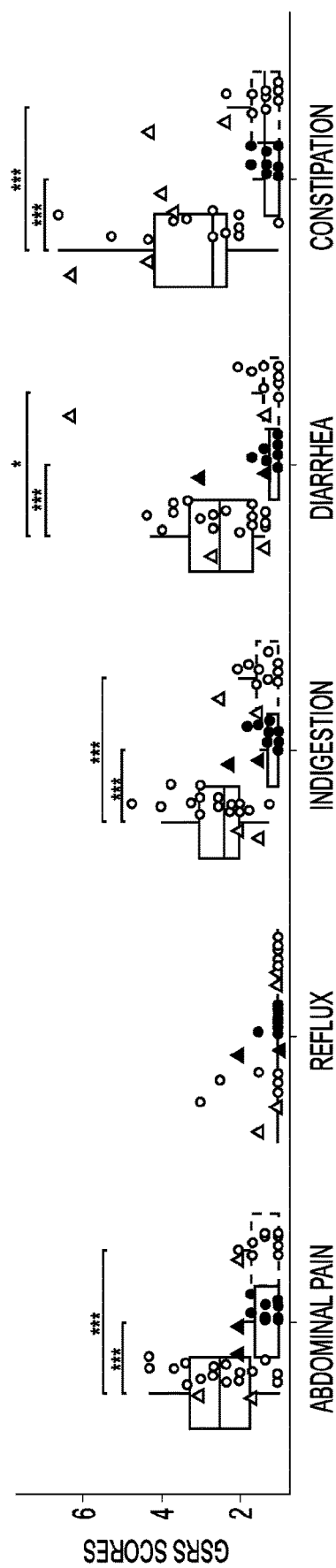
FIG. 10 (including panels a to c) provides a breakdown of GSRS components and improvements in patients. Panel a. GSRS subscores at baseline, MTT treatment end, and 8 weeks after treatment. Panel b. Results of daily stool records, averaged over 2 weeks. Panel c. Subscales of the ABC vs. time. *: $p<0.05$, : $p<0.01$, *: $p<0.001$ (two-tailed paired t-test).
Figure 10B:
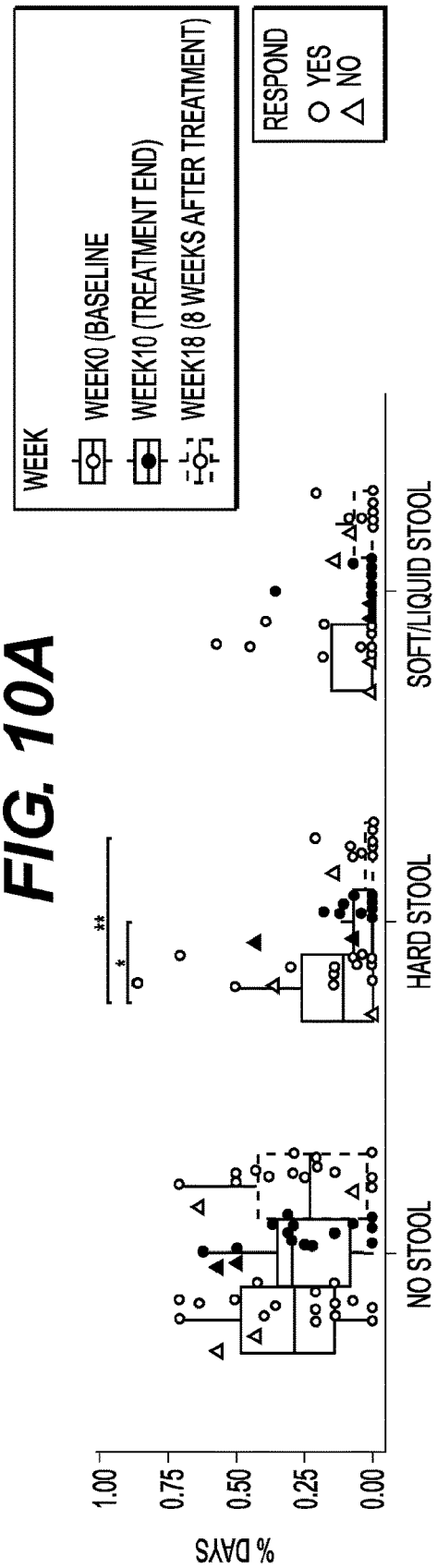
Figure 10C:
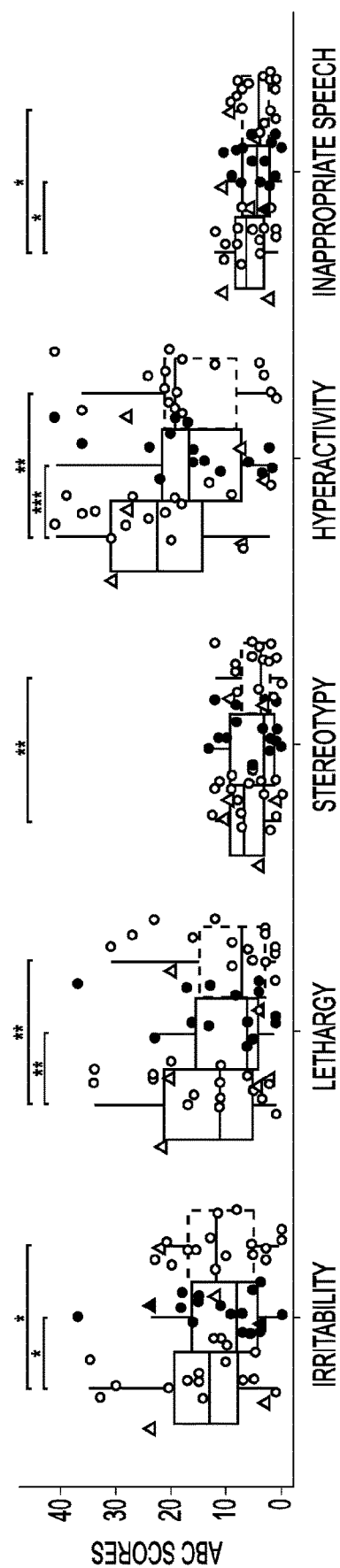

Similarly, the Daily Stool Record (DSR), showed significant decreases in the number of days with abnormal or no stools, and those improvements remained after 8 weeks of no treatment (Table 5, FIG. 10, panel b). The Daily Stool Record (DSR) is collected and averaged over two weeks in order to assess changes in stool hardness/softness during the study. Overall, a significant decrease is observed in "% days of abnormal stool" that combines % days of hard, soft/liquid, and no stool, from 62% to 34% (p=0.001) during the 10-week MTT treatment (Table 5 and FIG. 10, panel b). The improvements remained stable for the following 8 weeks during the observation period. In detail, both "% days of hard stools" (type 1 or 2) and "% days of soft/liquid stools" (type 6 or 7) significantly decreases during the 10-week MTT treatment, but the decrease in "% days of no stool" was not significant. (Table 5).

TABLE 5

Percent days of no stool, stool hardness and softness based on the daily stool record (DSR) and the Bristol Stool Form Scale.

|  | Baseline | Treatment end | p-value | 8 weeks after treatment | p-value |
|---|---|---|---|---|---|
| No stool | 33% | 26% | 0.27 | 26% | 0.38 |
| Hard stool (type 1 or 2) | 19% | 6% | 0.04 | 3% | 0.01 |
| Soft/liquid stool (type 6 or 7) | 10% | 2% | 0.05 | 3% | 0.11 |
| Abnormal stool (in total of hard, soft/liquid/, no stool) | 62% | 34% | 0.0007 | 32% | 0.001 |

Third, there are only temporary adverse effects (primarily mild to moderate hyperactivity and tantrums/aggression) from vancomycin treatment (Table 4), but no major changes in blood chemistry or long-term adverse effects.

Figure 11:
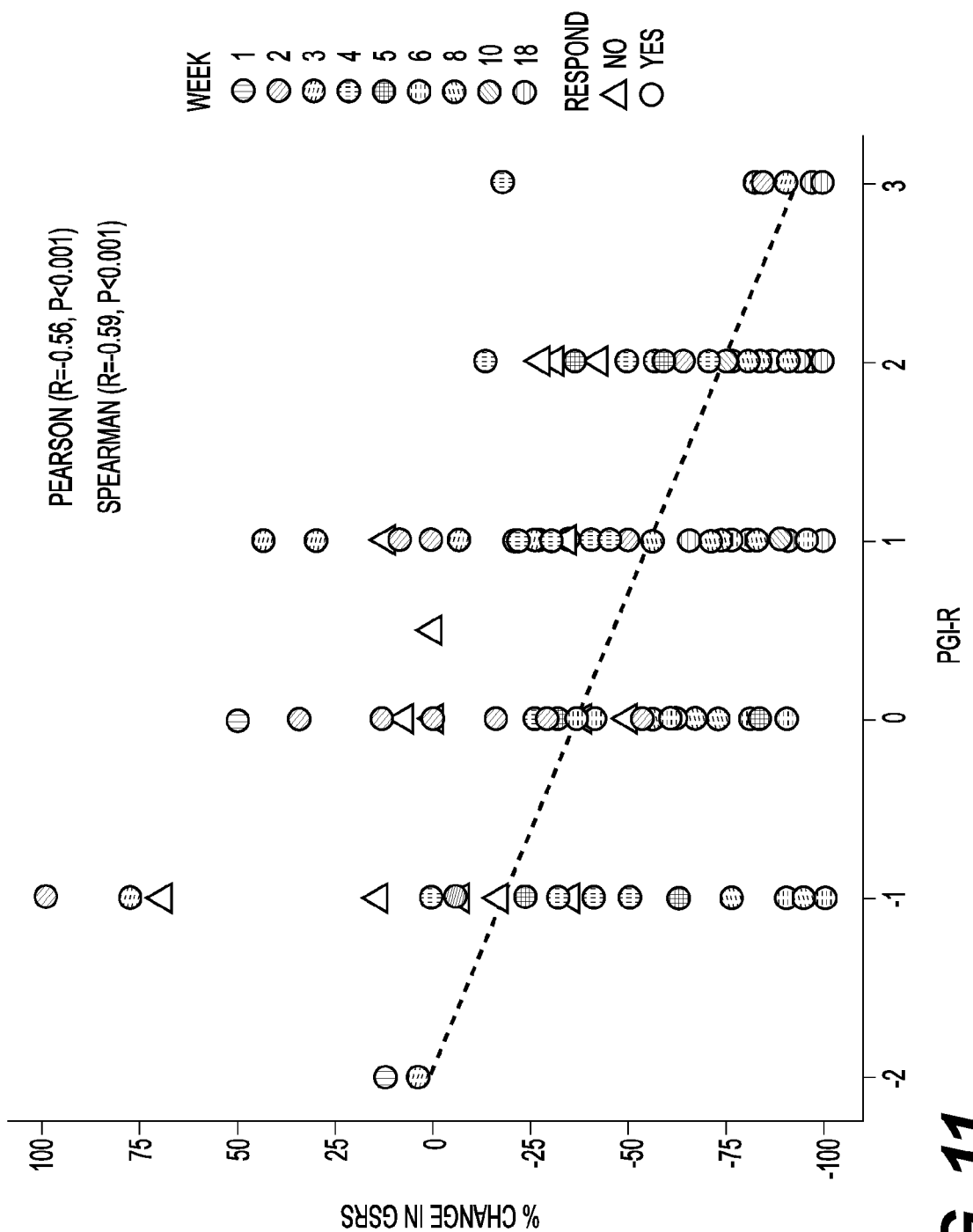
FIG. 11 demonstrates a correlation between GSRS and PGI-R (based on the data shown in FIG. 10, panels a and b). The Pearson correlation test showed $r=-0.56$ and $p<0.001$.
Figure 12:
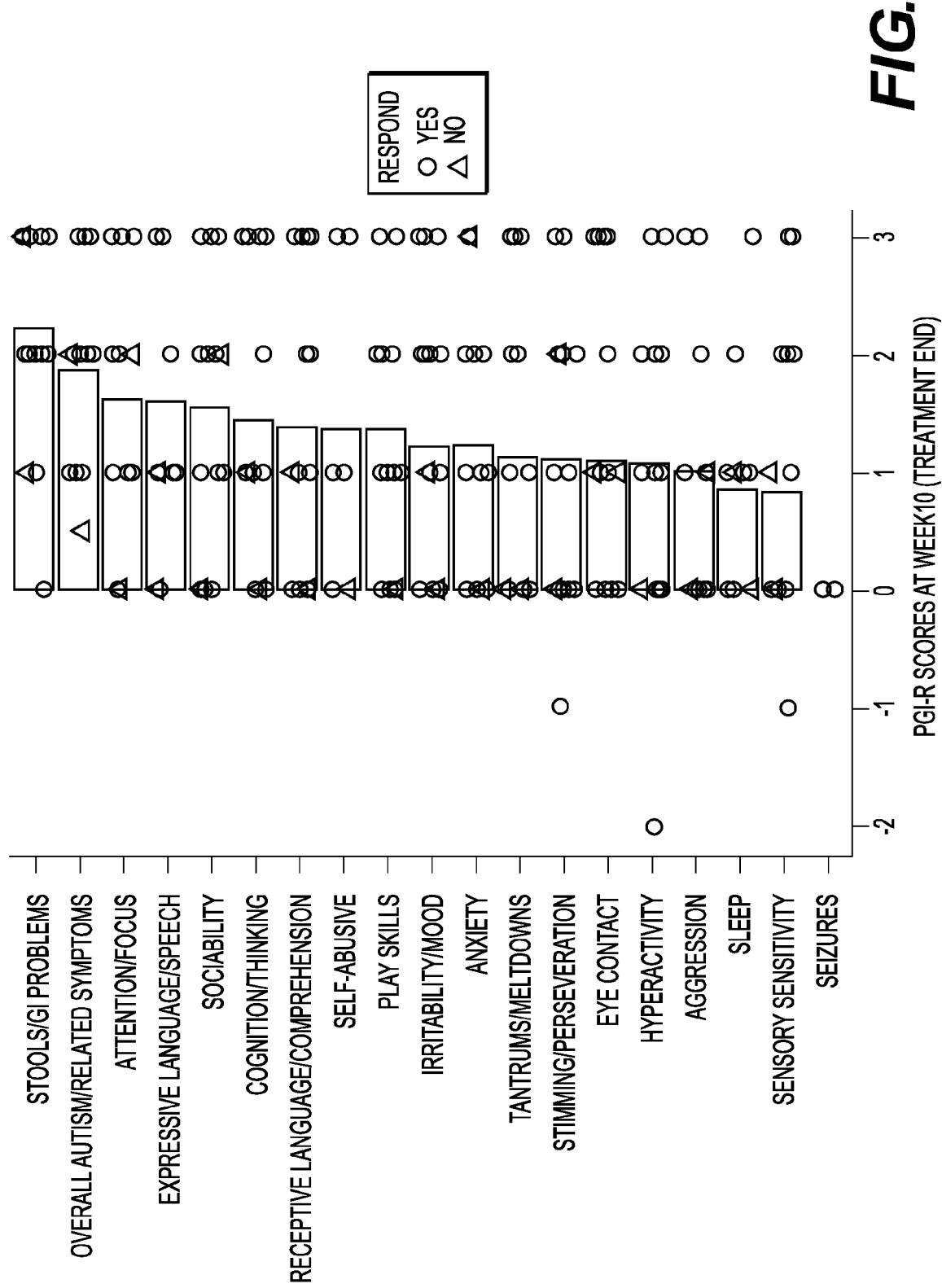
FIG. 12 shows Vineland Developmental Age (in years) for different subscales and for the average of all the subscales, measured at baseline and at the end of observation 4 months later. Note that the average chronological age is 10.9 years at the start of treatment, so at baseline there are delays in all areas, especially in the core autism areas of language and social (interpersonal) ability. *: $p<0.05$, : $p<0.01$, *: $p<0.001$ (two-tailed paired t-test).

Beyond these GI improvements, ASD-related behavior also improved following MTT. First, the Parent Global Impressions (PGI-R) assessment, which evaluates 17 ASD-related symptoms, revealed significant improvement during treatment and no reversion 8 weeks after treatment ended (FIG. 9, panel b). Further, a significant negative correlation between GSRS and PGI-R (Spearman correlation test showed r=−0.59 and p<0.001, FIG. 11) suggests that GI symptoms impact ASD behaviors, and that these can be altered via MTT. By the end of the MTT treatment at week 10, the parents rated the change in their children's autism symptoms using the PGI-R, and the largest improvements are in the GI subscore among 17 subscales and "Overall autism/related symptoms" of the PGI-R (FIG. 12). Specifically, the overall scale of PGI-R is rated as Much Better: n=4 (22%); Better: n=8 (44%); Slightly Better: n=5 (28%); Little/No change: n=1 (6%). The improvement in the other subscales is shown in FIG. 12.

Second, the Childhood Autism Rating Scale (CARS), which rates core ASD symptoms, decreases by 22% from beginning to end of treatment and 24% (relative to baseline) after 8 weeks of no treatment (p<0.001, FIG. 9, panel c).

Third, ASD-afflicted children saw improvement in their scores in the Social Responsiveness Scale (SRS), which assesses social skill deficits (FIG. 9, panel d), and the Aberrant Behavior Checklist (ABC), which evaluates irritability, hyperactivity, lethargy, stereotypy, and aberrant speech (FIG. 9, panel e). FIG. 10, panel c also shows a more detailed breakdown of ABC analysis to assess treatment effects on behaviors common in children with ASD: irritability, lethargy, stereotypy, hyperactivity, and inappropriate speech. In all five sub-scales, a significant reduction at the end of treatment is observed.

Figure 13:
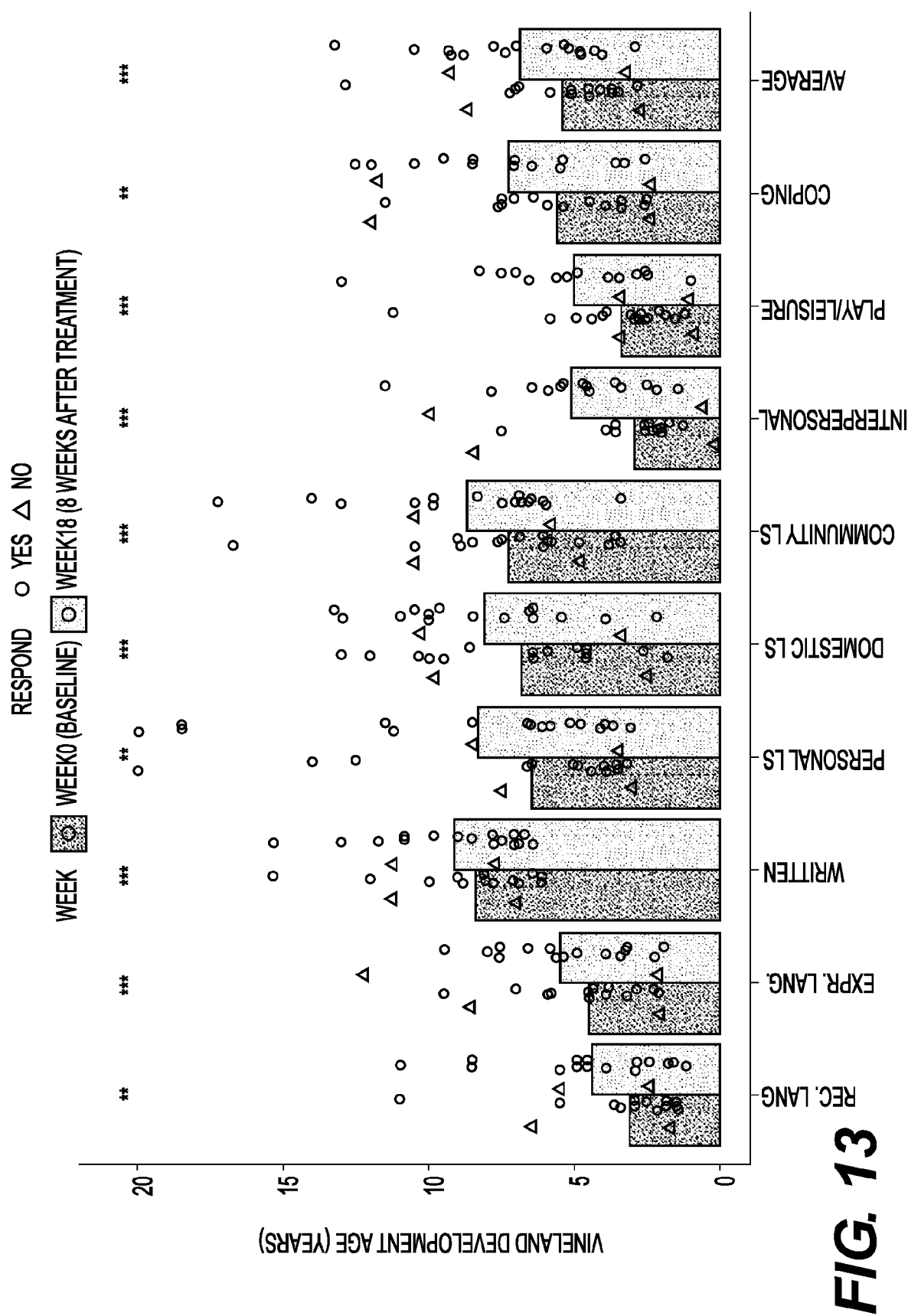
FIG. 13 shows subscores of the PGI-R at end of treatment (week 10). The scale goes from 3 (much better) to 2 (better) to 1 (slightly better) to 0 (no change) to minus 3 (much worse). Scores are similar after 8 weeks of no treatment (week 18). The data points represent 18 individual participants, and some data points overlap in the box plot.
Figure 14A:
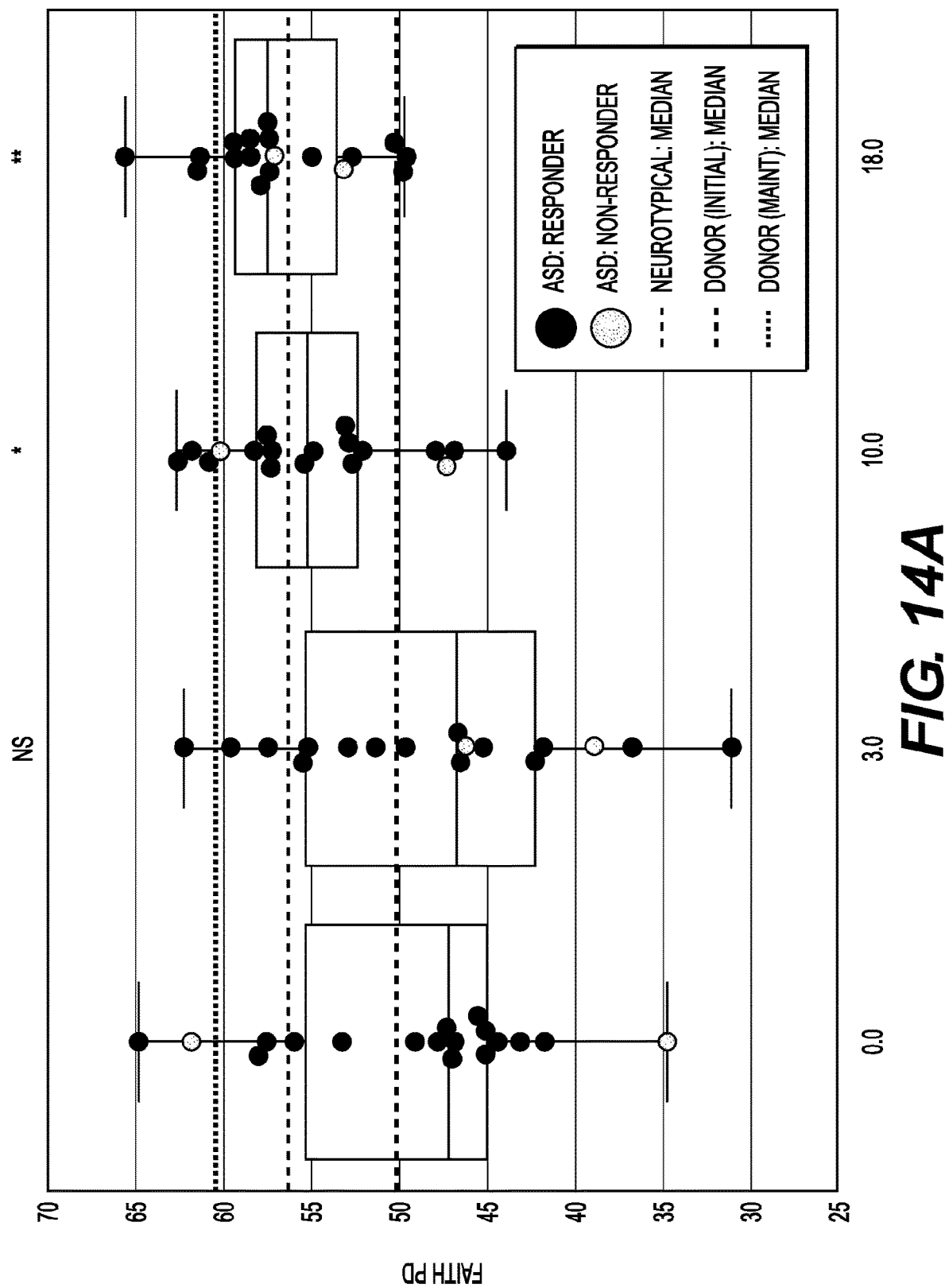
FIG. 14 (including panels a to h) describes stool microbiota changes in ASD patients receiving MTT. Panel a. Changes in Faith's Phylogenetic Diversity (PD) in the ASD microbiota as measured from stool samples. Orange line indicates median PD of the donor samples, and green line indicates median PD of neurotypical controls at week 0. Panel b. Change in Faith PD tracked on a per individual basis for all MTT recipients. Most individuals experienced an increase in gut microbiota PD. Panel c. Unweighted UniFrac distances between ASD gut microbiota and most relevant donor sample (initial donor sample at weeks 0 and 3, most recent maintenance dose sample at weeks 10 and 18). Green line indicates the median interpersonal variation between neurotypical controls and illustrates that prior to treatment the difference in gut microbiota composition between MTT recipients and donors is on the order of normal interpersonal variation. Following treatment, the MTT recipients are more similar to donors than normal interpersonal variation. Panel d. Distances between ASD gut microbiota and donor sample on a per individual basis. Most individuals become more similar to the donor over the study period. Panels e to h. Boxplots illustrating abundance of four genera, *Bifidobacterium, Prevotella, Desulfovibrio*, and *Bacteroides*, in the gut microbiota by group (top), and change in abundance 8 weeks after MTT in the ASD group (bottom).
Figure 14B:
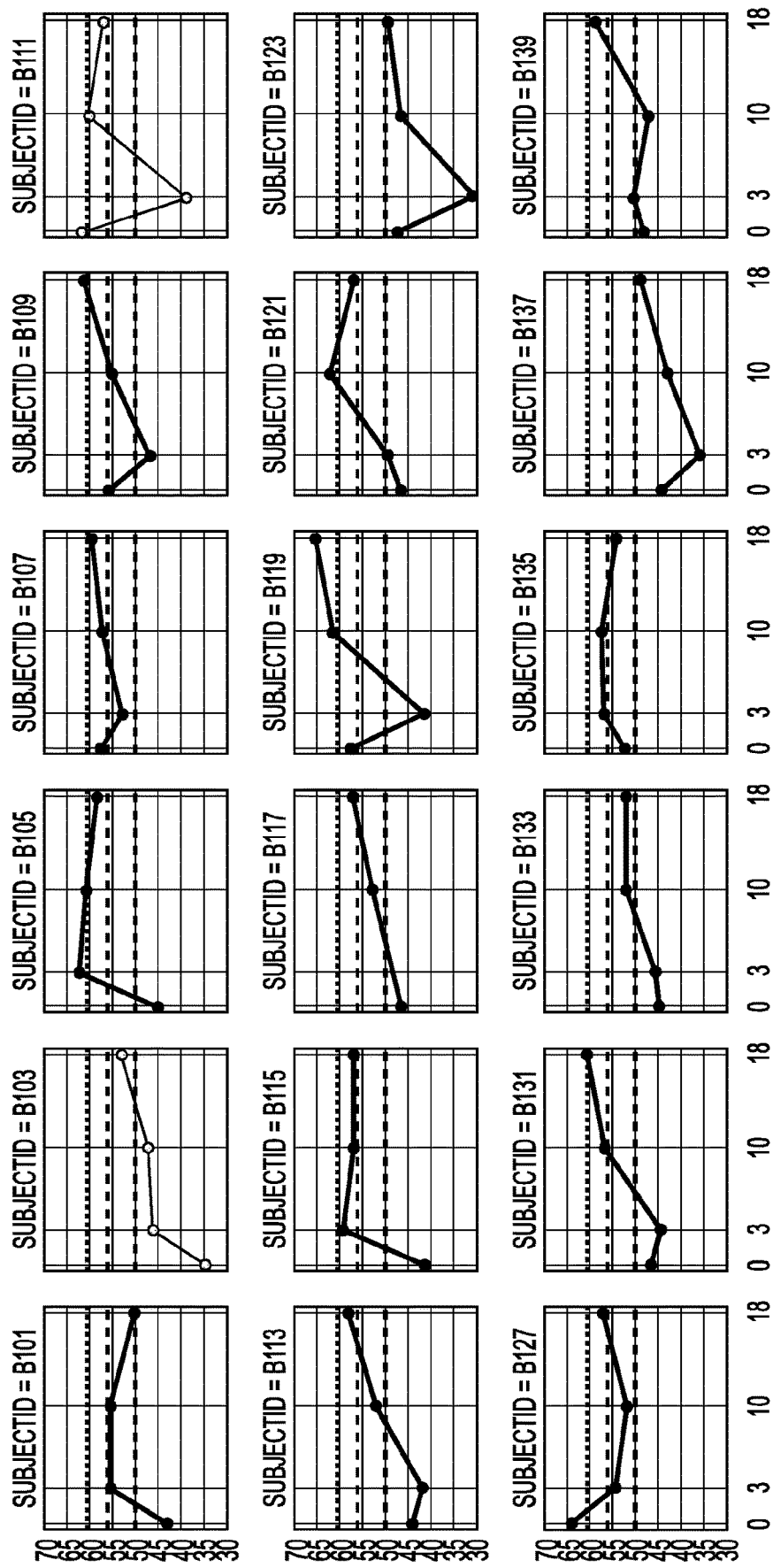
Figure 14C:
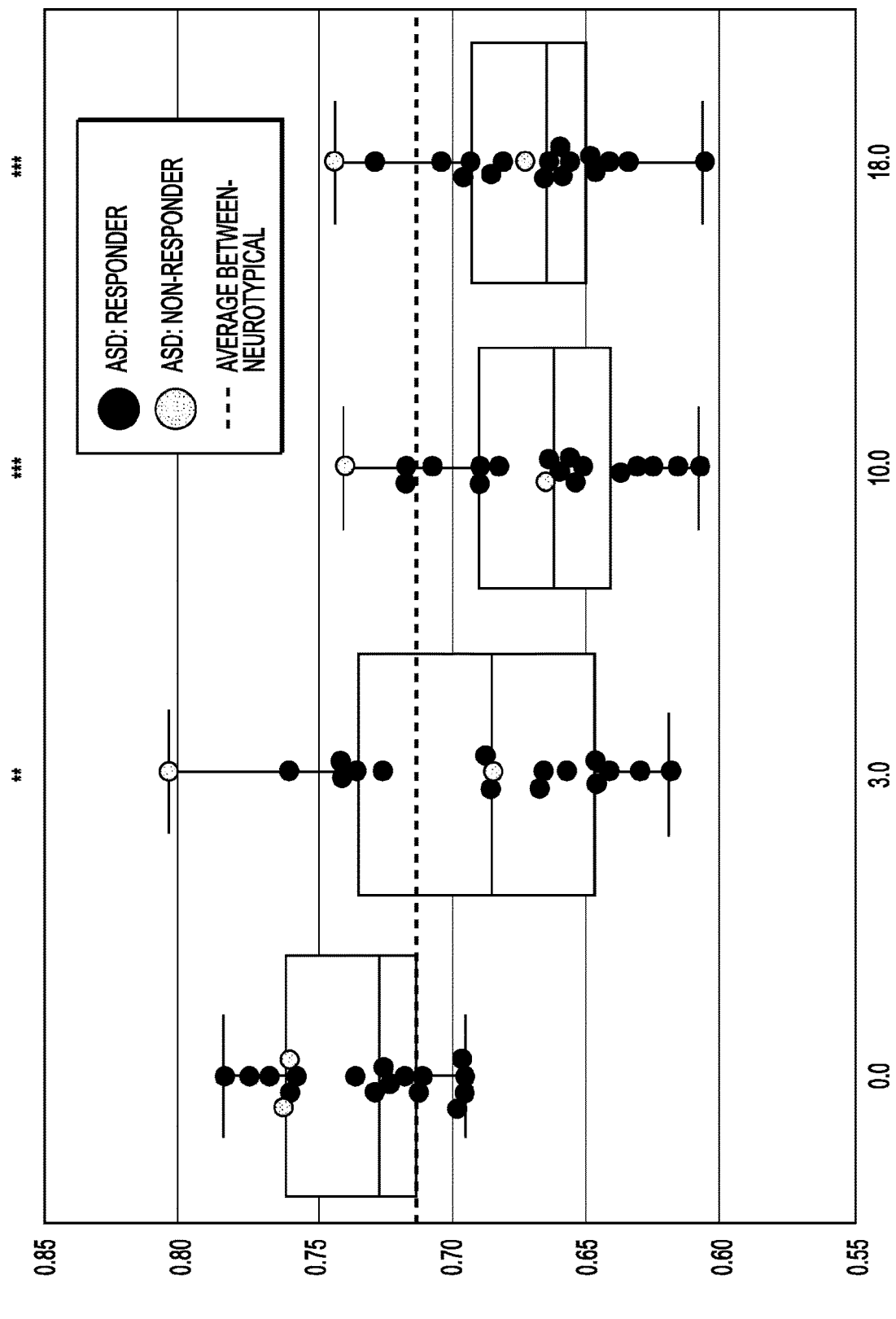
Figure 14D:
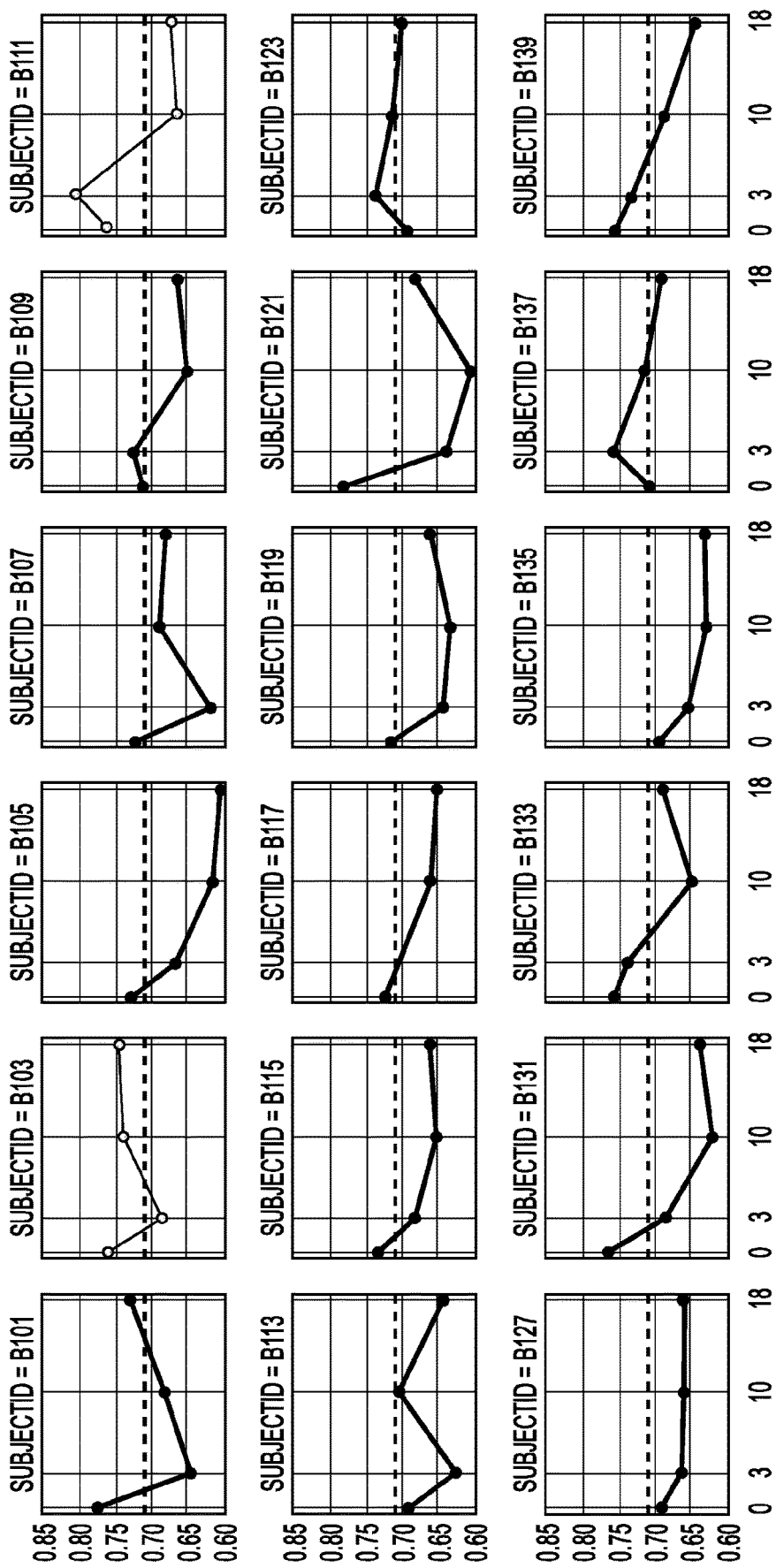
Figure 14E:
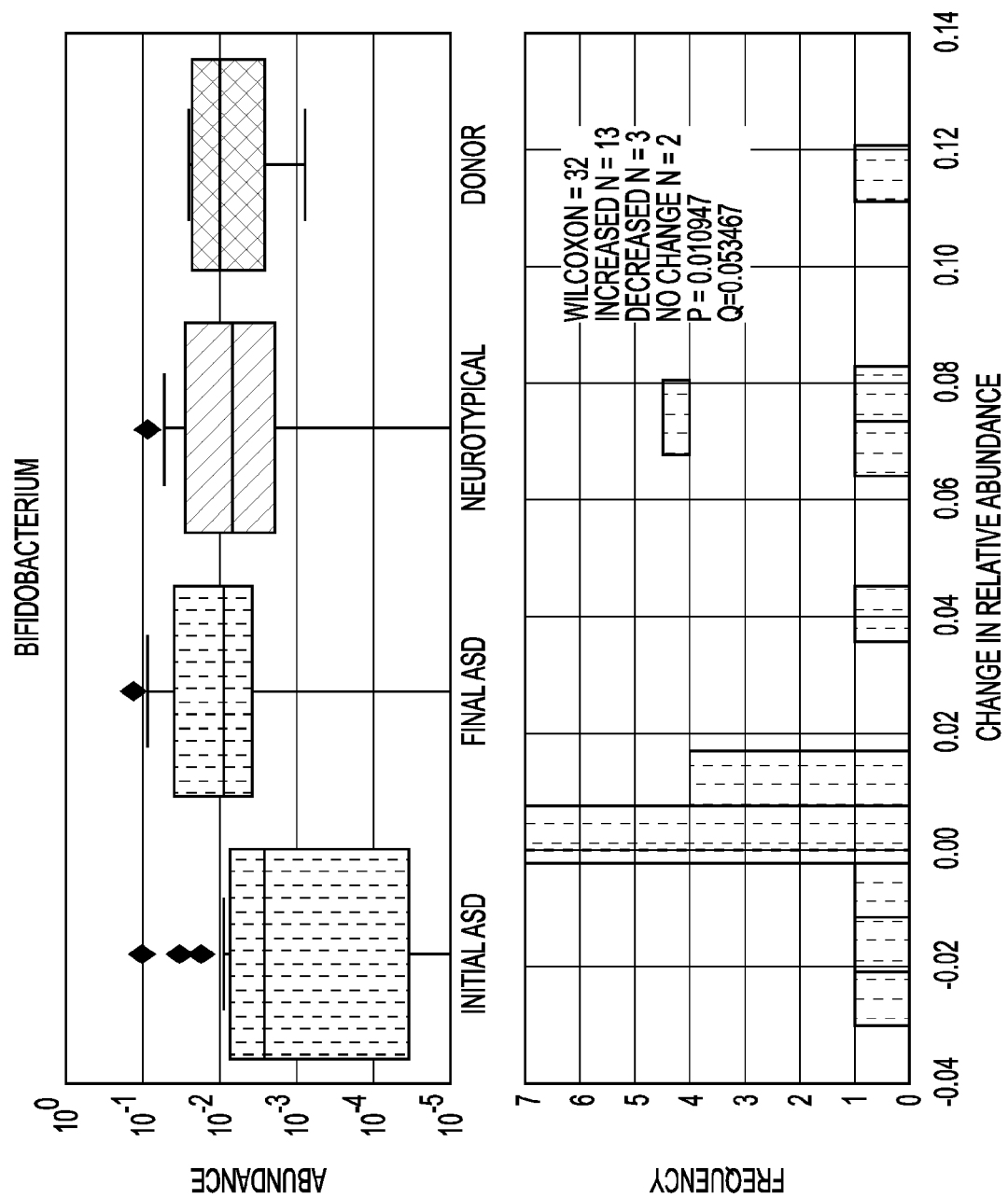
Figure 14F:
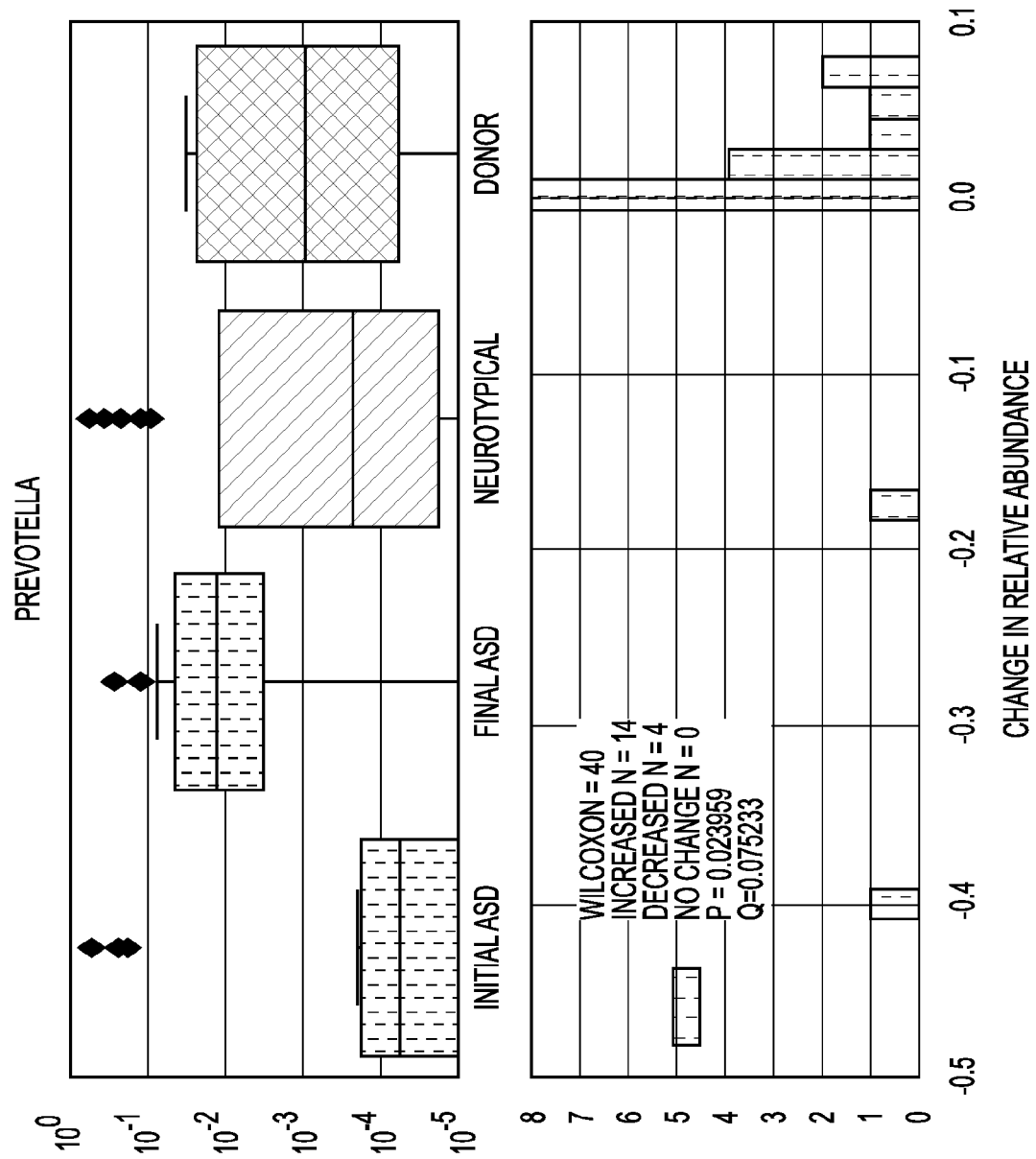
Figure 14G:
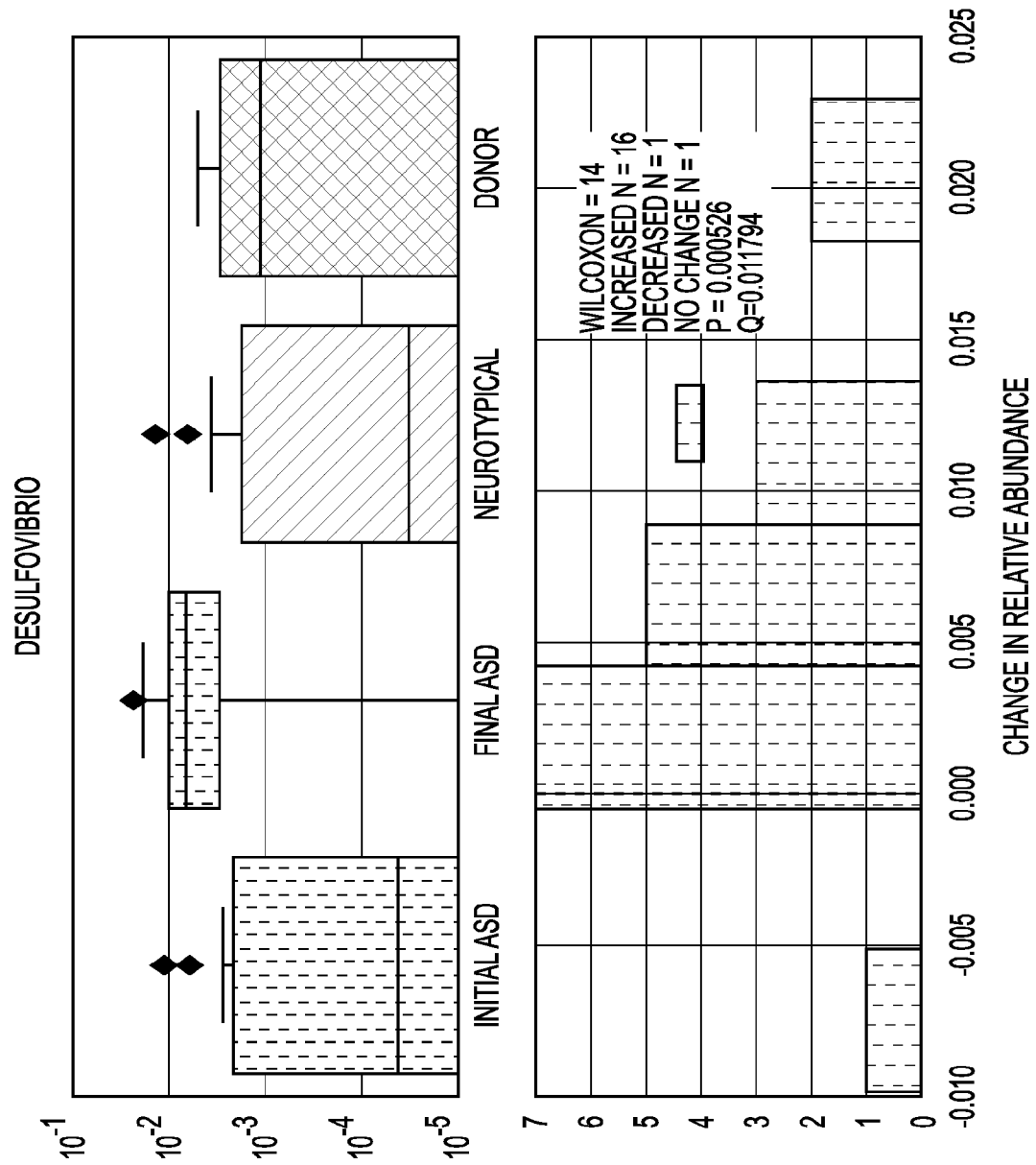
Figure 14H:
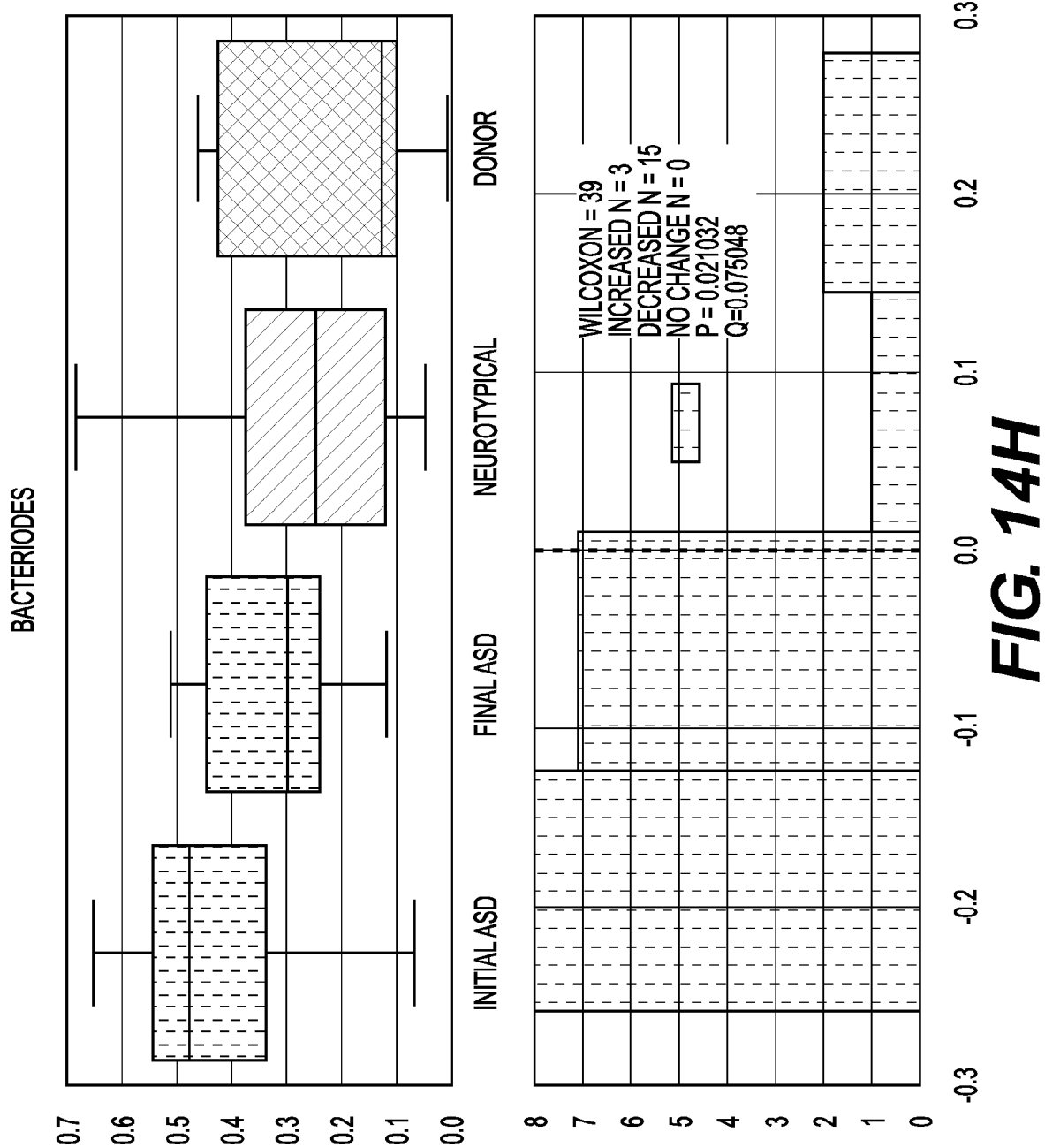

Fourth, the Vineland Adaptive Behavior Scale II (VABS-II) scoring found that the average developmental age increased by 1.4 years (p<0.001, VABS-II) and across all sub-domain areas (FIG. 13) during MTT; though the final VABS-II score is still lower than their chronological age. VABS-II is a measure of the functioning level in four different domains: Communication, Daily Living Skills, Socialization, and Motor Skills, based on 11 sub-domains. Among 11 subscales, Fine and Gross Motor skills are excluded, since these two subscales for the Vineland are only calculated up to 6.8 years and most children with ASD improved near to the limit of the scale. The other 9 subscales and their average are compared between the baseline and at the end of the study. The MTT treatment resulted in a significant increase in average developmental age, from 5.4 years at baseline to 6.8 years at the end of the study (p<0.001). A gain of 1.4 years within 18 weeks of the study is a substantial increase, but they still remained below their chronological age of 10.9 years. Significant improvements are also observed in all 9 subscale areas with the largest gains in Interpersonal Skills (2.2 years), Personal Living Skills (1.8 years), and Coping Skills (1.7 years) (FIG. 13). It is notable that the major impairments in ASD, namely Receptive language, Expressive language, and Interpersonal skills, are among the lowest initial scores, with initial developmental ages of 3.1 years, 4.5 years, and 2.9 years, respectively; all three areas had substantial improvements of 1.3, 1.1, and 2.2 years, respectively.

Finally, the MTT appears to be beneficial across both younger and older individuals (no significant correlations between age and GSRS or CARS improvement) and whether the initial MTT dose is received orally or rectally. Under our sample size, no difference is observed in efficacy of treatment or clinical outcomes whether MTT is initially administered rectally or orally.

Together these findings show that MTT is well-tolerated across an age-diverse cohort of 18 ASD-afflicted children. MTT is also effective as it led to significant improvements in both GI- and behavior-related symptoms that are sustained at least 8 weeks after treatment.

Example 12: Gut Microbiome Analysis

Changes in the bacterial diversity of gut samples from ASD patients or neurotypical participants are evaluated for correlates to the observed clinical improvements. Briefly, bacteria are surveyed by standard sequencing of 16S rRNA gene PCR-amplicons and definition of operational taxonomic units (OTUs). Abundance profiles of microbial OTUs are then statistically evaluated for changes over time.

It is observed that gut microbiota are significantly less diverse in ASD children than controls at baseline (FIG. 14, panel a; one-tailed t-test t=−2.25, p=0.015, n=18). After MTT, however, bacterial diversity increased in ASD children (FIG. 14, panel a; paired two-tailed t-test t=4.56, p=0.0003, n=18) such that median richness at week 18 is statistically indistinguishable across the ASD and control groups (FIG. 14, panel a; two-tailed t-test t=0.47, p=0.64, n=18). This increase is observed in nearly all individuals including one of the two non-responders (subjects whose GI symptoms do not improve) (FIG. 14, panel b). Higher gut microbiota richness is associated with healthy states. This is presumably, without being bound to any scientific theory, due to resilience afforded by higher functional redundancy.

It is also observed that the donor microbiota at least partially engrafted in the recipient gut. Specifically, the unweighted UniFrac distance, a qualitative measure of microbiota phylogenetic similarity, between the recipient gut and their most recent donor sample significantly decreases over time (FIG. 14, panel c; p<0.01 at three weeks and p<0.001 at 10 and 18 weeks), and remained more similar to the donor's microbiota 8 weeks after treatment stopped. By the end of treatment (week 10) and even 8 weeks after treatment stopped (week 18), the distance between the recipient and the donor microbiota is less than normal interpersonal microbiota variation (FIG. 14, panel c). Since exogenous bacteria are usually washed out within a month in the human gut, these signatures of engraftment indicate that MTT overcame "colonization resistance". The degree of engraftment varied across participants, which potentially reflects variation in starting gut microbiota and diets.

It was further observed that, consistent with a lack of difference in treatment efficacy between rectal and oral administration, receiving MTT either orally or rectally does not lead to different patterns in patients' gut microbiota diversity changes. (FIG. 15).

Procedures for microbiome 16S rDNA library preparation, sequencing, and analysis are summarized below.

Parents are asked to collect stool samples from their child on approximately days 0, 21, 70, and 126, and to collect fecal swabs bi-weekly on days 0, 14, 21, 28, 42, 56, 70, 84, 98, 112, and 126. The stool samples are analyzed to determine the types and amounts of gut microbiota present. For safety tests, blood and urine samples are also collected on approximately days 0, 19, 33, and 74. During the study, the participants met with the physician for an initial physical evaluation (including review of medical history) and following evaluations on days 16, 30, and 74. The physician had a phone consult with families on days 7, 21, 42, and 130, and more frequently if adverse symptoms occurred, or if families had any questions. Neurotypical participants do not receive any treatment. They simply provided stool samples (at weeks 0 and 19), and swab samples every 2 weeks.

Microbial DNA from stools, swabs, and donor samples is extracted with PowerSoil® DNA Isolation Kit (Mobio Carlsbard, Calif.). 16S rRNA library for MiSeq Illumina platform, is constructed according to the protocol from Earth Microbiome Project. The barcoded primer set 515f-806r for pair-ended sequencing of the 16s rRNA V4 region is used (Caporaso et al. *ISME Journal*, 6:1621-24 (2012)). Library preparation and sequencing work is performed at the Microbiome Analysis Laboratory in the Swette Center for Environmental Biotechnology. The used primers amplify both bacterial and archaeal 16S rRNA. No changes specific to archaea are observed.

Sequencing data are analyzed using QIIME 1.9.1 (Caporaso et al. *Nature Methods* 7:335-36 (2010)), biom-format version 2.1.5 (McDonald et al. *Gigascience,* 1:6 (2012)), vsearch version 1.7.0 (https://github.com/torognes/vsearch), SSU-ALIGN 0.1 (Nawrocki, *Bioinformatics,* 25:1335-37 (2009)) and FastTree (Price et al. *Molecular Biology and Evolution,* 26:1641-50 (2009)). Sequence quality control and demultiplexing is performed using QIIME's split libraries fastq.py with default parameters as described in (Bokulich et al, *Nature Methods,* 10:57-U11 (2013)) on a per run basis. The sequences are combined across runs by merging the resulting files using the cat Unix command, and sequences are clustered into OTUs at sequence similarities of 100% and 97%. All commands that are applied for these analyses are provided in the GitHub repository available at http://github.com/gregcaporaso/autism-fmtl.

Microbiome profiles across even sampling depths and OTU percent identity thresholds are analyzed to achieve the maximum resolution in OTUs. This can reveal important differences in microbiomes that are apparent only by observing differences in presence, absence, and abundance of closely related taxa that may be grouped into single OTUs at the commonly used 97% similarity threshold. Both 100% and 97% OTUs are therefore defined. The analysis here focused on the 100% OTUs, but also compared features of the microbiome to those computed based on 97% OTUs for validation.

To validate the method, it is further confirmed that the measures of community richness and composition used in our study are correlated between the 100% and 97% OTUs, such that if analyses are instead performed on 97% OTUs, similar results would be achieved. Specifically, Faith PD (Pearson r=0.97038, p<0.001, n=569), unweighted UniFrac (Mantel r: 0.92999, p<0.001, n=569), and weighted UniFrac (Mantel r: 0.76651, p<0.001, n=569) are all highly correlated across the two OTU clustering thresholds, suggesting that the same conclusions would be drawn with either approach. Small differences are expected, as there are many more 100% OTUs than 97% OTUs.

Similarly, the richness and composition metrics are computed at even sampling (rarefaction) depths of 5721 and 10,040 on our 100% OTU data. The lower depth allowed for maximizing the number of samples that could be analyzed, and comparison to the higher depth allows for confirming that results would be similar if more sequences are retained. Faith PD (Pearson r=0.99738, p<0.001, n=548), unweighted UniFrac (Mantel r: 0.97296, p<0.001), and weighted UniFrac (Mantel r: 0.99953, p<0.001) are all highly correlated across sampling depths, suggesting that the same conclusions would be drawn based from either sampling depth.

A customized pipeline is used to compute 100% OTUs. First, sequences are clustered into 100% OTUs with vsearch. The resulting data are loaded into a BIOM table using the biom from-uc command. OTUs that occurred in only one sample are filtered from the table for computational efficiency. OTU representative sequences are aligned with ssu-align, and high entropy positions are filtered with ssu-mask. A phylogenetic tree is built using FastTreeMP for phylogenetic diversity analyses. Taxonomy is assigned to the representative sequences using QIIME's RDP Classifier wrapper against the Greengenes 13_5 reference database. Alpha and beta diversity analyses are performed using QIIME's core_diversity_analyses.py, at rarefaction depths of 5721 (to retain as many samples as possible), and 10,000 to confirm that results are similar with more sequences per sample. Meanwhile, 97% OTUs are computed using QIIME's pick_open_reference_otus.py with the Greengenes 13_5 reference database and default parameters. Alpha and beta diversity analyses are performed using QIIME's core diversity analyses.py at a rarefaction depth of 5721.

Example 13: MTT Changes the Abundance of Selected Bacterial Genera in ASD Patients Several bacterial genera changed their abundance significantly following MTT. These genera include *Bifidobacterium* (FIG. 14, panel e), *Prevotella* (FIG. 15, panel f) and *Desulfovibrio* (FIG. 15, panel g) which both increased in abundance, and *Bacteroides* (FIG. 15, panel h), which decreased in abundance. Additional information for taxonomic changes accompanying MTT is provided in Table 6.

Previous reports asserted that *Bifidobacterium* are under-represented in ASD-afflicted children (Buie et al., *Pediatrics* 125, S1-S18 (2010); Bravo et al., *PNAS* 108:16050-55 (2011)). This is also observed in this study at baseline (two-tailed Mann-Whitney U-test p<0.05), but following MTT, *Bifidobacterium* significantly increased 4-fold to a median final relative abundance of 1.0% (FIG. 14, panel e), this suggests strong engraftment by these microbes in particular.

*Prevotella* are observed to be under-represented in ASD-afflicted children (at baseline median neurotypical and ASD abundances are 0.022% and 0.005%, respectively), but following MTT *Prevotella* increased 250-fold to a median final abundance of approximately 1.3% (Wilcoxon statistic: 40, p=0.024, FDR-corrected p=0.075). Along with *Prevotella*, *Desulfovibrio* also increased ~150-fold after MTT from baseline to 8 weeks after treatment. Without being bound to any scientific theory, this suggests strong engraftment by this microbe in particular. Both *Desulfovibrio* and *Prevotella* are on average more abundant in MTT recipients following treatment than in the donor samples, illustrating that the transferred microbiota adapts in its new host, but also that MTT changes the gut environment in a way that is more hospitable to recruit new commensal bacteria. Taken together, these data suggest that MTT successfully shifts the ASD microbiota toward that of age/gender matched healthy controls and to that of their donors.

TABLE 6

Selected fecal bacterial genera change their abundance in response to MTT. This table shows the abundance of different genera of bacteria at baseline and 8 weeks after MTT for the ASD group. The p-values show which results are statistically significant without correction for multiple hypothesis testing, and the q values show which results are significant (q < 0.05) or marginally significant (q < 0.10) after correction for multiple hypothesis testing. The following genera show a significant increase: *Bifidobacterium*, *Prevotella*, and *Desulfovibirio*; The following genus showed a marginally significant decrease: *Bacteroides* and *Eggerthella*.

| Taxonomy | Fold donor enrichment | Fold final enrichment | Donor median abundance | Neurotypical median abundance | Initial ASD median abundance |
|---|---|---|---|---|---|
| k_Bacteria; p_Proteobacteria; c_Betaproteobacteria; o_Burkholderiales; f_Oxalobacteraceae | inf | inf | 2.10E-05 | 0 | 0 |
| k_Bacteria; p_Proteobacteria; c_Betaproteobacteria; o_Burkholderiales; f_Oxalobacteraceae; g_Oxalobacter | inf | inf | 0 | 0 | 0 |
| k_Bacteria; p_Bacteroidetes; c_Bacteroidia; o_Bacteroidales; f_S24-7; g_ | inf | inf | 0.003035093 | 0 | 0 |
| k_Bacteria; p_Bacteroidetes; c_Bacteroidia; o_Bacteroidales; f_S24-7 | inf | inf | 0.003035093 | 0 | 0 |

TABLE 6-continued

Selected fecal bacterial genera change their abundance in response to MTT. This table shows the abundance of different genera of bacteria at baseline and 8 weeks after MTT for the ASD group. The p-values show which results are statistically significant without correction for multiple hypothesis testing, and the q values show which results are significant (q < 0.05) or marginally significant (q < 0.10) after correction for multiple hypothesis testing. The following genera show a significant increase: *Bifidobacterium*, *Prevotella*, and *Desulfovibirio*; The following genus showed a marginally significant decrease: *Bacteroides* and *Eggerthella*.

| | | | | | |
|---|---|---|---|---|---|
| k_Bacteria; p_Firmicutes; c_Clostridia; o_Clostridiales; f_Ruminococcaceae; g_Gemmiger | 2.001821375 | 6.148439423 | 0.005964801 | 0.007595364 | 0.002979687 |
| k_Bacteria; p_Proteobacteria; c_Betaproteobacteria; o_Burkholderiales; f_Comamonadaceae | inf | inf | 0.000505136 | 0 | 0 |
| k_Bacteria; p_Proteobacteria; c_Deltaproteobacteria; o_Desulfovibrionales; f_Desulfovibrionaceae; g_Desulfovibrio | 26.54064356 | 147.603739 | 0.001180314 | 3.36E-05 | 4.45E-05 |
| k_Bacteria; p_Firmicutes; c_Clostridia; o_Clostridiales; f_Ruminococcaceae; g_Anaerofilum | inf | inf | 0 | 0 | 0 |
| k_Bacteria; p_Proteobacteria; c_Betaproteobacteria; o_Burkholderiales; Other; Other | inf | inf | 0.00065189 | 0 | 0 |
| k_Bacteria; p_Proteobacteria; c_Betaproteobacteria; o_Burkholderiales; Other | inf | inf | 0.00065189 | 0 | 0 |
| k_Bacteria; p_Firmicutes; c_Clostridia; o_Clostridiales; f_Ruminococcaceae; g_Subdoligranulum | inf | inf | 0 | 4.21E-05 | 0 |
| k_Bacteria; p_Proteobacteria; c_Alphaproteobacteria; o_RF32 | inf | inf | 0.00035831 | 0 | 0 |
| k_Bacteria; p_Proteobacteria; c_Alphaproteobacteria; o_RF32; f_; g_ | inf | inf | 0.00035831 | 0 | 0 |
| k_Bacteria; p_Proteobacteria; c_Alphaproteobacteria; o_RF32; f_ | inf | inf | 0.00035831 | 0 | 0 |
| k_Bacteria; p_Lentisphaerae; c_[Lentisphaeria]; o_Victivallales | inf | inf | 0 | 0 | 0 |
| k_Bacteria; p_Lentisphaerae; c_[Lentisphaeria] | inf | inf | 0 | 0 | 0 |
| k_Bacteria; p_Lentisphaerae | inf | inf | 0 | 0 | 0 |
| k_Bacteria; p_Lentisphaerae; c_[Lentisphaeria]; o_Victivallales; f_Victivallaceae | inf | inf | 0 | 0 | 0 |
| k_Bacteria; p_Actinobacteria; c_Coriobacteriia; o_Coriobacteriales; f_Coriobacteriaceae; g_Adlercreutzia | 0 | 4.081749272 | 0 | 5.23E-05 | 4.89E-05 |
| k_Bacteria; p_Proteobacteria; c_Deltaproteobacteria; o_Desulfovibrionales; f_Desulfovibrionaceae | 1.313603645 | 3.843000937 | 0.002789742 | 0.001461841 | 0.002123732 |
| k_Bacteria; p_Proteobacteria; c_Deltaproteobacteria; o_Desulfovibrionales | 1.313603645 | 3.843000937 | 0.002789742 | 0.001461841 | 0.002123732 |
| k_Bacteria; p_Proteobacteria; c_Deltaproteobacteria | 1.313603645 | 3.843000937 | 0.002789742 | 0.001461841 | 0.002123732 |
| k_Bacteria; p_Bacteroidetes; c_Bacteroidia; o_Bacteroidales; f_[Odoribacteraceae]; g_Butyricimonas | inf | inf | 0.000105144 | 0 | 0 |
| k_Bacteria; p_Firmicutes; c_Clostridia; o_Clostridiales; f_Lachnospiraceae; g_Ruminococcus | 0 | 0 | 0 | 9.72E-05 | 0.000225701 |
| k_Bacteria; p_Firmicutes; c_Clostridia; o_Clostridiales; f_Peptostreptococcaceae; g_ | 6.827225474 | 2.419218284 | 0.007000977 | 0.002181422 | 0.00102545 |
| k_Bacteria; p_Proteobacteria; c_Alphaproteobacteria | inf | inf | 0.000505306 | 3.41E-05 | 0 |
| k_Bacteria; p_Firmicutes; c_Clostridia; o_Clostridiales; f_Veillonellaceae; g_Veillonella | 0.522843938 | 0 | 4.59E-05 | 4.54E-05 | 8.79E-05 |
| k_Bacteria; p_Actinobacteria | 2.88572859 | 3.028147004 | 0.010686058 | 0.00745319 | 0.003703071 |
| k_Bacteria; p_Firmicutes; c_Clostridia; o_Clostridiales; f_ | 5.713487631 | 6.369176097 | 0.018777814 | 0.015906199 | 0.003286576 |
| k_Bacteria; p_Firmicutes; c_Clostridia; o_Clostridiales; f_; g_ | 5.713487631 | 6.369176097 | 0.018777814 | 0.015906199 | 0.003286576 |
| k_Bacteria; p_Actinobacteria; c_Actinobacteria; o_Bifidobacteriales | 3.807675238 | 3.673005325 | 0.010264517 | 0.007225959 | 0.002695744 |
| k_Bacteria; p_Actinobacteria; c_Actinobacteria; o_Bifidobacteriales; f_Bifidobacteriaceae | 3.807675238 | 3.673005325 | 0.010264517 | 0.007225959 | 0.002695744 |
| k_Bacteria; p_Actinobacteria; c_Actinobacteria; o_Bifidobacteriales; f_Bifidobacteriaceae; g_Bifidobacterium | 3.807675238 | 3.664672999 | 0.010264517 | 0.007225959 | 0.002695744 |
| k_Bacteria; p_Actinobacteria; c_Actinobacteria | 3.742668409 | 3.626520891 | 0.010264517 | 0.007271405 | 0.002742566 |
| k_Bacteria; p_Actinobacteria; c_Coriobacteriia; o_Coriobacteriales; f_Coriobacteriaceae; g_Eggerthella | 0 | 0.585844581 | 0 | 0 | 9.42E-05 |
| k_Bacteria; p_Bacteroidetes | 0.344495799 | 0.826138917 | 0.210193161 | 0.404768129 | 0.610147241 |
| k_Bacteria; p_Bacteroidetes; c_Bacteroidia | 0.344418317 | 0.825842598 | 0.21011159 | 0.404637424 | 0.610047663 |
| k_Bacteria; p_Bacteroidetes; c_Bacteroidia; o_Bacteroidales | 0.344418317 | 0.825842598 | 0.21011159 | 0.404637424 | 0.610047663 |
| k_Bacteria; p_Firmicutes; Other; Other; Other; Other | 1.03418292 | 2.13255533 | 0.000147539 | 0.0002105 | 0.000142663 |
| k_Bacteria; p_Firmicutes; Other; Other | 1.03418292 | 2.13255533 | 0.000147539 | 0.0002105 | 0.000142663 |
| k_Bacteria; p_Firmicutes; Other; Other; Other | 1.03418292 | 2.13255533 | 0.000147539 | 0.0002105 | 0.000142663 |
| k_Bacteria; p_Firmicutes; Other | 1.03418292 | 2.13255533 | 0.000147539 | 0.0002105 | 0.000142663 |
| k_Bacteria; p_Firmicutes; c_Clostridia; o_Clostridiales; f_Ruminococcaceae; Other | 1.747310327 | 2.016617709 | 0.007878736 | 0.008887959 | 0.004509065 |
| k_Bacteria; p_Firmicutes; c_Clostridia; o_Clostridiales; f_Ruminococcaceae; g_Anaerotruncus | 0.247844155 | 0.709404861 | 1.63E-05 | 3.36E-05 | 6.58E-05 |
| k_Bacteria; p_Bacteroidetes; c_Bacteroidia; o_Bacteroidales; f_Bacteroidaceae | 0.268505262 | 0.630391858 | 0.127006656 | 0.248714588 | 0.473013658 |
| k_Bacteria; p_Bacteroidetes; c_Bacteroidia; o_Bacteroidales; f_Bacteroidaceae; g_Bacteroides | 0.268505262 | 0.630340467 | 0.127006656 | 0.248714588 | 0.473013658 |
| k_Bacteria; p_Bacteroidetes; c_Bacteroidia; o_Bacteroidales; f_Prevotellaceae | 17.65719148 | 248.1220024 | 0.000948467 | 0.000221251 | 5.37E-05 |
| k_Bacteria; p_Bacteroidetes; c_Bacteroidia; o_Bacteroidales; f_Prevotellaceae; g_Prevotella | 17.65719148 | 247.9923587 | 0.000948467 | 0.000221251 | 5.37E-05 |

TABLE 6-continued

Selected fecal bacterial genera change their abundance in response to MTT. This table shows the abundance of different genera of bacteria at baseline and 8 weeks after MTT for the ASD group. The p-values show which results are statistically significant without correction for multiple hypothesis testing, and the q values show which results are significant (q < 0.05) or marginally significant (q < 0.10) after correction for multiple hypothesis testing. The following genera show a significant increase: *Bifidobacterium*, *Prevotella*, and *Desulfovibirio*; The following genus showed a marginally significant decrease: *Bacteroides* and *Eggerthella*.

| | | | | | |
|---|---|---|---|---|---|
| k__Bacteria; p__Proteobacteria | 2.192234341 | 2.272050415 | 0.038251251 | 0.01496568 | 0.017448523 |
| k__Bacteria; p__Bacteroidetes; c__Bacteroidia; o__Bacteroidales; f__Porphyromonadaceae; g__Parabacteroides | 0.433529741 | 2.062863986 | 0.009768805 | 0.026376327 | 0.022533183 |
| k__Bacteria; p__Bacteroidetes; c__Bacteroidia; o__Bacteroidales; f__Porphyromonadaceae | 0.411630428 | 1.959236616 | 0.009768805 | 0.026376327 | 0.02373198 |
| k__Bacteria; p__Firmicutes; c__Clostridia; Other; Other; Other | inf | inf | 0 | 0 | 0 |
| k__Bacteria; p__Firmicutes; c__Clostridia; Other | inf | inf | 0 | 0 | 0 |
| k__Bacteria; p__Firmicutes; c__Clostridia; Other; Other | inf | inf | 0 | 0 | 0 |
| k__Bacteria; p__Actinobacteria; c__Coriobacteriia; o__Coriobacteriales; f__Coriobacteriaceae; g__Collinsella | 0.426757048 | 7.362725286 | 3.26E-05 | 0 | 7.65E-05 |
| k__Bacteria; p__Actinobacteria; c__Coriobacteriia; o__Coriobacteriales; f__Coriobacteriaceae | 0.517161809 | 1.879491712 | 0.0003426 | 0.000522821 | 0.000662462 |
| k__Bacteria; p__Actinobacteria; c__Coriobacteriia | 0.517161809 | 1.879491712 | 0.0003426 | 0.000522821 | 0.000662462 |
| k__Bacteria; p__Actinobacteria; c__Coriobacteriia; o__Coriobacteriales | 0.517161809 | 1.879491712 | 0.0003426 | 0.000522821 | 0.000662462 |
| k__Bacteria; p__Firmicutes; c__Clostridia; o__Clostridiales; f__Lachnospiraceae; Other | 3.017549229 | 0.696152119 | 0.036168755 | 0.013559835 | 0.011986136 |
| k__Bacteria; Other; Other; Other | 1.301001458 | 1.570025829 | 0.000513831 | 0.000716455 | 0.00039495 |
| k__Bacteria; Other; Other; Other; Other | 1.301001458 | 1.570025829 | 0.000513831 | 0.000716455 | 0.00039495 |
| k__Bacteria; Other; Other | 1.301001458 | 1.570025829 | 0.000513831 | 0.000716455 | 0.00039495 |
| k__Bacteria; Other; Other; Other | 1.301001458 | 1.570025829 | 0.000513831 | 0.000716455 | 0.00039495 |
| k__Bacteria; Other | 1.301001458 | 1.570025829 | 0.000513831 | 0.000716455 | 0.00039495 |
| k__Bacteria; p__Firmicutes; c__Clostridia; o__Clostridiales; f__Lachnospiraceae; g__Pseudobutyrivibrio | 2.683981412 | 0 | 0.000126462 | 0 | 4.71E-05 |
| k__Bacteria; p__Bacteroidetes; c__Bacteroidia; o__Bacteroidales; f__Rikenellaceae; g__Alistipes | 0.058011525 | 0.514869524 | 0.002008032 | 0.015744349 | 0.034614365 |
| k__Bacteria; p__Firmicutes; c__Clostridia; o__Clostridiales; f__Lachnospiraceae; g__Anaerostipes | 1.276736899 | 1.974407509 | 0.000542711 | 0.000836392 | 0.000425077 |
| k__Bacteria; p__Firmicutes; c__Clostridia; o__Clostridiales; f__Ruminococcaceae; g__Oscillospira | 0.524902192 | 1.417823714 | 0.01100073 | 0.020311601 | 0.020957675 |
| k__Bacteria; p__Firmicutes; c__Clostridia; o__Clostridiales; f__Ruminococcaceae; g__Butyricicoccus | 5.455129435 | 2.094743099 | 0.002339551 | 0.000637078 | 0.000428872 |
| k__Bacteria; p__Actinobacteria; c__Actinobacteria; o__Actinomycetales; f__Actinomycetaceae; g__Actinomyces | 0 | 0 | 0 | 0 | 3.15E-05 |
| k__Bacteria; p__Bacteroidetes; c__Bacteroidia; o__Bacteroidales; f__Rikenellaceae; g__ | 0.120110717 | 2.207642958 | 0.000967321 | 0.009714929 | 0.008053581 |
| k__Bacteria; p__Firmicutes; c__Bacilli; o__Lactobacillales | 0.769966567 | 0.649684935 | 0.00048844 | 0.000793279 | 0.000634366 |
| k__Bacteria; p__Proteobacteria; c__Gammaproteobacteria; o__Enterobacteriales; f__Enterobacteriaceae; g__Klebsiella | 0 | 0 | 0 | 0 | 9.56E-06 |
| k__Bacteria; p__Firmicutes; c__Clostridia; o__Clostridiales; f__[Tissierellaceae] | 0.994459647 | 1.599142849 | 3.26E-05 | 1.88E-05 | 3.28E-05 |
| k__Bacteria; p__Firmicutes; c__Clostridia; o__Clostridiales; f__Ruminococcaceae | 1.453704892 | 1.110880946 | 0.230557214 | 0.230537983 | 0.158599738 |
| k__Bacteria; p__Bacteroidetes; c__Bacteroidia; o__Bacteroidales; f__[Odoribacteraceae] | 0.831155585 | 4.796755878 | 0.001177609 | 0.001908744 | 0.001416833 |
| k__Bacteria; p__Firmicutes; c__Bacilli; o__Lactobacillales; f__Streptococcaceae | 0.699563524 | 0.706905977 | 0.000407857 | 0.000242931 | 0.000583016 |
| k__Bacteria; p__Proteobacteria; c__Gammaproteobacteria; o__Enterobacteriales; f__Enterobacteriaceae; g__Shigella | 1.193837765 | 0 | 4.59E-05 | 0 | 3.85E-05 |
| k__Bacteria; p__Firmicutes; c__Clostridia; o__Clostridiales; f__Lachnospiraceae; g__Lachnospira | 5.11663948 | 1.440152127 | 0.021681676 | 0.005215694 | 0.004237484 |
| k__Bacteria; p__Firmicutes; c__Clostridia; o__Clostridiales; f__Lachnospiraceae; g__Clostridium | 2.201981808 | 0.70751989 | 0.01978803 | 0.012243708 | 0.008986464 |
| k__Bacteria; p__Firmicutes; c__Clostridia; o__Clostridiales; f__Veillonellaceae; g__Phascolarctobacterium | 3.523547829 | 3.422413343 | 0.003709558 | 0.001636066 | 0.001052791 |
| k__Bacteria; p__Firmicutes; c__Bacilli; o__Lactobacillales; f__Streptococcaceae; g__Streptococcus | 0.590616304 | 0.722103841 | 0.000336757 | 0.000242931 | 0.000570179 |
| k__Bacteria; p__Proteobacteria; c__Gammaproteobacteria; o__Pasteurellales; f__Pasteurellaceae; g__Haemophilus | 6.817633863 | 0.337394452 | 0.000954145 | 6.29E-05 | 0.000139953 |
| k__Bacteria; p__Firmicutes; c__Clostridia; o__Clostridiales; f__Peptostreptococcaceae | 3.357260558 | 1.594334641 | 0.012807989 | 0.00340103 | 0.003815012 |
| k__Bacteria; p__Proteobacteria; c__Gammaproteobacteria; o__Pasteurellales | 7.00622958 | 0.430120039 | 0.00107048 | 0.00010618 | 0.00015279 |
| k__Bacteria; p__Proteobacteria; c__Gammaproteobacteria; o__Pasteurellales; f__Pasteurellaceae | 7.00622958 | 0.430120039 | 0.00107048 | 0.00010618 | 0.00015279 |
| k__Bacteria; p__Firmicutes; c__Bacilli | 1.467041864 | 0.940659447 | 0.00162713 | 0.001510384 | 0.001109123 |
| k__Bacteria; p__Firmicutes; c__Clostridia; o__Clostridiales; f__Lachnospiraceae | 1.813106928 | 0.790901395 | 0.282307099 | 0.178019629 | 0.155703503 |
| k__Bacteria; p__Bacteroidetes; Other; Other; Other; Other | 0.516176178 | 1.201854876 | 8.16E-05 | 7.56E-05 | 0.00015803 |
| k__Bacteria; p__Bacteroidetes; Other; Other | 0.516176178 | 1.201854876 | 8.16E-05 | 7.56E-05 | 0.00015803 |
| k__Bacteria; p__Bacteroidetes; Other | 0.516176178 | 1.201854876 | 8.16E-05 | 7.56E-05 | 0.00015803 |
| k__Bacteria; p__Bacteroidetes; Other; Other; Other | 0.516176178 | 1.201854876 | 8.16E-05 | 7.56E-05 | 0.00015803 |
| k__Bacteria; p__Firmicutes; c__Clostridia; o__Clostridiales; Other | 0.981525478 | 0.90949021 | 0.002480592 | 0.003488372 | 0.002527282 |

TABLE 6-continued

Selected fecal bacterial genera change their abundance in response to MTT. This table shows the abundance of different genera of bacteria at baseline and 8 weeks after MTT for the ASD group. The p-values show which results are statistically significant without correction for multiple hypothesis testing, and the q values show which results are significant (q < 0.05) or marginally significant (q < 0.10) after correction for multiple hypothesis testing. The following genera show a significant increase: *Bifidobacterium*, *Prevotella*, and *Desulfovibirio*; The following genus showed a marginally significant decrease: *Bacteroides* and *Eggerthella*.

| | | | | | |
|---|---|---|---|---|---|
| k__Bacteria; p__Firmicutes; c__Clostridia; o__Clostridiales; Other; Other | 0.981525478 | 0.90949021 | 0.002480592 | 0.003488372 | 0.002527282 |
| k__Bacteria; p__Firmicutes; c__Clostridia; o__Clostridiales; f__Lachnospiraceae; g__Coprococcus | 1.850680871 | 0.812111071 | 0.035388344 | 0.020691033 | 0.019121797 |
| k__Bacteria; p__Verrucomicrobia; c__Verrucomicrobiae; o__Verrucomicrobiales; f__Verrucomicrobiaceae; g__Akkermansia | 0.257961535 | 0.728898333 | 0.000551243 | 0.004473737 | 0.002136918 |
| k__Bacteria; p__Verrucomicrobia; c__Verrucomicrobiae; o__Verrucomicrobiales | 0.254058759 | 0.717870614 | 0.000551243 | 0.004473737 | 0.002169744 |
| k__Bacteria; p__Verrucomicrobia; c__Verrucomicrobiae; o__Verrucomicrobiales; f__Verrucomicrobiaceae | 0.254058759 | 0.717870614 | 0.000551243 | 0.004473737 | 0.002169744 |
| k__Bacteria; p__Verrucomicrobia | 0.254058759 | 0.717870614 | 0.000551243 | 0.004473737 | 0.002169744 |
| k__Bacteria; p__Verrucomicrobia; c__Verrucomicrobiae | 0.254058759 | 0.717870614 | 0.000551243 | 0.004473737 | 0.002169744 |
| k__Bacteria; p__Tenericutes | inf | inf | 0.000880971 | 0.000499909 | 0 |
| k__Bacteria; p__Firmicutes; c__Clostridia | 1.625088942 | 1.142513703 | 0.515044329 | 0.496217231 | 0.31693301 |
| k__Bacteria; p__Firmicutes; c__Clostridia; o__Clostridiales | 1.625088942 | 1.142513703 | 0.515044329 | 0.495923993 | 0.31693301 |
| k__Bacteria; p__Firmicutes; c__Erysipelotrichi; o__Erysipelotrichales; f__Erysipelotrichaceae; g__ | 1.269226262 | 0.43813951 | 0.0056043 | 0.005308983 | 0.004415525 |
| k__Bacteria; p__Actinobacteria; c__Coriobacteriia; o__Coriobacteriales; f__Coriobacteriaceae; g__ | 1.243790419 | 1.288374997 | 0.000105144 | 9.09E−05 | 8.45E−05 |
| k__Bacteria; p__Firmicutes | 1.601955527 | 1.167896058 | 0.521797051 | 0.523011392 | 0.325725054 |
| k__Bacteria; p__Proteobacteria; c__Betaproteobacteria | 3.265311462 | 1.561772748 | 0.023853623 | 0.008376604 | 0.00730516 |
| k__Bacteria; p__Proteobacteria; c__Betaproteobacteria; o__Burkholderiales | 3.265311462 | 1.557543063 | 0.023853623 | 0.008376604 | 0.00730516 |
| k__Bacteria; p__Firmicutes; c__Clostridia; o__Clostridiales; f__Lachnospiraceae; g__Lachnobacterium | 9.072677791 | 0.974782185 | 0.0007994 | 9.09E−05 | 8.81E−05 |
| k__Bacteria; p__Firmicutes; c__Erysipelotrichi; o__Erysipelotrichales | 0.908561486 | 0.469731563 | 0.006201479 | 0.007736019 | 0.006825602 |
| k__Bacteria; p__Firmicutes; c__Erysipelotrichi | 0.908561486 | 0.469731563 | 0.006201479 | 0.007736019 | 0.006825602 |
| k__Bacteria; p__Firmicutes; c__Erysipelotrichi; o__Erysipelotrichales; f__Erysipelotrichaceae | 0.908561486 | 0.469731563 | 0.006201479 | 0.007736019 | 0.006825602 |
| k__Bacteria; p__Proteobacteria; c__Betaproteobacteria; o__Burkholderiales; f__Alcaligenaceae | 3.148210789 | 1.472594374 | 0.02228209 | 0.008376604 | 0.0070777 |
| k__Bacteria; p__Proteobacteria; c__Betaproteobacteria; o__Burkholderiales; f__Alcaligenaceae; g__Sutterella | 3.140280787 | 1.464825274 | 0.022225964 | 0.008376604 | 0.0070777 |
| k__Bacteria; p__Firmicutes; c__Clostridia; o__Clostridiales; f__Lachnospiraceae; g__Blautia | 1.306385665 | 1.029190844 | 0.025648711 | 0.021260472 | 0.019633338 |
| k__Bacteria; p__Firmicutes; c__Erysipelotrichi; o__Erysipelotrichales; f__Erysipelotrichaceae; g__Coprobacillus | 0 | 0 | 0 | 6.29E−05 | 4.53E−05 |
| k__Bacteria; p__Bacteroidetes; c__Bacteroidia; o__Bacteroidales; Other | 0.536601183 | 1.743188226 | 0.0001142 | 0.000221251 | 0.000212821 |
| k__Bacteria; p__Bacteroidetes; c__Bacteroidia; o__Bacteroidales; Other; Other | 0.536601183 | 1.743188226 | 0.0001142 | 0.000221251 | 0.000212821 |
| k__Bacteria; p__Actinobacteria; c__Actinobacteria; o__Actinomycetales | 0 | 1.218333024 | 0 | 3.75E−05 | 4.61E−05 |
| k__Bacteria; p__Proteobacteria; c__Deltaproteobacteria; o__Desulfovibrionales; f__Desulfovibrionaceae; g__Bilophila | 0.869794269 | 1.174806104 | 0.001031152 | 0.000932554 | 0.001185512 |
| k__Bacteria; p__Firmicutes; c__Clostridia; o__Clostridiales; f__Peptostreptococcaceae; Other | 2.084966197 | 1.007207434 | 0.004700179 | 0.001875469 | 0.002254319 |
| k__Bacteria; p__Firmicutes; c__Clostridia; o__Clostridiales; f__Clostridiaceae; g__Clostridium | 1.518402522 | 0.797478568 | 0.005661055 | 0.003284265 | 0.003728296 |
| k__Bacteria; p__Firmicutes; c__Clostridia; o__Clostridiales; f__Lachnospiraceae; g__Dorea | 1.084132934 | 1.272777939 | 0.003169645 | 0.004715194 | 0.002923668 |
| k__Bacteria; p__Firmicutes; c__Clostridia; o__Clostridiales; f__Ruminococcaceae; g__Faecalibacterium | 3.022482575 | 1.27215778 | 0.157954842 | 0.071420012 | 0.052259968 |
| k__Bacteria; p__Firmicutes; c__Clostridia; o__Clostridiales; f__Peptostreptococcaceae; g__Clostridium | 1.048841882 | 1.267345199 | 0.000277343 | 0.000252042 | 0.000264428 |
| k__Bacteria; p__Firmicutes; c__Erysipelotrichi; o__Erysipelotrichales; f__Erysipelotrichaceae; g__Clostridium | 0.621776194 | 0.823944028 | 0.000309971 | 0.000388689 | 0.000498525 |
| k__Bacteria; p__Firmicutes; c__Clostridia; o__Clostridiales; f__Clostridiaceae; g__ | 2.504352946 | 13.14941079 | 4.21E−05 | 0.000971723 | 1.68E−05 |
| k__Bacteria; p__Firmicutes; c__Erysipelotrichi; o__Erysipelotrichales; f__Erysipelotrichaceae; g__Holdemania | 2.309460668 | 1.428020468 | 0.000183748 | 9.29E−05 | 7.96E−05 |
| k__Bacteria; p__Firmicutes; c__Clostridia; o__Clostridiales; f__Clostridiaceae | 1.362144975 | 0.610778314 | 0.008692301 | 0.006038584 | 0.006381333 |
| k__Bacteria; p__Firmicutes; c__Clostridia; o__Clostridiales; f__Ruminococcaceae; g__Clostridium | 0 | 0.901570882 | 0 | 6.29E−05 | 8.79E−05 |
| k__Bacteria; p__Firmicutes; c__Erysipelotrichi; o__Erysipelotrichales; f__Erysipelotrichaceae; g__[Eubacterium] | 0 | 0.419550281 | 0 | 0.000212359 | 0.000157073 |
| k__Bacteria; p__Firmicutes; c__Clostridia; o__Clostridiales; f__Lachnospiraceae; g__Roseburia | 2.583386922 | 0.717930175 | 0.074168314 | 0.042863063 | 0.02870972 |
| k__Bacteria; p__Actinobacteria; c__Actinobacteria; o__Actinomycetales; f__Actinomycetaceae | 0 | 0.647292947 | 0 | 0 | 3.47E−05 |
| k__Bacteria; p__Firmicutes; c__Clostridia; o__Clostridiales; f__Clostridiaceae; g__SMB53 | 3.296707194 | 0.766585538 | 0.000954145 | 0.000201633 | 0.000289424 |
| k__Bacteria; p__Firmicutes; c__Clostridia; o__Clostridiales; f__Lachnospiraceae; g__[Ruminococcus] | 1.00601522 | 1.062751999 | 0.007882812 | 0.007641034 | 0.007835678 |

TABLE 6-continued

Selected fecal bacterial genera change their abundance in response to MTT. This table shows the abundance of different genera of bacteria at baseline and 8 weeks after MTT for the ASD group. The p-values show which results are statistically significant without correction for multiple hypothesis testing, and the q values show which results are significant (q < 0.05) or marginally significant (q < 0.10) after correction for multiple hypothesis testing. The following genera show a significant increase: *Bifidobacterium*, *Prevotella*, and *Desulfovibirio*; The following genus showed a marginally significant decrease: *Bacteroides* and *Eggerthella*.

| Taxonomy | | | | | |
|---|---|---|---|---|---|
| k_Bacteria; p_Firmicutes; c_Clostridia; o_Clostridiales; f_Christensenellaceae; g_ | 0.536877265 | 1.443733623 | 0.000275621 | 0.001406267 | 0.000513379 |
| k_Bacteria; p_Firmicutes; c_Clostridia; o_Clostridiales; f_Lachnospiraceae; g_ | 2.670911283 | 0.683634656 | 0.033267443 | 0.014794342 | 0.012455465 |
| k_Bacteria; p_Proteobacteria; c_Gammaproteobacteria; o_Enterobacteriales; f_Enterobacteriaceae; g_Escherichia | 1.022906515 | 1.930806554 | 0.000505136 | 0.000243811 | 0.000493824 |
| k_Bacteria; p_Firmicutes; c_Clostridia; o_Clostridiales; f_[Mogibacteriaceae]; g_ | 1.137356676 | 1.741723987 | 0.00055665 | 0.001437758 | 0.000489424 |
| k_Bacteria; p_Firmicutes; c_Clostridia; o_Clostridiales; f_Christensenellaceae | 0.536877265 | 1.518256548 | 0.000275621 | 0.001406267 | 0.000513379 |
| k_Bacteria; p_Firmicutes; c_Clostridia; o_Clostridiales; f_Ruminococcaceae; g_Ruminococcus | 1.472940024 | 1.51485443 | 0.028288958 | 0.0437382 | 0.019205778 |
| k_Bacteria; p_Firmicutes; c_Bacilli; o_Turicibacterales; f_Turicibacteraceae; g_Turicibacter | 1.215935696 | 0.955712453 | 0.000299735 | 0.000145758 | 0.000246505 |
| k_Bacteria; p_Firmicutes; c_Bacilli; o_Turicibacterales; f_Turicibacteraceae | 1.215935696 | 0.955712453 | 0.000299735 | 0.000145758 | 0.000246505 |
| k_Bacteria; p_Firmicutes; c_Bacilli; o_Turicibacterales | 1.215935696 | 0.955712453 | 0.000299735 | 0.000145758 | 0.000246505 |
| k_Bacteria; p_Firmicutes; c_Clostridia; o_Clostridiales; f_Veillonellaceae; g_Dialister | 87.44384578 | 1.70820069 | 0.023443618 | 0.00337408 | 0.000268099 |
| k_Bacteria; p_Proteobacteria; c_Gammaproteobacteria; o_Enterobacteriales; f_Enterobacteriaceae | 2.302029237 | 1.663637994 | 0.001682405 | 0.0003368 | 0.000730836 |
| k_Bacteria; p_Proteobacteria; c_Gammaproteobacteria; o_Enterobacteriales | 2.302029237 | 1.663637994 | 0.001682405 | 0.0003368 | 0.000730836 |
| k_Bacteria; p_Proteobacteria; c_Gammaproteobacteria; o_Enterobacteriales; f_Enterobacteriaceae; Other | 0.509840777 | 1.391330932 | 5.43E-05 | 7.21E-05 | 0.000106447 |
| k_Bacteria; p_Bacteroidetes; c_Bacteroidia; o_Bacteroidales; f_Rikenellaceae; Other | 0.147361573 | 1.109505141 | 0.00033646 | 0.001516181 | 0.002283225 |
| k_Bacteria; p_Bacteroidetes; c_Bacteroidia; o_Bacteroidales; f_[Barnesiellaceae] | 9.667924155 | 25.23844637 | 0.000379898 | 0.007586842 | 3.93E-05 |
| k_Bacteria; p_Bacteroidetes; c_Bacteroidia; o_Bacteroidales; f_[Barnesiellaceae]; g_ | 9.667924155 | 25.23844637 | 0.000379898 | 0.007153308 | 3.93E-05 |
| k_Bacteria; p_Firmicutes; c_Clostridia; o_Clostridiales; f_[Mogibacteriaceae] | 1.137356676 | 1.741723987 | 0.00055665 | 0.001437758 | 0.000489424 |
| k_Bacteria; p_Firmicutes; c_Clostridia; o_Clostridiales; f_Veillonellaceae | 4.806417425 | 0.984253727 | 0.030337566 | 0.00905059 | 0.006311888 |
| k_Bacteria; p_Bacteroidetes; c_Bacteroidia; o_Bacteroidales; f_[Odoribacteraceae]; g_Odoribacter | 1.068251023 | 1.746723821 | 0.001072465 | 0.001052221 | 0.001003945 |
| k_Bacteria; p_Bacteroidetes; c_Bacteroidia; o_Bacteroidales; f_Rikenellaceae | 0.060561698 | 0.789582481 | 0.00330151 | 0.03397749 | 0.054514817 |
| k_Bacteria; p_Proteobacteria; c_Gammaproteobacteria | 1.745513701 | 1.302022307 | 0.002229045 | 0.000759536 | 0.001277014 |
| k_Bacteria; p_Firmicutes; c_Clostridia; o_Clostridiales; f_Ruminococcaceae; g_ | 0.708114468 | 0.856367273 | 0.010703294 | 0.031857844 | 0.015115203 |

| Taxonomy | Final ASD median abundance | Wilcoxon | p-value | FDR-corrected p-value (q) |
|---|---|---|---|---|
| k_Bacteria; p_Proteobacteria; c_Betaproteobacteria; o_Burkholderiales; f_Oxalobacteraceae | 0.000142986 | 0 | 6.32E-05 | 0.00273954 |
| k_Bacteria; p_Proteobacteria; c_Betaproteobacteria; o_Burkholderiales; f_Oxalobacteraceae; g_Oxalobacter | 0.000116622 | 0 | 7.90E-05 | 0.00273954 |
| k_Bacteria; p_Bacteroidetes; c_Bacteroidia; o_Bacteroidales; f_S24-7; g_ | 0.000957645 | 3 | 8.72E-05 | 0.00273954 |
| k_Bacteria; p_Bacteroidetes; c_Bacteroidia; o_Bacteroidales; f_S24-7 | 0.000957645 | 3 | 8.72E-05 | 0.00273954 |
| k_Bacteria; p_Firmicutes; c_Clostridia; o_Clostridiales; f_Ruminococcaceae; g_Gemmiger | 0.018320426 | 5 | 6.48E-05 | 0.00273954 |
| k_Bacteria; p_Proteobacteria; c_Betaproteobacteria; o_Burkholderiales; f_Comamonadaceae | 5.84E-05 | 13 | 0.00032 | 0.00840514 |
| k_Bacteria; p_Proteobacteria; c_Deltaproteobacteria; o_Desulfovibrionales; f_Desulfovibrionaceae; g_Desulfovibrio | 0.006564225 | 14 | 0.00053 | 0.01179367 |
| k_Bacteria; p_Firmicutes; c_Clostridia; o_Clostridiales; f_Ruminococcaceae; g_Anaerofilum | 4.71E-05 | 19 | 0.00238 | 0.02249607 |
| k_Bacteria; p_Proteobacteria; c_Betaproteobacteria; o_Burkholderiales; Other; Other | 5.62E-05 | 20 | 0.00115 | 0.02011689 |
| k_Bacteria; p_Proteobacteria; c_Betaproteobacteria; o_Burkholderiales; Other | 5.62E-05 | 20 | 0.00115 | 0.02011689 |
| k_Bacteria; p_Firmicutes; c_Clostridia; o_Clostridiales; f_Ruminococcaceae; g_Subdoligranulum | 5.58E-05 | 22 | 0.00297 | 0.02249607 |
| k_Bacteria; p_Proteobacteria; c_Alphaproteobacteria; o_RF32 | 0.001304964 | 23 | 0.00295 | 0.02249607 |
| k_Bacteria; p_Proteobacteria; c_Alphaproteobacteria; o_RF32; f_; g_ | 0.001304964 | 23 | 0.00295 | 0.02249607 |

TABLE 6-continued

Selected fecal bacterial genera change their abundance in response to MTT. This table shows the abundance of different genera of bacteria at baseline and 8 weeks after MTT for the ASD group. The p-values show which results are statistically significant without correction for multiple hypothesis testing, and the q values show which results are significant (q < 0.05) or marginally significant (q < 0.10) after correction for multiple hypothesis testing. The following genera show a significant increase: *Bifidobacterium*, *Prevotella*, and *Desulfovibirio*; The following genus showed a marginally significant decrease: *Bacteroides* and *Eggerthella*.

| Taxon | | | |
|---|---|---|---|
| k__Bacteria; p__Proteobacteria; c__Alphaproteobacteria; o__RF32; f__ | 0.001304964 | 23 | 0.00295 | 0.02249607 |
| k__Bacteria; p__Lentisphaerae; c__[Lentisphaeria]; o__Victivallales | 3.00E−05 | 24 | 0.00228 | 0.02249607 |
| k__Bacteria; p__Lentisphaerae; c__[Lentisphaeria] | 3.00E−05 | 24 | 0.00228 | 0.02249607 |
| k__Bacteria; p__Lentisphaerae | 3.00E−05 | 24 | 0.00228 | 0.02249607 |
| k__Bacteria; p__Lentisphaerae; c__[Lentisphaeria]; o__Victivallales; f__Victivallaceae | 3.00E−05 | 24 | 0.00228 | 0.02249607 |
| k__Bacteria; p__Actinobacteria; c__Coriobacteriia; o__Coriobacteriales; f__Coriobacteriaceae; g__Adlercreutzia | 0.000199396 | 26 | 0.00315 | 0.02249607 |
| k__Bacteria; p__Proteobacteria; c__Deltaproteobacteria; o__Desulfovibrionales; f__Desulfovibrionaceae | 0.008161503 | 26 | 0.00315 | 0.02249607 |
| k__Bacteria; p__Proteobacteria; c__Deltaproteobacteria; o__Desulfovibrionales | 0.008161503 | 26 | 0.00315 | 0.02249607 |
| k__Bacteria; p__Proteobacteria; c__Deltaproteobacteria | 0.008161503 | 26 | 0.00315 | 0.02249607 |
| k__Bacteria; p__Bacteroidetes; c__Bacteroidia; o__Bacteroidales; f__[Odoribacteraceae]; g__Butyricimonas | 0.004541428 | 28 | 0.00433 | 0.02954072 |
| k__Bacteria; p__Firmicutes; c__Clostridia; o__Clostridiales; f__Lachnospiraceae; g__Ruminococcus | 0 | 28 | 0.00625 | 0.03922132 |
| k__Bacteria; p__Firmicutes; c__Clostridia; o__Clostridiales; f__Peptostreptococcaceae; g__ | 0.002480787 | 29 | 0.00505 | 0.033057 |
| k__Bacteria; p__Proteobacteria; c__Alphaproteobacteria | 0.001329582 | 30 | 0.0083 | 0.04495085 |
| k__Bacteria; p__Firmicutes; c__Clostridia; o__Clostridiales; f__Veillonellaceae; g__Veillonella | 0 | 30 | 0.01124 | 0.0534674 |
| k__Bacteria; p__Actinobacteria | 0.011213443 | 31 | 0.00684 | 0.04132322 |
| k__Bacteria; p__Firmicutes; c__Clostridia; o__Clostridiales; f__ | 0.020932784 | 32 | 0.00794 | 0.04450209 |
| k__Bacteria; p__Firmicutes; c__Clostridia; o__Clostridiales; f__; g__ | 0.020932784 | 32 | 0.00794 | 0.04450209 |
| k__Bacteria; p__Actinobacteria; c__Actinobacteria; o__Bifidobacteriales | 0.009901481 | 32 | 0.01095 | 0.0534674 |
| k__Bacteria; p__Actinobacteria; c__Actinobacteria; o__Bifidobacteriales; f__Bifidobacteriaceae | 0.009901481 | 32 | 0.01095 | 0.0534674 |
| k__Bacteria; p__Actinobacteria; c__Actinobacteria; o__Bifidobacteriales; f__Bifidobacteriaceae; g__Bifidobacterium | 0.009879019 | 32 | 0.01095 | 0.0534674 |
| k__Bacteria; p__Actinobacteria; c__Actinobacteria | 0.009945975 | 35 | 0.01221 | 0.05640206 |
| k__Bacteria; p__Actinobacteria; c__Coriobacteriia; o__Coriobacteriales; f__Coriobacteriaceae; g__Eggerthella | 5.52E−05 | 36 | 0.02229 | 0.07523254 |
| k__Bacteria; p__Bacteroidetes | 0.50406638 | 37 | 0.0161 | 0.06831558 |
| k__Bacteria; p__Bacteroidetes; c__Bacteroidia | 0.503803347 | 37 | 0.0161 | 0.06831558 |
| k__Bacteria; p__Bacteroidetes; c__Bacteroidia; o__Bacteroidales | 0.503803347 | 37 | 0.0161 | 0.06831558 |
| k__Bacteria; p__Firmicutes; Other; Other; Other; Other | 0.000304236 | 38 | 0.01842 | 0.06886366 |
| k__Bacteria; p__Firmicutes; Other; Other; Other | 0.000304236 | 38 | 0.01842 | 0.06886366 |
| k__Bacteria; p__Firmicutes; Other; Other; Other | 0.000304236 | 38 | 0.01842 | 0.06886366 |
| k__Bacteria; p__Firmicutes; Other | 0.000304236 | 38 | 0.01842 | 0.06886366 |
| k__Bacteria; p__Firmicutes; c__Clostridia; o__Clostridiales; f__Ruminococcaceae; Other | 0.00909306 | 38 | 0.01842 | 0.06886366 |
| k__Bacteria; p__Firmicutes; c__Clostridia; o__Clostridiales; f__Ruminococcaceae; g__Anaerotruncus | 4.67E−05 | 39 | 0.027 | 0.08312852 |
| k__Bacteria; p__Bacteroidetes; c__Bacteroidia; o__Bacteroidales; f__Bacteroidaceae | 0.298183959 | 39 | 0.02103 | 0.07504768 |
| k__Bacteria; p__Bacteroidetes; c__Bacteroidia; o__Bacteroidales; f__Bacteroidaceae; g__Bacteroides | 0.29815965 | 39 | 0.02103 | 0.07504768 |
| k__Bacteria; p__Bacteroidetes; c__Bacteroidia; o__Bacteroidales; f__Prevotellaceae | 0.013328022 | 40 | 0.02396 | 0.07523254 |
| k__Bacteria; p__Bacteroidetes; c__Bacteroidia; o__Bacteroidales; f__Prevotellaceae; g__Prevotella | 0.013321059 | 40 | 0.02396 | 0.07523254 |
| k__Bacteria; p__Proteobacteria | 0.039643924 | 40 | 0.02396 | 0.07523254 |
| k__Bacteria; p__Bacteroidetes; c__Bacteroidia; o__Bacteroidales; f__Porphyromonadaceae; g__Parabacteroides | 0.046482891 | 40 | 0.02396 | 0.07523254 |
| k__Bacteria; p__Bacteroidetes; c__Bacteroidia; o__Bacteroidales; f__Porphyromonadaceae | 0.046496563 | 40 | 0.02396 | 0.07523254 |
| k__Bacteria; p__Firmicutes; c__Clostridia; Other; Other; Other | 3.28E−05 | 41 | 0.045 | 0.10868376 |
| k__Bacteria; p__Firmicutes; c__Clostridia; Other | 3.28E−05 | 41 | 0.045 | 0.10868376 |
| k__Bacteria; p__Firmicutes; c__Clostridia; Other; Other | 3.28E−05 | 41 | 0.045 | 0.10868376 |
| k__Bacteria; p__Actinobacteria; c__Coriobacteriia; o__Coriobacteriales; f__Coriobacteriaceae; g__Collinsella | 0.000562932 | 41 | 0.03992 | 0.10275249 |
| k__Bacteria; p__Actinobacteria; c__Coriobacteriia; o__Coriobacteriales; f__Coriobacteriaceae | 0.001245091 | 42 | 0.03089 | 0.08979861 |
| k__Bacteria; p__Actinobacteria; c__Coriobacteriia | 0.001245091 | 42 | 0.03089 | 0.08979861 |
| k__Bacteria; p__Actinobacteria; c__Coriobacteriia; o__Coriobacteriales | 0.001245091 | 42 | 0.03089 | 0.08979861 |
| k__Bacteria; p__Firmicutes; c__Clostridia; o__Clostridiales; f__Lachnospiraceae; Other | 0.008344174 | 43 | 0.03495 | 0.09977185 |

TABLE 6-continued

Selected fecal bacterial genera change their abundance in response to MTT. This table shows the abundance of different genera of bacteria at baseline and 8 weeks after MTT for the ASD group. The p-values show which results are statistically significant without correction for multiple hypothesis testing, and the q values show which results are significant (q < 0.05) or marginally significant (q < 0.10) after correction for multiple hypothesis testing. The following genera show a significant increase: *Bifidobacterium*, *Prevotella*, and *Desulfovibirio*; The following genus showed a marginally significant decrease: *Bacteroides* and *Eggerthella*.

| | | | | |
|---|---|---|---|---|
| k__Bacteria; Other; Other; Other | 0.000620082 | 44 | 0.03947 | 0.10275249 |
| k__Bacteria; Other; Other; Other; Other | 0.000620082 | 44 | 0.03947 | 0.10275249 |
| k__Bacteria; Other; Other | 0.000620082 | 44 | 0.03947 | 0.10275249 |
| k__Bacteria; Other; Other; Other | 0.000620082 | 44 | 0.03947 | 0.10275249 |
| k__Bacteria; Other | 0.000620082 | 44 | 0.03947 | 0.10275249 |
| k__Bacteria; p__Firmicutes; c__Clostridia; o__Clostridiales; f__Lachnospiraceae; g__Pseudobutyrivibrio | 0 | 44 | 0.06007 | 0.13667366 |
| k__Bacteria; p__Bacteroidetes; c__Bacteroidia; o__Bacteroidales; f__Rikenellaceae; g__Alistipes | 0.017821882 | 45 | 0.04447 | 0.10868376 |
| k__Bacteria; p__Firmicutes; c__Clostridia; o__Clostridiales; f__Lachnospiraceae; g__Anaerostipes | 0.000839275 | 46 | 0.04999 | 0.11714052 |
| k__Bacteria; p__Firmicutes; c__Clostridia; o__Clostridiales; f__Ruminococcaceae; g__Oscillospira | 0.029714289 | 46 | 0.04999 | 0.11714052 |
| k__Bacteria; p__Firmicutes; c__Clostridia; o__Clostridiales; f__Ruminococcaceae; g__Butyricicoccus | 0.000898376 | 47 | 0.05608 | 0.12947425 |
| k__Bacteria; p__Actinobacteria; c__Actinobacteria; o__Actinomycetales; f__Actinomycetaceae; g__Actinomyces | 0 | 47 | 0.07548 | 0.16459142 |
| k__Bacteria; p__Bacteroidetes; c__Bacteroidia; o__Bacteroidales; f__Rikenellaceae; g__ | 0.017779431 | 48 | 0.06277 | 0.13880434 |
| k__Bacteria; p__Firmicutes; c__Bacilli; o__Lactobacillales | 0.000412138 | 48 | 0.06277 | 0.13880434 |
| k__Bacteria; p__Proteobacteria; c__Gammaproteobacteria; o__Enterobacteriales; f__Enterobacteriaceae; g__Klebsiella | 0 | 48 | 0.08672 | 0.18192579 |
| k__Bacteria; p__Firmicutes; c__Clostridia; o__Clostridiales; f__[Tissierellaceae] | 5.25E-05 | 49 | 0.07673 | 0.16501965 |
| k__Bacteria; p__Firmicutes; c__Clostridia; o__Clostridiales; f__Ruminococcaceae | 0.176185427 | 51 | 0.08691 | 0.18192579 |
| k__Bacteria; p__Bacteroidetes; c__Bacteroidia; o__Bacteroidales; f__[Odoribacteraceae] | 0.006796202 | 52 | 0.09645 | 0.19924207 |
| k__Bacteria; p__Firmicutes; c__Bacilli; o__Lactobacillales; f__Streptococcaceae | 0.000412138 | 53 | 0.10681 | 0.21778096 |
| k__Bacteria; p__Proteobacteria; c__Gammaproteobacteria; o__Enterobacteriales; f__Enterobacteriaceae; g__Shigella | 0 | 53 | 0.14088 | 0.2764745 |
| k__Bacteria; p__Firmicutes; c__Clostridia; o__Clostridiales; f__Lachnospiraceae; g__Lachnospira | 0.006102621 | 54 | 0.11803 | 0.23457433 |
| k__Bacteria; p__Firmicutes; c__Clostridia; o__Clostridiales; f__Lachnospiraceae; g__Clostridium | 0.006358102 | 54 | 0.11803 | 0.23457433 |
| k__Bacteria; p__Firmicutes; c__Clostridia; o__Clostridiales; f__Veillonellaceae; g__Phascolarctobacterium | 0.003603085 | 57 | 0.1573 | 0.29754187 |
| k__Bacteria; p__Firmicutes; c__Bacilli; o__Lactobacillales; f__Streptococcaceae; g__Streptococcus | 0.000411728 | 57 | 0.1573 | 0.29754187 |
| k__Bacteria; p__Proteobacteria; c__Gammaproteobacteria; o__Pasteurellales; f__Pasteurellaceae; g__Haemophilus | 4.72E-05 | 57 | 0.1573 | 0.29754187 |
| k__Bacteria; p__Firmicutes; c__Clostridia; o__Clostridiales; f__Peptostreptococcaceae | 0.006082406 | 58 | 0.17238 | 0.31469611 |
| k__Bacteria; p__Proteobacteria; c__Gammaproteobacteria; o__Pasteurellales | 6.57E-05 | 58 | 0.17238 | 0.31469611 |
| k__Bacteria; p__Proteobacteria; c__Gammaproteobacteria; o__Pasteurellales; f__Pasteurellaceae | 6.57E-05 | 58 | 0.17238 | 0.31469611 |
| k__Bacteria; p__Firmicutes; c__Bacilli | 0.001043307 | 59 | 0.18852 | 0.34020243 |
| k__Bacteria; p__Firmicutes; c__Clostridia; o__Clostridiales; f__Lachnospiraceae | 0.123146118 | 60 | 0.20575 | 0.36707003 |
| k__Bacteria; p__Bacteroidetes; Other; Other; Other | 0.000189929 | 61 | 0.2348 | 0.39217229 |
| k__Bacteria; p__Bacteroidetes; Other; Other | 0.000189929 | 61 | 0.2348 | 0.39217229 |
| k__Bacteria; p__Bacteroidetes; Other | 0.000189929 | 61 | 0.2348 | 0.39217229 |
| k__Bacteria; p__Bacteroidetes; Other; Other; Other | 0.000189929 | 61 | 0.2348 | 0.39217229 |
| k__Bacteria; p__Firmicutes; c__Clostridia; o__Clostridiales; Other | 0.002298538 | 61 | 0.22409 | 0.3909104 |
| k__Bacteria; p__Firmicutes; c__Clostridia; o__Clostridiales; Other; Other | 0.002298538 | 61 | 0.22409 | 0.3909104 |
| k__Bacteria; p__Firmicutes; c__Clostridia; o__Clostridiales; f__Lachnospiraceae; g__Coprococcus | 0.015529023 | 63 | 0.26421 | 0.43211663 |
| k__Bacteria; p__Verrucomicrobia; c__Verrucomicrobiae; o__Verrucomicrobiales; f__Verrucomicrobiaceae; g__Akkermansia | 0.001557596 | 63 | 0.27523 | 0.43211663 |
| k__Bacteria; p__Verrucomicrobia; c__Verrucomicrobiae; o__Verrucomicrobiales | 0.001557596 | 63 | 0.27523 | 0.43211663 |
| k__Bacteria; p__Verrucomicrobia; c__Verrucomicrobiae; o__Verrucomicrobiales; f__Verrucomicrobiaceae | 0.001557596 | 63 | 0.27523 | 0.43211663 |
| k__Bacteria; p__Verrucomicrobia | 0.001557596 | 63 | 0.27523 | 0.43211663 |
| k__Bacteria; p__Verrucomicrobia; c__Verrucomicrobiae | 0.001557596 | 63 | 0.27523 | 0.43211663 |
| k__Bacteria; p__Tenericutes | 0.000126247 | 64 | 0.32999 | 0.49815875 |
| k__Bacteria; p__Firmicutes; c__Clostridia | 0.362100306 | 64 | 0.28603 | 0.43599322 |
| k__Bacteria; p__Firmicutes; c__Clostridia; o__Clostridiales | 0.362100306 | 64 | 0.28603 | 0.43599322 |
| k__Bacteria; p__Firmicutes; c__Erysipelotrichi; o__Erysipelotrichales; f__Erysipelotrichaceae; g__ | 0.001934616 | 64 | 0.28603 | 0.43599322 |

TABLE 6-continued

Selected fecal bacterial genera change their abundance in response to MTT. This table shows the abundance of different genera of bacteria at baseline and 8 weeks after MTT for the ASD group. The p-values show which results are statistically significant without correction for multiple hypothesis testing, and the q values show which results are significant (q < 0.05) or marginally significant (q < 0.10) after correction for multiple hypothesis testing. The following genera show a significant increase: *Bifidobacterium*, *Prevotella*, and *Desulfovibirio*; The following genus showed a marginally significant decrease: *Bacteroides* and *Eggerthella*.

| Taxonomy | p-value | | q | q |
|---|---|---|---|---|
| k__Bacteria; p__Actinobacteria; c__Coriobacteriia; o__Coriobacteriales; f__Coriobacteriaceae; g__ | 0.000108913 | 66 | 0.34435 | 0.51488091 |
| k__Bacteria; p__Firmicutes | 0.380413007 | 67 | 0.35862 | 0.53116324 |
| k__Bacteria; p__Proteobacteria; c__Betaproteobacteria | 0.011409 | 68 | 0.38519 | 0.54481563 |
| k__Bacteria; p__Proteobacteria; c__Betaproteobacteria; o__Burkholderiales | 0.011378101 | 68 | 0.38519 | 0.54481563 |
| k__Bacteria; p__Firmicutes; c__Clostridia; o__Clostridiales; f__Lachnospiraceae; g__Lachnobacterium | 8.59E−05 | 68 | 0.41288 | 0.56373387 |
| k__Bacteria; p__Firmicutes; c__Erysipelotrichi; o__Erysipelotrichales | 0.003206201 | 68 | 0.38519 | 0.54481563 |
| k__Bacteria; p__Firmicutes; c__Erysipelotrichi | 0.003206201 | 68 | 0.38519 | 0.54481563 |
| k__Bacteria; p__Firmicutes; c__Erysipelotrichi; o__Erysipelotrichales; f__Erysipelotrichaceae | 0.003206201 | 68 | 0.38519 | 0.54481563 |
| k__Bacteria; p__Proteobacteria; c__Betaproteobacteria; o__Burkholderiales; f__Alcaligenaceae | 0.010422581 | 69 | 0.41293 | 0.56373387 |
| k__Bacteria; p__Proteobacteria; c__Betaproteobacteria; o__Burkholderiales; f__Alcaligenaceae; g__Sutterella | 0.010367593 | 69 | 0.41293 | 0.56373387 |
| k__Bacteria; p__Firmicutes; c__Clostridia; o__Clostridiales; f__Lachnospiraceae; g__Blautia | 0.020206452 | 69 | 0.41293 | 0.56373387 |
| k__Bacteria; p__Firmicutes; c__Erysipelotrichi; o__Erysipelotrichales; f__Erysipelotrichaceae; g__Coprobacillus | 0 | 69 | 0.45471 | 0.58515603 |
| k__Bacteria; p__Bacteroidetes; c__Bacteroidia; o__Bacteroidales; Other | 0.000370987 | 70 | 0.44181 | 0.57326273 |
| k__Bacteria; p__Bacteroidetes; c__Bacteroidia; o__Bacteroidales; Other; Other | 0.000370987 | 70 | 0.44181 | 0.57326273 |
| k__Bacteria; p__Actinobacteria; c__Actinobacteria; o__Actinomycetales | 5.62E−05 | 70 | 0.44181 | 0.57326273 |
| k__Bacteria; p__Proteobacteria; c__Deltaproteobacteria; o__Desulfovibrionales; f__Desulfovibrionaceae; g__Bilophila | 0.001392747 | 70 | 0.44181 | 0.57326273 |
| k__Bacteria; p__Firmicutes; c__Clostridia; o__Clostridiales; f__Peptostreptococcaceae; Other | 0.002270567 | 70 | 0.44181 | 0.57326273 |
| k__Bacteria; p__Firmicutes; c__Clostridia; o__Clostridiales; f__Clostridiaceae; g__Clostridium | 0.002973236 | 70 | 0.44181 | 0.57326273 |
| k__Bacteria; p__Firmicutes; c__Clostridia; o__Clostridiales; f__Lachnospiraceae; g__Dorea | 0.00372118 | 71 | 0.47183 | 0.59261272 |
| k__Bacteria; p__Firmicutes; c__Clostridia; o__Clostridiales; f__Ruminococcaceae; g__Faecalibacterium | 0.066482925 | 71 | 0.47183 | 0.59261272 |
| k__Bacteria; p__Firmicutes; c__Clostridia; o__Clostridiales; f__Peptostreptococcaceae; g__Clostridium | 0.000335121 | 71 | 0.47183 | 0.59261272 |
| k__Bacteria; p__Firmicutes; c__Erysipelotrichi; o__Erysipelotrichales; f__Erysipelotrichaceae; g__Clostridium | 0.000410757 | 71 | 0.48196 | 0.60054299 |
| k__Bacteria; p__Firmicutes; c__Clostridia; o__Clostridiales; f__Clostridiaceae; g__ | 0.000220828 | 72 | 0.5276 | 0.64211601 |
| k__Bacteria; p__Firmicutes; c__Erysipelotrichi; o__Erysipelotrichales; f__Erysipelotrichaceae; g__Holdemania | 0.000113618 | 72 | 0.51269 | 0.62884726 |
| k__Bacteria; p__Firmicutes; c__Clostridia; o__Clostridiales; f__Clostridiaceae | 0.00389758 | 72 | 0.50293 | 0.62172928 |
| k__Bacteria; p__Firmicutes; c__Clostridia; o__Clostridiales; f__Ruminococcaceae; g__Clostridium | 7.92E−05 | 73 | 0.55219 | 0.66178605 |
| k__Bacteria; p__Firmicutes; c__Erysipelotrichi; o__Erysipelotrichales; f__Erysipelotrichaceae; g__[Eubacterium] | 6.59E−05 | 73 | 0.53508 | 0.64621276 |
| k__Bacteria; p__Firmicutes; c__Clostridia; o__Clostridiales; f__Lachnospiraceae; g__Roseburia | 0.020611574 | 74 | 0.56824 | 0.6758595 |
| k__Bacteria; p__Actinobacteria; c__Actinobacteria; o__Actinomycetales; f__Actinomycetaceae | 2.25E−05 | 74 | 0.59051 | 0.69707032 |
| k__Bacteria; p__Firmicutes; c__Clostridia; o__Clostridiales; f__Clostridiaceae; g__SMB53 | 0.000221868 | 75 | 0.60235 | 0.70573682 |
| k__Bacteria; p__Firmicutes; c__Clostridia; o__Clostridiales; f__Lachnospiraceae; g__[Ruminococcus] | 0.008327383 | 76 | 0.63735 | 0.74121664 |
| k__Bacteria; p__Firmicutes; c__Clostridia; o__Clostridiales; f__Christensenellaceae; g__ | 0.000741182 | 78 | 0.70977 | 0.81936988 |
| k__Bacteria; p__Firmicutes; c__Clostridia; o__Clostridiales; f__Lachnospiraceae; g__ | 0.008514988 | 79 | 0.74704 | 0.8557764 |
| k__Bacteria; p__Proteobacteria; c__Gammaproteobacteria; o__Enterobacteriales; f__Enterobacteriaceae; g__Escherichia | 0.000953478 | 80 | 0.78492 | 0.8557764 |
| k__Bacteria; p__Firmicutes; c__Clostridia; o__Clostridiales; f__[Mogibacteriaceae]; g__ | 0.000852442 | 80 | 0.78492 | 0.8557764 |
| k__Bacteria; p__Firmicutes; c__Clostridia; o__Clostridiales; f__Christensenellaceae | 0.00077944 | 80 | 0.78492 | 0.8557764 |
| k__Bacteria; p__Firmicutes; c__Clostridia; o__Clostridiales; f__Ruminococcaceae; g__Ruminococcus | 0.029093957 | 80 | 0.78492 | 0.8557764 |
| k__Bacteria; p__Firmicutes; c__Bacilli; o__Turicibacterales; f__Turicibacteraceae; g__Turicibacter | 0.000235588 | 80 | 0.78492 | 0.8557764 |
| k__Bacteria; p__Firmicutes; c__Bacilli; o__Turicibacterales; f__Turicibacteraceae | 0.000235588 | 80 | 0.78492 | 0.8557764 |

TABLE 6-continued

Selected fecal bacterial genera change their abundance in response to MTT. This table shows the abundance of different genera of bacteria at baseline and 8 weeks after MTT for the ASD group. The p-values show which results are statistically significant without correction for multiple hypothesis testing, and the q values show which results are significant (q < 0.05) or marginally significant (q < 0.10) after correction for multiple hypothesis testing. The following genera show a significant increase: *Bifidobacterium*, *Prevotella*, and *Desulfovibirio*; The following genus showed a marginally significant decrease: *Bacteroides* and *Eggerthella*.

| | | | | |
|---|---|---|---|---|
| k__Bacteria; p__Firmicutes; c__Bacilli; o__Turicibacterales | 0.000235588 | 80 | 0.78492 | 0.8557764 |
| k__Bacteria; p__Firmicutes; c__Clostridia; o__Clostridiales; f__Veillonellaceae; g__Dialister | 0.000457967 | 82 | 0.86212 | 0.90840897 |
| k__Bacteria; p__Proteobacteria; c__Gammaproteobacteria; o__Enterobacteriales; f__Enterobacteriaceae | 0.001215846 | 82 | 0.86212 | 0.90840897 |
| k__Bacteria; p__Proteobacteria; c__Gammaproteobacteria; o__Enterobacteriales | 0.001215846 | 82 | 0.86212 | 0.90840897 |
| k__Bacteria; p__Proteobacteria; c__Gammaproteobacteria; o__Enterobacteriales; f__Enterobacteriaceae; Other | 0.000148103 | 82 | 0.86212 | 0.90840897 |
| k__Bacteria; p__Bacteroidetes; c__Bacteroidia; o__Bacteroidales; f__Rikenellaceae; Other | 0.00253325 | 82 | 0.86212 | 0.90840897 |
| k__Bacteria; p__Bacteroidetes; c__Bacteroidia; o__Bacteroidales; f__[Barnesiellaceae] | 0.000991737 | 83 | 0.90127 | 0.92483534 |
| k__Bacteria; p__Bacteroidetes; c__Bacteroidia; o__Bacteroidales; f__[Barnesiellaceae]; g__ | 0.000991737 | 83 | 0.90127 | 0.92483534 |
| k__Bacteria; p__Firmicutes; c__Clostridia; o__Clostridiales; f__[Mogibacteriaceae] | 0.000852442 | 83 | 0.90127 | 0.92483534 |
| k__Bacteria; p__Firmicutes; c__Clostridia; o__Clostridiales; f__Veillonellaceae | 0.006212499 | 83 | 0.90127 | 0.92483534 |
| k__Bacteria; p__Bacteroidetes; c__Bacteroidia; o__Bacteroidales; f__[Odoribacteraceae]; g__Odoribacter | 0.001753614 | 84 | 0.94067 | 0.95280405 |
| k__Bacteria; p__Bacteroidetes; c__Bacteroidia; o__Bacteroidales; f__Rikenellaceae | 0.043043944 | 84 | 0.94067 | 0.95280405 |
| k__Bacteria; p__Proteobacteria; c__Gammaproteobacteria | 0.0016627 | 85 | 0.98021 | 0.98020591 |
| k__Bacteria; p__Firmicutes; c__Clostridia; o__Clostridiales; f__Ruminococcaceae; g__ | 0.012944165 | 85 | 0.98021 | 0.98020591 |

Example 14: Microbiome Analysis Across Common Diversity Metrics

Figure 16:
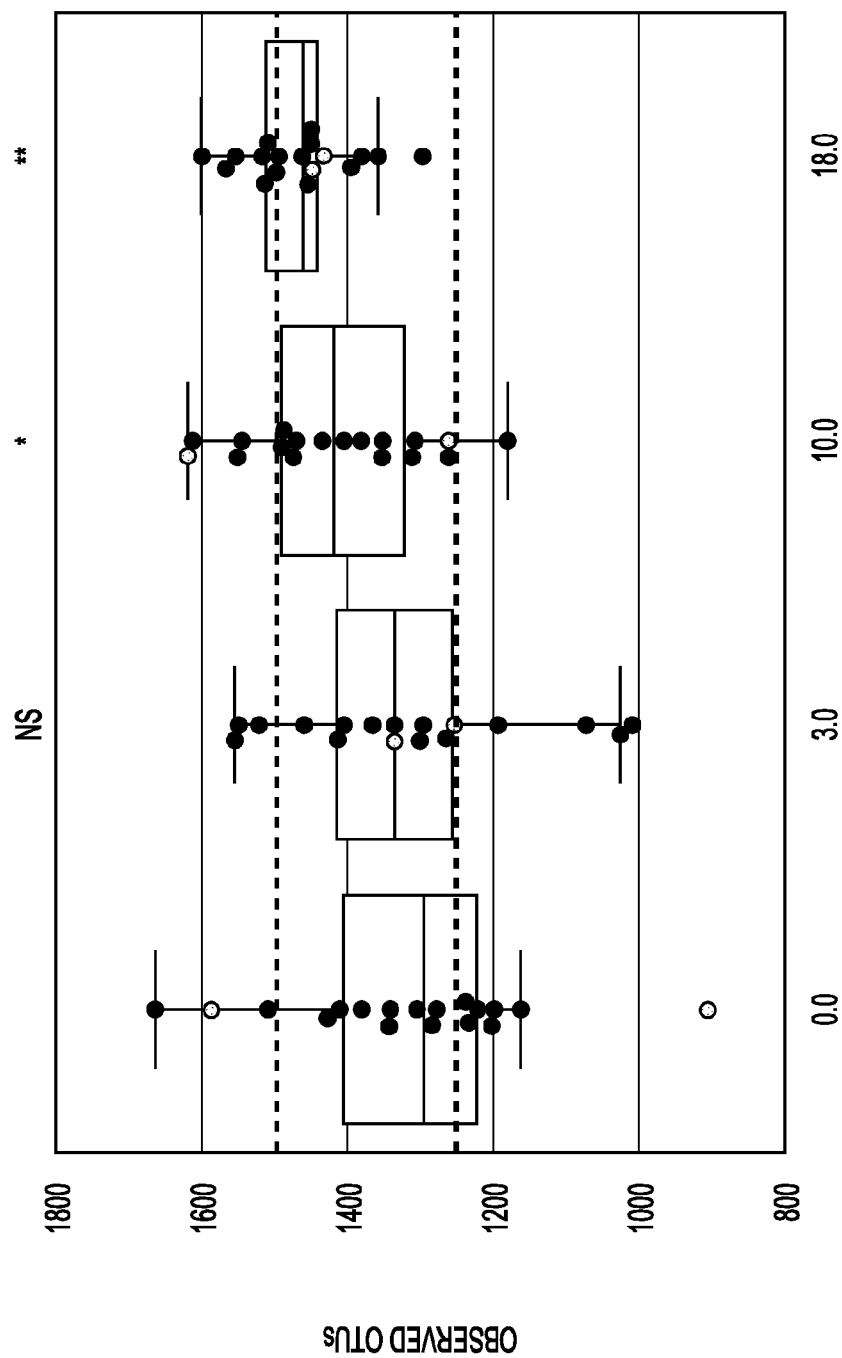
FIG. 16 presents Change in community richness, as measure with a non-phylogenetic diversity metric.

Parallel analyses are performed for multiple diversity metrics to understand the effect of metric on the microbiome findings. With the Observed OTUs metric (a count of the number of OTUs observed at least two times in a sample (FIG. 16), the same patterns as in FIG. 14, panel a are observed. This confirms that both phylogenetic and non-phylogenetic metrics illustrate the same patterns of change in community richness with MTT.

Figure 17:
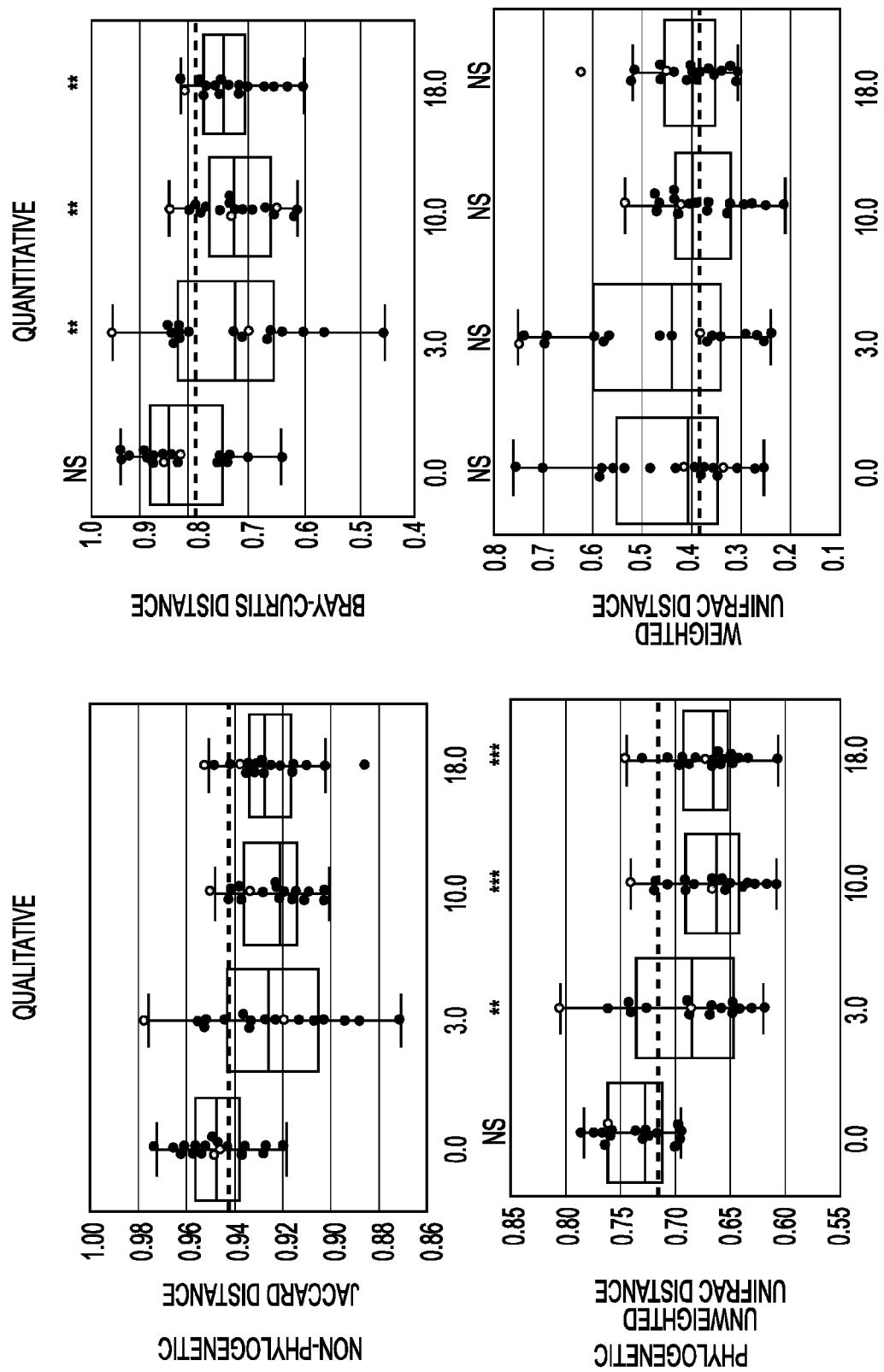
FIG. 17 describes engraftment plots with four diversity metrics.
Figure 18A:
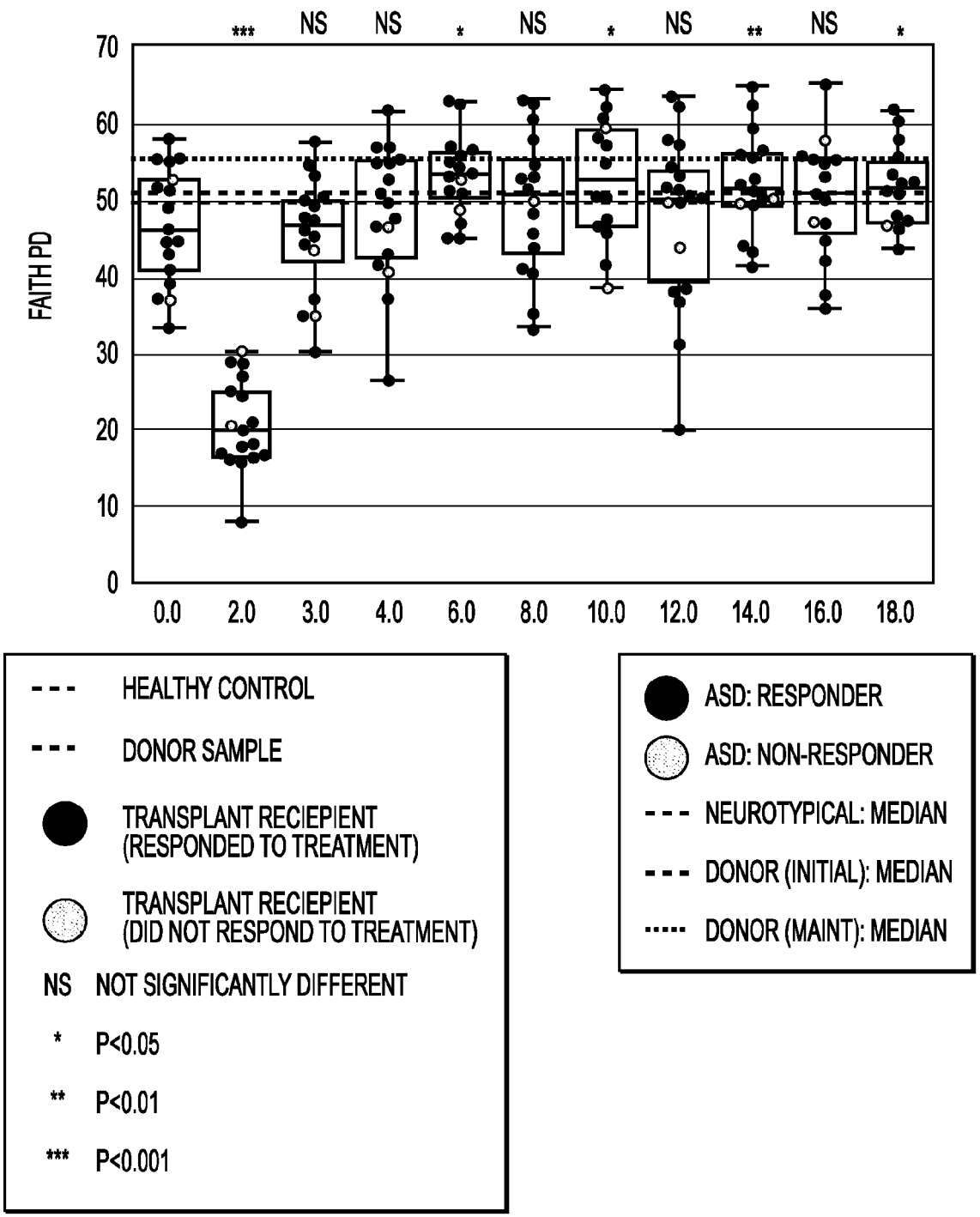
FIG. 18 (including panels a to d) describes microbiota analysis of fecal swab samples from ASD patients received MTT. Each of panels a to d correspond to panels a to d of FIG. 14, respectively. Panel a. Changes in Faith's Phylogenetic Diversity (PD) in the ASD microbiota (n=20). Orange lines indicates median PD of the donor samples (dashed line represents initial donor samples (n=4), and dashed line represents maintenance dose samples (n=2)), and green line indicates median PD of neurotypical controls at week 0 (n=18). Panel b. Change in Faith PD tracked on a per individual basis for all MTT recipients. Panel c. Unweighted UniFrac distances between ASD gut microbiota and most relevant donor sample (initial donor sample at weeks 0 and 3, most recent maintenance dose sample at weeks 10 and 18). Green line indicates the median interpersonal variation between neurotypical controls. Panel d. Distances between ASD gut microbiota and donor sample on a per individual basis.
Figure 18B:
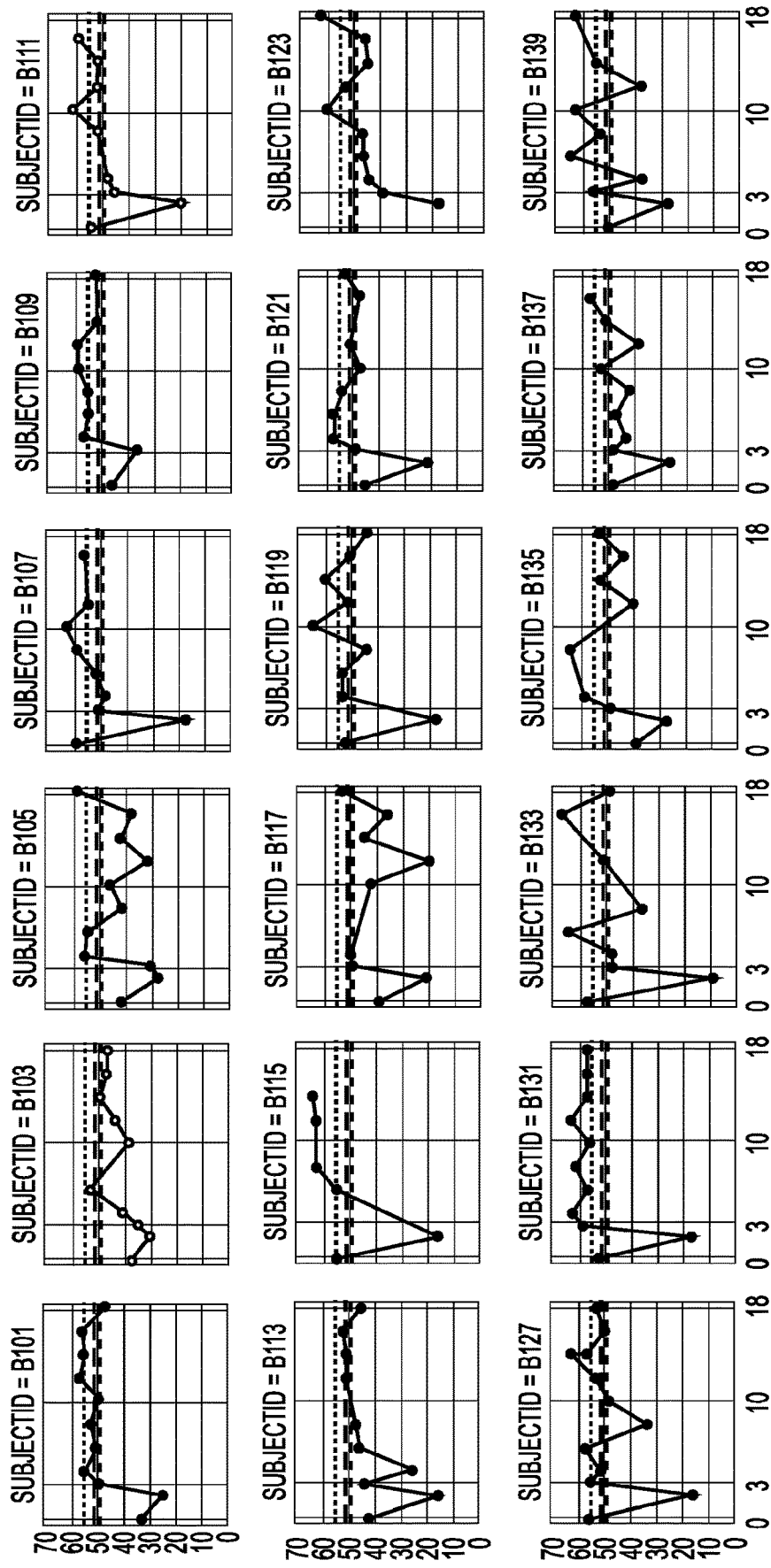
Figure 18C:
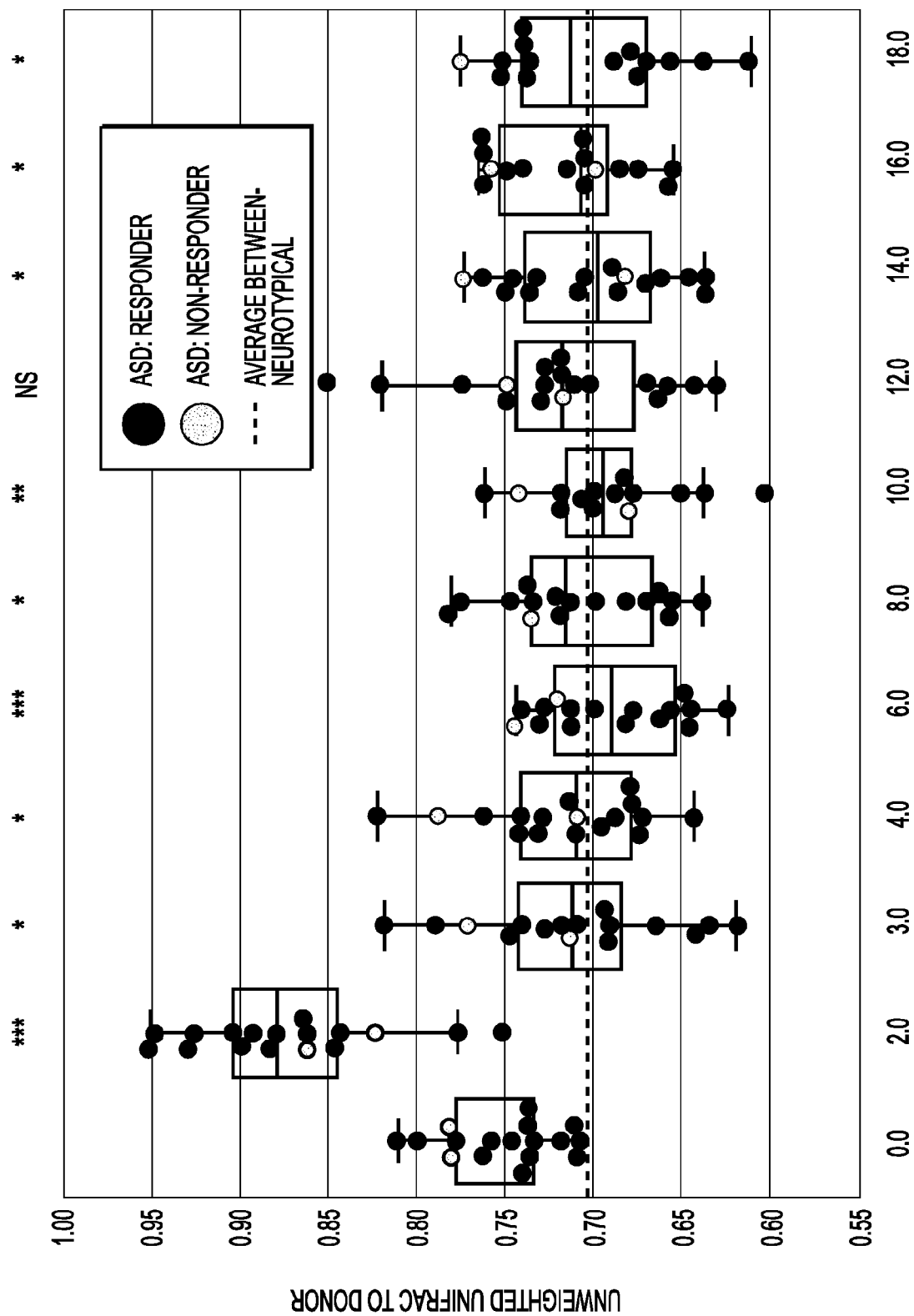
Figure 18D:
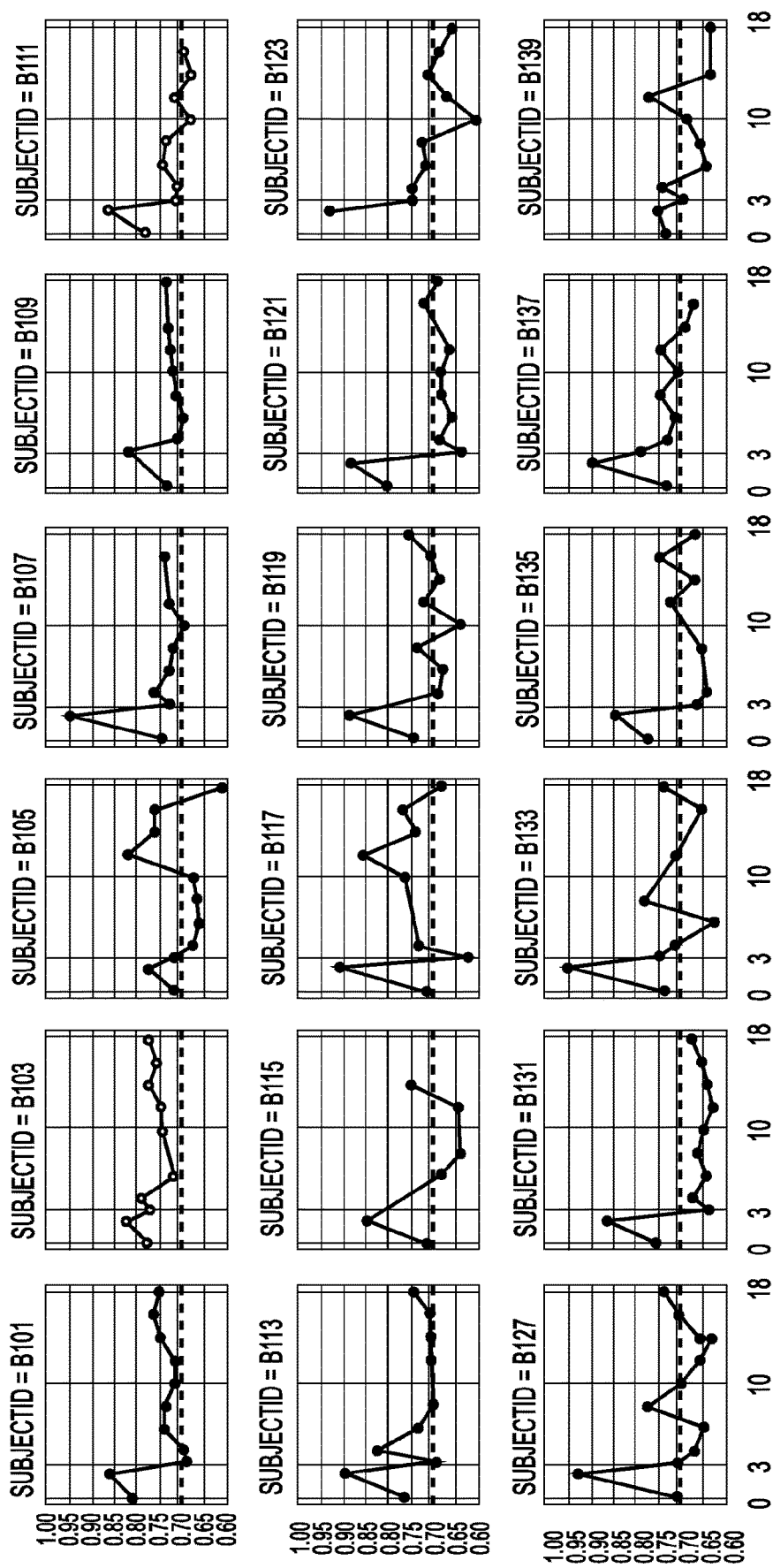
Figure 19A:
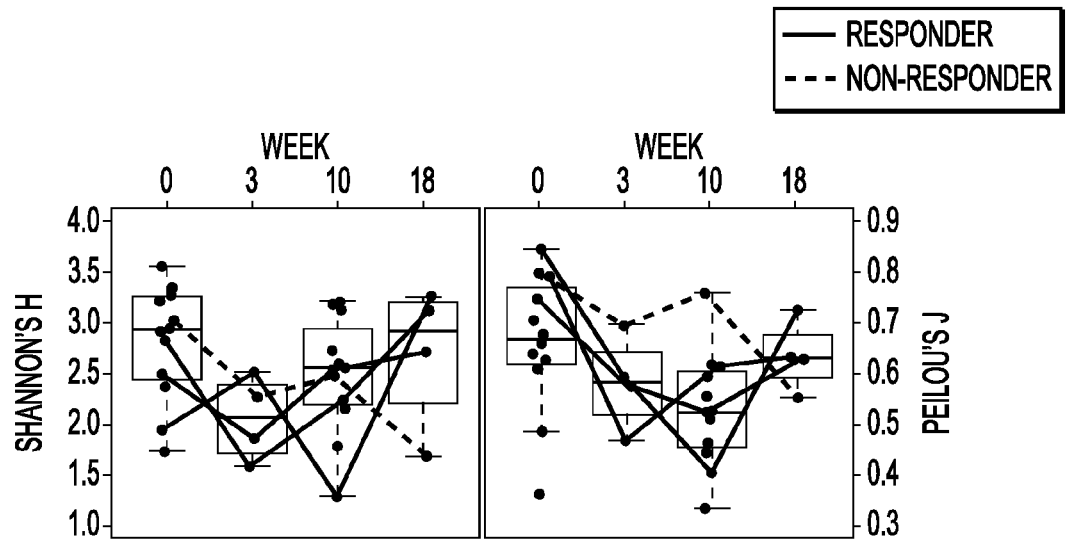
FIG. 19 (including panels a to d) describes stool virome changes in ASD patients receiving MTT. Panel a. Diversity indices, Shannon's H' (a measure of biodiversity and richness; right) and Peilou's J (a measure of evenness; left), of ASD participants. ASD diversity indices decrease at week 3 following vancomycin and the initial high dose MMT treatment and then rebound over time and stabilized following treatment with maintenance doses of MMT. Fecal samples are collected at all four time points for four out of the 12 ASD subjects where the bacteriophage communities are assessed. The responders (indicated by a grey line) rebounded in biodiversity, richness and evenness following FMT. In contrast, the non-responder (indicated by a red line) does not recover. Panel b. Nonmetric multidimensional scaling of Bray-Curtis dissimilarity (right; 2D-stress= 0.2467) and Jaccard (left; 2D-stress=0.2212) distances reveal that ASD gut bacteriophage communities are more similar to donor gut bacteriophage communities following both the high and low MTT doses. Panel c, Analyses of ASD virome composition at week 10 shows engraftment of donor bacteriophage populations across all ASD subjects. In >80% of the subjects, the starting (week 0) bacteriophage populations make up <20% of the virome at week 10. Panel d. In contrast, analyses of virome composition of the untreated neurotypical children at week 18 reveals a high percentage (>60%) of starting (week 0) bacteriophage populations.
Figure 19B:
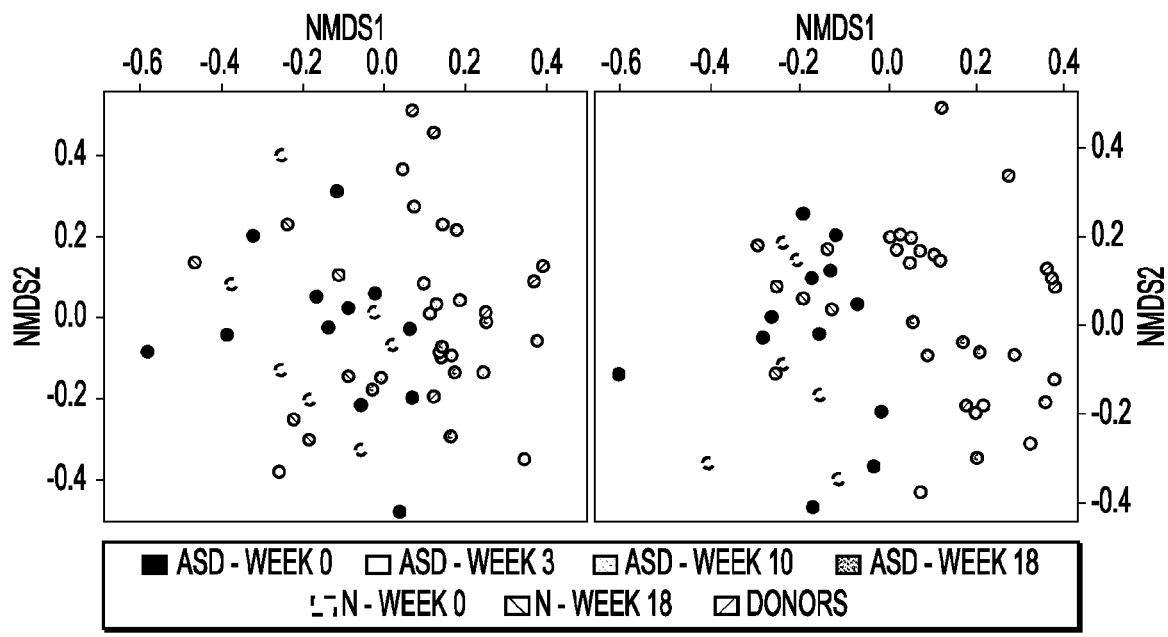
Figure 19C:
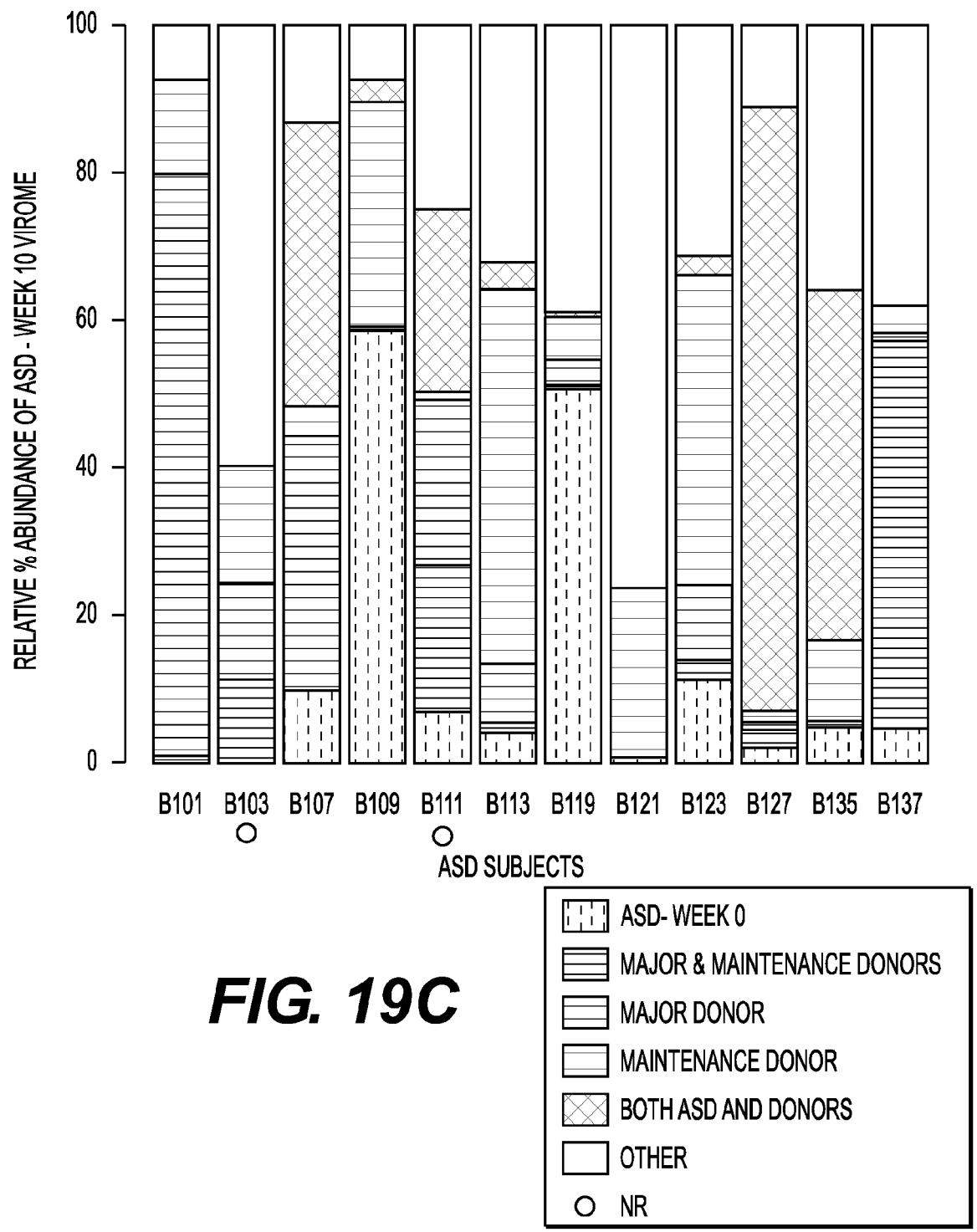
Figure 19D:
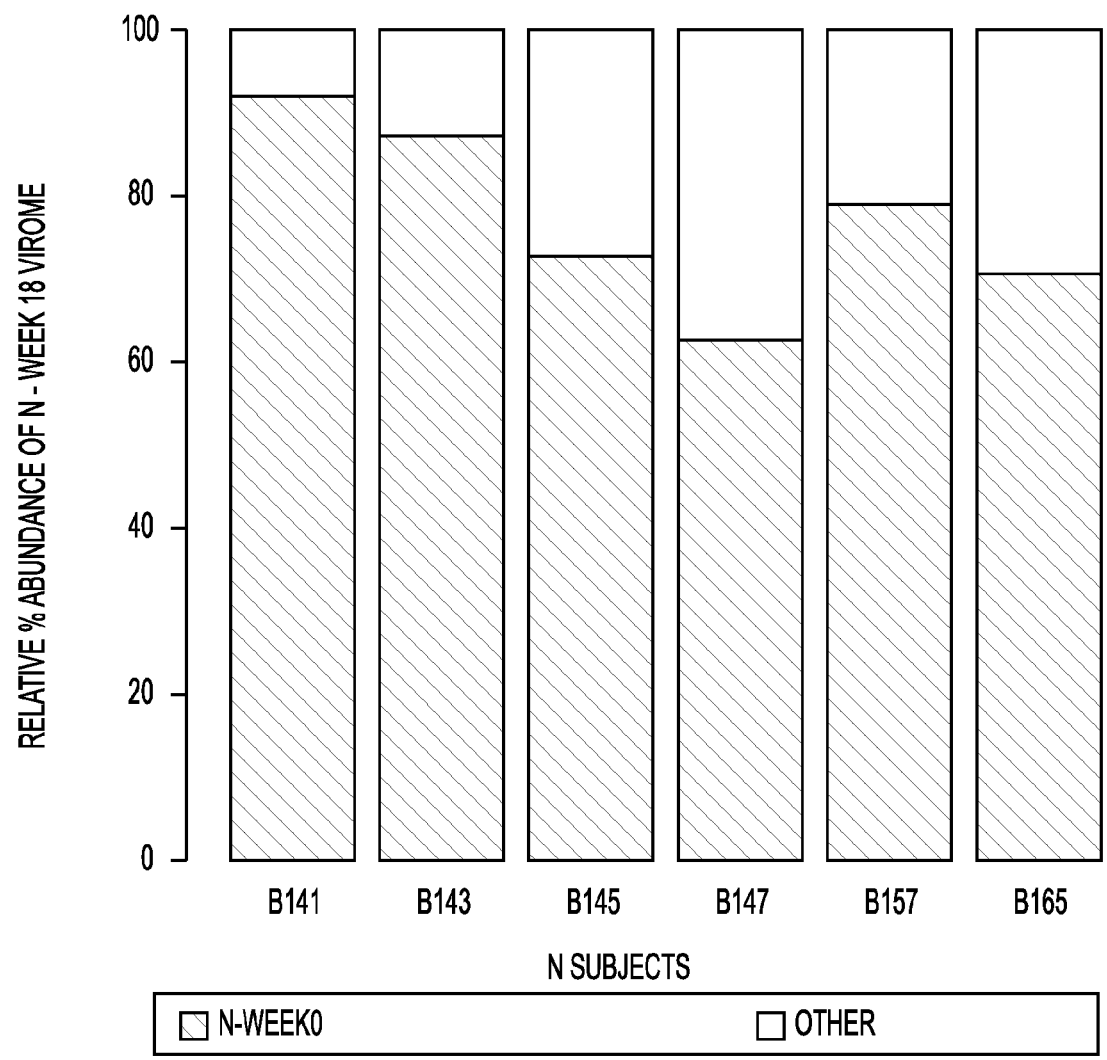

Similarly, pairwise distances are computed between samples using four diversity metrics, a qualitative non-phylogenetic metric (Jaccard distance), and quantitative non-phylogenetic diversity metric (Bray-Curtis distance), a qualitative phylogenetic diversity metric (unweighted UniFrac), and a quantitative phylogenetic diversity metric (weighted UniFrac) (FIG. 17). While the same pattern is observed with the first three metrics, no significant engraftment is seen with weighted UniFrac (though less variation is observed across individuals at weeks 10 and 18 than in earlier timepoints). Quantitative metrics give more weight to higher abundance OTUs than qualitative metrics. Because differences are observed in composition with our quantitative non-phylogenetic metric but not our quantitative phylogenetic metric, without being bound to any scientific theory, this may suggest that when changes occur in high abundance OTUs, those OTUs are generally closely related (thus the change is down-weighted with a phylogenetic diversity metric relative to a non-phylogenetic diversity metric).

Example 15: Microbiome Analysis Based on Fecal Swab Samples

In addition to stool collection over the 18 week period, fecal swab samples are collected nearly every other week. These samples are obtained by swabbing bottoms or used toilet paper with a sterile swab, and thus are easier to collect than stool samples. The general patterns observed from the stool data are present in the swab data. However, the fecal swab samples do not achieve the same statistical significance as in the stool samples (FIG. 18). This could be due to greater variability in the handling of the swab samples, which are shipped to our collection facility at ASU, and thus spent a varied amount of time at ambient temperature, ranging from a few hours to multiple days.

Example 16: Bacteriophage Virome Analysis

Changes in the phage diversity of gut samples from ASD or neurotypical participants are also evaluated. Briefly, phages are surveyed by sequencing community DNA from purified viral fraction samples, assembling them, and defining phage populations from the assembled contigs as established in Brum et al., Patterns and ecological drivers of ocean viral communities. *Science* 348, doi:10.1126/science.1261498 (2015). Abundance profiles of phage populations are then statistically evaluated for changes over time.

In contrast to the microbiota, phage richness and evenness do not significantly change following MTT during the timeframe of this study (FIG. 19, panel a). Without being bound to any scientific theory, at the population level, phage communities are reliant on their host communities and, thus, significant changes in phage diversity can lag behind bacterial community changes (Rodriguez-Brito et al. 2010). However, a number of metrics suggested phage communities also responded to MTT as follows.

First, in four individuals tracked across all four stool samples, phage diversity of three MTT responders decrease and then recover, while the non-responder decreases but does not recover. Second, analyses of quantitative (Bray-Curtis; FIG. 19, panel b, right) and qualitative (Jaccard; FIG. 19, panel b, left) measures of community dissimilarity between samples revealed phage communities of ASD-afflicted children are significantly more similar to those from the donor following MTT. Permutation based fitting of subject variables to Bray-Curtis and Jaccard NMDS plots uncovered significant clustering based on subject type (e.g. autism, neutrotypic and donor; $r^2 \geq 0.2120$, p-value $\leq 0.0001$, 9999 permutations) and among ASD subjects based on treatment stage ($r^2 \geq 0.4021$, p$\leq 0.0002$, 9999 permutations), and high ($r^2 \geq 0.2066$, p$\leq 0.0149$, 9999 permutations) and low ($r^2 \geq 0.1851$, p$\leq 0.0023$, 9999 permutations) dose donor. Not surprisingly, in addition to microbiota, FMT also transfers phages. Indeed, phage communities of ASD children appear driven by the successful transfer of donor viral populations during MTT (FIG. 19, panel c). Following the high and low doses of MTT, phage populations from the donor engrafted across all ASD subjects, while the abundance of phage populations originally in their pre-MTT virome are completely eliminated or decrease (FIG. 19, panel c). In contrast, across neurotypical subjects high abundance (>60%) of phage populations of the starting virome remained indicating that the changes observed are not due to normal temporal variability (FIG. 19, panel d). The results indicate that MTT shifts phage communities of ASD children towards those of donors Procedures for gut virome preparation, sequence, and analysis are summarized below. Viral DNA is isolated from stool samples as previously described by (Minot et al. *Genome Research* 21:1616-25 (2011)) with slight modifications. Briefly, 0.5 g of stool is resuspended into 40 mL of SM buffer and spun down at 4000 rpm for 30 min and the supernatant is filtered at 0.2 um. The filtrate is then ultracentrifuged in a step CsCl gradient as detailed in (Thurber et al., *Environmental Microbiology* 11:2148-63 (2009)). To target dsDNA bacteriophages, the 1.35-1.5 g/mL fraction is collected from the CsCl column, treated with chloroform (Vega Thurber et al 2009) and then with DNase I (100 U/mL) followed by the addition of 0.1M EDTA and 0.1M EGTA to halt enzyme activity as described (Hurwitz et al., *Environmental Microbiology* 15:1428-40 (2013)). Viral DNA is then extracted using the DNeasy Blood and Tissue Kit.

Following DNA extraction, the NexteraXT kit is used to prepare the sequencing libraries with two minor changes. During the library preparation, input DNA is PCR amplified with 18-25 cycles. When input DNA concentrations are low, the buffer ATM is added at a 1:10 dilution. Sequencing is performed on a MiSeq v3 2×300 at one-sixth of a lane per sequencing library.

For Virome bioinformatic analysis, reads are QC'd using Trimmomatic (Bolger et al., *Bioinformatics* 30:2114-20 (2014)) to remove adaptors, trim low-quality ends of reads (reads are cut as soon as the base quality dropped below 20 on a 4 bp window), and discard short reads (<50 bp). The reads from each sample are then assembled using Idba_ud (Peng et al., *Bioinformatics* 28(11):1420-8(2012)) with kmer size varying from 20 to 100 by increment of 10.

The assembled contigs are screened with VirSorter (Roux et al., 2015) to identify and remove all microbial genomes sequences (i.e. all contigs >10 kb and not detected as viral by VirSorter in "virome decontamination" mode). Then, a non-redundant dataset of viral contigs is generated by clustering all viral contigs with Cd-hit (Li et al., *Bioinformatics* 22:1658-59 (2006), threshold of 95% ANI on 80% of the shortest sequence). This resulted in 4,759 non-redundant viral sequences longer than 10 kb.

To determine the viral population relative abundances in the initial samples, the QC reads are mapped back to this non-redundant contigs database with bowtie2 (Langmead et al., *Nature Methods* 9:357-U354 (2012), option-non-deterministic and -sensitive, default otherwise). A contig is considered as detected in a sample if covered by reads on more than 75% of its length, and its abundance is computed as the contig average coverage (number of bp mapped to the contig divided by contig length) normalized by the total number of bp sequenced in the metagenome (as in Brum et al., *Science* 348, doi:10.1126/science.1261498 (2015)).

The diversity indices, Shannon's H' and Peilou's J, and Bray-Curtis distances analyses are calculated using the vegan package (Oksanen et al., Community ecology package, version 2 (2013)) in R version 3.2.3 (R Core Team, 2015). Bray-Curtis distances are statistically ordinated using the nonmetric multidimensional scaling (NMDS) and then the influence of the metadata on sample ordination is evaluated using the "envfit" function with a total of 9999 permutations in the vegan package.

Example 17: Long-Term Trial Outcome and Analysis

Figure 23A:
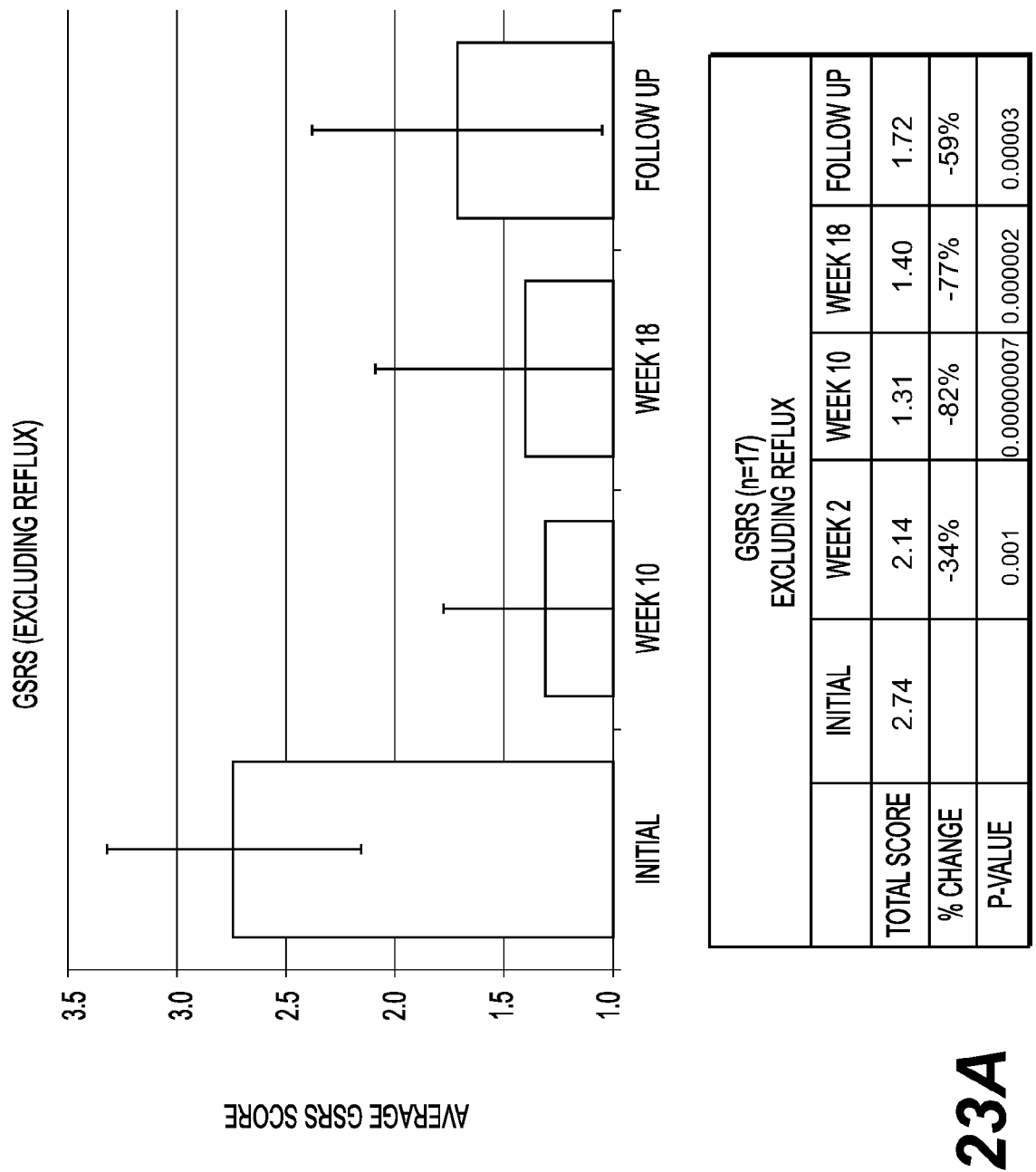
FIG. 23 (including panels a to c) provides a breakdown of GSRS components and improvements in patients. GSRS average scores of all, Panel a. and individual participants, Panel b. at baseline, MTT treatment end (week 10), 8 weeks after treatment, and 2-years after treatment (follow-up). Panel c. Results of average GSRS subscale scores patient at baseline, MTT treatment end (week 10), 8 weeks after treatment (week 18), and 2-years after treatment (follow-up). Analysis for 2-year follow-up is between 1.7 and 2.1 years after end of treatment.
Figure 23B:
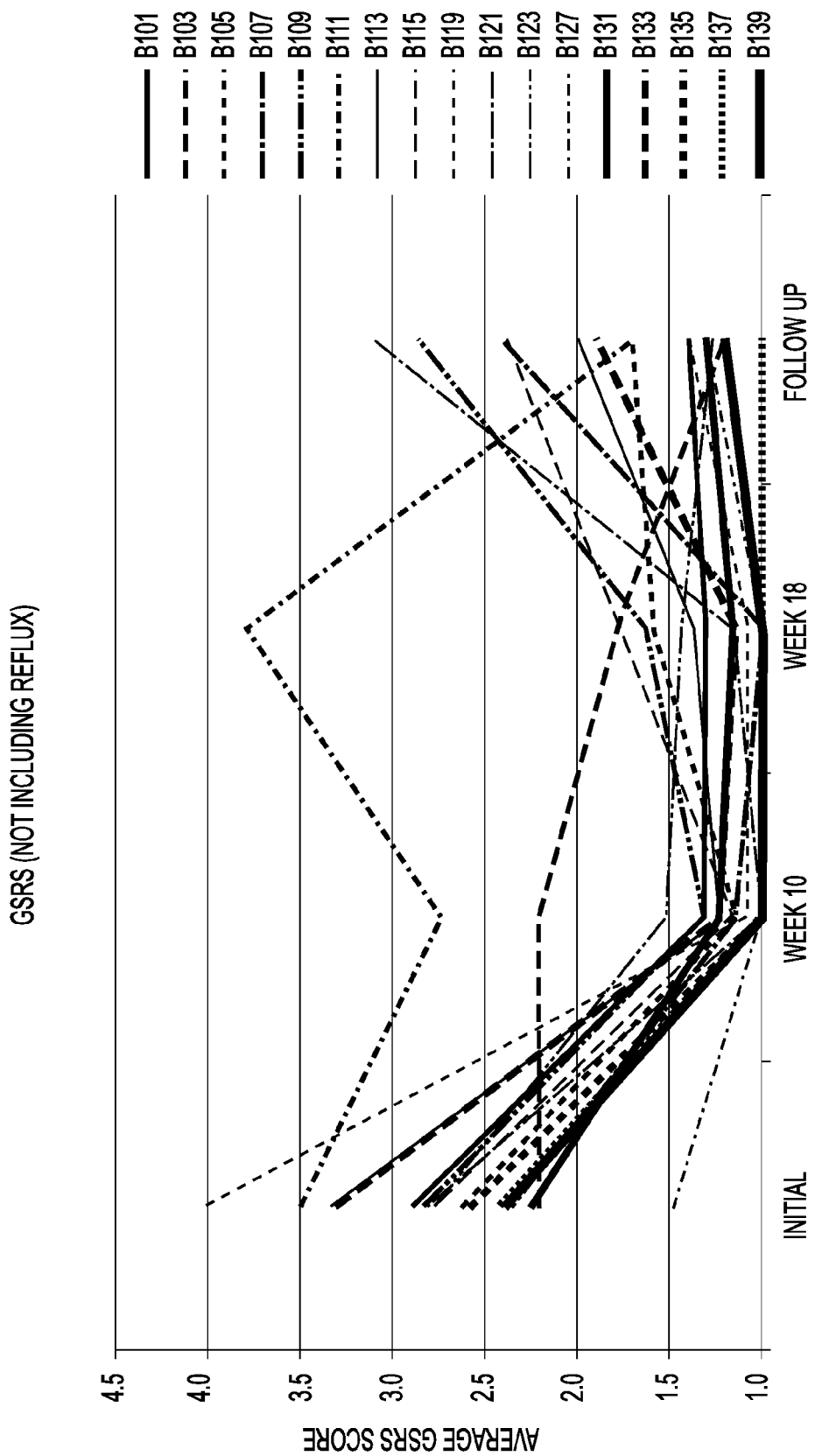
Figure 23C:
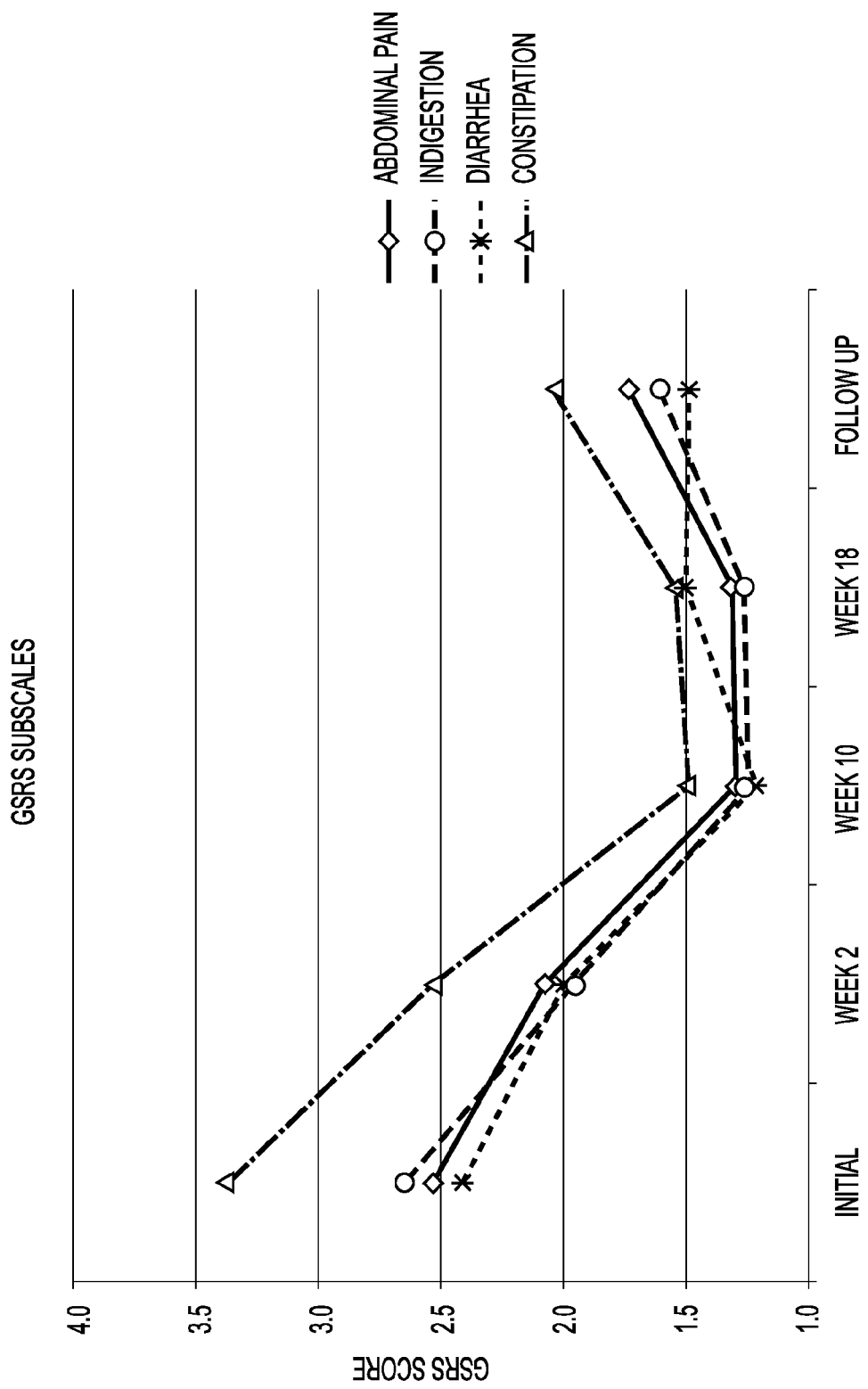

Clinically, this study remains broadly successful over a two year period of time. All ASD participants are further assessed for continued improvements during a 2 year follow-up. Specifically, overall GI symptoms, as assessed by the Gastrointestinal Symptom Rating Scale (GSRS), remain significantly improved when assessed at a 2 year follow-up (comparing approximately 2.74 average GRS score at the beginning to approximately 1.72 average GSRS score at the 2 year follow-up) (FIG. 23, panel a; and panel b (showing individual patient scores)). The percent change of average GSRS score is 82, 77, and 59% for week 10, week 18, and 2-year follow-up, respectively. GSRS scores remain improved for subscales including abdominal pain, indigestion, diarrhea, and constipation, (FIG. 23, panel c). The two-year results do not include reflux since no children had significant reflux at the start of the study. Notably, two seemingly opposite GI symptoms—diarrhea and constipation—continues to respond two years after MTT treatment.

Figure 24:
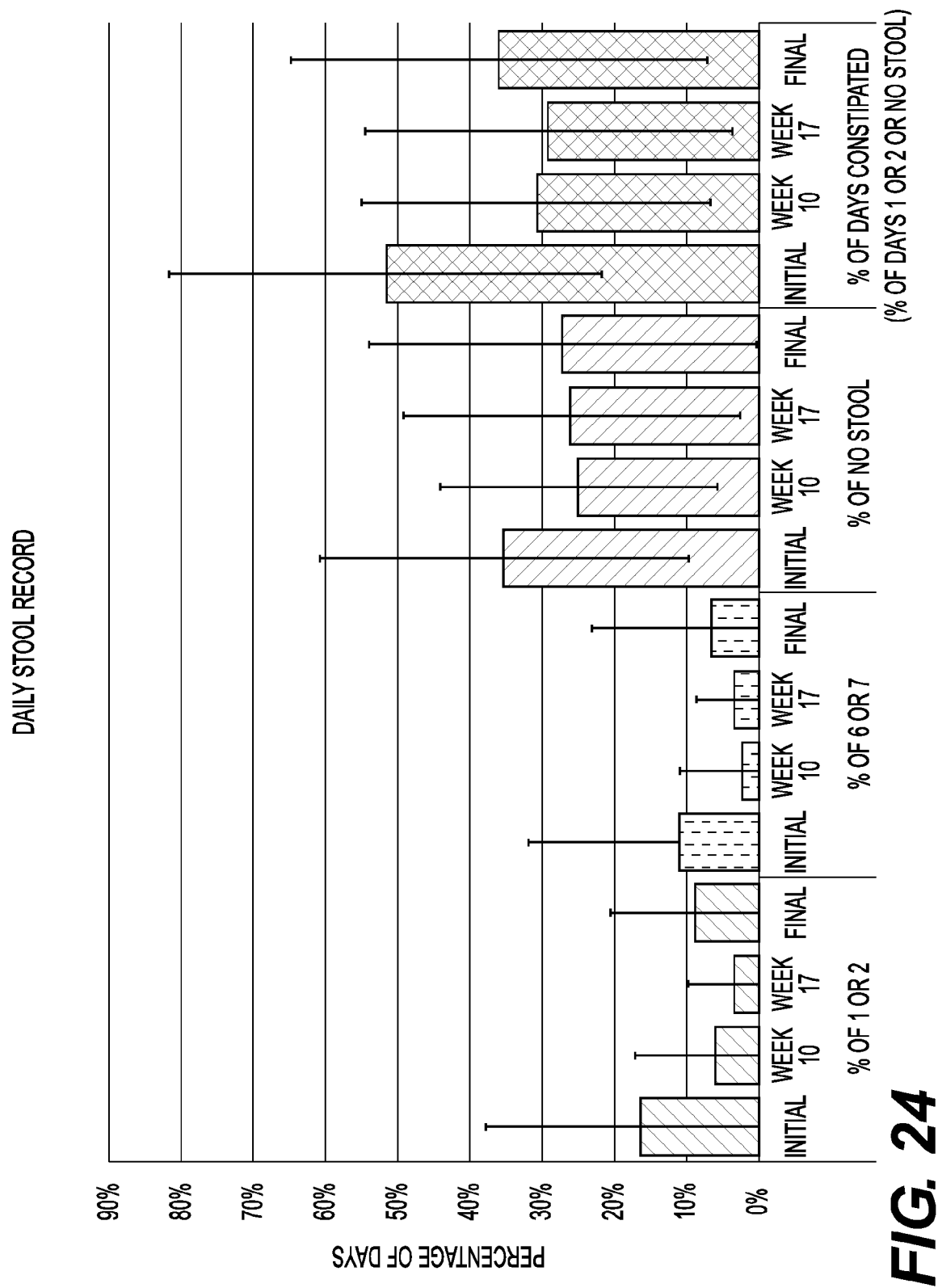
FIG. 24 provides the results of daily stool records, averaged over 2 weeks. Type 1 stool: Separate hard lumps, like nuts (hard to pass); Type 2: Sausage-shaped, but lumpy; Type 6: Fluffy pieces with ragged edges, a mushy stool; and Type 7: Watery, no solid pieces, entirely liquid.

Similarly, the Daily Stool Record (DSR), shows significant decreases in the number of days with abnormal or no stools at week 10, and these improvements remain after 8 weeks of no treatment (Table 7, column 3; and FIG. 24), and at the 2-year follow-up (Table 6, column 9; FIG. 24. Further, significant decreases in constipation is seen at week 10, after 8 weeks of no treatment, and at the 2-year follow-up. The Daily Stool Record (DSR) is collected and averaged over two weeks in order to assess changes in stool as described in Example 11. Table 7 and FIG. 24 show changes in stool for initial, week 10, after 8 weeks of no treatment, and during the 2-year follow-up. Overall, participant's show improvements in defecation.

TABLE 7

Percent days of no stool, constipation, stool hardness and softness based on the daily stool record (DSR).

| | Initial | Week 10 | Change Initial to Week 10 | P-Value | Week 17 | Change Initial to Week 17 | P-Value | 2-year Follow Up | Change Initial to Follow Up | P-Value |
|---|---|---|---|---|---|---|---|---|---|---|
| Hard stool (type 1 or 2) | 16% | 6% | −10% | 0.03 | 3% | −13% | 0.005 | 9% | −8% | 0.03 |
| Soft/liquid stool (type 6 or 7) | 11% | 2% | −9% | 0.04 | 3% | −8% | 0.05 | 6% | −5% | 0.2 |
| No stool | 35% | 25% | −10% | 0.06 | 26% | −9% | 0.13 | 27% | −8% | 0.2 |
| constipated | 52% | 31% | −21% | 0.007 | 29% | −22% | 0.01 | 36% | −16% | 0.06 |
| Abnormal stool (in total of hard, soft/liquid/, no stool) | 63% | 33% | −29% | 0.0005 | 32% | −30% | 0.001 | 42% | −20% | 0.009 |
| Type 1 or 2 & Type 6 or 7 | 27% | 8% | −19% | 0.004 | 7% | −21% | 0.001 | 15% | −12% | 0.02 |

Figure 25A:
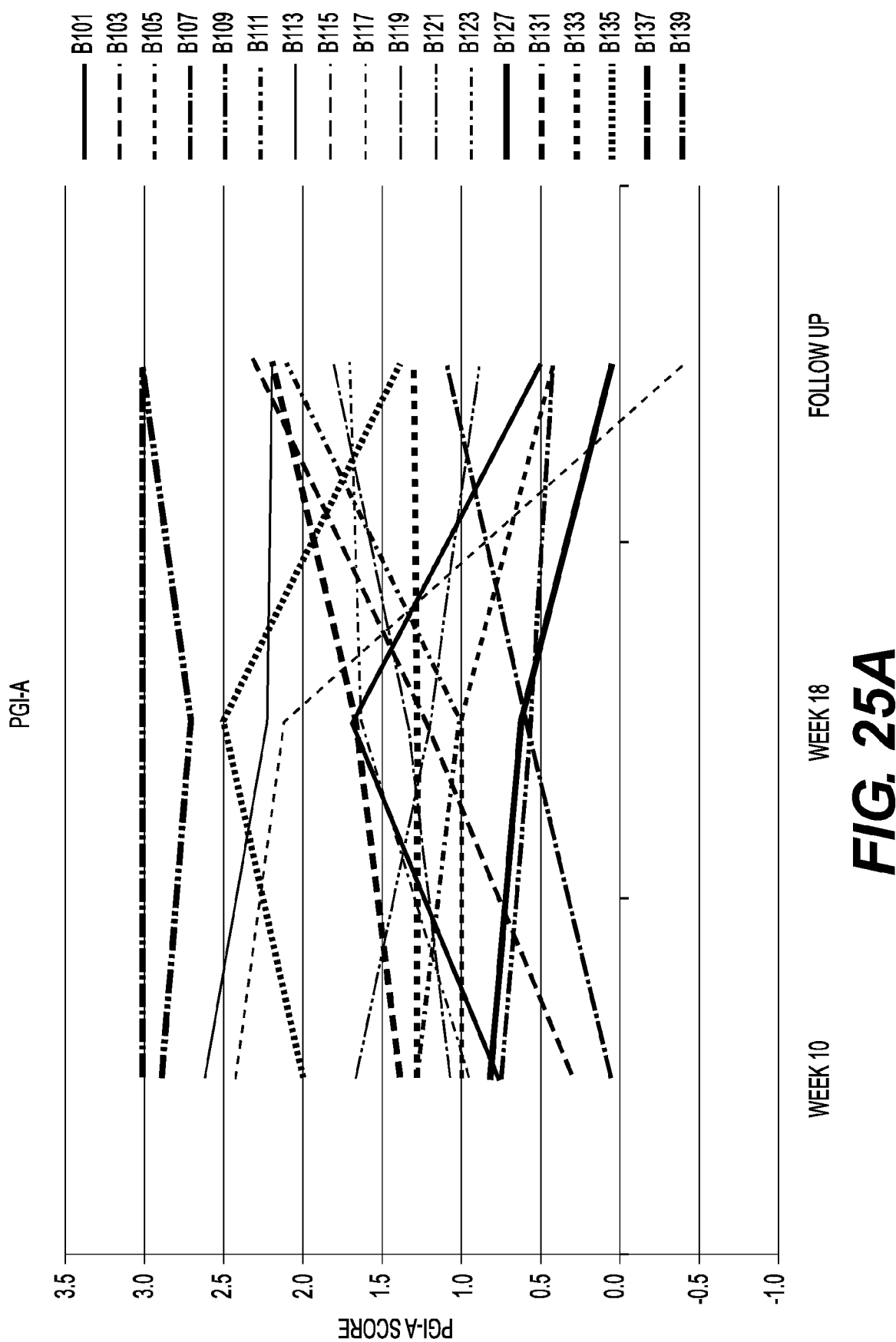
FIG. 25 (including panels a and b) provides the scores of the PGI-R at end of treatment (week 10), 8 weeks after treatment (week 18), and at the 2-year follow-up. The scale goes from 3 (much better) to 2 (better) to 1 (slightly better) to 0 (no change). Scores are similar after 8 weeks of no treatment (week 18) and 2-years of no treatment (Follow-up). The data points represent 17 individual participants.
Figure 25B:
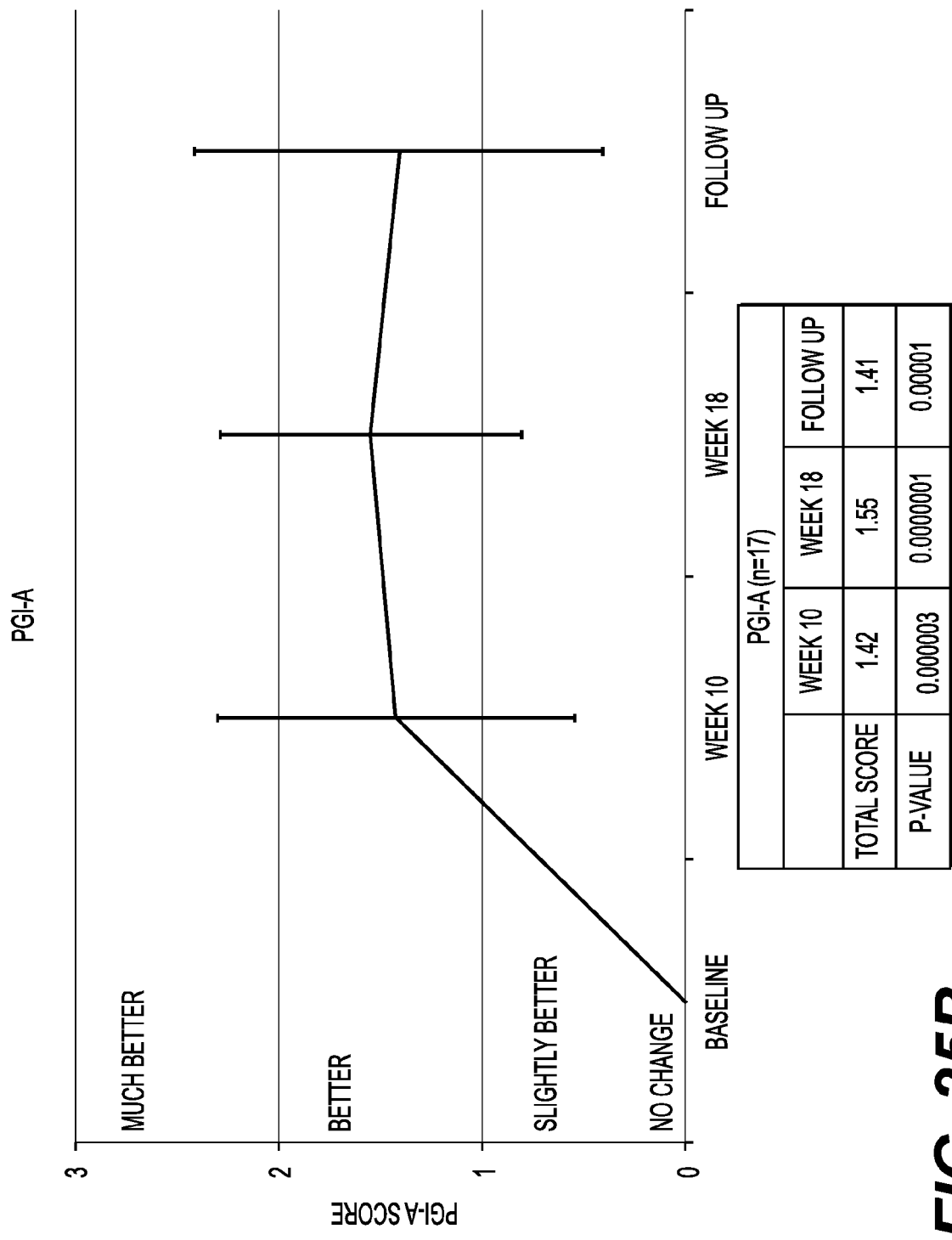

Beyond these GI improvements, ASD-related behavior also improve following MTT. First, the Parent Global Impressions (PGI-R) assessment, which evaluates 17 ASD-related symptoms, reveal significant improvement during treatment and no reversion 8 weeks after treatment ended or at the 2-year follow-up (FIG. 25, panel a, showing independent patient results; and panel b showing average of all ASD patients).

Figure 26A:
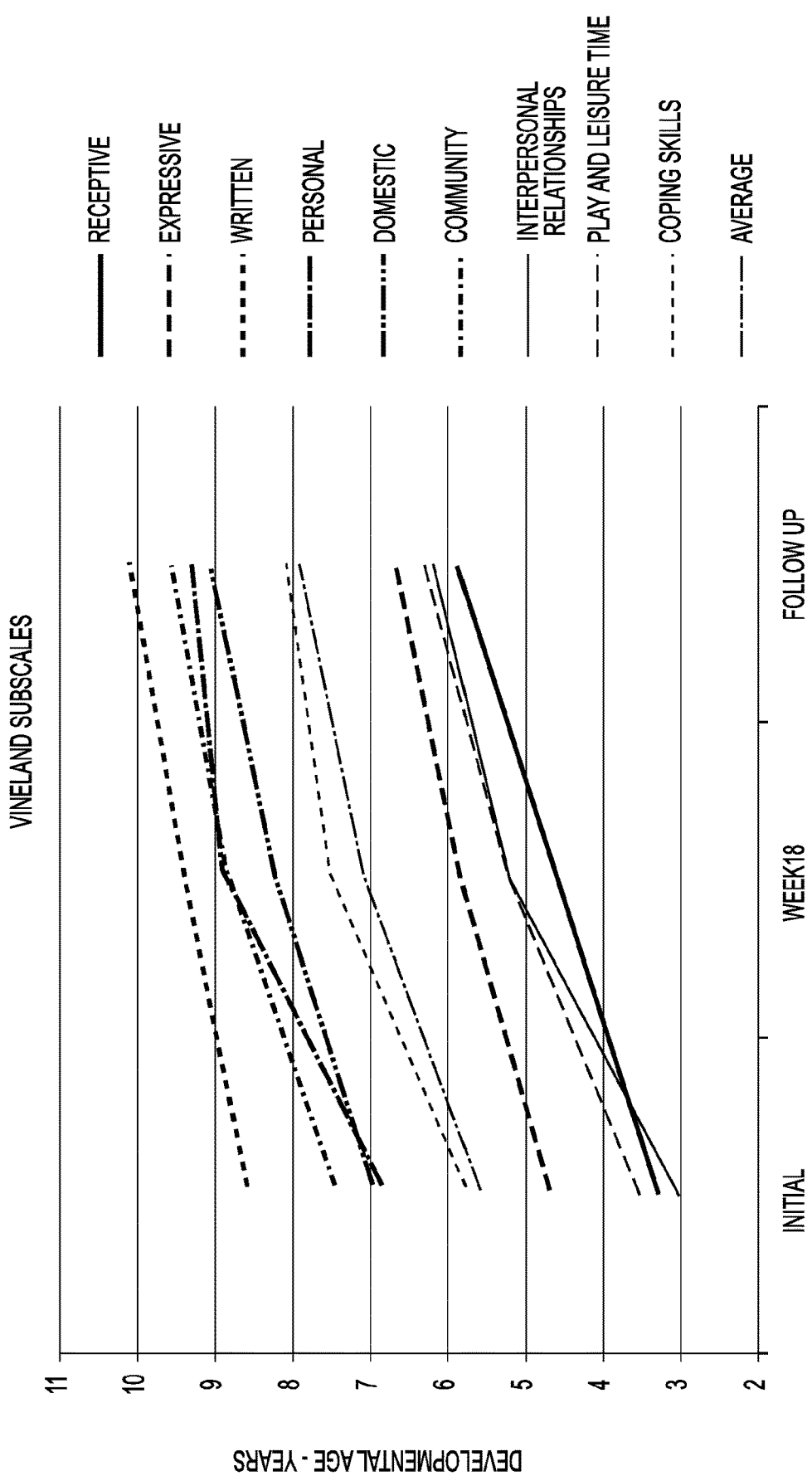
FIG. 26 (including panels a and b) shows Vineland Developmental Age in years (not including motor skills) for Panel a. different subscales and for Panel b. the average of all the subscales, measured at baseline, 8 weeks after treatment, and 2-years after treatment (Follow-up). Note that the average initial developmental age is 5.57 years vs. a chronological age of 10.9 years, so at baseline there are delays in all areas, especially in the core autism areas of language and social (interpersonal) ability.
Figure 26B:
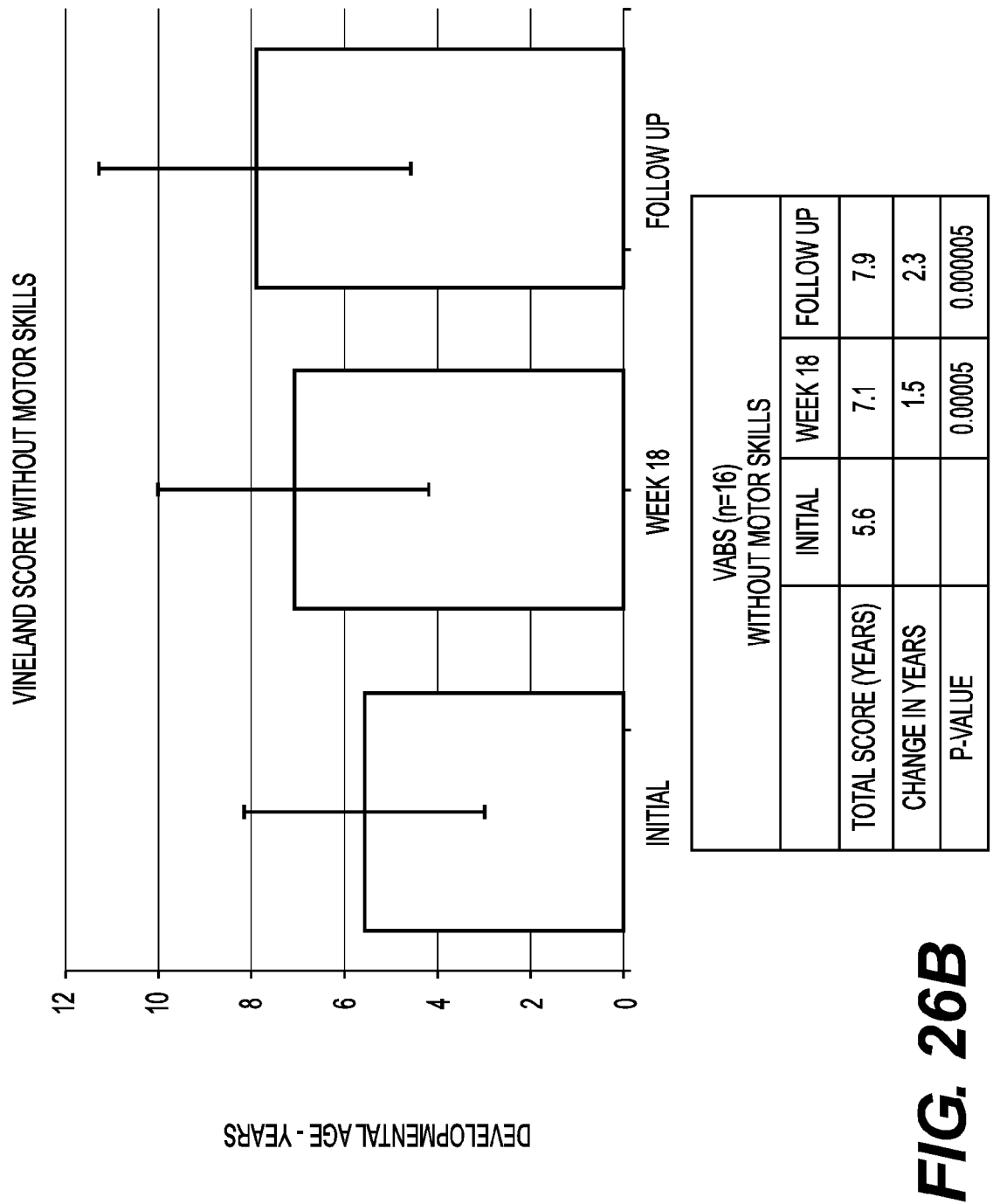

Second, the Vineland Adaptive Behavior Scale II (VABS-II) scoring shows that the average developmental age increases across 9 of the 11 sub-domain areas (FIG. 26, panel a) after 8 weeks of no treatment and the 2-year follow-up. Among 11 subscales, Fine and Gross Motor skills are excluded, since these two subscales for the Vineland are only calculated up to 6.8 years and most children with ASD improved near to the limit of the scale. The other 9 subscales and their average are compared between the baseline and at the end of the study. Significant improvements are also observed in all 9 subscale areas, at the 2-year follow-up, with the largest gains in Interpersonal Skills (3.3 years), Personal Living Skills (2.45 years), and Coping Skills (2.3 years) (FIG. 26, panel a). It is notable that the major impairments in ASD, namely Receptive language, Expressive language, and Interpersonal skills, are among the lowest initial scores, with initial developmental ages of 3.3 years, 4.7 years, and 3.04 years, respectively; all three areas had substantial improvements of 2.6, 0.8, and 3.3 years, respectively. The VABS-II scoring also shows an overall increase in the average developmental age by 1.5 years ($p<0.001$, VABS-II) after 8 weeks with no treatment and 2.3 years ($p<0.001$, VABS-II), for the 2-year follow-up (FIG. 26, panel b).

Figure 27A:
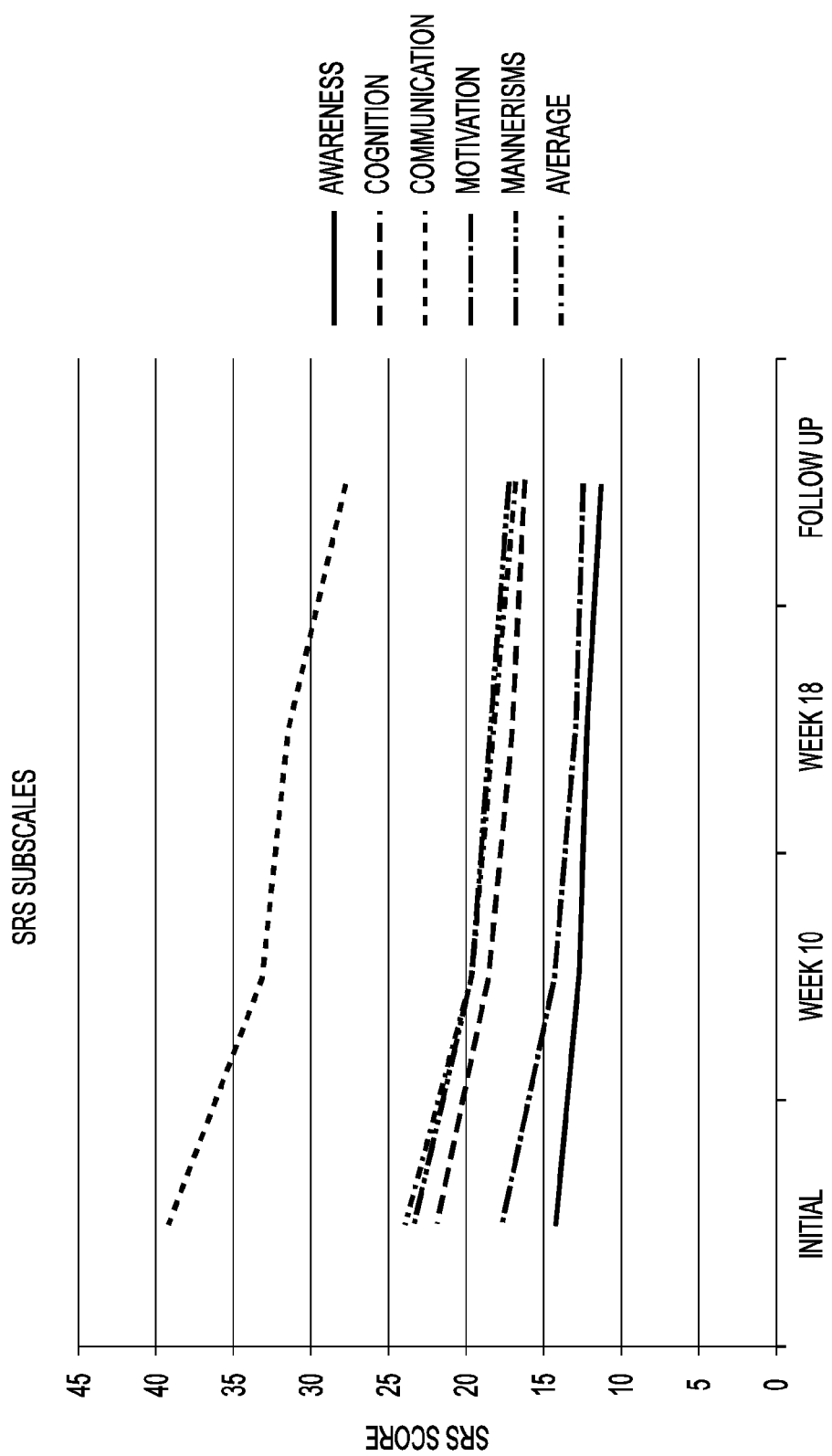
FIG. 27 (including panels a and b) shows SRS subscales scores at baseline, MTT treatment end (week 10), 8 weeks after treatment, and 2-years after treatment (follow-up). Panel b, shows average overall SRS scores. The scores range from severe range, to mild-to-moderate range, to normal range. The data points represent 17 individual participants.
Figure 27B:
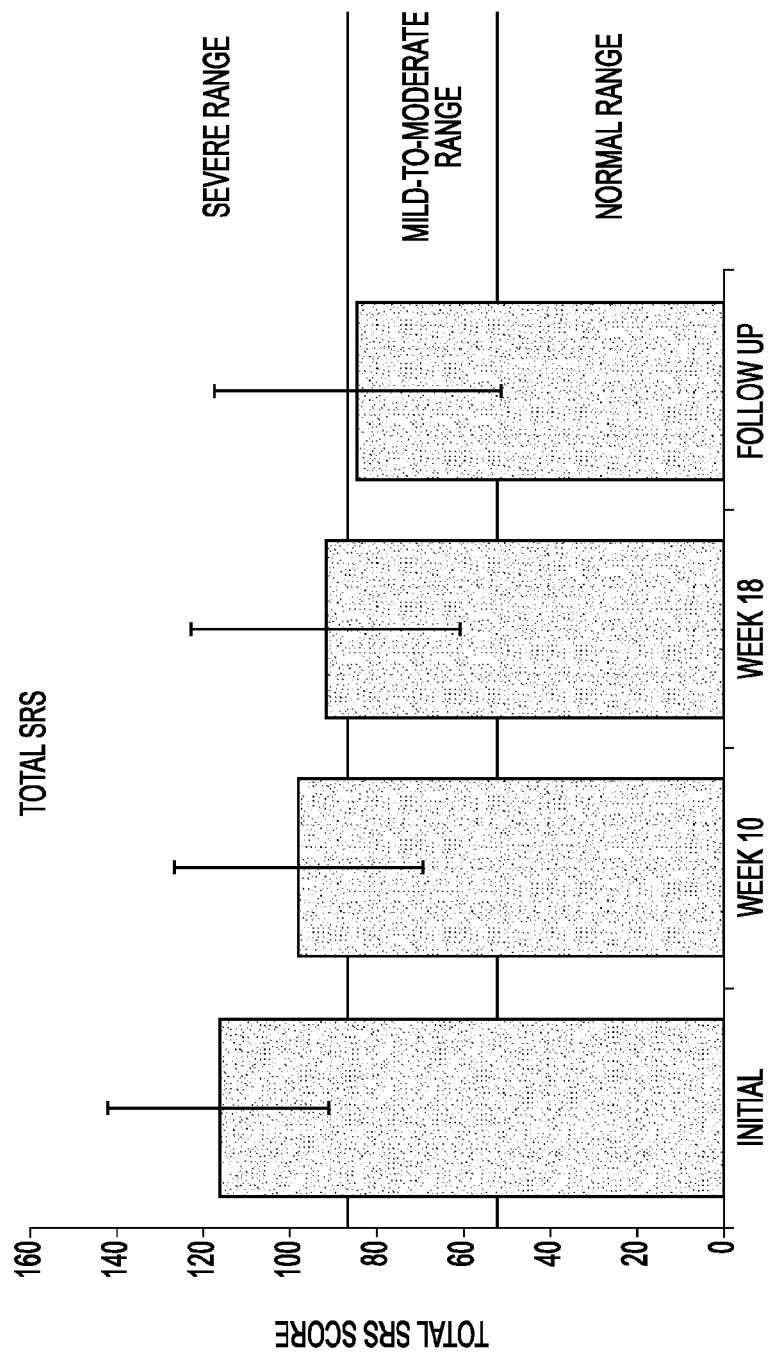
Figure 28A:
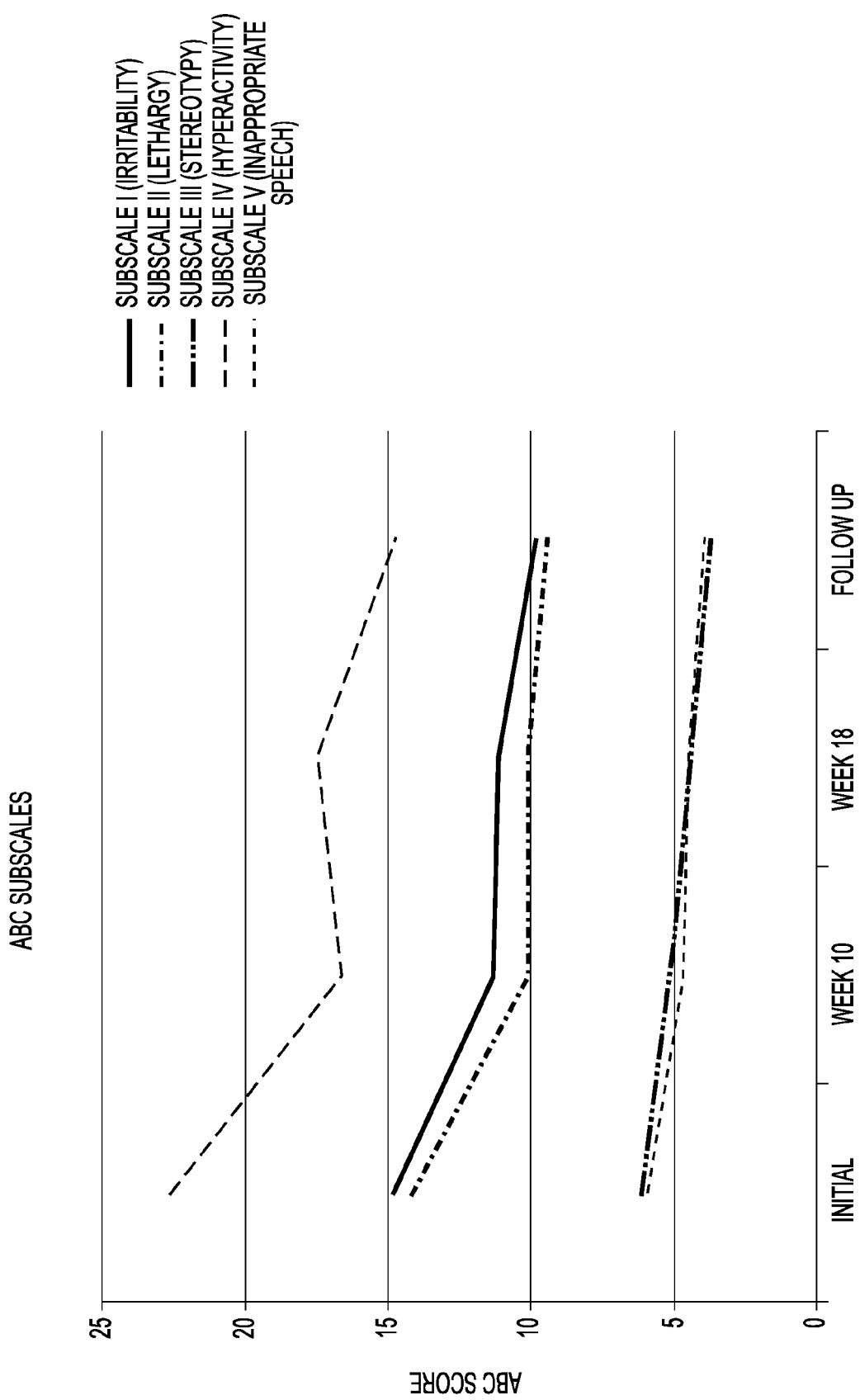
FIG. 28 (including panels a and b) shows ABC subscales scores at baseline, MTT treatment end (week 10), 8 weeks after treatment, and 2-years after treatment (follow-up). Panel b, shows average overall ABC scores. The data points represent 18 individual participants.
Figure 28B:
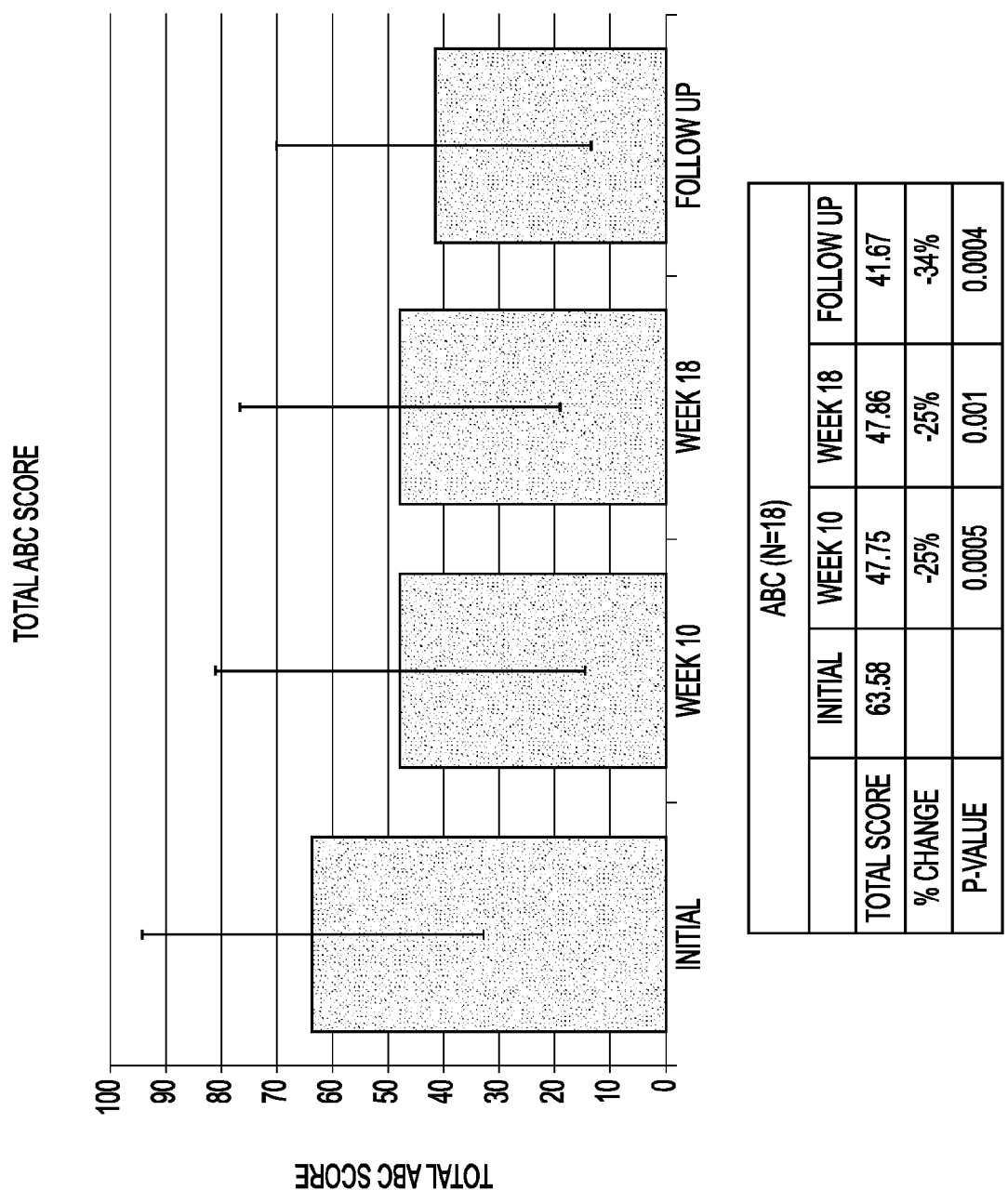
Figure 29A:
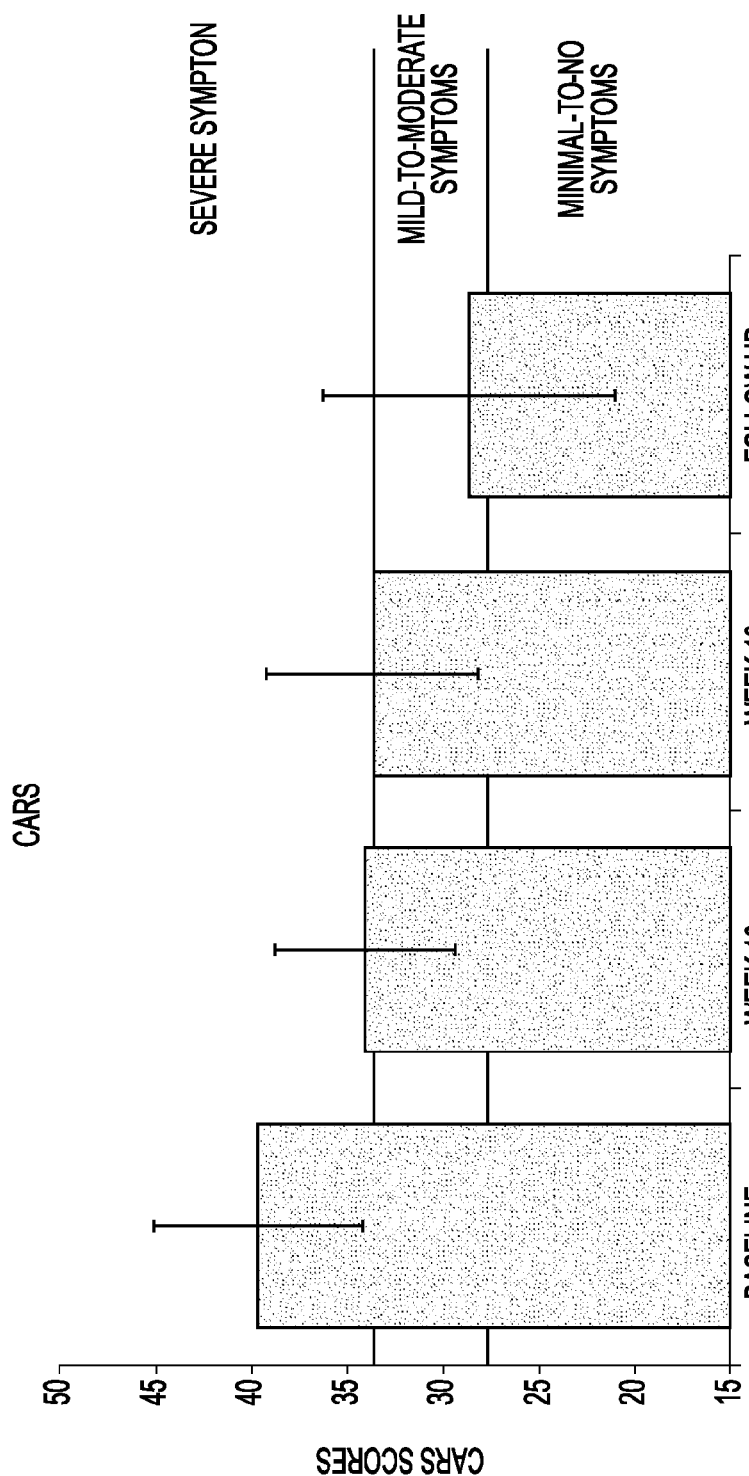
FIG. 29 (including panels a to d) show total CARS scores at baseline, MTT treatment end (week 10), 8 weeks after treatment, and 2-years after treatment (follow-up). The scores range from severe symptoms, to mild-to-moderate symptoms, to minimal-to-no symptoms. Panel b. shows the percentage of participants with severe symptoms, mild-to-moderate symptoms, and minimal-to-no symptoms, at baseline, end of treatment, and follow-up. The data points represent 18 individual participants. Panels c and d. demonstrate a correlation between GSRS and CARS based on percentage change and difference.
Figure 29B:
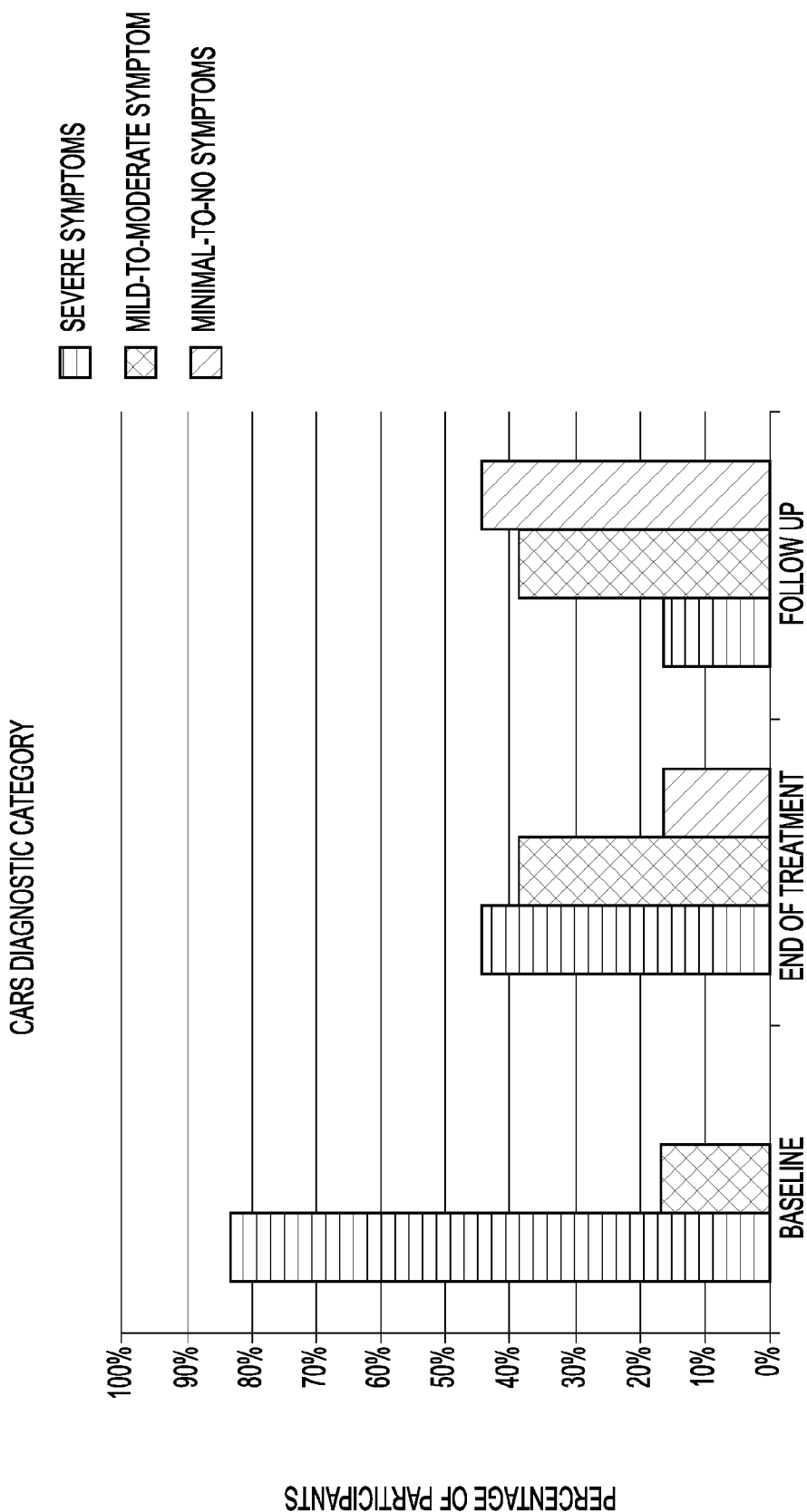
Figure 29C:
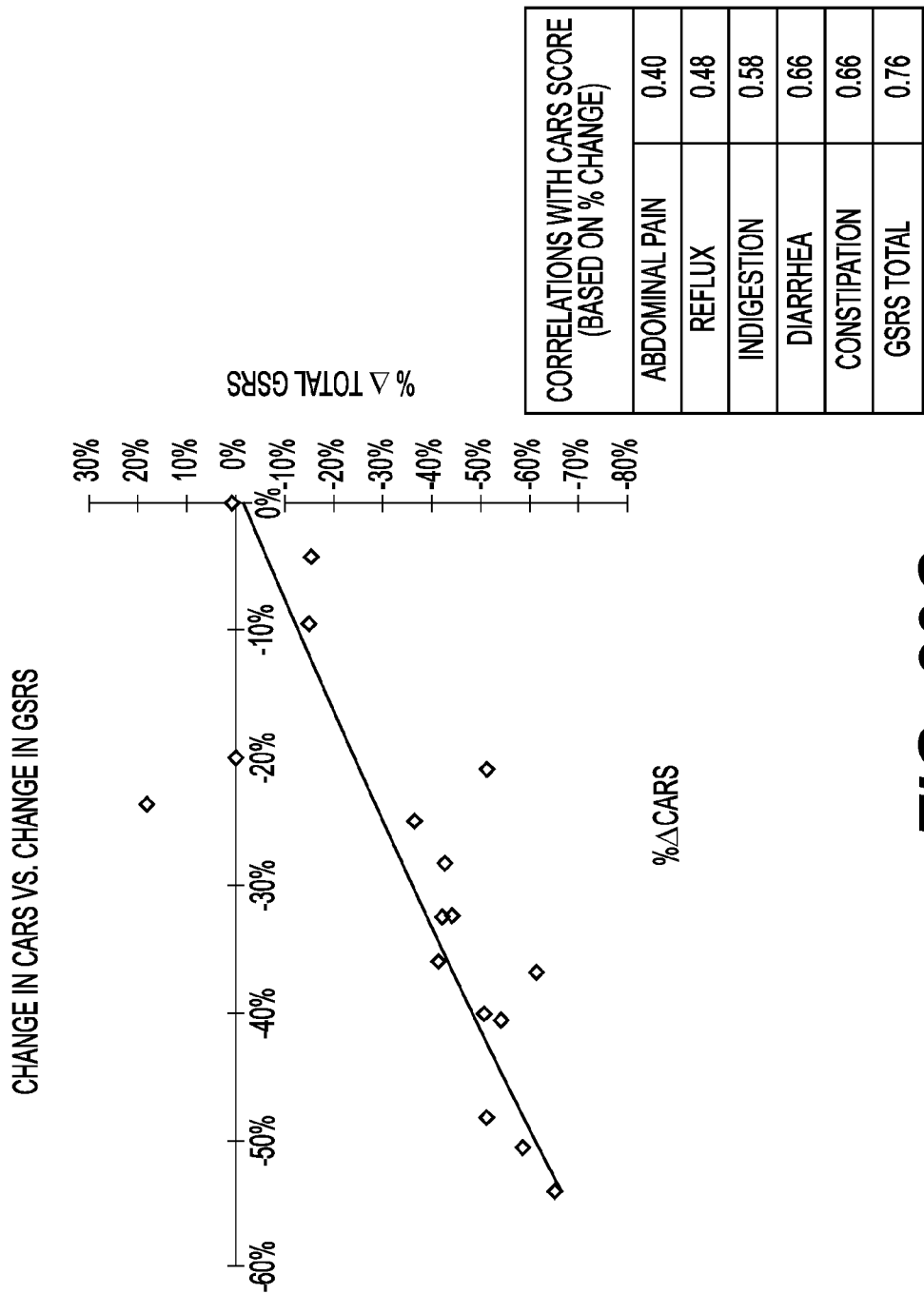
Figure 29D:
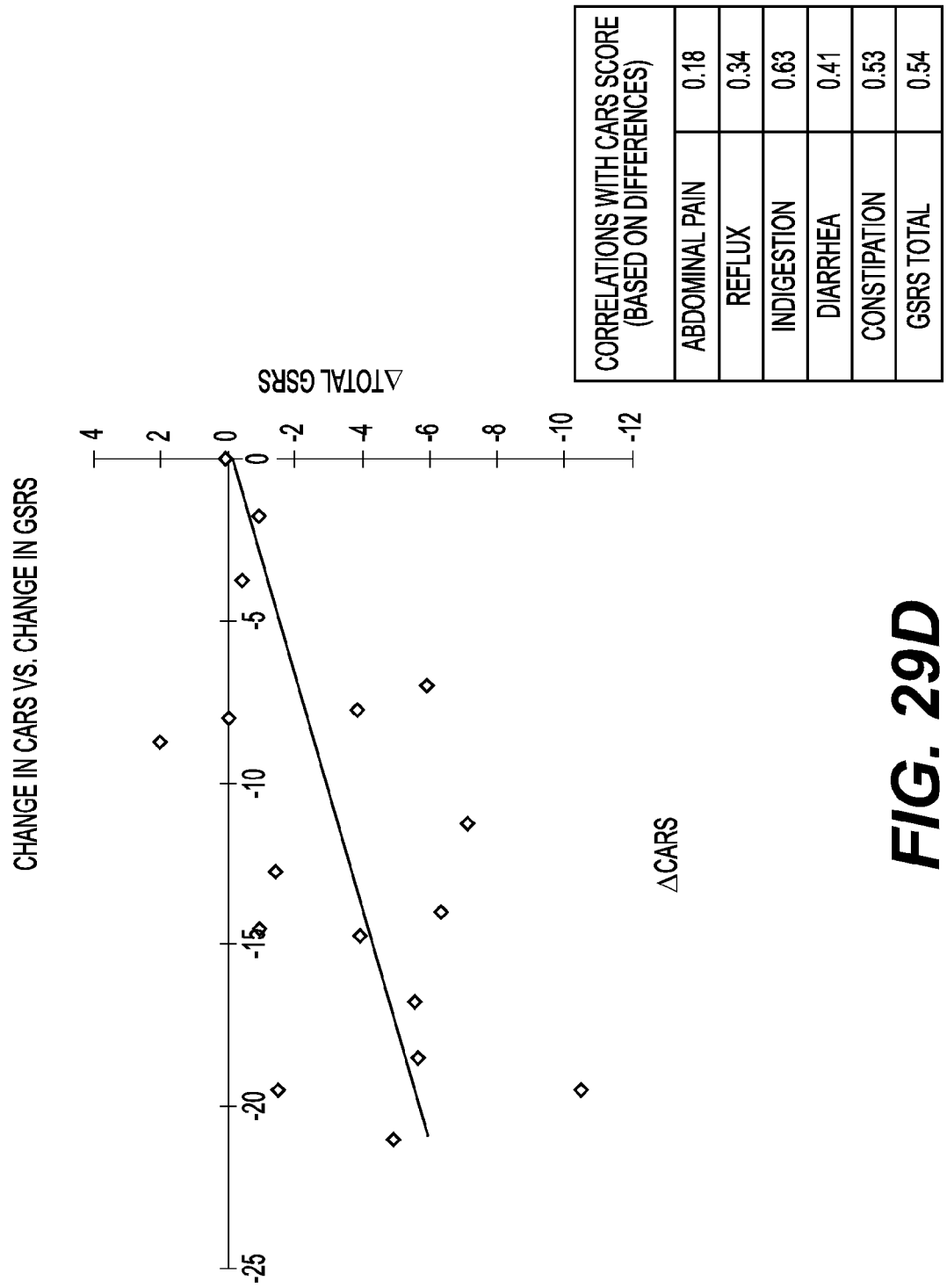

Third, ASD-afflicted children show improvements in their scores in the Social Responsiveness Scale (SRS), which assesses social skill deficits including awareness, cognition, communication, motivation, and mannerisms (FIG. 27, panel a and panel b). ASD-afflicted children also show improvements in their scores in the Aberrant Behavior Checklist (ABC), which evaluates irritability, hyperactivity, lethargy, stereotypy, and inappropriate speech (FIG. 28, panel a). In all five sub-scales, a significant reduction at the end of treatment is observed. FIG. 28, panel b, shows an overall improvement in ABC scores at week 10, after 8 weeks of no treatment, and at the 2-year follow-up.

Fourth, the Childhood Autism Rating Scale (CARS), which rates core ASD symptoms, decrease from the severe symptoms range at the beginning of the treatment, to the mild-to-moderate symptoms range after 8 weeks of no treatment and close to the minimal-to-no symptoms range (with some participants within the minimal-to-no symptoms range) at the 2-year follow-up ($p<0.001$, FIG. 29, panel a). The percentage of participants with severe symptoms decrease overtime and the percentage of participants with minimal-to-no symptoms increase overtime (17% and 44% of participants with minimal-to-no symptoms at the end of treatment and at the 2-year follow-up, respectively) (FIG. 29, panel b). Further, a significant correlation between GSRS and CARS suggests that GI symptoms impact ASD behaviors, and that these can be altered via MTT (FIG. 29, panels c and d)

Together these findings show that MTT is well-tolerated across an age-diverse cohort of 18 ASD-afflicted children. MTT is also effective as it led to significant improvements in GI-symptoms that are mostly sustained at least 2-years after treatment, and improvements in behavior-related symptoms by the end of treatment, with greater improvements at the two-year follow-up.

Figure 30A:
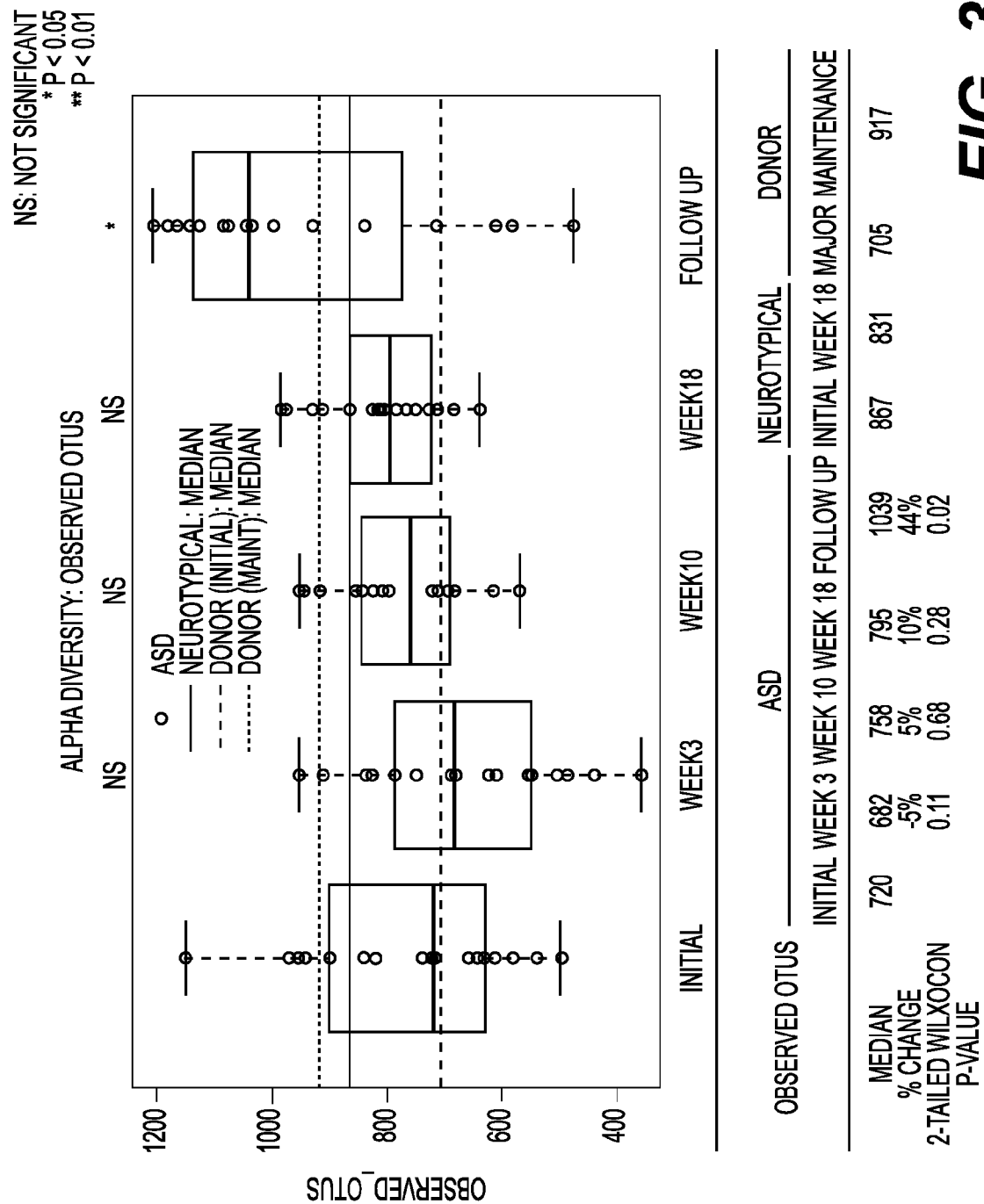
FIG. 30 (including panels a to d) describes stool microbiota changes in ASD patients receiving MTT, as measured with an observed OTU diversity metric, Panel a. and Faith's Phylogenetic Diversity (PD), Panel b. Most individuals experienced an increase in gut microbiota PD. Panel c, shows Mann-Whitney test of diversity comparisons 2-years after treatment between participants receiving oral and rectal administration of MTT. Panel d. shows a Mann-Whitney test of diversity comparisons 2-years after treatment between male and female participants. ns: not significant, *: $p<0.05$, **: $p<0.01$ (two-tailed Wilcoxon signed-rank test).
Figure 30B:
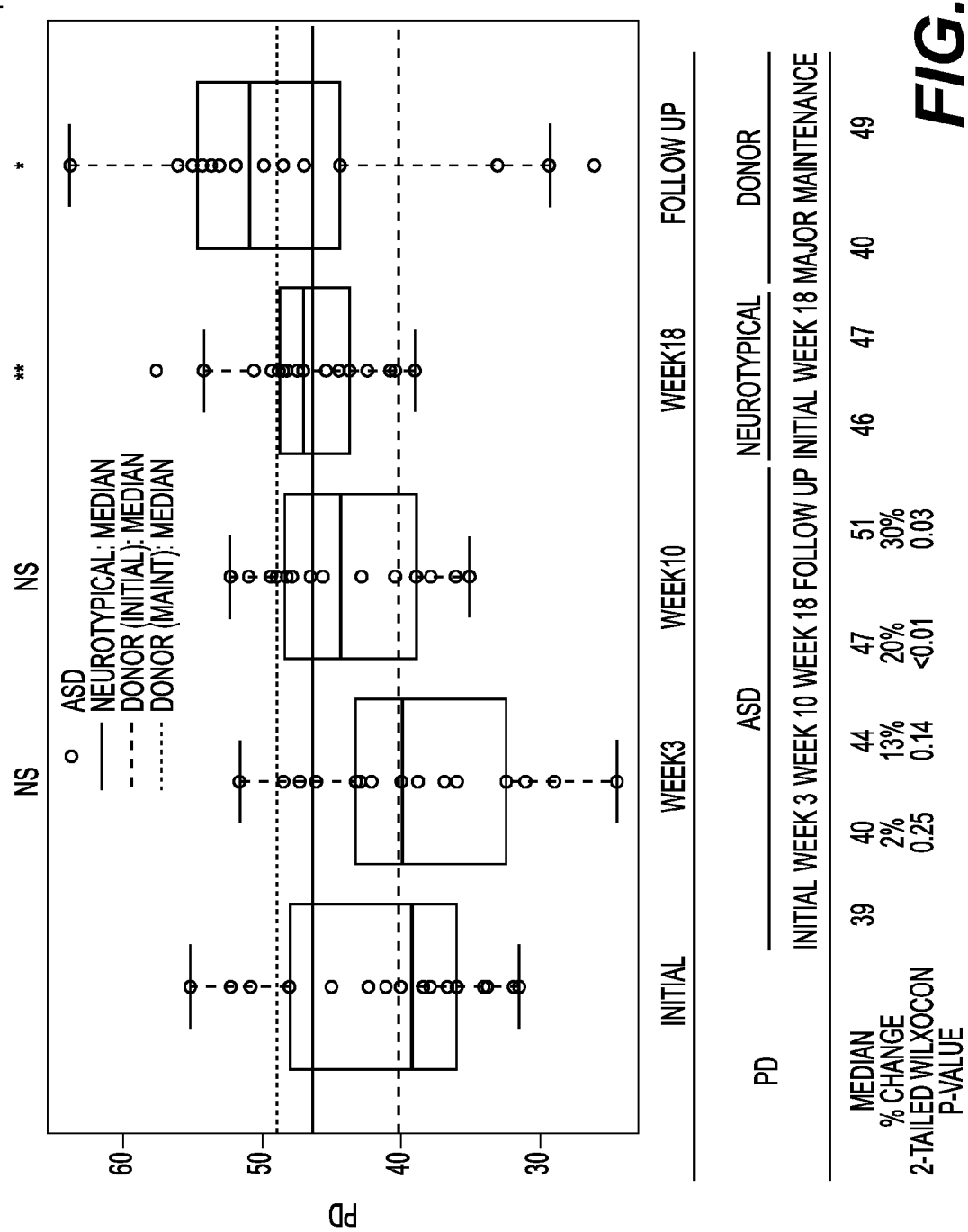

Example 18: Microbiome Analysis Across Common Diversity Metrics Up to the 2-Year Follow-Up Parallel analyses are performed for multiple diversity metrics, as identified in Examples 12 and 14 above, to understand the effect of metric on the microbiome findings. The Observed OTUs metric shows a count of the number of OTUs observed at least two times in a sample (FIG. 30, panel a). FIG. 30, panel b, describes Faith's Phylogenetic Diversity (PD) changes in ASD participants receiving MTT. Similar to the results of the Observed OTUs, microbial bacterial diversity increased in stools of children with ASD, and remained higher than baseline 2-years after the treatment (Follow-up). This confirms that both phylogenetic and non-phylogenetic metrics illustrate the same patterns of change in community richness with MTT for at least 2-years.

The Observed OTUs at the 2-years follow-up are also analyzed based on route of administration, oral vs. rectal. Mann-whitney tests show a marginally higher diversity in participants who receive oral administration (2-tailed $p=0.09$), compared to patients receiving MTT rectally (FIG.

30, panel c). No significant difference is observed between male and female participants at the 2-year follow-up (FIG. 30, panel d).

Figure 31A:
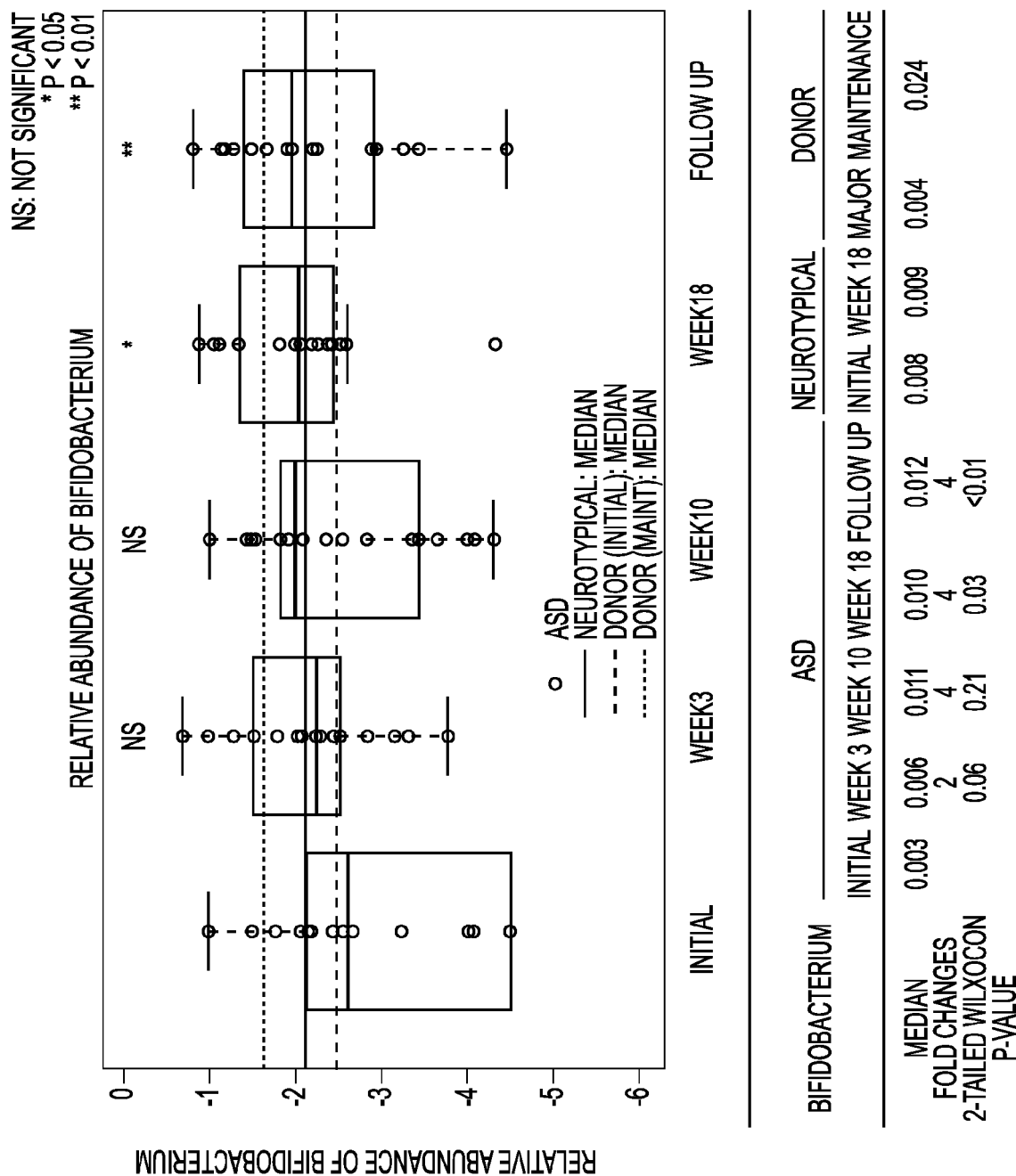
FIG. 31 (including panels a to c) shows boxplots illustrating abundance of three genera, *Bifidobacterium* (Panel a.), *Prevotella* (Panel b.), and *Desulfovibrio* (Panel c.), in the gut microbiota, and change in abundance at week 3 during treatment, week 10 at treatment end, 8 weeks after no treatment, and 2-years after no treatment (Follow-up) in the ASD participants. ns: not significant, *: $p<0.05$, **: $p<0.01$ (two-tailed Wilcoxon signed-rank test).
Figure 31B:
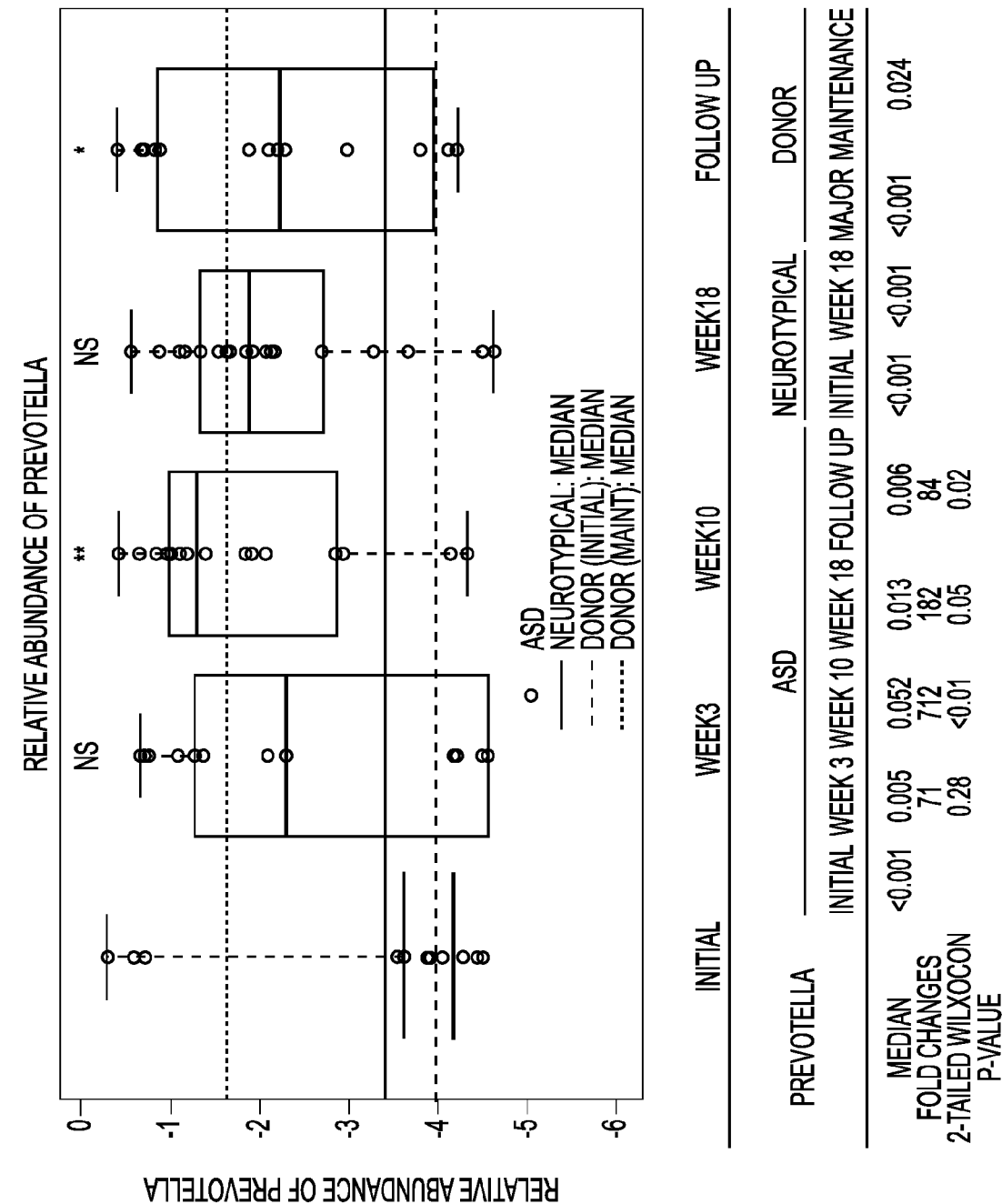
Figure 31C:
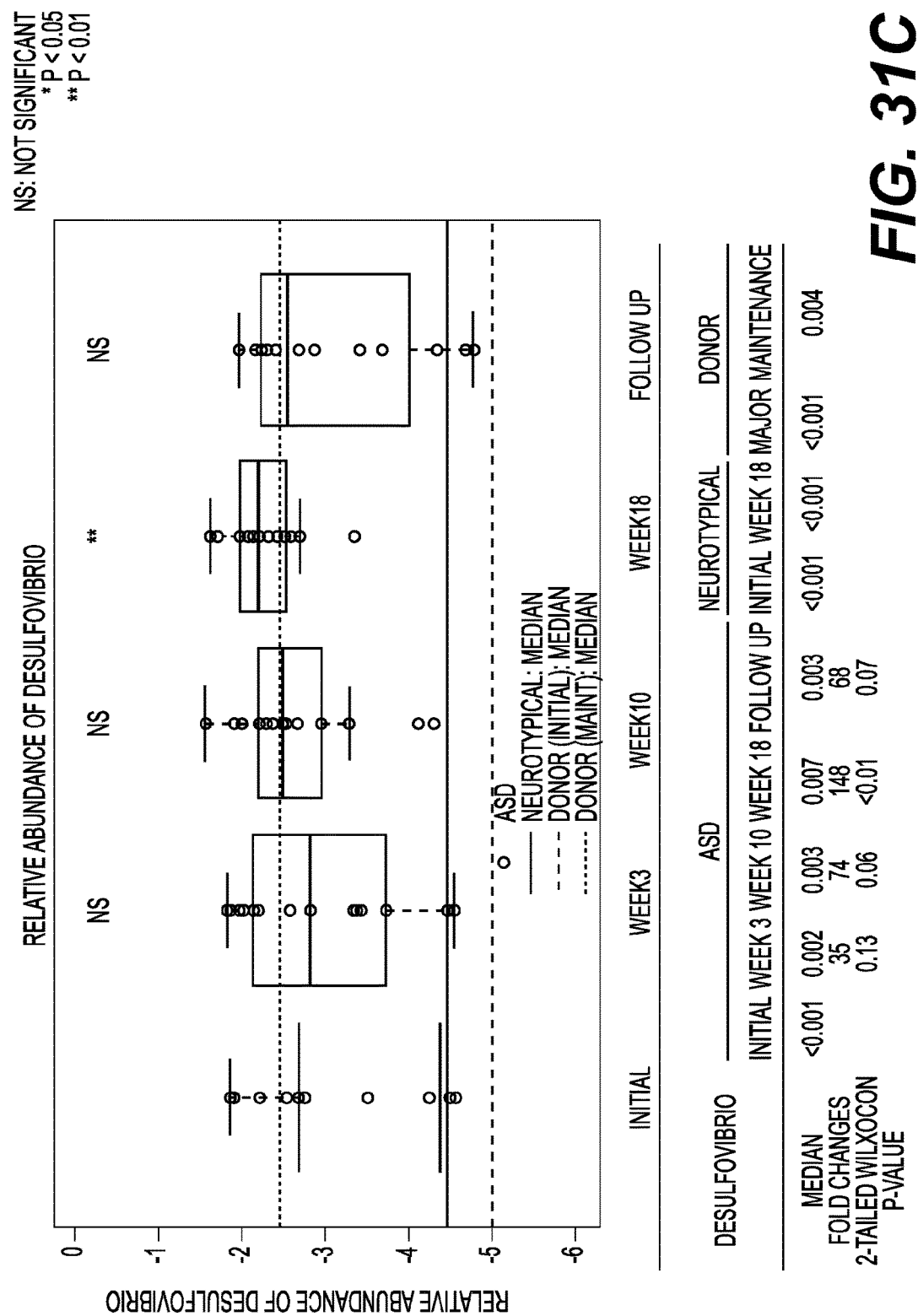

Example 18: MTT Changes and Maintains the Abundance of Selected Bacterial Genera in ASD Patients for at Least 2-Years Several bacterial genera maintain their increase in abundance compared to the initial treatment when assessed at the 2-year follow-up. These genera include *Bifidobacterium* (FIG. 31, panel a), *Prevotella* (FIG. 31, panel b) and *Desulfovibrio* (FIG. 31, panel c) which all maintaining their abundance above the Neurotypical participant median. As outlined above in Example 13 (and FIG. 31, panel a and b), *Bifidobacterium*, and *Prevotella* are both under-represented in ASD-afflicted children, but at the 2-year follow-up to MTT, *Bifidobacterium* significantly increases 4-fold (FIG. 30, panel a; $p<0.01$), and *Prevotella* significantly increases 84-fold (FIG. 31, panel b; $p<0.05$). These genera also show a significant increase in abundance at weeks 3 and 10 of treatment, and after 8 weeks of no treatment. *Desulfovibrio* also increases 68-fold after MTT from baseline to the 2-year follow-up. This suggests strong engraftment by these microbes in particular.

Without being bound to any scientific theory, this suggests strong engraftment by these microbes in particular. *Bifidobacterium*, *Desulfovibrio* and *Prevotella* are on average more abundant in MTT recipients at 2-years following treatment than the neurotypical median, illustrating that the transferred microbiota adapts in its new host, but also that MTT changes the gut environment in a way that is more hospitable to recruit new commensal bacteria. Taken together, these data suggest that MTT successfully shifts the ASD microbiota toward that of age/gender matched neurotypical controls.

The invention claimed is:

1. A method for increasing the relative abundance of gut microorganisms in a subject having an autism spectrum disorder (ASD), said method comprising treating said subject by administering a therapeutically effective amount of a pharmaceutical composition comprising a fecal microbe preparation comprising a community of fecal bacteria from a stool of a human donor, thereby improving one or more ASD symptoms in said subject and causing said subject to exhibit at least a 2-fold increase of the relative abundance of each of *Bifidobacterium* and *Desulfovibrio* in the gut of said subject after said treatment as compared to before initiating said treatment.

2. The method of claim 1, wherein said method further comprises determining in said subject the relative abundance of said *Bifidobacterium* and *Desulfovibrio*.

3. The method of claim 1, wherein said one or more ASD symptoms comprise an impairment in sociability.

4. The method of claim 1, wherein said subject exhibits at least a 10% reduction in ASD symptom severity after said treatment as compared to before initiating said treatment, and based on an assessment system selected from the group consisting of Childhood Autism Rating Scale (CARS), Childhood Autism Rating Scale 2-Standard Form (CARS2-ST), Childhood Autism Rating Scale 2-High Functioning (CARS2-HF), Aberrant Behavior Checklist (ABC), Social Responsiveness Scale (SRS), and Vineland Adaptive Behavior Scale II (VABS-II).

5. The method of claim 1, where said subject exhibits the at least 2-fold increase after 2 or more weeks of initiating said administering of the therapeutically effective amount of the pharmaceutical composition.

6. The method of claim 1, where said subject exhibits the at least 2-fold increase for at least 8 weeks after discontinuing said administering of the therapeutically effective amount of the pharmaceutical composition.

7. The method of claim 1, where said subject further exhibits one or more GI symptoms prior to initiating said treatment.

8. The method of claim 7, where said subject exhibits at least a 50% reduction in GI symptom severity based on the Gastrointestinal Symptom Rating Scale (GSRS) after said treatment as compared to before initiating said treatment.

9. The method of claim 1, where said treating further comprises administering an antibiotic to said subject prior to administering said pharmaceutical composition.

10. The method of claim 1, wherein said pharmaceutical composition is administered orally.

11. The method of claim 1, wherein said fecal microbe preparation is lyophilized.

12. The method of claim 1, wherein said fecal microbe preparation comprises a non-selected and substantially complete fecal microbiota from a single donor.

13. The method of claim 1, wherein said fecal microbe preparation comprises a preparation of viable flora in proportional content that resembles a normal healthy human fecal flora and comprises no antibiotic resistant populations.

14. The method of claim 1, wherein said pharmaceutical composition is formulated as an acid-resistant capsule.

15. The method of claim 1, wherein said fecal microbe preparation comprises bacteria from the genus *Lactobacillus*.

16. The method of claim 15, wherein said bacteria from the genus *Lactobacillus* are cultured.

17. The method of claim 16, wherein said fecal microbe preparation further comprises a non-selected fecal microbiota.

18. The method of claim 1, wherein said fecal microbe preparation is spray-dried.

19. The method of claim 1, wherein said pharmaceutical composition is formulated as acid-resistant microcapsules.

20. The method of claim 19, wherein said pharmaceutical composition is administered to the subject with a food or drink.

* * * * *